(12) United States Patent
Coffman et al.

(10) Patent No.: US 10,722,591 B2
(45) Date of Patent: Jul. 28, 2020

(54) CLEAVABLE CONJUGATES OF TLR7/8 AGONIST COMPOUNDS, METHODS FOR PREPARATION, AND USES THEREOF

(71) Applicant: Dynavax Technologies Corporation, Berkeley, CA (US)

(72) Inventors: Robert L. Coffman, Portola Valley, CA (US); Stewart D. Chipman, Bainbridge Island, WA (US); Radwan Kiwan, Richmond, CA (US); Samuel Zalipsky, Redwood City, CA (US); Gary S. Ott, Oakland, CA (US)

(73) Assignee: Dynavax Technologies Corporation, Emeryville, CA (US)

( * ) Notice: Subject to any disclaimer, the term of this patent is extended or adjusted under 35 U.S.C. 154(b) by 0 days.

(21) Appl. No.: 16/190,010

(22) Filed: Nov. 13, 2018

(65) Prior Publication Data

US 2019/0151462 A1    May 23, 2019

Related U.S. Application Data

(60) Provisional application No. 62/586,110, filed on Nov. 14, 2017.

(51) Int. Cl.
| | |
|---|---|
| *A61K 31/4745* | (2006.01) |
| *A61K 47/65* | (2017.01) |
| *A61K 47/69* | (2017.01) |
| *A61K 47/54* | (2017.01) |
| *C07D 471/04* | (2006.01) |
| *C07D 519/00* | (2006.01) |
| *A61K 47/68* | (2017.01) |
| *A61K 47/60* | (2017.01) |
| *A61P 35/00* | (2006.01) |

(52) U.S. Cl.
CPC .......... *A61K 47/65* (2017.08); *A61K 31/4745* (2013.01); *A61K 47/54* (2017.08); *A61K 47/545* (2017.08); *A61K 47/60* (2017.08); *A61K 47/6803* (2017.08); *A61K 47/6855* (2017.08); *A61K 47/6889* (2017.08); *A61K 47/6939* (2017.08); *A61P 35/00* (2018.01); *C07D 471/04* (2013.01); *C07D 519/00* (2013.01)

(58) Field of Classification Search
CPC .......................... A61K 31/4745; C07D 471/04
USPC ............................................ 514/293; 546/82
See application file for complete search history.

(56) References Cited

U.S. PATENT DOCUMENTS

| | | |
|---|---|---|
| 4,689,338 A | 8/1987 | Gerster |
| 5,446,153 A | 8/1995 | Lindstrom |
| 6,110,929 A | 8/2000 | Gerster |
| 6,180,095 B1 | 1/2001 | Greenwald et al. |
| 6,194,425 B1 | 2/2001 | Gerster |
| 7,199,131 B2 | 4/2007 | Lindstrom |
| 7,276,248 B2 | 10/2007 | Zalipsky et al. |
| 7,375,180 B2 | 5/2008 | Gorden |
| 7,387,271 B2 | 6/2008 | Noelle |
| 7,427,629 B2 | 9/2008 | Kedl |
| 7,592,307 B2 | 9/2009 | Zalipsky et al. |
| 7,799,800 B2 | 9/2010 | Wightman |
| 7,923,560 B2 | 4/2011 | Wightman |
| 7,993,659 B2 | 8/2011 | Noelle |
| 8,329,197 B2 | 12/2012 | Noelle |
| 8,728,486 B2 | 5/2014 | David et al. |
| 8,951,528 B2 | 2/2015 | Stoermer |
| 9,161,976 B2 | 10/2015 | Noelle |
| 9,441,005 B2 | 9/2016 | David |
| 9,801,947 B2 | 10/2017 | Miller |
| 9,962,453 B2 | 5/2018 | Georges |
| 10,105,426 B2 | 10/2018 | Noelle |
| 2004/0202720 A1 | 10/2004 | Wightman |
| 2004/0265351 A1 | 12/2004 | Miller |
| 2011/0280903 A1 | 11/2011 | Noelle |
| 2012/0294885 A1 | 11/2012 | David |
| 2014/0141033 A1 | 5/2014 | Vernejoul et al. |
| 2015/0141625 A1 | 5/2015 | Stoermer |
| 2017/0319712 A1 | 11/2017 | Miller |
| 2018/0311334 A1 | 11/2018 | Gautam et al. |
| 2019/0015516 A1 | 1/2019 | Jackson et al. |
| 2019/0062329 A1 | 2/2019 | Chipman |
| 2019/0083592 A1 | 3/2019 | Noelle |
| 2019/0125889 A1 | 5/2019 | Georges |

FOREIGN PATENT DOCUMENTS

| | | |
|---|---|---|
| EP | 2674170 A1 | 12/2013 |
| EP | 2769738 A1 | 8/2014 |
| JP | H1180156 A | 3/1999 |

(Continued)

OTHER PUBLICATIONS

Agarwal, P. et al. (2013; e-pub. May 28, 2013). "Hydrazino-Pictet-Spengler Ligation as a Biocompatible Method for the Generation of Stable Protein Conjugates," *Bioconjug Chem* 24(6):846-851.

(Continued)

*Primary Examiner* — Jeffrey H Murray
(74) *Attorney, Agent, or Firm* — Morrison & Foerster LLP

(57) ABSTRACT

The present disclosure relates to cleavable conjugates (for example, particle-based or antibody-based conjugates) of TLR7/8 agonists (for example, 1H-imidazo[4,5-c]quinoline derivatives) containing a conjugation linker, a cleavable linker, and a self-eliminating linker. The present disclosure also related to methods for preparation of the cleavable conjugates, uses thereof for stimulating an effective immune response, and uses thereof for the treatment of cancer.

121 Claims, 19 Drawing Sheets

(56) References Cited

FOREIGN PATENT DOCUMENTS

| | | |
|---|---|---|
| WO | WO2004028539 A2 | 4/2004 |
| WO | WO2004058759 A1 | 7/2004 |
| WO | WO2005054237 A1 | 6/2005 |
| WO | WO2006028545 A2 | 3/2006 |
| WO | WO2007079086 A1 | 7/2007 |
| WO | WO-2013/166110 A1 | 11/2013 |
| WO | WO2014113634 A1 | 7/2014 |
| WO | WO-2015/023958 A1 | 2/2015 |
| WO | WO-2015/103987 A1 | 7/2015 |
| WO | WO-2015/168279 A1 | 11/2015 |
| WO | WO2016055812 A1 | 4/2016 |
| WO | WO-2017/044803 A1 | 3/2017 |
| WO | WO-2017/044803 A8 | 3/2017 |
| WO | WO-2017/072662 A1 | 5/2017 |
| WO | WO-2018/198091 A1 | 11/2018 |
| WO | WO2019040491 A1 | 2/2019 |

OTHER PUBLICATIONS

Beck, A. et al. (May 2017; e-pub. Mar. 17, 2017). "Strategies and Challenges for the Next Generation of Antibody-Drug Conjugates," *Nature Rev Drug Discovery* 16(5):315-337.

Beesu, M. et al. (2015; e-pub. Sep. 9, 2015). "Structure-Based Design of Human TLR8-Specific Agonists with Augmented Potency and Adjuvanticity,"*J Med Chem* 58(19):7833-7849.

Blencowe, C.A. et al. (2011). "Self-immolative Linkers in Polymeric Delivery Systems," *Polymer Chem* 2:773-790.

Brülisauer, L. et al. (Dec. 10, 2014; e-pub. Jun. 18, 2014). "Disulfide-Containing Parenteral Delivery Systems and their Redox-Biological Fate," *J Controlled Release* 195:147-154.

Caballero, O.L. et al. (Nov. 2009; e-pub. Aug. 27, 2009). "Cancer/testis (CT) Antigens: Potential Targets for Immunotherapy," *Cancer Science* 100(11):2014-2021.

Carlmark, A. et al. (Apr. 30, 2013). "Dendritic Architectures Based on bis-MPA: Functional Polymeric Scaffolds for Application-Driven Research," *Chem. Soc. Rev.* 42:5858-5879.

Cheever, M.A. et al. (Sep. 1, 2009). "The Prioritization of Cancer Antigens: A National Cancer Institute Pilot Project for the Acceleration of Translational Research," *Clinical Cancer Research* 15(17):5323-5337.

Desrichard, A. et al. (Feb. 15, 2016; e-pub. Oct. 29, 2015). "Cancer Neoantigens and Applications for Immunotherapy," *Clinical Cancer Res.* 22(4):807-812.

Doronina, S.O. et al. (Jul. 2003; e-pub. Jun. 1, 2003). "Development of Potent Monoclonal Antibody Auristatin Conjugates for Cancer Therapy," *Nature Biotechnology* 21(7):778-784, also includes the Erratum 21(8):941, total 8 pages.

Dorywalska, M. et al. (Apr. 15, 2015; e-pub. Feb. 2, 2015). "Effect of Attachment Site on Stability of Cleavable Antibody Drug Conjugates," *Bioconjug Chem* 26(4):650-659.

Dubowchik, G.M. et al. (2002; e-pub. Jun. 18, 2002). "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity," *Bioconj Chem* 13(4):855-869.

Eisenhauer, E.A. et al. (Jan. 2009). "New Response Evaluation Criteria in Solid Tumours: Revised RECIST Guideline (Version 1.1)," *Eur J Cancer* 45(2):228-247.

Flygare, J.A. et al. (Jan. 2013). "Antibody-Drug Conjugates for the Treatment of Cancer," *Chem Biol Drug Des* 81(1):113-121.

Gadd, A.J.R. et al. (Jul. 1, 2015). "Targeted Activation of Toll-Like Receptors: Conjugation of a Toll-Like Receptor 7 Agonist to a Monoclonal Antibody Maintains Antigen Binding and Specificity," *Bioconjugate Chem* 26:1743-1752.

Grünewald, J. et al. (Jul. 19, 2017; e-pub. Jun. 7, 2017). "Optimization of an Enzymatic Antibody-Drug Conjugation Approach Based on Coenzyme A Analogs," *Bioconjug Chem* 28(7):1906-1915.

Hamann, P.R. et al. (Jan.-Feb. 2002; e-pub. Dec. 19, 2001). "An Anti-CD33 Antibody-Calicheamicin Conjugate for Treatment of Acute Myeloid Leukemia. Choice of Linker," *Bioconjugate Chem* 13(1):40-46.

Jacobsen, F.W. et al. (Feb. 3, 2017). "Engineering an IgG Scaffold Lacking Effector Function with Optimized Developability," *J Biol Chem* 292(5):1865-1875.

Jain, N. et al. (Nov. 2015, e-pub. Mar. 11, 2015). "Current ADC Linker Chemistry," *Pharma Res* 32(11):3526-3540.

Junutula, J.R. et al. (Aug. 2008; e-pub. Jul. 20, 2008). "Site-Specific Conjugation of a Cytotoxic Drug to an Antibody Improves the Therapeutic Index," *Nat Biotechnol* 26(8):925-932.

Kato, A. et al. (2017; e-pub. Jul. 20, 2017). "Extensive Survey of Antibody Invariant Positions for Efficient Chemical Conjugation Using Expanded Genetic Codes," *Bioconjug Chem* 28(8):2099-2108.

Kim, M.T. et al. (Jul. 16, 2014; e-pub. May 29, 2014). "Statistical Modeling of the Drug Load Distribution on Trastuzumab Emtansine (Kadcyla), a Lysine-Linked Antibody Drug Conjugate," *Bioconjugate Chem* 25(7):1223-1232.

Kolb, H.C. et al. (Dec. 2003). "The Growing Impact of Click Chemistry on Drug Discovery," *Drug Discov Today* 8(24):1128-1137.

Kolb, H.C. et al. (Jun. 1, 2001; e-pub. May 28, 2001). "Click Chemistry: Diverse Chemical Function from a Few Good Reactions," *Angew Chem Int Ed Engl* 40(11):2004-2021.

Kunert, R. et al. (Apr. 2016, e-pub. Mar. 3, 2016). "Advances in Recombinant Antibody Manufacturing," *Appl Microbiol Biotechnol* 100(8):3451-3461.

Kung-Sutherland, M.S. et al. (Aug. 2013; e-pub. Jun. 14, 2013). "SGN-CD33A: A Novel CD33-targeting Antibody-Drug Conjugate Utilizing a Pyrrolobenzodiazepine Dimer is Active in Models of Drug-Resistant AML," *Blood* 122(8):1455-1463.

Lambert, J.M. (2012; e-pub. Nov. 23, 2012). "Drug-Conjugated Antibodies for the Treatment of Cancer," *Br J Clin Pharmacol* 76(2):248-262.

Lebeau, A.M. et al. (Jan. 2, 2013; e-pub. Dec. 17, 2012). "Imaging a Functional Tumorigenic Biomarker in the Transformed Epithelium," *Proc Nat Acad Sci USA* 110(1):93-98.

Liu, C. et al. (Jun. 1, 2003). "Overexpression of Legumain in Tumors Is Significant for Invasion/Metastasis and a Candidate Enzymatic Target for Prodrug Therapy," *Cancer Res* 63:2957-2964.

Lu, J. et al. (Apr. 14, 2016). "Linkers Having a Crucial Role in Antibody-Drug Conjugates," *Int J Mol Sci* 17(4):561, pp. 1-22.

Lyon, R.P. et al. (Oct. 2014, e-pub. Sep. 7, 2014). "Self-hydrolyzing Maleimides Improve the Stability and Pharmacological Properties of Antibody-Drug Conjugates," *Nat Biotechnol* 32(10):1059-1062.

Lyon, R.P. et al. (Jul. 2015; e-pub. Jun. 15, 2015). "Reducing Hydrophobicity of Homogeneous Antibody-Drug Conjugates Improves Pharmacokinetics and Therapeutic Index," *Nat Biotechnol* 33(7):733-735.

Mason, S.D. et al. (Apr. 2011; e-pub. Jan. 12, 2011). "Proteolytic Networks in Cancer," *Trends Cell Biol* 21(4):228-237, 18 pages.

Okeley, N.M. et al. (Oct. 16, 2013; e-pub. Sep. 19, 2013). "Metabolic Engineering of Monoclonal Antibody Carbohydrates for Antibody-Drug Conjugation," *Bioconjug Chem* 24(10):1650-1655.

Pramanick, S. et al. (Mar. 2013). "Excipient Selection in Parenteral Formulation Development," *Pharma Times* 45(3):65-77.

Puthenveetil, S. et al. (May 30, 2017). "Multivalent Peptidic Linker Enables Identification of Preferred Sites of Conjugation for a Potent Thialanstatin Antibody Drug Conjugate," *PlosOne* 12(5):e0178452, 16 pages.

Sabado, R.L. et al. (Mar. 2015; e-pub. Jan. 29, 2015). "Resiquimod as an Immunologic Adjuvant for NY-ESO-1 Protein Vaccination in Patients With High-Risk Melanoma," *Cancer Immunol Res* 3(3):278-287.

Sadowsky, J.D. et al. (Aug. 16, 2017; e-pub. Jun. 21, 2017). "Development of Efficient Chemistry to Generate Site-Specific Disulfide-Linked Protein-and Peptide-Payload Conjugates: Application to THIOMAB Antibody-Drug Conjugates," *Bioconjug Chem* 28(8):2086-2098.

(56) References Cited

OTHER PUBLICATIONS

Sau, S. et al. (Oct. 2017; Jun. 13, 2017). "Advances in Antibody-Drug Conjugates: A New Era of Targeted Cancer Therapy," *Drug Discov Today* 22(10):1547-1556.
Schumacher, T.N. et al. (Apr. 3, 2015). "Neoantigens in Cancer Immunotherapy," *Science* 348(6230):69-74.
Shukla, N.M. et al. (Jun. 10, 2010). "Structure-Activity Relationships in Human Toll-like Receptor 7-Active Imidazoquinoline Analogues," *J. Med. Chem.* 53(11):4450-4465, 52 pages.
Singh, M. et al. (2014; e-pub. Sep. 24, 2014). "Effective Innate and Adaptive Antimelanoma Immunity through Localized TLR7/8 Activation," *J. Immunol.*193:4722-4731.
Smirnov, D. et al. (Jul. 26, 2011). "Vaccine Adjuvant Activity of 3M-052: An Imidazoquinoline Designed for Local Activity Without Systemic Cytokine Induction," *Vaccine* 29(33):5434-5442.
Sun, M.C. et al. (2005). "Reduction-Alkylation Strategies for the Modification of Specific Monoclonal Antibody Disulfides," *Bioconjug Chem* 16(5):1282-1290, 22 pages.
Sun, X. et al. (2017; e-pub. Apr. 7, 2017). "Effects of Drug-Antibody Ratio on Pharmacokinetics, Biodistribution, Efficacy, and Tolerability of Antibody-Maytansinoid Conjugates," *Bioconjug Chem* 28(5):1371-1381.
Takeuchi, O. et al. (Mar. 19, 2010). "Pattern Recognition Receptors and Inflammation," *Cell* 140(6):805-820.
Tanabe, L.M. et al. (2017). "The Role of Type II Transmembrane Serine Protease-Mediated Signaling in Cancer," *FEBS J* 284:1421-1436.
Tang, F. et al. (Aug. 2017; e-pub. Jul. 27, 2017). "Chemoenzymatic Synthesis of Glycoengineered IgG Antibodies and Glycosite-Specific Antibody-Drug Conjugates," *Nature Protocols* 12(8):1702-1721, 44 pages.
Tian. F. et al. (Feb. 4, 2014). "A General Approach to Site-Specific Antibody Drug Conjugates," *Proc Nat Acad Sci USA* 111(5):1766-1771.
Uhland, K. (Dec. 2006). "Matriptase and its Putative Role in Cancer," *Cell Mol Life Sci* 63(24):2968-2978.
Ulisse, S. et al. (2009). "The Urokinase Plasminogen Activator System: A Target for Anti-Cancer Therapy," *Curr Cancer Drug Targets* 9(1):32-71.
Vasilakos, J.P. et al. (2013). "The Use of Toll-Like Receptor 7/8 Agonists as Vaccine Adjuvants," *Exp Rev Vaccines* 12(7):809-819.
Wagh, A. et al. (Feb.-Mar. 2018; e-pub. Jan. 2018). "Challenges and New Frontiers in Analytical Characterization of Antibody-Drug Conjugates," *MABS* 10(2):222-243.
Wang, R.-F. et al. (Jan. 2017; e-pub. Dec. 27, 2016). "Immune Targets and Neoantigens for Cancer Immunotherapy and Precision Medicine," *Cell Research* 27(1):11-37.
Wang, S. et al. (Nov. 15, 2016; e-pub. Oct. 31, 2016). "Intratumoral Injection of a CpG Oligonucleotide Reverts Resistance to PD-1 Blockade by Expanding Multifunctional CD8+ T Cells," *Proc. Nat. Acad. Sci. USA* 113(46):E7240-E7249.
Warncke, M. et al. (2012; e-pub. Mar. 28, 2012). "Different Adaptations of IgG Effector Function in Human and Nonhuman Primates and Implications for Therapeutic Antibody Treatment," *J Immunol* 188:4405-4411.
Weidle, U.H. et al. (2014). "Proteases as Activators for Cytotoxic Prodrugs in Antitumor Therapy," *Cancer Genomics Proteomics* 11:67-79.
Weidle, U.H. et al. (Oct. 2014). "Tumor-Antigen-Binding Bispecific Antibodies for Cancer Treatment," *Seminars in Oncology* 41(5):653-660.
Wille-Reece, U. et al. (Oct. 18, 2005; e-pub. Oct. 11, 2005). "HIV Gag Protein Conjugated to a Toll-Like Receptor 7/8 Agonist Improves The Magnitude and Quality of Th1 and CD8+ T Cell Responses In Nonhuman Primates," *Proc. Nat'l Acad. Sci.* 102(42):15190-15194.
Yang et al. (Sep. 12, 2006). "Evaluation of Disulfide Reduction During Receptor-Mediated Endocytosis by Using FRET Imaging," *PNAS* 103(37):13872-13877.
Zhou, Q. et al. (2014; e-pub. Feb. 17, 2014). "Site-Specific Antibody-Drug Conjugation through Glycoengineering," *Bioconjug Chem* 25(3):510-520.
Francica, J.R. et al. (Sep. 1, 2016). "Thermoresponsive Polymer Nanoparticles Co-Deliver RSV F Trimers with a TLR-7/8 Adjuvant," *Bioconjugate Chemistry* 27(10):2372-2385.
Kim, W.G. et al. (Aug. 9, 2016). "Covalent Conjugation of Small-Molecule Adjuvants to Nanoparticles Induces Robust Cytotoxic T Cell Responses via DC Activation," *Bioconjugate Chemistry* 27(9):2007-2013.
International Search Report and Written Opinion dated Mar. 1, 2019 for PCT Application No. PCT/US2018/060849 filed on Nov. 13, 2018, 19 pages.
Bao, M. et al. (Jan. 2013). "Regulation of TLR7/9 Signaling in Plasmacytoid Dendritic Cells," *Protein Cell* 4 (1):40-52.
Brito, L.A. et al. (2013). "Vaccine Adjuvant Formulations: A Pharmaceutical Perspective," *Seminar Immunol* 25:130-145.
Dowling, D.J. et al. (Jan. 26, 2017). "TLR7/8 Adjuvant Overcomes Newborn Hyporesponsiveness to Pneumococcal Conjugate Vaccine at Birth," *JCI Insight* 2:e91020, 18 pages.
Eigenbrod, T. et al. (2015; e-pub. Jun. 22, 2015). "TLR8 Senses Bacterial RNA in Human Monocytes and Plays a Nonredundant Role for Recognition of *Streptococcus pyogenes*," *J Immunol* I95:1092-1099.
Ganapathi, L. et al. (Aug. 14, 2015). "The Imidazoquinoline Toll-Like Receptor-7/8 Agonist Hybrid-2 Potently Induces Cytokine Production by Human Newborn and Adult Leukocytes," *PLoS One* 10(8):e0134640, 12 pages.
Gorden, K.B. et al. (2005). "Synthetic TLR Agonists Reveal Functional Differences Between Human TLR7 and TLR8," *J Immunol* 174:1259-1268.
Gosu, V. et al. (Nov. 14, 2012). "Therapeutic Applications of Nucleic Acids and Their Analogues in Toll-like Receptor Signaling," *Molecules* 17:13503-13529.
Hemmi, H. et al. (Feb. 2002, e-pub. Jan. 22, 2002). "Small Anti-Viral Componunds Activate Immune Cell via the TLR7 MyD88-Dependent Signaling Pathway," *Nat Immunol* 3(2):196-200.
International Search Report and Written Opinion dated Nov. 6, 2018 for PCT Application No. PCT/US2018/047323 filed on Aug. 21, 2018, 12 pages.
Lu, H. et al. (Jan. 15, 2012; e-pub. Nov. 29, 2011). "VTX-2337 is a Novel TLR8 Agonist That Activates NK Cells and Augments ADCC," *Clin Cancer Res* 18(2):499-509.
Patil, S.A. et al. (2016). "Imidazoquinolines: Recent Developments in Anticancer Activity," *Mini Rev Med Chem.* 16(4):309-322.
Pockros, P. et al. (Aug. 2007). "Oral Resiquimod in Chronic HCV Infection: Safety and Efficacy in 2 Placebo-Controlled, Double-Blind Phase Iia Studies," *J Hepatol* 47(2):174-182.
Rice, J. et al. (2002). "Critical Components of a DNA Fusion Vaccine Able to Induce Protective Cytotoxic T Cells Against a Single Epitope of a Tumor Antigen," *J Immunol* 169:3908-3913.
Savage, P. et al. (1996). "A Phase I Clinical Trial of Imiquimod, an Oral Interferon Inducer, Administered Daily," *Br J Cancer* 74:1482-1486.
Shukla, N.M. et al. (Aug. 28, 2012). "Potent Adjuvanticity Of a Pure TLR7-Agonistic Imidazoquinoline Dendrimer," *PLoS One* 7(8):e43612, 11 pages.
Shukla, N.M. et al. (Feb. 9, 2012, e-pub. Jan. 27, 2012). "Toll-Like Receptor (TLR)-7 and -8 Modulatory Activities of Dimeric Imidazoquinolines," *Journal of Medicinal Chemistry* 55(3):1106-1116, 26 pages.
Shukla, N.M. et al. (Jun. 1, 2011). "Toward Self-Adjuvanting Subunit Vaccines: Model Peptide and Protein Antigens Incorporating Covalently Bound Toll-Like Receptor-7 Agonistic Imidazoquinolines," *Bioorganic & Medicinal Chemistry Letters* 21(11):3232-3236, 15 pages.
Shukla, N.M. et al. (Nov. 15, 2010). "Syntheses of Fluorescent Imidazoquinoline Conjugates as Probes of Toll-Like Receptor 7," *Bioorg Med Chem Lett* 20(22):6384-6386, 9 pages.
Spinetti, T. et al. (2016). "TLR7-Based Cancer Immunotherapy Decreases Intratumoral Myeloid-Derived Suppressor Cells and Blocks Their Immunosuppressive Function,"*Oncoimmunol* 5(11):eI230578, 8 pages.

(56) References Cited

OTHER PUBLICATIONS

Tanji, H. et al. (Feb. 2015; e-pub. Jan. 19, 2015). "Toll-Like Receptor 8 Senses Degradation Products of Single-Stranded RNA," Nat Struct Mol Biol 22(2):109-115.

Van Haren, S.D. et al. (2016; e-pub. Oct. 28, 2016). "Age-Specific Adjuvant Synergy: Dual TLR7/8 and Mincle Activation of Human Newborn Dendritic Cells Enables Th1 Polarization," J Immunol 197:4413-4424.

Van Hoeven, N. et al. (Apr. 21, 2017). "A Formulated TLR7/8 Agonist is a Flexible, Highly Potent and Effective Adjuvant for Pandemic Influenza Vaccines," Sci Rep 7:46426, pp. 1-15.

Zhang, Z. et al. (Oct. 18, 2016). "Structural Analysis Reveals that Toll-like Receptor 7 Is a Dual Receptor for Guanosine and Single-Stranded RNA," Immunity 45:737-748.

FIG. 1
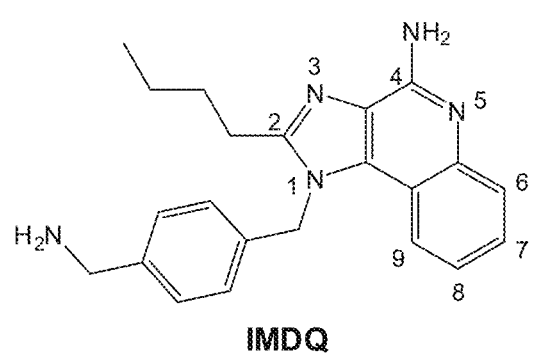
IMDQ
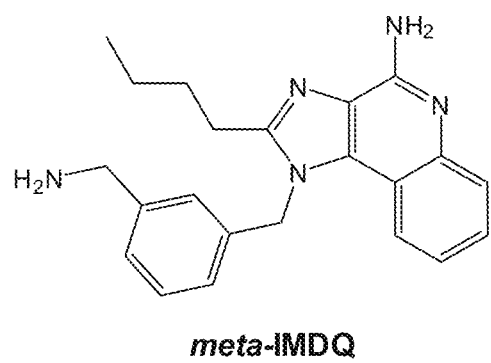
meta-IMDQ

FIG. 8
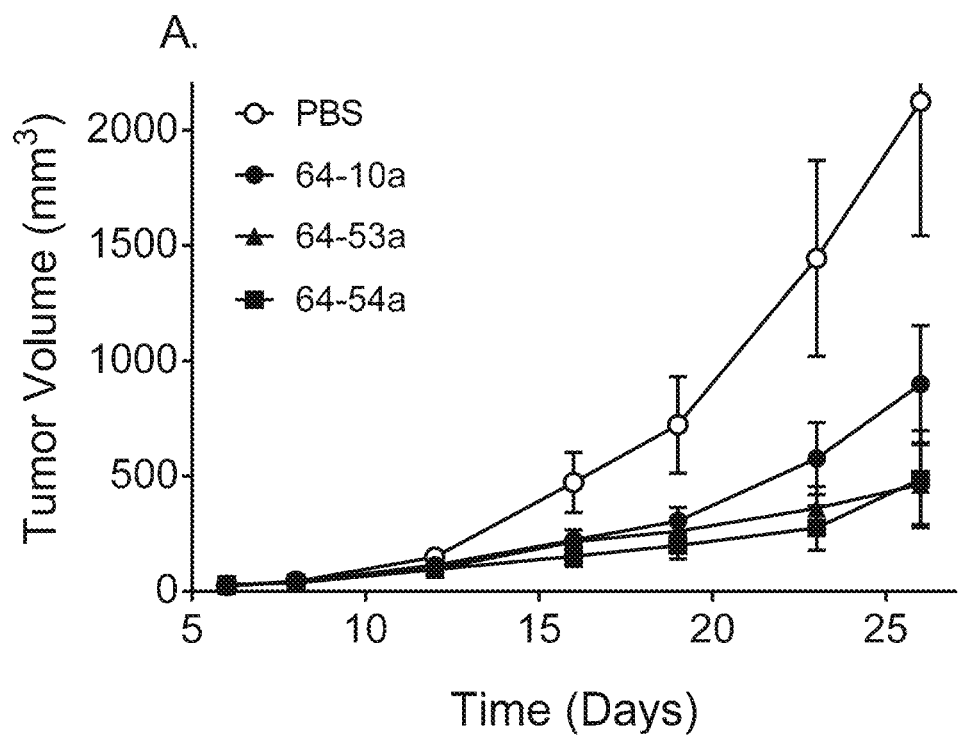
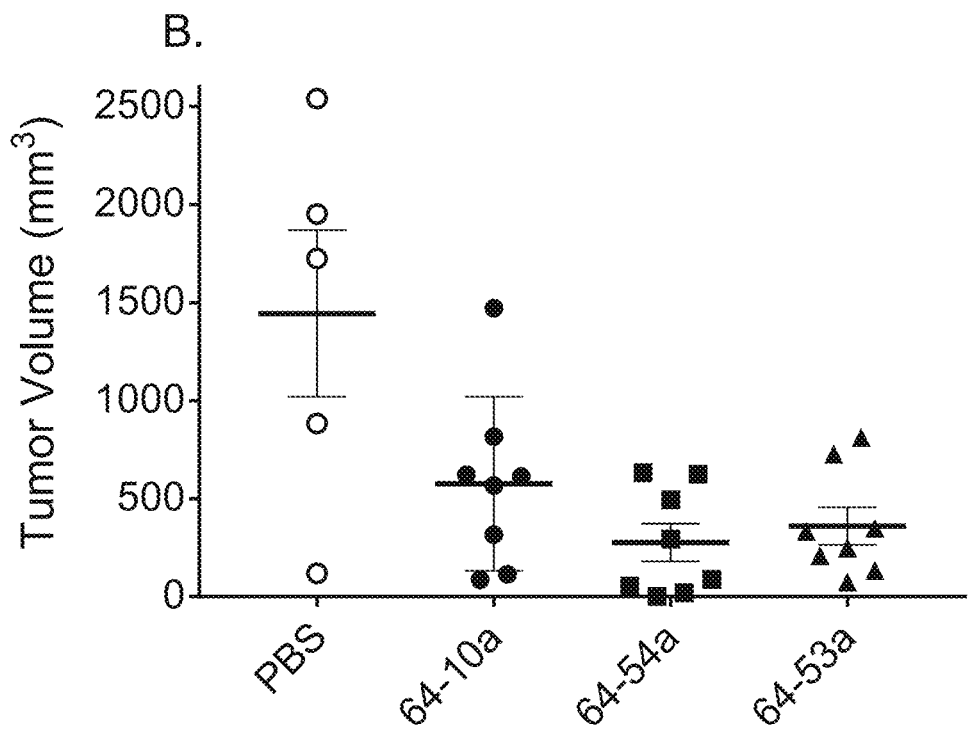

FIG. 10
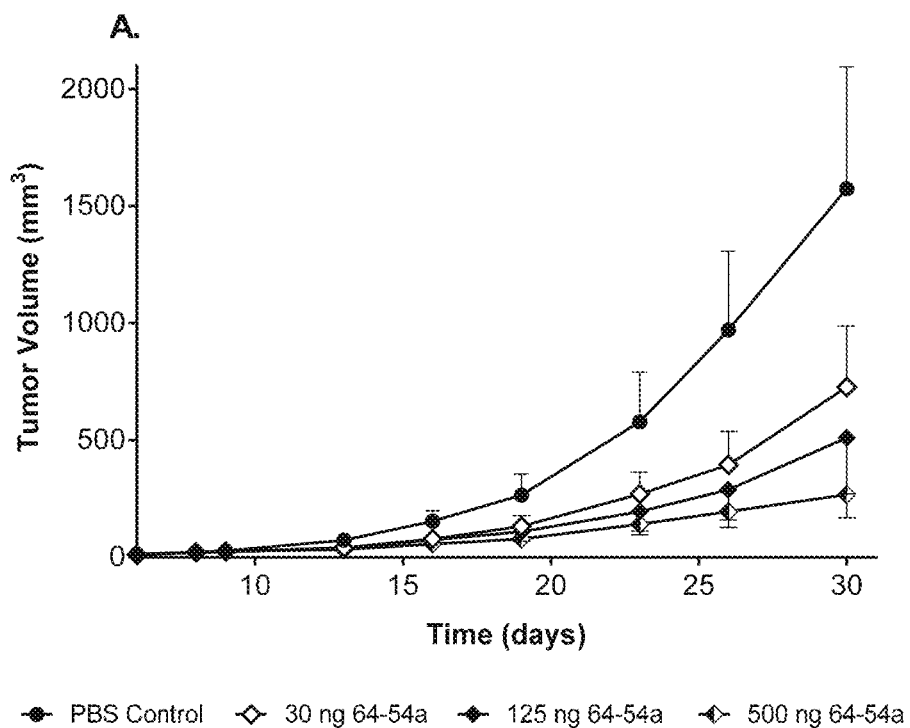
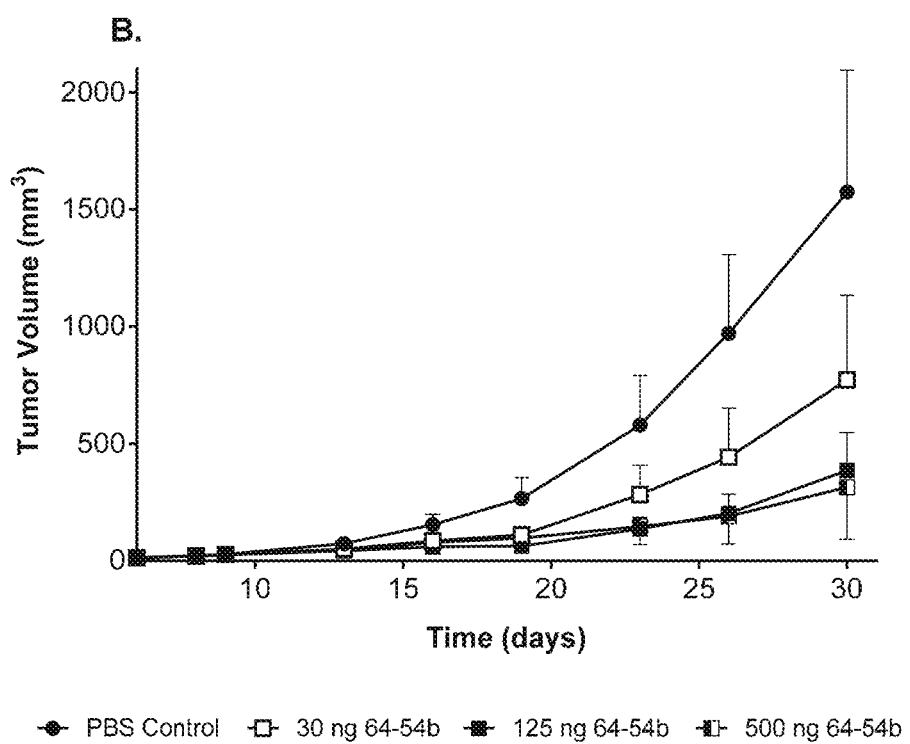

formula (F-1)

CLEAVABLE CONJUGATES OF TLR7/8 AGONIST COMPOUNDS, METHODS FOR PREPARATION, AND USES THEREOF

CROSS-REFERENCE TO RELATED APPLICATIONS

This application claims priority to and the benefit of U.S. Provisional Patent Application No. 62/586,110, filed Nov. 14, 2017, the disclosure of which is incorporated herein by reference in its entirety.

FIELD OF THE INVENTION

The present disclosure relates to Toll-like Receptor 7/8 agonist compounds that are covalently conjugated to an agent, for example a tumor-specific targeting agent or a polymeric nanoparticle agent, via a cleavable linker moiety to promote local release and/or local retention of a bioactive form of the TLR7/8 agonist, and reduce unwanted systemic pro-inflammatory cytokine responses. The present disclosure also relates to methods for preparation of the cleavable conjugates, uses thereof for stimulating an effective immune response, and uses thereof for the treatment of cancer.

BACKGROUND OF THE INVENTION

Toll-like receptors (TLRs) are a family of transmembrane proteins, which recognize structurally conserved molecules that are derived from pathogens, referred to as pathogen-associated molecular patterns. As such, TLRs function in the mammalian immune system as front-line sensors of pathogen-associated molecular patterns, detecting the presence of invading pathogens (Takeuchi and Akira 2010, *Cell* 140: 805-820). The human genome contains 10 known TLRs; of these, TLR7 and TLR8 sense single stranded RNA ligands and their (oligo)nucleotide degradation products. The distribution of TLR7 and TLR8 is restricted to the endolysosomal compartment and the receptors are preferentially expressed in antigen presenting cells (APCs), a key cell type that modulates immune system activation.

TLR engagement in sentinel immune cells causes biosynthesis of selected cytokines (e.g., type I interferons), induction of co-stimulatory molecules, and increased antigen presentation capacity by APCs; important molecular mechanisms that activate innate and adaptive immune responses. Engagement of TLR7 in plasmacytoid dendritic cells leads to the induction of IFN-$\alpha$/$\beta$, which plays essential functions in the control of adaptive immunity. TLR8 is expressed in myeloid dendritic cells, monocytes, and monocyte-derived dendritic cells and agonist engagement of TLR8 induces a prominent pro-inflammatory cytokine profile, characterized by increased production of tumor necrosis factor $\alpha$ (TNF-$\alpha$), interleukin-12 (IL-12), and IL-18. Thus, virtually all major types of monocytic and dendritic cells can be activated by agonists of either TLR7 or TLR8 to become highly effective antigen-presenting cells. As most antigen presenting cell types express only one of these two receptors, agonists that can stimulate both receptors are potentially more effective adjuvants than agonists specific for only one of these TLR (Wille-Reece, et al. *Proc. Nat'l Acad. Sci.* 2005, 102:15190-15194). Additionally, TLR7 and TLR7/8 agonists can also be effective in stimulating anti-tumor immune responses in cancer, based on studies in animal models (Singh, et al. *J Immunol* 2014, 193:4722-4731). Accordingly, TLR agonists have been extensively investigated as stimulators of innate and adaptive immune responses, including for use as cancer therapeutic agents and vaccine adjuvants (Sabado et al. 2015, *Ca Immunol Res* 3:278-287; Vasilakos and Tomai 2013, *Exp Rev Vaccines* 12:809-819).

Although a number of small molecule structural classes are known to interact at the guanosine/uridine ligand binding site and possess varying levels of TLR7 and/or TLR8 agonist bioactivity, many such agonists are derivatives of the 1H-imidazo[4,5-c]quinoline privileged chemical template. One early example is 1-isobutyl-1H-imidazo[4,5-c]quinolin-4-amine (Imiquimod), a modest potency TLR7 agonist that was approved in 1997 as a topical formulation for actinic keratosis, superficial basal cell carcinoma, and genital warts. Subsequent medicinal chemistry efforts have produced several derivatives with significantly improved dual TLR7/8 agonist activity, most notably 1-(4-amino-2-(ethoxymethyl)-1H-imidazo[4,5-c]quinolin-1-yl)-2-methylpropan-2-ol (R848, Resiquimod), as well as 1-(4-aminomethylbenzyl)-2-butyl-1H-imidazo[4,5-c]quinolin-4-amine (IMDQ, FIG. 1) and 1-(3-(aminomethyl)benzyl)-2-butyl-1H-imidazo[4,5-c]quinolin-4-amine (meta-IMDQ, FIG. 1; see, e.g., Beesu, M. et al. 2015, *J Med Chem* 50:7833-7849; U.S. Pat. Nos. 8,728,486 and 9,441,005, incorporated herein by reference). However, rapid systemic diffusion of these small molecule compounds following local administration (e.g., subcutaneous [SC], intratumoral [IT], or intramuscular [IM]) of pharmacologically relevant doses, leads to systemic induction of pro-inflammatory cytokine responses, elevating the risk of adverse events in humans (e.g., fever, malaise, lymphopenia, etc.), see, e.g., Vasilakos and Tomai 2013, *Exp Rev Vaccines* 12:809-819; Smirnov, D. et al. 2011, *Vaccine* 29:5434-5442).

Therefore, there remains a need for immunotherapeutic agents that: 1) possess TLR7/8 agonist activity with potent bioactivity against both receptors and with potent immunostimulatory activities that activate larger subsets of APCs than exclusively TLR7 or TLR8 agonists alone; 2) preferentially target a stable prodrug form of the TLR7/8 agonist to the tumor microenvironment or locally retain a stable prodrug form of the TLR7/8 agonist at the tumor microenvironment following SC or intravenous administration, and subsequently release the active form within the tumor microenvironment; and 3) possess physiochemical properties that restrict subsequent distribution of the released, active form (i.e., unconjugated) of the TLR7/8 agonist from the tumor microenvironment.

The present invention provides for conjugates of TLR7/8 agonist compounds containing a cleavable linker and an agent for tissue-specific targeting or for local retention following administration, methods for preparation thereof, uses thereof for stimulating local immune responses and reducing unwanted systemic immune activation, and uses thereof for the treatment of cancer.

BRIEF SUMMARY OF THE INVENTION

The present disclosure provides for modified 1H-imidazo[4,5-c]quinoline derivatives that are potent TLR7/8 agonists, covalently conjugated to an agent for tumor-specific targeting or for local retention following administration via combinations of a self-eliminating linker, a cleavable linker, and a conjugation linker. These cleavable conjugates promote local release and/or local retention of a bioactive form of the TLR7/8 agonist, and reduce unwanted systemic pro-inflammatory cytokine responses. The present disclosure also relates to methods for preparation of the cleavable conjugates, uses thereof for stimulating an effective immune response, and uses thereof for the treatment of cancer.

In one aspect, provided is a compound of formula (I):

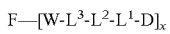

F—[W-L³-L²-L¹-D]$_x$     (I)

wherein:
D is a TLR7/8 agonist moiety;
L¹ is a bond or a self-eliminating linker;
L² is a cleavable linker;
L³ is a conjugation linker;
W is O, S, or NR$^{10}$;
R$^{10}$ is H or C$_1$-C$_8$ alkyl;
x is an integer from 1 to 500;
F is a conjugation moiety; and
the TLR7/8 agonist moiety is a 1H-imidazo[4,5-c]quinoline derivative.

In one aspect, provided is a compound of formula (I), wherein D is of the formula (D-1):

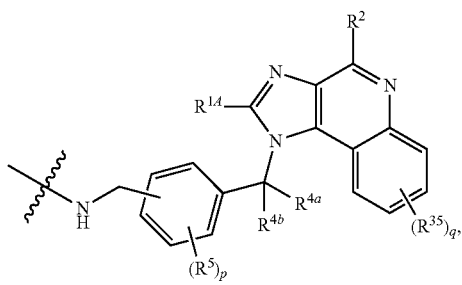

wherein:
R$^{1A}$ is C$_1$-C$_8$ alkyl, C$_1$-C$_8$ hydroxyalkyl, or C$_3$-C$_8$ cycloalkyl;
R$^2$ is NHR$^{2a}$, where R$^{2a}$ is H or C$_1$-C$_8$ alkyl;
each R$^{35}$ is independently halogen or C$_1$-C$_8$ alkyl;
R$^{4a}$ and R$^{4b}$ are independently H or C$_1$-C$_8$ alkyl;
each R$^5$ is independently halogen or C$_1$-C$_8$ alkyl;
p and q are independently 0, 1, 2, 3, or 4; and
the wave line represents the point of attachment of D in formula (I).

In one aspect, provided is a compound of formula (I), wherein D is of the formula (D-2):

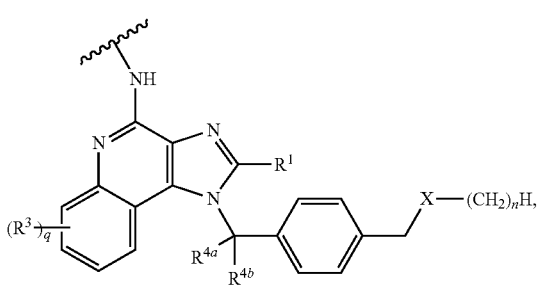

wherein:
n is an integer from 4 to 21;
X is —NH— or —NH(C=O)—;
R$^1$ is C$_3$-C$_6$ alkyl, —(CH$_2$)$_p$OR$^{1a}$, —(CH$_2$)$_p$NHR$^{1b}$, or —(CH$_2$)$_p$R$^{1c}$; where R$^{1a}$ and R$^{1b}$ are independently C$_1$-C$_3$ alkyl; R$^{1c}$ is C$_3$-C$_4$ cycloalkyl; and p is 1 or 2;
each R$^3$ is independently halogen, C$_1$-C$_8$ alkyl, —(C$_1$-C$_7$ alkylene)-NH$_2$, or —CH$_2$-phenylene-CH$_2$NH$_2$;
q is 0, 1, 2, 3, or 4;
R$^{4a}$ and R$^{4b}$ are independently H or C$_1$-C$_8$ alkyl; and
the wave line represents the point of attachment of D in formula (I).

In another aspect, provided is a compound of formula (I), wherein D is of the formula (D-2a) or (D-2b):

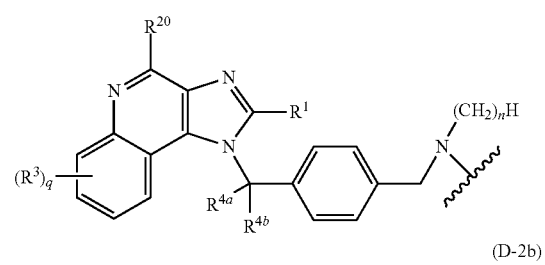

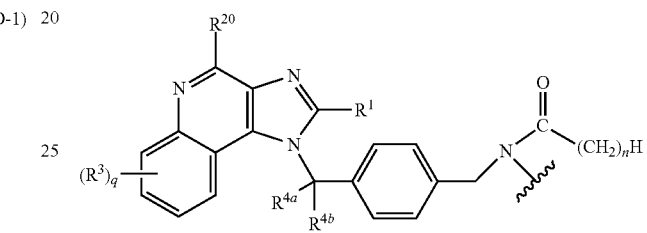

wherein:
n is an integer from 4 to 21;
R$^1$ is C$_3$-C$_6$ alkyl, —(CH$_2$)$_p$OR$^{1a}$, —(CH$_2$)$_p$NHR$^{1b}$, or —(CH$_2$)$_p$R$^{1c}$; where R$^{1a}$ and R$^{1b}$ are independently C$_1$-C$_3$ alkyl; R$^{1c}$ is C$_3$-C$_4$ cycloalkyl; and p is 1 or 2;
R$^{20}$ is NHR$^{20a}$; where R$^{20a}$ is H, OH, NH$_2$, or methyl;
each R$^3$ is independently halogen, C$_1$-C$_8$ alkyl, —(C$_1$-C$_7$ alkylene)-NH$_2$, or —CH$_2$-phenylene-CH$_2$NH$_2$;
q is 0, 1, 2, 3, or 4;
R$^{4a}$ and R$^{4b}$ are independently H or C$_1$-C$_8$ alkyl; and
the wave line represents the point of attachment of D in formula (I).

In another aspect, provided is a compound of formula (I), wherein D is of the formula (D-3):

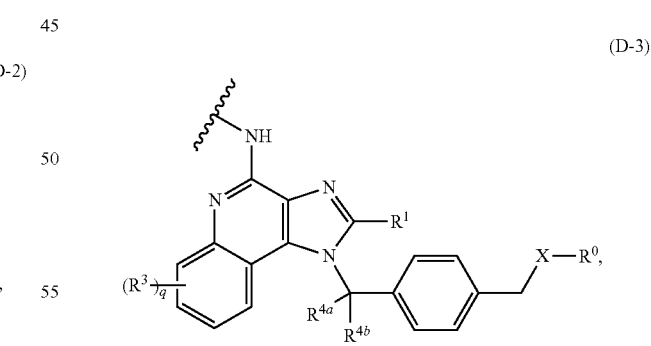

wherein:
R$^0$ is C$_4$-C$_{21}$ hydrocarbyl optionally substituted by 1 to 4 halogen atoms;
X is —NH— or —NH(C=O)—;
R$^1$ is C$_3$-C$_6$ alkyl, —(CH$_2$)$_p$OR$^{1a}$, —(CH$_2$)$_p$NHR$^{1b}$, or —(CH$_2$)$_p$R$^{1c}$; where R$^{1a}$ and R$^{1b}$ are independently C$_1$-C$_3$ alkyl; R$^{1c}$ is C$_3$-C$_4$ cycloalkyl; and p is 1 or 2;
each R$^3$ is independently halogen, C$_1$-C$_8$ alkyl, —(C$_1$-C$_7$ alkylene)-NH$_2$, or —CH$_2$-phenylene-CH$_2$NH$_2$;

q is 0, 1, 2, 3, or 4;

$R^{4a}$ and $R^{4b}$ are independently H or $C_1$-$C_8$ alkyl; and the wave line represents the point of attachment of D in formula (I).

In a further aspect, provided is a compound of formula (I), wherein D is of the formula (D-3a) or (D-3b):

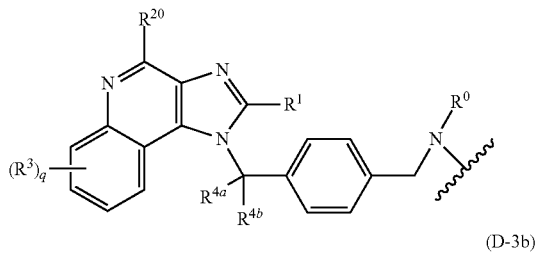

(D-3a)

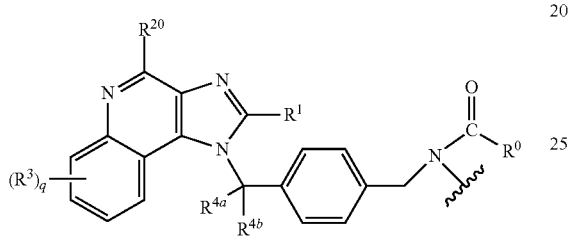

(D-3b)

wherein:

$R^0$ is $C_4$-$C_{21}$ hydrocarbyl optionally substituted by 1 to 4 halogen atoms;

$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;

$R^{20}$ is $NHR^{20a}$; where $R^{20a}$ is H, OH, $NH_2$, or methyl;

each $R^3$ is independently halogen, $C_1$-$C_8$ alkyl, —$(C_1$-$C_7$ alkylene)-$NH_2$, or —$CH_2$-phenylene-$CH_2NH_2$;

q is 0, 1, 2, 3, or 4;

$R^{4a}$ and $R^{4b}$ are independently H or $C_1$-$C_8$ alkyl; and the wave line represents the point of attachment of D in formula (I).

In yet another aspect, provided is a compound of formula (I), wherein D is of the formula (D-4):

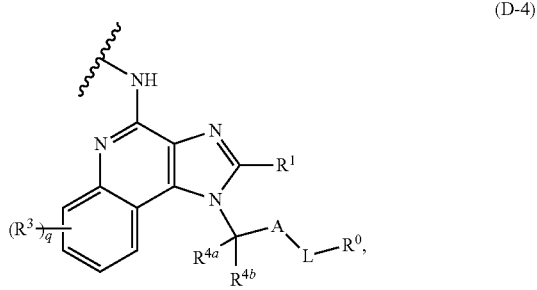

(D-4)

wherein:

$R^0$ is $C_4$-$C_{21}$ hydrocarbyl optionally substituted by 1 to 4 halogen atoms;

L is X or —$CH_2$—X—;

X is —NH— or —NH(C=O)—;

A is $C_6$-$C_{14}$ arylene optionally substituted by 1 to 4 groups independently selected from the group consisting of halogen and $C_1$-$C_8$ alkyl optionally substituted by 1 to 8 halogen atoms, or 5- to 14-membered heteroarylene optionally substituted by 1 to 4 groups independently selected from the group consisting of halogen and $C_1$-$C_8$ alkyl optionally substituted by 1 to 8 halogen atoms;

$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;

each $R^3$ is independently halogen, $C_1$-$C_8$ alkyl, —$(C_1$-$C_7$ alkylene)-$NH_2$, or —$CH_2$-phenylene-$CH_2NH_2$;

q is 0, 1, 2, 3, or 4;

$R^{4a}$ and $R^{4b}$ are independently H or $C_1$-$C_8$ alkyl; and the wave line represents the point of attachment of D in formula (I).

In another aspect, provided is a compound of formula (I), wherein D is of the formula (D-4a) or (D-4b):

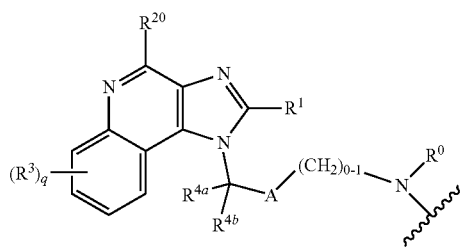

(D-4a)

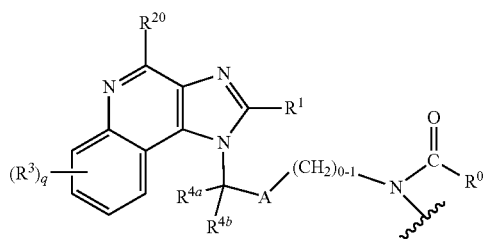

(D-4b)

wherein:

$R^0$ is $C_4$-$C_{21}$ hydrocarbyl optionally substituted by 1 to 4 halogen atoms;

A is $C_6$-$C_{14}$ arylene optionally substituted by 1 to 4 groups independently selected from the group consisting of halogen and $C_1$-$C_8$ alkyl optionally substituted by 1 to 8 halogen atoms, or 5- to 14-membered heteroarylene optionally substituted by 1 to 4 groups independently selected from the group consisting of halogen and $C_1$-$C_8$ alkyl optionally substituted by 1 to 8 halogen atoms;

$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;

$R^{20}$ is $NHR^{20a}$; where $R^{20a}$ is H, OH, $NH_2$, or methyl;

each $R^3$ is independently halogen, $C_1$-$C_8$ alkyl, —$(C_1$-$C_7$ alkylene)-$NH_2$, or —$CH_2$-phenylene-$CH_2NH_2$;

q is 0, 1, 2, 3, or 4;

$R^{4a}$ and $R^{4b}$ are independently H or $C_1$-$C_8$ alkyl; and the wave line represents the point of attachment of D in formula (I).

In one aspect, provided is a compound of formula (I), wherein $L^1$ is of the formula (L-1):

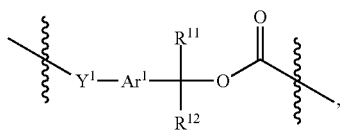
(L-1)

wherein $Y^1$ is S, O, or NH; $Ar^1$ is an optionally substituted arylene; and $R^{11}$ and $R^{12}$ are independently H or optionally substituted $C_1$-$C_8$ alkyl.

In another aspect, provided is a compound of formula (I), wherein $L^2$ is of the formula (L-2):

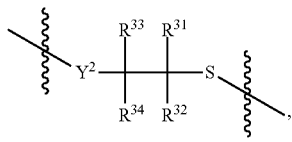
(L-2)

wherein $Y^2$ is $NR^{30}$, O, or S; and $R^{30}$, $R^{31}$, $R^{32}$, $R^{33}$ and $R^{34}$ are independently H, $C_1$-$C_8$ alkyl, or $C_3$-$C_8$ cycloalkyl. In some embodiments, $L^2$ is a peptide linker cleavable by one or more endosomal or lysosomal peptidase(s) or protease(s), or one or more pericellular peptidase(s) or protease(s), that are expressed by cells in the tumor microenvironment. In some embodiments, $L^2$ is a peptide linker cleavable by an endosomal cathepsin or a pericellular type II transmembrane serine protease.

In another aspect, provided is a compound of formula (I), wherein $L^3$ is -$L^{3a}$-$Y^3$-$L^{3b}$-, wherein $Y^3$, $L^{3a}$, and $L^{3b}$ are independently optional spacer fragments. In some embodiments, $Y^3$ is:

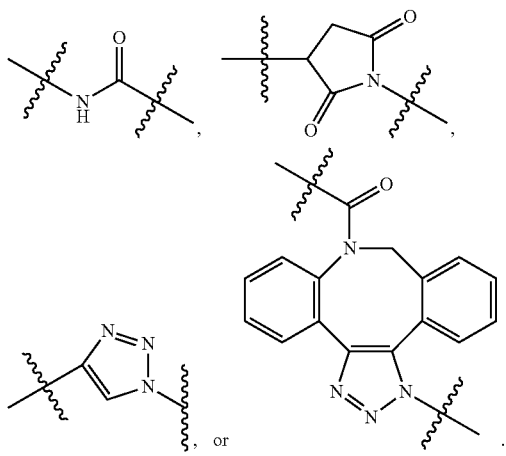 [SMILES: *NC(*)=O ; *C1CC(=O)N(*)C1=O ; *c1cn(*)nn1 ; *C(=O)N1Cc2ccccc2-c2c(nnn2*)-c2ccccc21]

In some embodiments, $L^{3a}$ is:

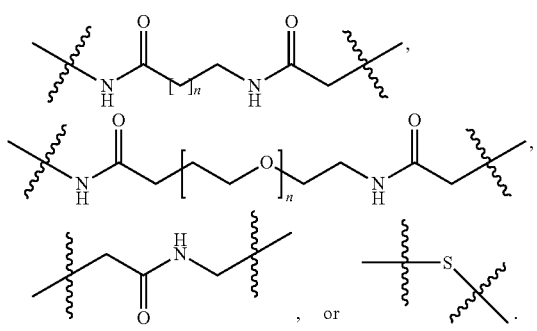

In some embodiments, $L^{3b}$ is an acyl spacer fragment of the formula:

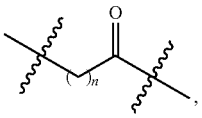

or a PEG-acyl spacer fragment of the formula:

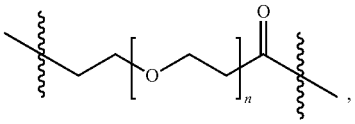

where n is 0 to 200. In some embodiments, $L^{3b}$ is an acyl spacer fragment of the formula:

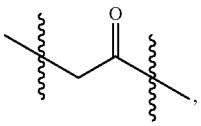 [SMILES: *CC(*)=O]

or a PEG-acyl spacer fragment of the formula:

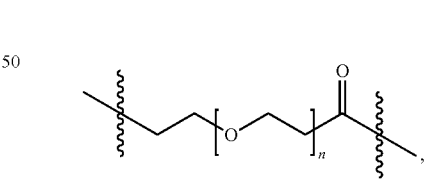

where n is 0 to 200. In some embodiments, $L^3$ is:

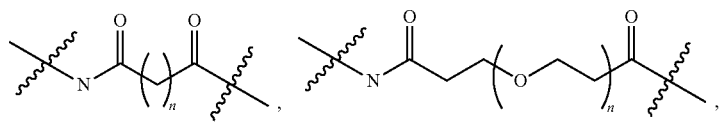

-continued
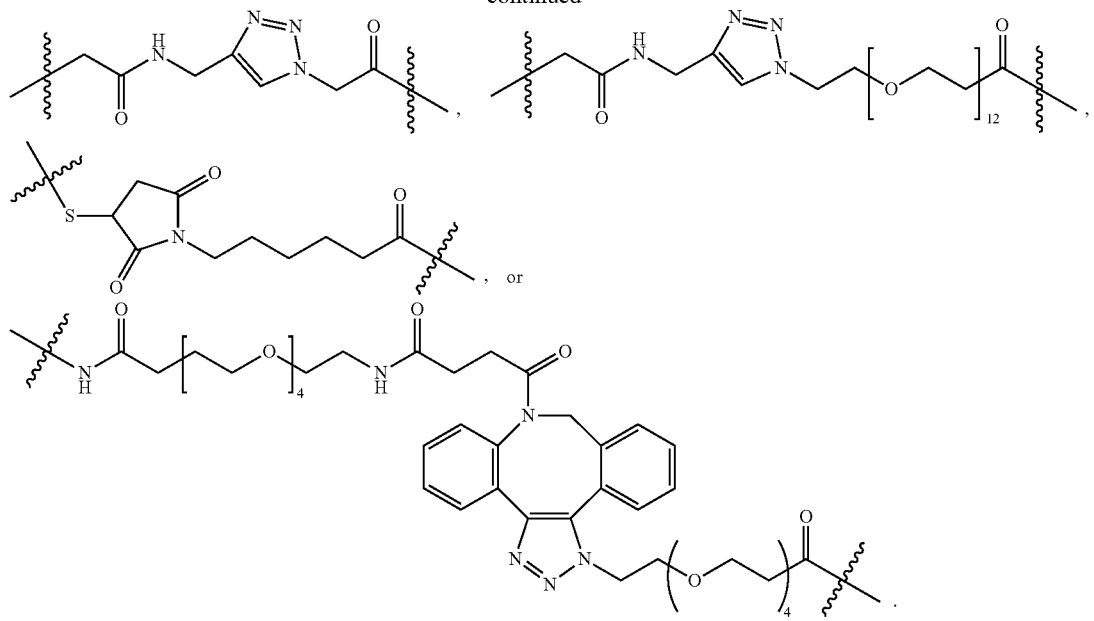
In another aspect, provided herein is a compound of formula (I), wherein the -L³-L²-L¹-D moiety is:
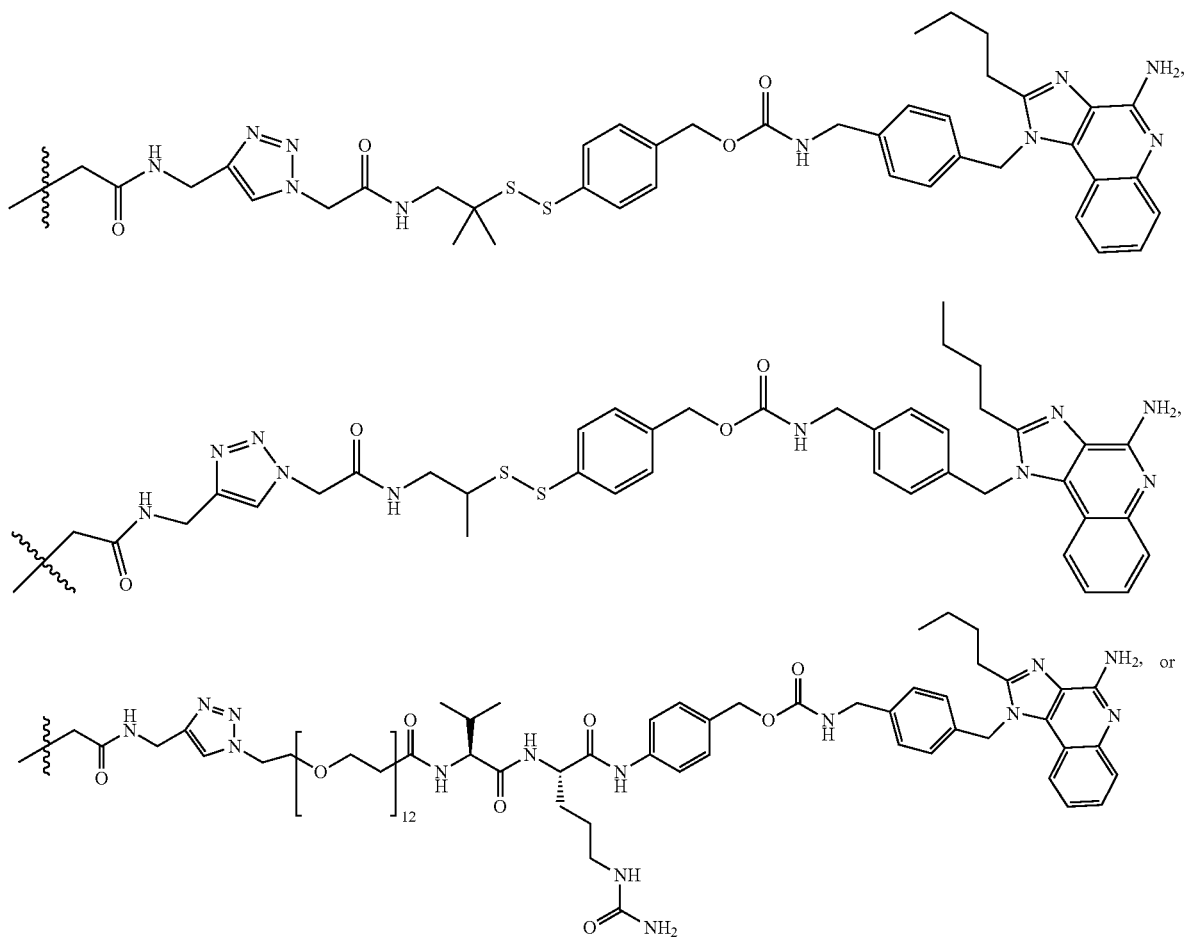

-continued

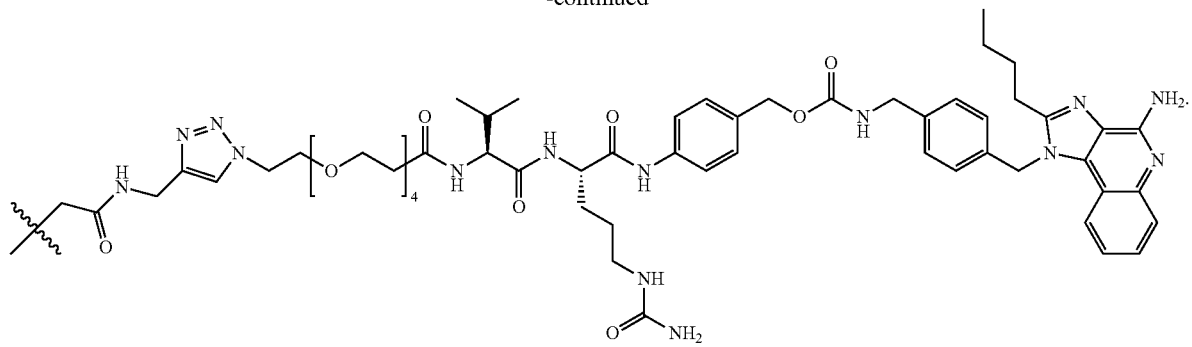

In one aspect, provided herein is a compound of formula (I), wherein F is a tumor targeting agent. In some embodiments, the tumor targeting agent is an antibody or binding ligand, which preferentially binds to tumor cell surface antigens, unique structural elements of the tumor microenvironment extracellular matrix, or unique structural elements of the tumor vasculature. In some embodiments, F possesses physical properties or chemical modifications of the surface designed to cause preferential distribution to the tumor microenvironment.

In another aspect, provided herein is a compound of formula (I), wherein F is an agent that promotes local retention of the compound of formula (I). In some embodiments, F is a liposome, virus-like particle, nanoparticle, microparticle, macromolecule or supramolecule, dendrimer, or polypeptide.

Further provided is a pharmaceutical composition comprising a compound of formula (I) and a pharmaceutically acceptable excipient. In some embodiments of the pharmaceutical composition the excipient is a solvent, bulking agent, emulsifier/surfactant, buffering agent, tonicity adjusting agent and/or a preservative. In some embodiments of the pharmaceutical composition the form is a solution or a freeze-dried solid.

In another aspect, provided is a method of stimulating an immune response in a mammalian subject in need thereof, comprising administering to the mammalian subject a pharmaceutical composition comprising a compound of formula (I) in an amount sufficient to stimulate an immune response in the mammalian subject.

Also provided is a method of inducing an antigen-specific antibody response and/or an antigen-specific T cell response in a mammalian subject in need thereof, comprising administering to the mammalian subject a pharmaceutical composition comprising a compound of formula (I) in an amount, and on a dosing schedule, sufficient to induce an antigen-specific antibody response and/or an antigen-specific T cell response in the mammalian subject.

Also provided is a plurality of methods of treating cancer in a mammalian subject in need thereof comprising administering an effective amount of a pharmaceutical composition by a parenteral route of administration, either as a single agent or in combination with other agents for the treatment of cancer (e.g., chemotherapies, targeted therapies, and/or immunotherapies). Also provided in the invention are kits comprising pharmaceutical compositions of the invention, and instructions for use in the treatment of cancers.

BRIEF DESCRIPTION OF THE DRAWINGS

FIG. 1 shows chemical structure representations of 1-(4-aminomethylbenzyl)-2-butyl-1H-imidazo[4,5-c]quinolin-4-amine (IMDQ) and 1-(3-aminomethylbenzyl)-2-butyl-1H-imidazo[4,5-c]quinolin-4-amine (meta-IMDQ). The atom numbering is also shown on IMDQ for the imidazoquinoline core structure.

FIG. 8 shows the effect on tumor growth of weekly intratumoral administration of Compound No. 64-53a, Compound No. 64-54a, Compound No. 64-10a, or PBS vehicle control to syngeneic CT26 tumor bearing BALB/c mice with a single subcutaneous tumor. Panel A shows the effect on tumor volume over 27 days post tumor implantation. Panel B shows a scatter plot of the tumor growth for the treatments on day 27 (3 days after the last of 3 weekly doses of the administered compounds). Datapoints are the average+/− standard error of the mean for groups of 8 mice.

FIG. 10 shows the effect on tumor growth of weekly intratumoral administration of 30, 125 or 500 ng of an IMDQ equivalent mass of Compound No. 64-54a (Panel A) or Compound No. 64-54b (Panel B), plus a PBS vehicle control, to syngeneic CT26 tumor bearing BALB/c mice with a single subcutaneous tumor. Time is days post tumor implantation and datapoints are the average+/−standard error of the mean for groups of 10 mice.

DETAILED DESCRIPTION OF THE INVENTION

Figure 2:
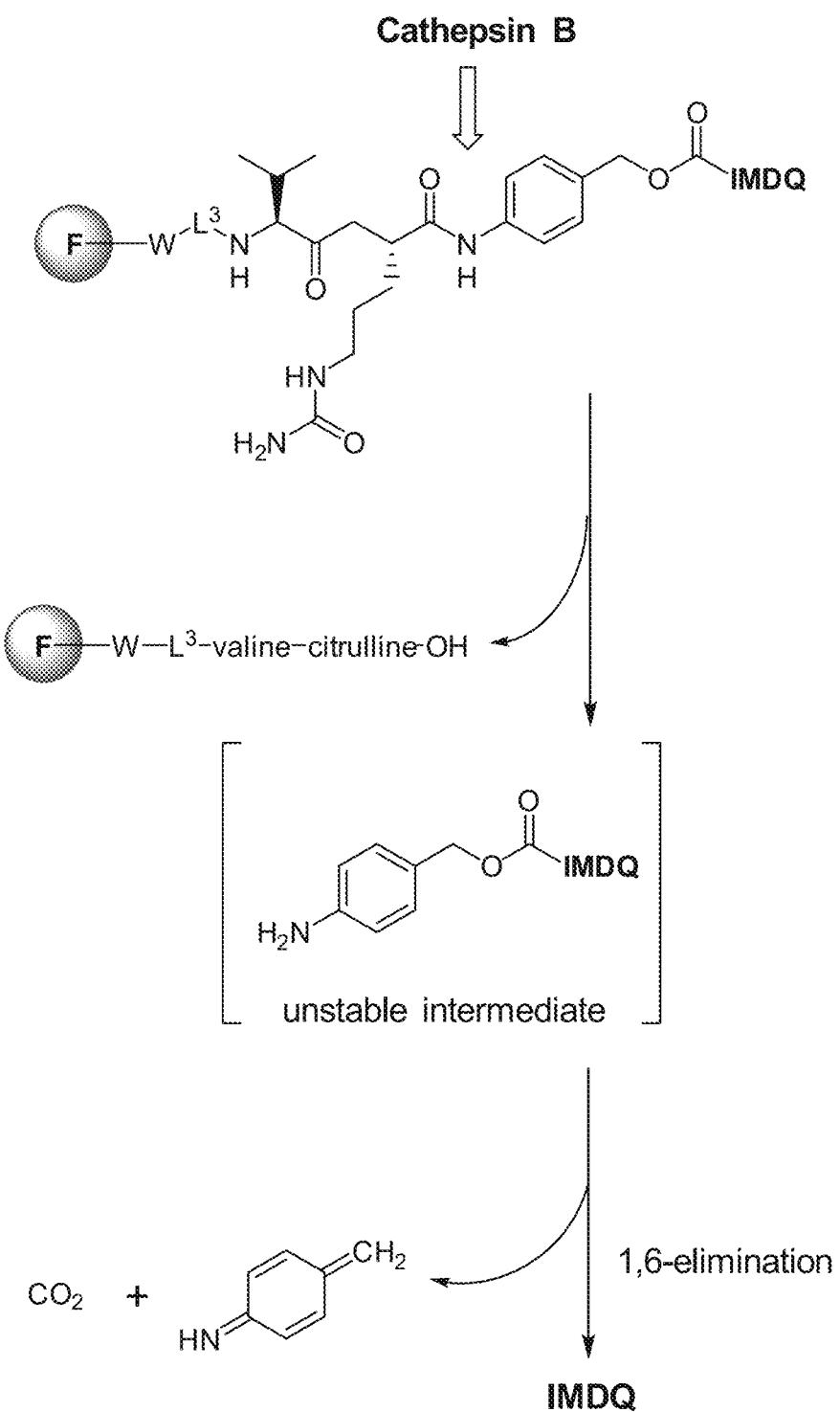
FIG. 2 depicts a mechanism of release of IMDQ from an exemplary compound of formula (I) containing a valine-citrulline dipeptide cleavable linker.

The present disclosure relates to TLR7/8 agonist compounds exhibiting potent bioactivity against both receptors, that are covalently conjugated to a conjugation moiety, that enables tumor-specific targeting or local retention following administration, via a cleavable linker that promotes local release of a bioactive form of the TLR7/8 agonist and reduces unwanted systemic pro-inflammatory cytokine responses. The TLR7/8 agonist compounds include modified 1H-imidazo[4,5-c]quinoline derivatives modified with alkyl or hydrocarbyl groups, aryl groups, heteroaryl groups, or combinations thereof. The conjugation moiety is a tumor-specific targeting agent or an agent that promotes local retention following administration. The conjugation moiety can be an antibody, ligand, liposome, virus-like particle, nanoparticle, microparticle, macromolecule or supramolecule, dendrimer, or polypeptide. The cleavable linker moiety allows for the release of the TLR7/8 agonist compounds within the tumor microenvironment. The present disclosure also relates to uses thereof for stimulating an immune response (e.g., an antigen-specific CD4+/CD8+ T cell response), to uses thereof for the treatment of cancer, and to methods for preparation of the cleavable conjugates.

I. GENERAL METHODS AND DEFINITIONS

The practice of the present disclosure will employ, unless otherwise indicated, conventional techniques of organic chemistry, analytical chemistry, molecular biology, microbiology, cell biology, biochemistry, and immunology, which are within the skill of the art. Such techniques are fully described in the literature, see for example: *Fiesers' Reagents for Organic Synthesis*, $25^{th}$ edition (Ho, ed., Wiley, 2016); *Comprehensive Organic Functional Group Transformations*, $2^{nd}$ edition (Katritsky and Taylor, eds., Elsevier, 2004); *Comprehensive Organic Synthesis*, version 1-8 (Trost and Flemming, eds., Permagon Press, 1991); *Beilsteins Handbuch der Organischen Chemie*, 4 (Auflage, ed., Springer-Verlag, 1934); *Animal Cell Culture*, sixth edition (Freshney, Wiley-Blackwell, 2010); *Current Protocols in Cell Biology* (Bonifacino et al., ed., John Wiley and Sons, Inc., 1996, including supplements through 2014); *Current Protocols in Immunology* (Coligan et al., eds., John Wiley & Sons, Inc., 1991 including supplements through 2014); *Current Protocols in Molecular Biology* (Ausubel et al., eds., John Wiley and Sons, Inc., 1987, including supplements through 2014); *Molecular Cloning: A Laboratory Manual*, third edition (Sambrook and Russell, Cold Spring Harbor Laboratory Press, 2001); and *Molecular Cloning: A Laboratory Manual*, fourth edition (Green and Sambrook, Cold Spring Harbor Laboratory Press, 2012).

The terms "individual" and "subject" refer to mammals. "Mammals" include, but are not limited to, humans, non-human primates (e.g., monkeys), farm animals, sport animals (e.g., horses), rodents (e.g., mice and rats), and pets (e.g., dogs and cats).

The term "antigen" refers to a substance that is recognized and bound specifically by an antibody or by a T cell antigen receptor. Antigens can include peptides, polypeptides, proteins, glycoproteins, polysaccharides, complex carbohydrates, sugars, gangliosides, lipids, and phospholipids; portions thereof, and combinations thereof.

Antigens, when present in the compositions of the present disclosure, can be synthetic or isolated from nature. Antigens suitable for administration in the methods of the present disclosure include any molecule capable of eliciting an antigen-specific B cell or T cell response. Haptens are included within the scope of "antigen." A "hapten" is a low molecular weight compound that is not immunogenic by itself but is rendered immunogenic when conjugated with a generally larger immunogenic molecule.

"Polypeptide antigens" can include purified native peptides, synthetic peptides, engineered peptides, recombinant peptides, crude peptide extracts, or peptides in a partially purified or unpurified active state (such as peptides that are part of attenuated or inactivated viruses, microorganisms, or cells), or fragments of such peptides. Polypeptide antigens are preferably at least six amino acid residues in length, preferably from 8 to 1800 amino acids in length, more preferably from 9 to 1000 amino acids in length, or from 10 to 100 amino acids in length. Similarly, in some embodiments, the polypeptide is about 9 to about 2000, about 9 to about 1000, about 9 to about 100, or about 9 to about 60 amino acids in length. In some embodiments, the polypeptide is at least (lower limit) 9, 10, 11, 12, 13, 14, 15, 16, 17, 18, 19, 20, 25, 30, 35, 40, 45, 50, 60, 70, 80, or 90 amino acids in length. In some embodiments, the polypeptide is at most (upper limit) 1000, 900, 800, 700, 600, 500, 400, 300, 250, 200, 150, 100, 50, or 25 amino acids in length. In some embodiments, the polypeptide antigen is from 9 to 35 amino acids in length.

As used herein, the term "immunogenic" refers to an agent (e.g., endogenous or externally administered polypeptide antigen) that elicits an adaptive immune response upon administration under suitable conditions to a mammalian subject. The immune response can be a B cell (humoral) and/or T cell (cellular) mediated response.

"Adjuvant" refers to a substance which, when mixed with an immunogenic agent such as an antigen, nonspecifically enhances or potentiates an immune response to the agent in the recipient upon exposure to the mixture.

The term "agonist" is used in the broadest sense and includes any molecule that activates signaling through a receptor. For instance, a TLR7 agonist binds a toll-like receptor 7 protein and activates a TLR7-signaling pathway; a TLR8 agonist binds a toll-like receptor 8 protein and activates a TLR8-signaling pathway; a dual TLR7/8 agonist binds to both toll-like receptor 7 and toll-like receptor 8 proteins and activates both TLR7- and TLR8-signaling pathways.

"Stimulation" of a response or parameter includes eliciting and/or enhancing that response or parameter when compared to conditions that are otherwise the same except for the agent or molecule or, alternatively, as compared to another condition (e.g., increase in TLR-signaling in the presence of a TLR agonist as compared to the absence of the TLR agonist). For example, "stimulation" of an immune response means an increase in the response.

An "effective amount" of an agent disclosed herein is an amount sufficient to carry out a specifically stated purpose. An "effective amount" can be determined empirically and in a routine manner, in relation to the stated purpose. An "effective amount" or an "amount sufficient" of an agent is that amount adequate to produce a desired biological effect, such as a beneficial result, including a beneficial clinical result. The term "therapeutically effective amount" refers to an amount of an agent (e.g., TLR modulator) effective to "treat" a disease or disorder in a subject (e.g., a mammal such as a human).

The terms "treating" or "treatment" of a disease refers to executing a protocol, which can include administering one or more drugs to an individual (human or otherwise), in an effort to alleviate signs or symptoms of the disease. Thus, "treating" or "treatment" does not require complete alleviation of signs or symptoms, does not require a cure, and specifically includes protocols that have only a palliative effect on the individual. As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival of an individual not receiving treatment. "Palliating" a disease or disorder means that the extent and/or undesirable clinical manifestations of the disease or disorder are lessened and/or time course of progression of the disease or disorder is slowed, as compared to the expected untreated outcome. Especially in the cancer context, palliation can occur upon causing stable disease, or disease remission that lead to increases in overall survival rates. Further, palliation does not necessarily occur by administration of one dose, but often occurs upon administration of a series of doses. Thus, an amount sufficient to palliate a response or disorder can be administered in one or more doses.

"Alkyl" as used herein refers to a saturated linear (i.e., unbranched) or branched univalent hydrocarbon chain or combination thereof. Particular alkyl groups are those having a designated number of carbon atoms, for example, an alkyl group having 1 to 20 carbon atoms (a "$C_1$-$C_{20}$ alkyl"), having 1 to 10 carbon atoms (a "$C_1$-$C_{10}$" alkyl), having 1 to 8 carbon atoms (a "$C_1$-$C_8$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e., unbranched) or branched univalent hydrocarbon chain or combination thereof, having at least one site of olefinic unsaturation (i.e., having at least one moiety of the formula C=C). Particular alkenyl groups are those having a designated number of carbon atoms, for example, an alkenyl group having 2 to 20 carbon atoms (a "$C_2$-$C_{20}$ alkenyl"), having 2 to 10 carbon atoms (a "$C_2$-$C_{10}$" alkenyl), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). The alkenyl group can be in "cis" or "trans" configurations or, alternatively, in "E" or "Z" configurations. Examples of alkenyl groups include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs, and isomers thereof, and the like.

"Alkynyl" as used herein refers to an unsaturated linear (i.e., unbranched) or branched univalent hydrocarbon chain or combination thereof, having at least one site of acetylenic unsaturation (i.e., having at least one moiety of the formula C≡C). Particular alkynyl groups are those having a designated number of carbon atoms, for example, an alkynyl group having 2 to 20 carbon atoms (a "$C_2$-$C_{20}$ alkynyl"), having 2 to 10 carbon atoms (a "$C_2$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl groups include, but are not limited to, groups such as ethynyl (or acetylenyl), prop-1-ynyl, prop-2-ynyl (or propargyl), but-1-ynyl, but-2-ynyl, but-3-ynyl, homologs, and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene"), or 1 to 3 carbon atoms (a "$C_1$-$C_3$ alkylene"). Examples of alkylene groups include, but are not limited to, groups such as methylene (—$CH_2$— or =$CH_2$), ethylene (—$CH_2CH_2$— or =$CHCH_3$), propylene (—$CH_2CH_2CH_2$— or =$CHCH_2CH_3$), butylene (—$CH_2CH_2CH_2CH_2$— or =$CHCH_2CH_2CH_3$), and the like.

"Cycloalkyl" as used herein refers to non-aromatic, saturated, or unsaturated cyclic univalent hydrocarbon structures. Particular cycloalkyl groups are those having a designated number of annular (i.e., ring) carbon atoms, for example, a cycloalkyl group having from 3 to 12 annular carbon atoms (a "$C_3$-$C_{12}$ cycloalkyl"). A preferred cycloalkyl is a cyclic hydrocarbon having from 3 to 8 annular carbon atoms (a "$C_3$-$C_8$ cycloalkyl"), or having 3 to 6 annular carbon atoms (a "$C_3$-$C_6$ cycloalkyl"). Cycloalkyl can consist of one ring, such as cyclohexyl, or multiple rings, such as adamantyl, but excludes aryl groups. A cycloalkyl comprising more than one ring can be fused, spiro, or bridged, or combinations thereof. Examples of cycloalkyl groups include, but are not limited to, cyclopropyl, cyclobutyl, cyclopentyl, cyclohexyl, 1-cyclohexenyl, 3-cyclohexenyl, cycloheptyl, norbornyl, and the like.

"Cycloalkylene" as used herein refers to the same residues as cycloalkyl, but having bivalency. Particular cycloalkylene groups are those having 3 to 12 annular carbon atoms (a "$C_3$-$C_{12}$ cycloalkylene"), having from 3 to 8 annular carbon atoms (a "$C_3$-$C_8$ cycloalkylene"), or having 3 to 6 annular carbon atoms (a "$C_3$-$C_6$ cycloalkylene"). Examples of cycloalkylene groups include, but are not limited to, cyclopropylene, cyclobutylene, cyclopentylene, cyclohexylene, 1,2-cyclohexenylene, 1,3-cyclohexenylene, 1,4-cyclohexenylene, cycloheptyl, norbornyl, and the like.

"Hydrocarbyl" as used herein refers to and includes a univalent group formed by removing a hydrogen atom from a non-aromatic hydrocarbon, which can be fully saturated, mono- or polyunsaturated, having the number of carbon atoms designated (i.e., $C_1$-$C_{20}$ means one to twenty carbon atoms). A hydrocarbyl group can contain one or more linear, branched, or cyclic moieties, or combinations thereof. Alkyl, alkenyl, alkynyl, and cycloalkyl groups are particular subsets of hydrocarbyl groups. A hydrocarbyl group can also contain an alkyl, alkenyl, or alkynyl group further substituted by one or more cycloalkyl groups; and/or a cycloalkyl group further substituted by one of more alkyl, alkenyl, and/or alkynyl groups. Examples of hydrocarbyl groups include, but are not limited to, groups such as the following:

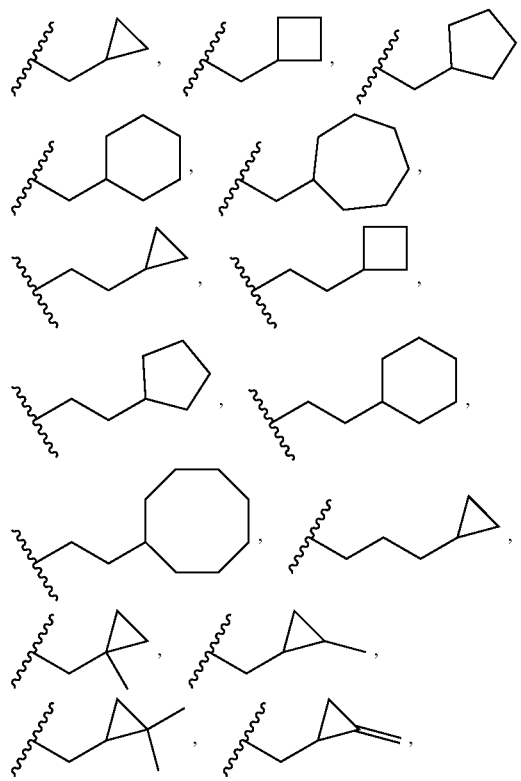

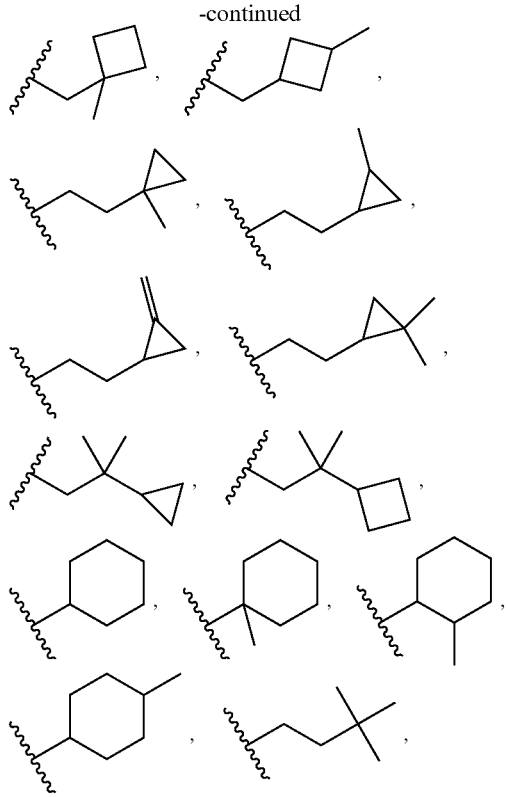

and the like. A hydrocarbyl group can be substituted, at one or more positions, by one or more substituents, such as halogen atoms, for example chlorine or fluorine. Examples of substituted hydrocarbyl groups include, but are not limited to, groups such as the following:

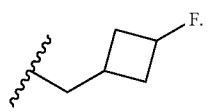 [SMILES: *CC1CC(F)C1]

"Aryl" as used herein refers to an unsaturated aromatic carbocyclic group having a single ring (e.g., phenyl) or multiple condensed rings (e.g., naphthyl or anthryl) where one or more of the condensed rings can not be aromatic. Particular aryl groups are those having from 6 to 14 annular (i.e., ring) carbon atoms (a "$C_6$-$C_{14}$ aryl"). An aryl group having more than one ring where at least one ring is non-aromatic can be connected to the parent structure at either an aromatic ring position or at a non-aromatic ring position. In one variation, an aryl group having more than one ring where at least one ring is non-aromatic is connected to the parent structure at an aromatic ring position. Examples of aryl include, but are not limited to, groups such as phenyl, naphthyl, 1-naphthyl, 2-naphthyl, and the like.

"Arylene" as used herein refers to the same residues as aryl, but having bivalency. Particular arylene groups are those having from 6 to 14 annular carbon atoms (a "$C_6$-$C_{14}$ arylene"). Examples of arylene include, but are not limited to, groups such as phenylene, o-phenylene (i.e., 1,2-phenylene), m-phenylene (i.e., 1,3-phenylene), p-phenylene (i.e., 1,4-phenylene), naphthylene, 1,2-naphthylene, 1,3-naphthylene, 1,4-naphthylene, 2,7-naphthylene, 2,6-naphthylene, and the like.

"Heteroaryl" as used herein refers to an unsaturated aromatic cyclic group having from 1 to 14 annular carbon atoms and at least one annular heteroatom, including, but not limited to, heteroatoms such as nitrogen, oxygen, and sulfur. A heteroaryl group can have a single ring (e.g., pyridyl or imidazolyl) or multiple condensed rings (e.g., indolizinyl or pyrazolo-pyridazinyl) where at least one of the condensed rings is aromatic. Particular heteroaryl groups are 5- to 14-membered rings having 1 to 12 annular carbon atoms and 1 to 6 annular heteroatoms independently selected from the group consisting of nitrogen, oxygen, and sulfur (a "5- to 14-membered heteroaryl"); 5- to 10-membered rings having 1 to 8 annular carbon atoms and 1 to 4 annular heteroatoms independently selected from the group consisting of nitrogen, oxygen, and sulfur (a "5- to 10-membered heteroaryl"); or 5-, 6-, or 7-membered rings having 1 to 5 annular carbon atoms and 1 to 4 annular heteroatoms independently selected from the group consisting of nitrogen, oxygen, and sulfur (a "5- to 17-membered heteroaryl"). In one variation, heteroaryl includes monocyclic aromatic 5-, 6-, or 7-membered rings having from 1 to 6 annular carbon atoms and 1 to 4 annular heteroatoms independently selected from the group consisting of nitrogen, oxygen, and sulfur. In another variation, heteroaryl includes polycyclic aromatic rings having from 1 to 12 annular carbon atoms and 1 to 6 annular heteroatoms independently selected from the group consisting of nitrogen, oxygen, and sulfur. A heteroaryl group having more than one ring where at least one ring is non-aromatic can be connected to the parent structure at either an aromatic ring position or at a non-aromatic ring position. In one variation, a heteroaryl group having more than one ring where at least one ring is non-aromatic is connected to the parent structure at an aromatic ring position. Examples of heteroaryl include, but are not limited to, groups such as pyridyl, benzimidazolyl, benzotriazolyl, benzo[b]thienyl, quinolinyl, indolyl, benzothiazolyl, and the like.

"Heteroarylene" as used herein refers to the same residues as heteroaryl, but having bivalency. Particular heteroarylene groups are 5- to 14-membered rings having 1 to 12 annular carbon atoms and 1 to 6 annular heteroatoms independently selected from the group consisting of nitrogen, oxygen, and sulfur (a "5- to 14-membered heteroarylene"); 5- to 10-membered rings having 1 to 8 annular carbon atoms and 1 to 4 annular heteroatoms independently selected from the group consisting of nitrogen, oxygen, and sulfur (a "5- to 10-membered heteroarylene"); or 5-, 6-, or 7-membered rings having 1 to 5 annular carbon atoms and 1 to 4 annular heteroatoms independently selected from the group consisting of nitrogen, oxygen, and sulfur (a "5- to 7-membered heteroarylene"). Examples of heteroarylene include, but are not limited to, groups such as pyridylene, benzimidazolylene, benzotriazolylene, benzo[b]thienylene, quinolinylene, indolylene, benzothiazolylene, and the like.

"Halo" or "halogen" refers to elements of the Group 17 series having atomic number 9 to 85. Preferred halo groups include fluoro, chloro, bromo, and iodo. Where a residue is substituted with more than one halogen, it can be referred to by using a prefix corresponding to the number of halogen moieties attached. For example, dihaloaryl, dihaloalkyl, and trihaloaryl, etc., refer to aryl and alkyl substituted with two ("di") or three ("tri") halo groups, which can be, but are not necessarily, the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Amino" refers to the group —$NH_2$.

"Substituted amino" refers to the group —NR'R" where R' and R" are independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl, provided that at least one of R' and R" is not hydrogen.

"Optionally substituted", unless otherwise specified, means that a group can be unsubstituted or substituted by one or more (e.g., 1, 2, 3, 4, or 5) of the substituents listed for that group in which the substituents can be the same or different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, or 1 to 5 substituents.

"Substituted alkyl" unless otherwise specified refers to an alkyl group having one or more substituents (e.g., from 1 to 5 substituents, or from 1 to 3 substituents) selected from acyloxy, hydroxy, mercapto, acyl, alkoxy, substituted alkoxy, cycloalkyl, substituted cycloalkyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclyloxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Substituted alkenyl" unless otherwise specified refers to an alkenyl group having one or more substituents (e.g., from 1 to 5 substituents, or from 1 to 3 substituents) selected from acyloxy, hydroxy, mercapto, acyl, alkoxy, substituted alkoxy, cycloalkyl, substituted cycloalkyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclyloxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Substituted alkynyl" unless otherwise specified refers to an alkynyl group having one or more substituents (e.g., from 1 to 5 substituents, or from 1 to 3 substituents) selected from acyloxy, hydroxy, mercapto, acyl, alkoxy, substituted alkoxy, cycloalkyl, substituted cycloalkyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclyloxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Substituted cycloalkyl" unless otherwise specified refers to a cycloalkyl group having one or more substituents (e.g., from 1 to 5 substituents, or from 1 to 3 substituents) selected from acyloxy, hydroxy, thiol, acyl, alkyl, substituted alkyl, alkoxy, substituted alkoxy, alkenyl, substituted alkenyl, alkynyl, substituted alkynyl, cycloalkyl, substituted cycloalkyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Substituted aryl" unless otherwise specified refers to an aryl group having one or more substituents (e.g., from 1 to 5 substituents, or from 1 to 3 substituents) selected from acyloxy, hydroxy, thiol, acyl, alkyl, substituted alkyl, alkoxy, substituted alkoxy, alkenyl, substituted alkenyl, alkynyl, substituted alkynyl, cycloalkyl, substituted cycloalkyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Substituted heteroaryl" unless otherwise specified refers to a heteroaryl group having one or more substituents (e.g., from 1 to 5 substituents, or from 1 to 3 substituents) selected from acyloxy, hydroxy, thiol, acyl, alkyl, substituted alkyl, alkoxy, substituted alkoxy, alkenyl, substituted alkenyl, alkynyl, substituted alkynyl, cycloalkyl, substituted cycloalkyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Substituted heterocyclyl" unless otherwise specified refers to a heterocyclyl group having one or more substituents (e.g., from 1 to 5 substituents, or from 1 to 3 substituents) selected from acyloxy, hydroxy, thiol, acyl, alkyl, substituted alkyl, alkoxy, substituted alkoxy, alkenyl, substituted alkenyl, alkynyl, substituted alkynyl, cycloalkyl, substituted cycloalkyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —S(O)R$^{70}$, —SO$_2$R$^{70}$, —SO$_2$O$^-$M$^+$, —SO$_2$OR$^{70}$, —OSO$_2$R$^{70}$, —OSO$_2$$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)R$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heterocycloalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 3-, 4-, 5-, 6-, or 7-membered heterocycloalkyl which can optionally include from 1 to 4 of the same or different additional heteroatoms selected from the group consisting of O, N and S, of which N can have —H, C$_1$-C$_4$ alkyl, —C(O)C$_{1-4}$alkyl, —CO$_2$C$_{1-4}$alkyl, or —SO$_2$C$_{1-4}$alkyl substitution; and each M$^+$ is a counter ion with a net single positive charge. Each M$^+$ can independently be, for example, an alkali ion, such as K$^+$, Na$^+$, Li$^-$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the embodiments and the other a typical counter ion such as chloride, or two ionized compounds disclosed herein can serve as counter ions for such divalent alkali earth ions, or a doubly ionized compound of the embodiments can serve as the counter ion for such divalent alkali earth ions).

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{80}$, SR$^{70}$, S$^-$M$^+$, —NR$^{80}$R$^{80}$, trihalomethyl, —CF$_3$, —CN, —OCN, —SCN, —NO, —NO$_2$, —N$_3$, —S(O)R$^{70}$, —SO$_2$R$^{70}$, —SO$_3$$^{-M+}$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —SR$^{70}$, or —S$^-$M$^+$.

In addition to the substituent groups disclosed with respect to the individual terms herein, substituent groups for hydrogens on nitrogen atoms in "substituted" heterocycloalkyl and cycloalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)R$^{70}$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, that such groups do not contain any substitution or substitution patterns which are sterically impractical and/or synthetically non-feasible. In addition, the subject compounds include all stereochemical isomers arising from the substitution of these compounds.

"Polyalkylene glycol" refers to straight or branched polyalkylene glycol polymers such as polyethylene glycol ("PEG" or polyethylene oxide), polypropylene glycol ("PPG" or polypropylene oxide), and polybutylene glycol. A polyalkylene glycol subunit is a single polyalkylene glycol unit. For example, an example of a polyethylene glycol subunit would be an ethylene glycol, —[CH$_2$—CH$_2$—O]—; or propylene glycol, —[CH$_2$—CH(CH$_3$)—O]—; capped with a hydrogen at the chain termination point. Other examples of poly(alkylene glycol) include, but are not limited to, PEG; PEG derivatives such as methoxypoly (ethylene glycol) (mPEG); poly(ethylene oxide); PPG; poly (tetramethylene glycol), also known as poly(tetrahydrofuran) or poly THF; poly(ethylene oxide-co-propylene oxide); or copolymers and combinations thereof.

"Organic modifier", unless otherwise specified, means one of a group of solvents typically used to solubilize organic chemical compounds. This group can include, but is not limited to, acetic acid, acetone, anisole, 1-butanol, 2-butanol, butyl acetate, tert-butyl methyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylenthylketone, methylisobutylketone, 2-methyl-1-propanol, pentane, 1-pentanol, 1-propanol, 2-propanol (isopropanol), propyl acetate, and combinations thereof.

In addition to the disclosure herein, the term "substituted", when used to modify a specified group or radical, can also mean that one or more hydrogen atoms of the specified group or radical are each, independently of one another, replaced with the same or different substituent groups as defined herein. In some embodiments, a group that is substituted has 1, 2, 3, or 4 substituents, 1, 2, or 3 substituents, 1 or 2 substituents, or 1 substituent.

In addition to the disclosure herein, in a certain embodiment, a group that is substituted has 1, 2, 3, or 4 substituents, 1, 2, or 3 substituents, 1 or 2 substituents, or 1 substituent.

Unless a specific isotope of an element is indicated in a formula, the invention includes all isotopologues of the compounds disclosed herein, such as, for example, deuterated derivatives of the compounds (where H can be $^2$H, i.e., D). Isotopologues can have isotopic replacements at any or at all locations in a structure, or can have atoms present in natural abundance at any or all locations in a structure.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

It will be appreciated that the term "or a salt or solvate or stereoisomer thereof" is intended to include all permutations of salts, solvates, and stereoisomers, such as a solvate of a pharmaceutically acceptable salt of a stereoisomer of subject compound.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such subcombination of chemical groups was individually and explicitly disclosed herein.

It is understood that aspects and embodiments described herein as "comprising" include "consisting of" and "consisting essentially of" embodiments.

As used herein and in the appended claims, the singular forms "a", "an", and "the" include plural referents unless otherwise indicated or clear from context.

Unless clearly indicated otherwise, the term "about" is used to indicate that a value includes the standard deviation of error for the device or method being employed to determine the value. Reference to "about" a value or parameter herein includes (and describes) embodiments that are directed to that value or parameter per se. For example, description referring to "about X" includes description of "X."

II. TUMOR TARGETED CLEAVABLE CONJUGATES OF TLR7/8 AGONIST COMPOUNDS

The present disclosure provides for modified 1H-imidazo [4,5-c]quinoline derivatives that are potent TLR7/8 agonists covalently conjugated to an agent for tumor-specific targeting or for local retention following administration via a combination of a self-eliminating linker, a cleavable linker, and a conjugation linker to promote local release of a bioactive form of the TLR7/8 agonist. Within the tumor microenvironment, covalently conjugated TLR7/8 agonist compounds of the present disclosure are chemically cleaved, thereby promoting release of a maximally bioactive form (i.e., unconjugated form) of the TLR7/8 agonists. Accordingly, these locally released TLR7/8 agonists can induce effective immune responses. Additionally, systemic distribution of covalently conjugated TLR7/8 agonist compounds of the present disclosure can be restricted due to their chemical properties, thereby reducing unwanted systemic pro-inflammatory cytokine responses. The present disclosure also relates to methods for preparation of a therapeutic agent or vaccine adjuvant comprised of the covalent conjugates of TLR7/8 agonists, uses thereof for stimulating an immune response with reduced systemic pro-inflammatory cytokine responses, and uses thereof as a therapeutic agent for the treatment of cancer.

In one aspect, provided is a compound of formula (I):

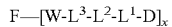 (I)

wherein:
D is a TLR7/8 agonist moiety;
$L^1$ is a bond or a self-eliminating linker;
$L^2$ is a cleavable linker;
$L^3$ is a conjugation linker;
W is O, S, or $NR^{10}$;
$R^{10}$ is H or $C_1$-$C_8$ alkyl;
x is an integer from 1 to 500; and
F is a conjugation moiety.

In another aspect, provided is a compound of formula (I-a):

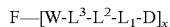 (I-a)

wherein:
D is a TLR7/8 agonist moiety;
$L^1$ is a self-eliminating linker;
$L^2$ is a cleavable linker;
$L^3$ is a conjugation linker;
W is O, S, or $NR^{10}$;
$R^{10}$ is H or $C_1$-$C_8$ alkyl;
x is an integer from 1 to 500; and
F is a conjugation moiety.

A. TLR7/8 Agonists

In some embodiments, the TLR7/8 agonist moiety of D in formula (I) is an 1H-imidazo[4,5-c]quinoline derivative. In some embodiments, the TLR7/8 agonist moiety of D is a 2-butyl-1H-imidazo[4,5-c]quinolin-4-amine derivative.

In some embodiments, the TLR7/8 agonist moiety of D in formula (I) is of the formula (D-1):

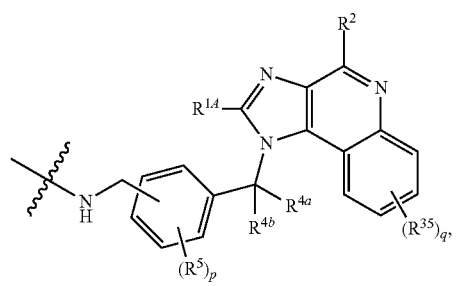 (D-1)

wherein:
$R^{1A}$ is $C_1$-$C_8$ alkyl, $C_1$-$C_8$ hydroxyalkyl, or $C_3$-$C_8$ cycloalkyl;
$R^2$ is $NHR^{2a}$, where $R^{2a}$ is H or $C_1$-$C_8$ alkyl;
each $R^{35}$ is independently halogen or $C_1$-$C_8$ alkyl;
$R^{4a}$ and $R^{4b}$ are independently H or $C_1$-$C_8$ alkyl;
each $R^5$ is independently halogen or $C_1$-$C_8$ alkyl;
p and q are independently 0, 1, 2, 3, or 4; and
the wave line represents the point of attachment of D in formula (I).

In some embodiments, $R^{1A}$ is an optionally substituted $C_1$-$C_8$ alkyl, $C_1$-$C_8$ hydroxyalkyl, or an optionally substituted $C_3$-$C_8$ cycloalkyl. In one variation, $R^{1A}$ is $C_1$-$C_8$ alkyl optionally substituted by hydroxy. In a particular variation, $R^{1A}$ is $C_1$-$C_8$ alkyl (e.g., n-butyl or isobutyl). In another particular variation, $R^{1A}$ is $C_1$-$C_8$ hydroxyalkyl. In one variation, $R^{1A}$ is $C_3$-$C_8$ cycloalkyl.

In some embodiments, $R^2$ is $NH_2$ or $NHR^{2a}$, where $R^{2a}$ is an optionally substituted alkyl. In one variation, $R^2$ is $NH_2$. In another variation, $R^2$ is $NHR^{2a}$, where $R^{2a}$ is an optionally substituted $C_1$-$C_8$ alkyl. In a particular variation, $R^2$ is $NHR^{2a}$ where $R^{2a}$ is $C_1$-$C_8$ alkyl.

In some embodiments, q is 0 (i.e., $R^{35}$ is absent). In some embodiments, q is 1 and $R^{35}$ is attached to the 6, 7, 8, or 9 position of the imidazo[4,5-c]quinoline core. In some embodiments, q is 1 and $R^{35}$ is amino or substituted amino attached to the 7 or 8 position of the imidazo[4,5-c]quinoline core. In some embodiments, q is 2 and the two $R^{35}$ groups are attached to the 7 and 8 position of the imidazo[4,5-c]quinoline core, and are taken together with the carbon to which they are attached to form a cycloalkyl, aryl, heteroaryl, or heterocyclyl. In some embodiments, q is 1 or 2, and each $R^{35}$ is independently halogen or $C_1$-$C_8$ alkyl.

In some embodiments, $R^{4a}$ and $R^{4b}$ are each H. In some embodiments, $R^{4a}$ and $R^{4b}$ are taken together with the carbon to which they are attached to form an optionally substituted $C_3$-$C_8$ cycloalkyl (e.g., cyclopropyl).

In some embodiments, p is 0 (i.e., $R^5$ is absent). In some embodiments, p is 1 or 2, and each $R^5$ is independently halogen or $C_1$-$C_8$ alkyl.

It is intended and understood that each and every variation of $R^{1A}$, $R^2$, $R^{35}$, $R^{4a}$, $R^{4b}$, $R^5$, p, and q detailed herein for formula (D-1) can be combined with each and every variation of another of $R^{1A}$, $R^2$, $R^{35}$, $R^{4a}$, $R^{4b}$, $R^5$, p, and q detailed herein for formula (D-1) as if each and every combination is individually described. For example, in some embodiments, D is of the formula (D-1), wherein $R^{1A}$ is $C_1$-$C_8$ alkyl, $C_1$-$C_8$ hydroxyalkyl, or $C_3$-$C_8$ cycloalkyl; $R^2$ is $NH_2$ or $NHR^{2a}$, where $R^{2a}$ is $C_1$-$C_8$ alkyl; each $R^{35}$ is independently halogen or $C_1$-$C_8$ alkyl; $R^{4a}$ and $R^{4b}$ are independently H or $C_1$-$C_8$ alkyl; each $R^5$ is independently halogen or $C_1$-$C_8$ alkyl; and p and q are independently 0, 1, 2, 3 or 4.

In some embodiments, the TLR7/8 agonist moiety of formula (D-1) is a p-aminomethylbenzyl-1H-imidazo[4,5-c]quinoline moiety of formula (D-1a) or a m-aminomethylbenzyl-1H-imidazo[4,5-c]quinoline moiety of formula (D-1b):

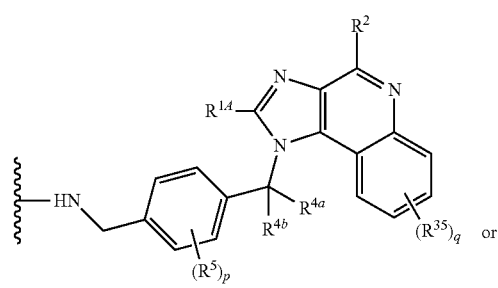 (D-1a)

or

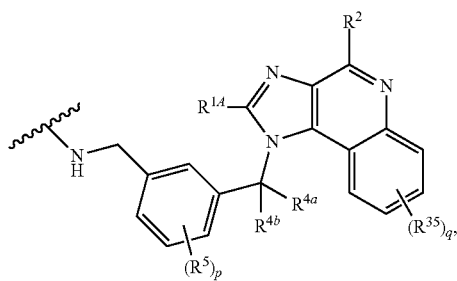

(D-1b)

where the wave line represents the point of attachment of D in formula (I).

In some embodiments, D is of the formula (D-1a) or (D-1b), wherein $R^{14}$ is butyl, $R^2$ is $NH_2$, and q is 0. In one variation, $R^{4a}$ and $R^{4b}$ are each H.

In some embodiments, D is of formula (D-1a-1) or (D-1b-1):

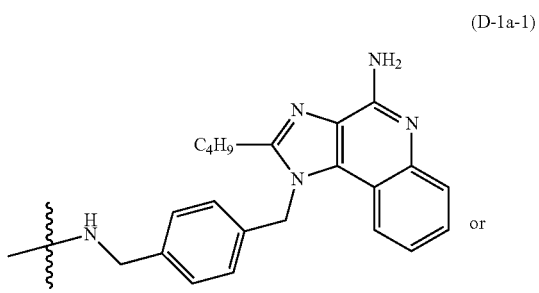

(D-1a-1)

or

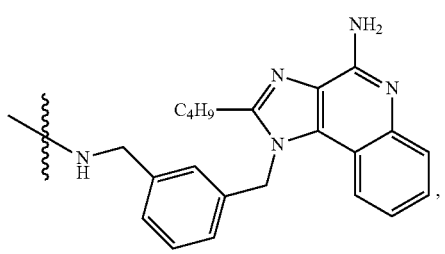

(D-1b-1)

where the wave line represents the point of attachment of D in formula (I).

Other TLR7/8 agonists known in the art are also embraced by the present disclosure. In some embodiments, the TLR7/8 agonist is an aminoquinoline TLR8 agonist compound described in Beesu et al. 2015, *J Med Chem* 58:7833-7849; incorporated herein by reference in their entireties. For example, compounds listed in Table 1 in Beesu et al. *J. Med. Chem.* 2015, 58:7833-7849, that contain a reactive amino group can be converted to a conjugate of formula (D-1), or any variation thereof, as described herein.

In some embodiments, D is an aminoquinoline moiety of formula (D-1c) or (D-1d):

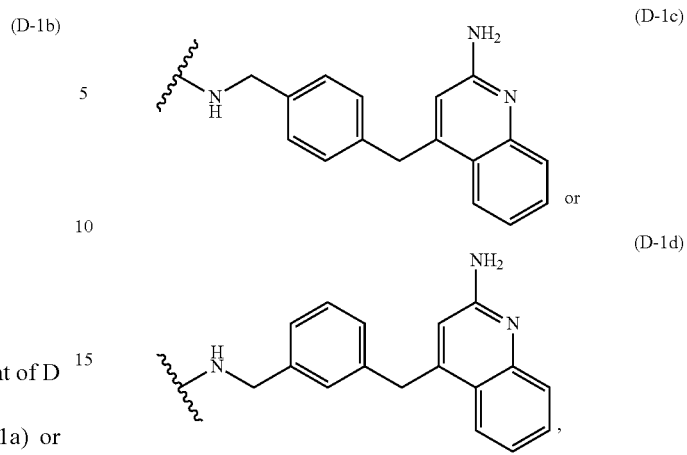

(D-1c)

or (D-1d)

where the wave line represents the point of attachment of D in formula (I).

In some embodiments, the TLR7/8 agonist is an imidazoquinoline compound, or an aminomethyl derivative thereof, described in Shukla et al. *J. Med. Chem.* 2010, 53:4450-4465; and WO 2015/023958; incorporated herein by reference in their entireties. For example, a compound listed in Table 1 in Shukla et al. *J. Med. Chem.* 2010, 53:4450-4465, or a derivative thereof, can be covalently linked (or conjugated) to the conjugation moiety (i.e., moiety F in formula (I)) via an amino group derivatized from the benzyl group or any other applicable portion of the molecule. Likewise, a compound of Formula 11 or Formula 11A as described in WO 2015/023958, or a derivative thereof, can be covalently linked (or conjugated) to the conjugation moiety (i.e., moiety F in formula (I)) via an amino group derivatized from the benzyl group.

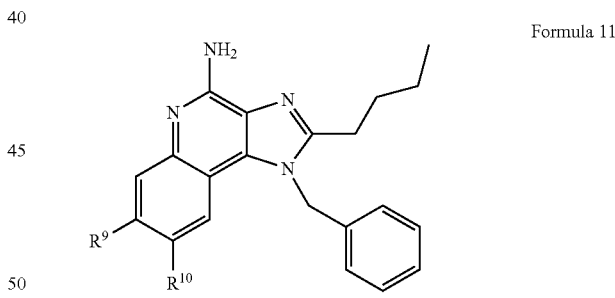

Formula 11

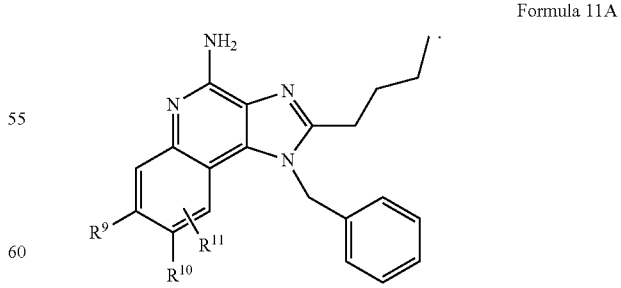

Formula 11A

Formula 11 and Formula 11A, where $R^9$, $R^{10}$, and $R^{11}$ are as described in WO 2015/023958.

In some embodiments, the TLR7/8 agonist moiety of D is of the formula (D-2):

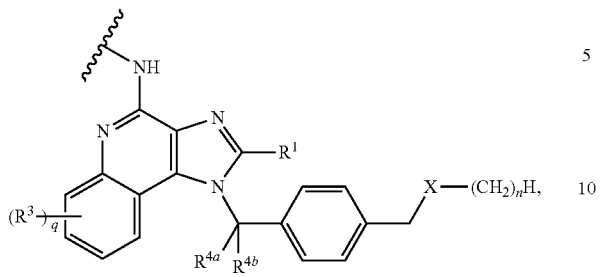

(D-2)

wherein:

n is an integer from 4 to 21;

X is —NH— or —NH(C=O)—;

$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;

each $R^3$ is independently halogen, $C_1$-$C_8$ alkyl, —($C_1$-$C_7$ alkylene)-$NH_2$, or —$CH_2$-phenylene-$CH_2NH_2$;

q is 0, 1, 2, 3, or 4;

$R^{4a}$ and $R^{4b}$ are independently H or $C_1$-$C_8$ alkyl; and the wave line represents the point of attachment of D in formula (I).

In some embodiments, X is —NH—. In some embodiments, X is —NH(C=O)—

In some embodiments, X is —NH—. In some embodiments, n is an integer from 4 to 15. In some embodiments, n is 4, 5, 6, or 7. In some embodiments, n is 8, 9, 10, 11, 12, 13, 14, or 15. In some embodiments, n is 16, 17, 18, 19, 20, or 21.

In some embodiments, X is —NH(C=O)—. In some embodiments, n is 11, 12, 13, or 14. In some embodiments, n is 4, 5, 6, 7, 8, 9, or 10. In some embodiments, n is 15, 16, 17, 18, 19, 20, or 21.

In some embodiments, $R^1$ is $C_3$-$C_6$ alkyl. In some embodiments, $R^1$ is propyl, butyl, pentyl or hexyl. In some embodiments, $R^1$ is n-butyl. In some embodiments, $R^1$ is n-pentyl.

In some embodiments, $R^1$ is —$(CH_2)_pOR^{1a}$, where p is 1 or 2, and $R^{1a}$ is $C_1$-$C_3$ alkyl. In some embodiments, $R^1$ is —$CH_2OCH_2CH_3$.

In some embodiments, $R^1$ is —$(CH_2)_pNHR^{1b}$, where $R^{1b}$ is $C_1$-$C_3$ alkyl. In some embodiments, $R^1$ is —$CH_2NHCH_2CH_3$.

In some embodiments, $R^1$ is —$(CH_2)_pR^{1c}$, where p is 1 or 2, and $R^{1c}$ is cyclopropyl or cyclobutyl. In some embodiments, $R^1$ is —$CH_2$-cyclopropyl or —$CH_2CH_2$-cyclopropyl.

In some embodiments, the phenyl moiety of the 1H-imidazo[4,5-c]quinoline core is unsubstituted (i.e., q is 0). In some embodiments, the phenyl moiety of the 1H-imidazo[4,5-c]quinoline core is substituted by 1, 2, 3, or 4 substituents independently selected from the group consisting of halogen, $C_1$-$C_8$ alkyl, —($C_1$-$C_7$ alkylene)-$NH_2$, and —$CH_2$-phenylene-$CH_2NH_2$. In some embodiments, q is 1 and $R^3$ is $C_1$-$C_8$ alkyl.

In some embodiments, $R^{4a}$ and $R^{4b}$ are independently H or $C_1$-$C_8$ alkyl. In some embodiments, each $R^{4a}$ and $R^{4b}$ is H.

It is intended and understood that where present, each and every variation of X and n described for formula (D-2) can be combined with each and every variation of $R^1$, q, p, $R^3$, $R^{4a}$, and $R^{4b}$ described for formula (D-2), the same as if each and every combination is specifically and individually described. For example, in some embodiments, $R^1$ is $C_3$-$C_6$ alkyl (e.g., n-butyl), q is 0, X is —NH—, and n is 4, 5, 6, or 7. In some embodiments, $R^1$ is $C_3$-$C_6$ alkyl (e.g., n-butyl), q is 0, X is —NH(C=O)—, and n is 11, 12, 13, or 14.

In some embodiments, the TLR7/8 agonist moiety of D is of the formula (D-2a) or (D-2b):

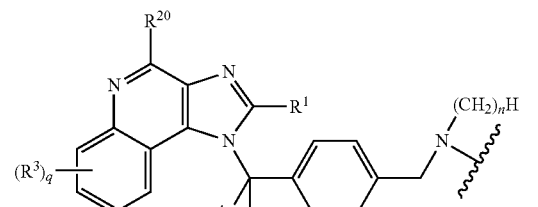

(D-2a)

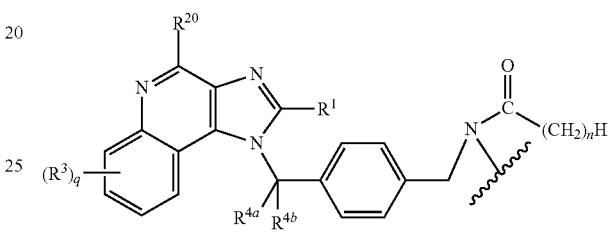

(D-2b)

wherein:

n is an integer from 4 to 21;

$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;

$R^{20}$ is $NHR^{20a}$; where $R^{20a}$ is H, OH, $NH_2$, or methyl;

each $R^3$ is independently halogen, $C_1$-$C_8$ alkyl, —($C_1$-$C_7$ alkylene)-$NH_2$, or —$CH_2$-phenylene-$CH_2NH_2$;

q is 0, 1, 2, 3, or 4;

$R^{4a}$ and $R^{4b}$ are independently H or $C_1$-$C_8$ alkyl; and the wave line represents the point of attachment of D in formula (I).

In some embodiments, the TLR7/8 agonist moiety of D is of the formula (D-2a). In other embodiments, the TLR7/8 agonist moiety of D is of the formula (D-2b).

In some embodiments, the TLR7/8 agonist moiety of D is of the formula (D-2a), and n is an integer from 4 to 15. In some variations, n is 4, 5, 6, or 7. In some variations, n is 8, 9, 10, 11, 12, 13, 14, or 15. In some embodiments, the TLR7/8 agonist moiety of D is of the formula (D-2a), and n is 16, 17, 18, 19, 20, or 21.

In some embodiments, the TLR7/8 agonist moiety of D is of the formula (D-2b), and n is 11, 12, 13, or 14. In some variations, n is 4, 5, 6, 7, 8, 9, or 10. In some embodiments, the TLR7/8 agonist moiety of D is of the formula (D-2b), and n is 15, 16, 17, 18, 19, 20, or 21.

In some embodiments, $R^1$ is $C_3$-$C_6$ alkyl. In some embodiments, $R^1$ is propyl, butyl, pentyl or hexyl. In some embodiments, $R^1$ is n-butyl. In some embodiments, $R^1$ is n-pentyl.

In some embodiments, $R^1$ is —$(CH_2)_pOR^{1a}$, where p is 1 or 2, and $R^{1a}$ is $C_1$-$C_3$ alkyl. In some embodiments, $R^1$ is —$CH_2OCH_2CH_3$.

In some embodiments, $R^1$ is —$(CH_2)_pNHR^{1b}$, where $R^{1b}$ is $C_1$-$C_3$ alkyl. In some embodiments, $R^1$ is —$CH_2NHCH_2CH_3$.

In some embodiments, $R^1$ is —$(CH_2)_pR^{1c}$, where p is 1 or 2, and $R^{1c}$ is cyclopropyl or cyclobutyl. In some embodiments, $R^1$ is —$CH_2$-cyclopropyl or —$CH_2CH_2$-cyclopropyl.

In some embodiments, the phenyl moiety of the 1H-imidazo[4,5-c]quinoline core is unsubstituted (i.e., q is 0). In some embodiments, the phenyl moiety of the 1H-imidazo[4,5-c]quinoline core is substituted by 1, 2, 3, or 4 substituents independently selected from the group consisting of halogen, $C_1$-$C_8$ alkyl, —($C_1$-$C_7$ alkylene)-$NH_2$, and —$CH_2$-phenylene-$CH_2NH_2$. In some embodiments, q is 1 and $R^3$ is $C_1$-$C_8$ alkyl.

In some embodiments, $R^{20}$ is $NHR^{20a}$, where $R^{20a}$ is H, OH, $NH_2$, or methyl. In some embodiments, $R^{20}$ is $NH_2$. In some embodiments, $R^{20}$ is NHOH, $NHNH_2$, or $NHCH_3$.

In some embodiments, $R^{4a}$ and $R^{4b}$ are independently H or $C_1$-$C_8$ alkyl. In some embodiments, each $R^{4a}$ and $R^{4b}$ is H.

It is intended and understood that where present, each and every variation of n described for formula (D-2a) can be combined with each and every variation of $R^1$, $R^{20}$, q, p, $R^3$, $R^{4a}$, and $R^{4b}$ described for formula (D-2a), the same as if each and every combination is specifically and individually described. Similarly, it is intended and understood that where present, each and every variation of n described for formula (D-2b) can be combined with each and every variation $R^1$, $R^{20}$, q, p, $R^3$, $R^{4a}$, and $R^{4b}$ described for formula (D-2b), the same as if each and every combination is specifically and individually described. For example, in some embodiments of formula (D-2a), $R^1$ is $C_3$-$C_6$ alkyl (e.g., n-butyl), $R^{20}$ is $NH_2$, q is 0, and n is 4, 5, 6, or 7. In some embodiments of formula (D-2b), $R^1$ is $C_3$-$C_6$ alkyl (e.g., n-butyl), $R^{20}$ is $NH_2$, q is 0, and n is 11, 12, 13, or 14.

Representative compounds of formula (D-2), (D-2a), and (D-2b) are listed in Table 1, where the wave line represents the point of attachment of D in formula (I).

TABLE 1

| Compound No. | Formula | Compound No. | Formula | Name[1] |
|---|---|---|---|---|
| 64-01 | | 64-01a | | N-(4-((4-amino-2-butyl-1H-imidazo[4,5-c]quinolin-1-yl)methyl)benzyl)pentanamide |
| 64-02 | | 64-02a | | N-(4-((4-amino-2-butyl-1H-imidazo[4,5-c]quinolin-1-yl)methyl)benzyl)hexanamide |

TABLE 1-continued
| Compound No. | Formula | Compound No. | Formula | Name[1] |
|---|---|---|---|---|
| 64-03 | 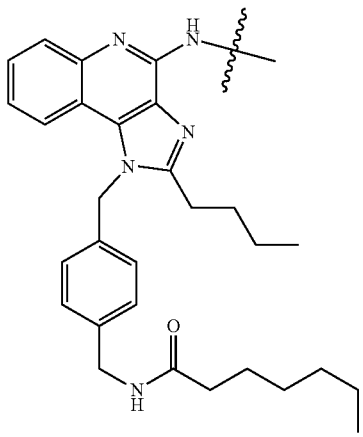 | 64-03a | 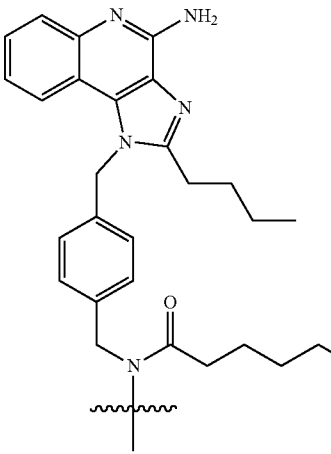 | N-(4-((4-amino-2-butyl-1H-imidazo[4,5-c]quinolin-1-yl)methyl)benzyl) heptanamide |
| 64-04 | 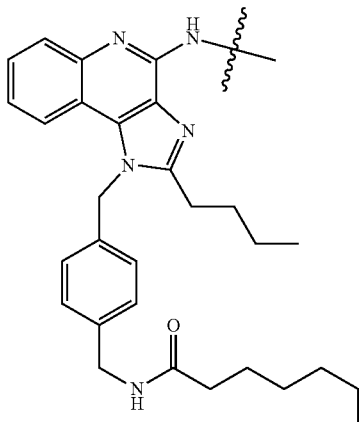 | 64-04a | 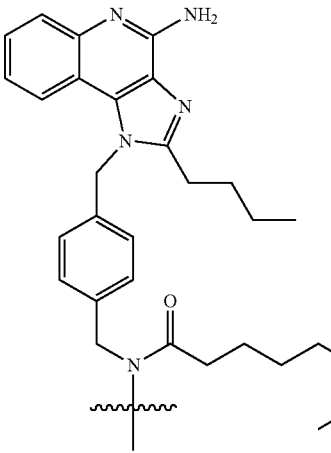 | N-(4-((4-amino-2-butyl-1H-imidazo[4,5-c]quinolin-1-yl)methyl)benzyl) octanamide |
| 64-05 | 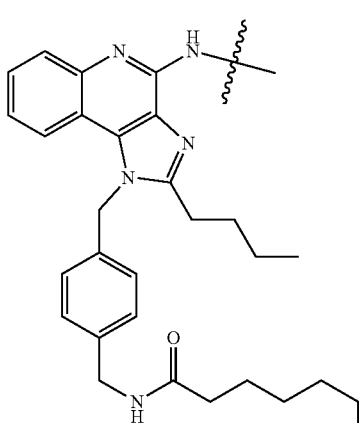 [SMILES: *Nc1nc2ccccc2c2c1nc(CCCC)n2Cc1ccc(CNC(=O)CCCCC)cc1] | 64-05a | 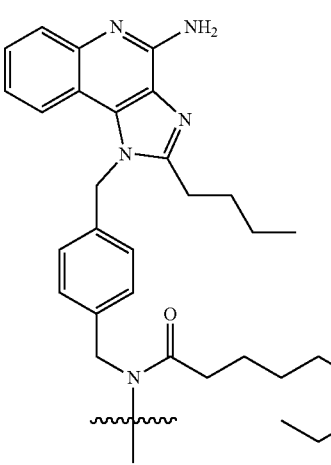 | N-(4-((4-amino-2-butyl-1H-imidazo[4,5-c]quinolin-1-yl)methyl)benzyl) nonanamide |

TABLE 1-continued
| Compound No. | Formula | Compound No. | Formula | Name |
|---|---|---|---|---|
| 64-06 | 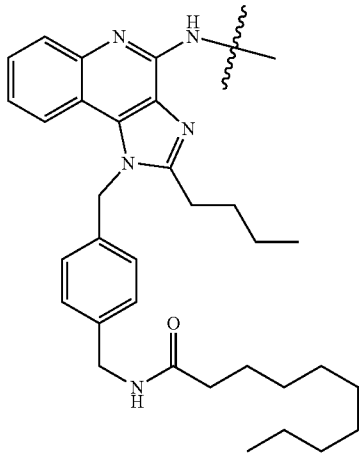 [SMILES: *Nc1nc2ccccc2c2c1nc(CCCC)n2Cc1ccc(CNC(=O)CCCCCCCCC)cc1] | 64-06a | 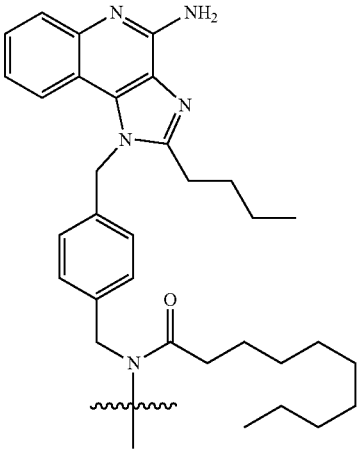 [SMILES: *N(Cc1ccc(Cn2c(CCCC)nc3c(N)nc4ccccc4c32)cc1)C(=O)CCCCCCCCC] | N-(4-((4-amino-2-butyl-1H-imidazo[4,5-c]quinolin-1-yl)methyl)benzyl) decanamide |
| 64-07 | 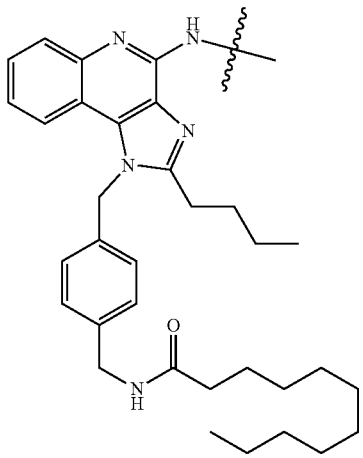 [SMILES: *Nc1nc2ccccc2c2c1nc(CCCC)n2Cc1ccc(CNC(=O)CCCCCCCCCC)cc1] | 64-07a | 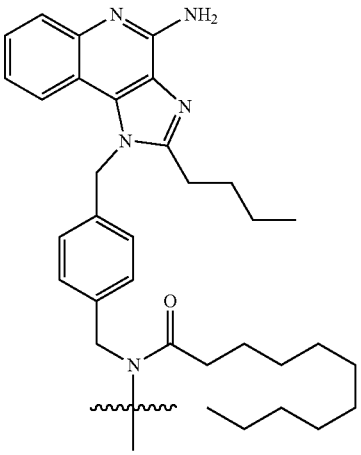 [SMILES: *N(Cc1ccc(Cn2c(CCCC)nc3c(N)nc4ccccc4c32)cc1)C(=O)CCCCCCCCCC] | N-(4-((4-amino-2-butyl-1H-imidazo[4,5-c]quinolin-1-yl)methyl)benzyl) undecanamide |
| 64-08 | 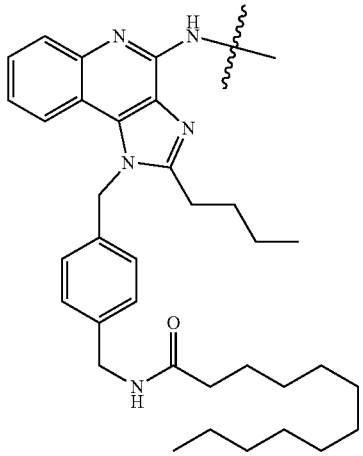 [SMILES: *Nc1nc2ccccc2c2c1nc(CCCC)n2Cc1ccc(CNC(=O)CCCCCCCCCCC)cc1] | 64-08a | 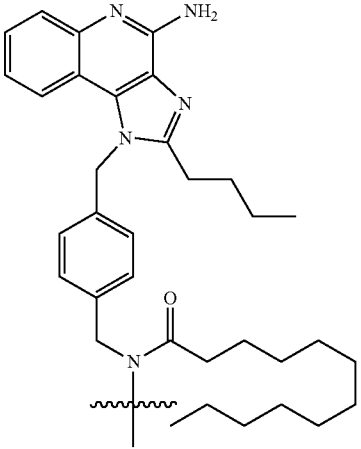 [SMILES: *N(Cc1ccc(Cn2c(CCCC)nc3c(N)nc4ccccc4c32)cc1)C(=O)CCCCCCCCCCC] | N-(4-((4-amino-2-butyl-1H-imidazo[4,5-c]quinolin-1-yl)methyl)benzyl) dodecanamide |

TABLE 1-continued
| Compound No. | Formula | Compound No. | Formula | Name[1] |
|---|---|---|---|---|
| 64-09 | 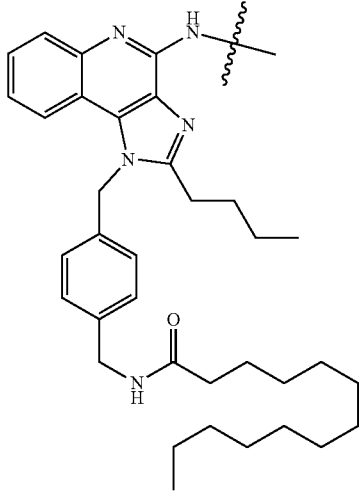 [SMILES: *Nc1nc2ccccc2c2c1nc(CCCC)n2Cc1ccc(CNC(=O)CCCCCCCCCCCC)cc1] | 64-09a | 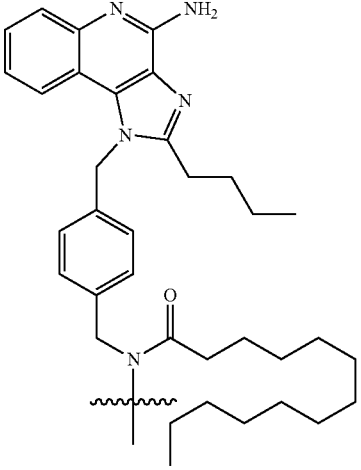 [SMILES: *N(Cc1ccc(Cn2c(CCCC)nc3c(N)nc4ccccc4c32)cc1)C(=O)CCCCCCCCCCCC] | N-(4-((4-amino-2-butyl-1H-imidazo[4,5-c]quinolin-1-yl)methyl)benzyl)tridecanamide |
| 64-10 | 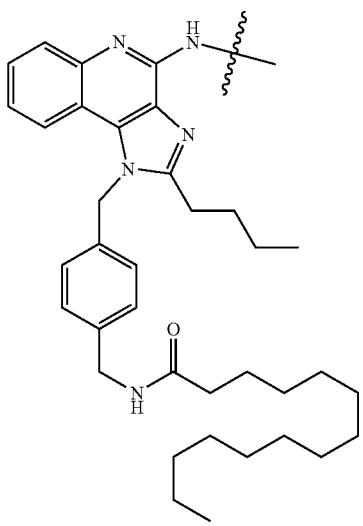 [SMILES: *Nc1nc2ccccc2c2c1nc(CCCC)n2Cc1ccc(CNC(=O)CCCCCCCCCCCCC)cc1] | 64-10a | 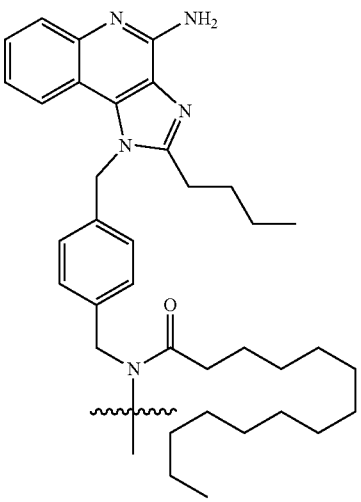 [SMILES: *N(Cc1ccc(Cn2c(CCCC)nc3c(N)nc4ccccc4c32)cc1)C(=O)CCCCCCCCCCCCC] | N-(4-((4-amino-2-butyl-1H-imidazo[4,5-c]quinolin-1-yl)methyl)benzyl)tetradecanamide |
| 64-11 | 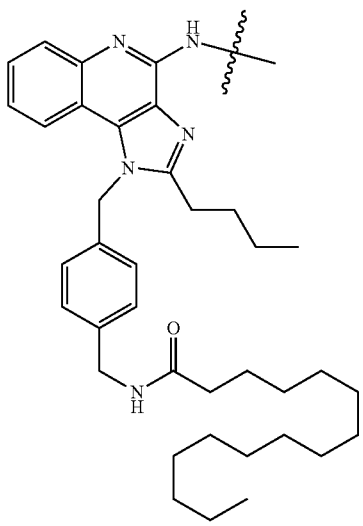 [SMILES: *Nc1nc2ccccc2c2c1nc(CCCC)n2Cc1ccc(CNC(=O)CCCCCCCCCCCCCC)cc1] | 64-11a | 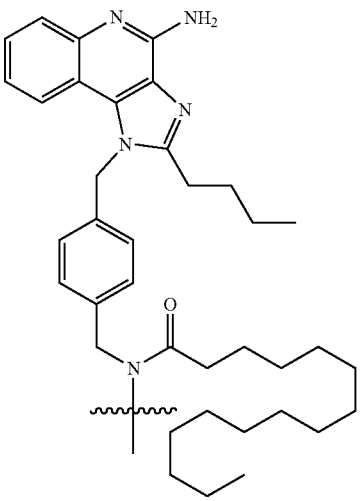 [SMILES: *N(Cc1ccc(Cn2c(CCCC)nc3c(N)nc4ccccc4c32)cc1)C(=O)CCCCCCCCCCCCCC] | N-(4-((4-amino-2-butyl-1H-imidazo[4,5-c]quinolin-1-yl)methyl)benzyl)pentadecanamide |

TABLE 1-continued
| Compound No. | Formula | Compound No. | Formula | Name |
|---|---|---|---|---|
| 64-12 | 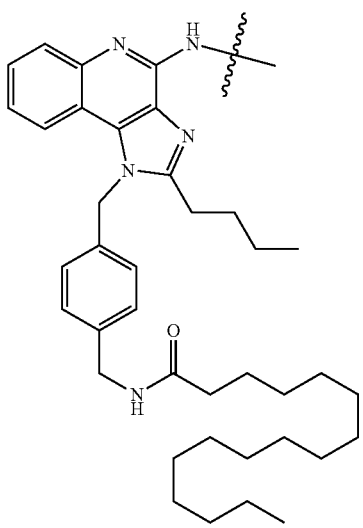 [SMILES: *Nc1nc2ccccc2c2c1nc(CCCC)n2Cc1ccc(CNC(=O)CCCCCCCCCCCCCCC)cc1] | 64-12a | 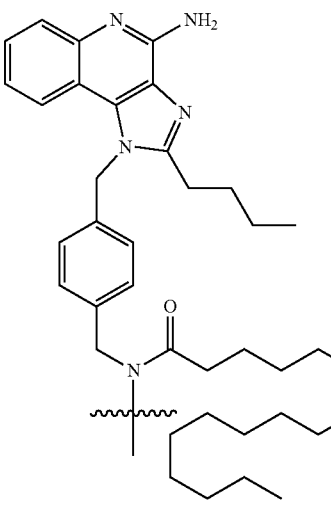 | N-(4-((4-amino-2-butyl-1H-imidazo[4,5-c]quinolin-1-yl)methyl)benzyl) palmitamide |
| 64-13 | 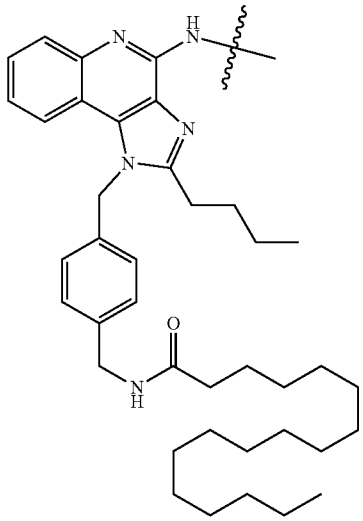 [SMILES: *Nc1nc2ccccc2c2c1nc(CCCC)n2Cc1ccc(CNC(=O)CCCCCCCCCCCCCCCC)cc1] | 64-13a | 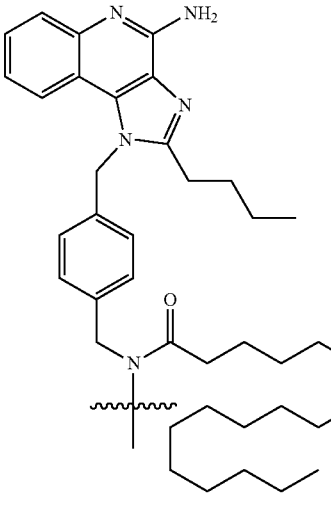 | N-(4-((4-amino-2-butyl-1H-imidazo[4,5-c]quinolin-1-yl)methyl)benzyl) heptadecanamide |
| 64-14 | 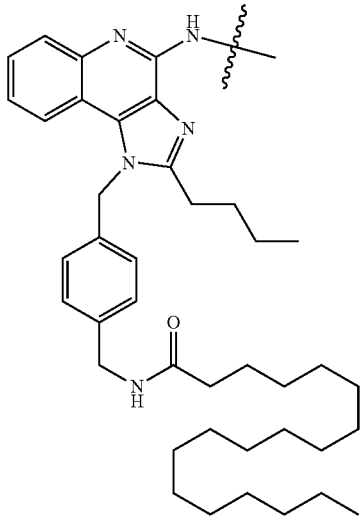 [SMILES: *Nc1nc2ccccc2c2c1nc(CCCC)n2Cc1ccc(CNC(=O)CCCCCCCCCCCCCCCCC)cc1] | 64-14a | 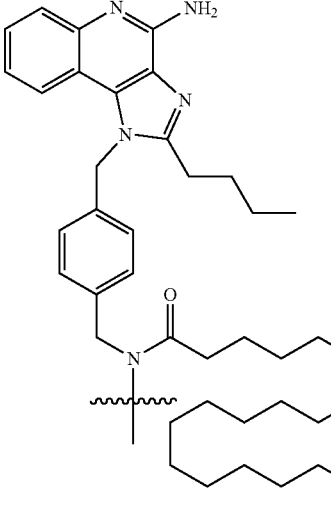 | N-(4-((4-amino-2-butyl-1H-imidazo[4,5-c]quinolin-1-yl)methyl)benzyl) stearamide |

TABLE 1-continued

| Compound No. | Formula | Compound No. | Formula | Name[1] |
|---|---|---|---|---|
| 64-15 | | 64-15a | | N-(4-((4-amino-2-butyl-1H-imidazo[4,5-c]quinolin-1-yl)methyl)benzyl) nonadecanamide |
| 64-16 | | 64-16a | | N-(4-((4-amino-2-butyl-1H-imidazo[4,5-c]quinolin-1-yl)methyl)benzyl) icosanamide |
| 64-17 | | 64-17a | | 2-butyl-1-(4-((butylamino)methyl)benzyl)-1H-imidazo[4,5-c]quinolin-4-amine |

TABLE 1-continued

| Compound No. | Formula | Compound No. | Formula | Name |
|---|---|---|---|---|
| 64-18 | | 64-18a | | 2-butyl-1-(4-((pentylamino)methyl)benzyl)-1H-imidazo[4,5-c]quinolin-4-amine |
| 64-19 | | 64-19a | | 2-butyl-1-(4-((hexylamino)methyl)benzyl)-1H-imidazo[4,5-c]quinolin-4-amine |
| 64-20 | | 64-20a | | 2-butyl-1-(4-((heptylamino)methyl)benzyl)-1H-imidazo[4,5-c]quinolin-4-amine |

TABLE 1-continued

| Compound No. | Formula | Compound No. | Formula | Name |
|---|---|---|---|---|
| 64-21 | | 64-21a | | 2-butyl-1-(4-((octylamino)methyl)benzyl)-1H-imidazo[4,5-c]quinolin-4-amine |
| 64-22 | | 64-22a | | 2-butyl-1-(4-((nonylamino)methyl)benzyl)-1H-imidazo[4,5-c]quinolin-4-amine |
| 64-23 | | 64-23a | | 2-butyl-1-(4-((decylamino)methyl)benzyl)-1H-imidazo[4,5-c]quinolin-4-amine |

TABLE 1-continued

| Compound No. | Formula | Compound No. | Formula | Name[1] |
|---|---|---|---|---|
| 64-24 | | 64-24a | | 2-butyl-1-(4-((undecylamino)methyl)benzyl)-1H-imidazo[4,5-c]quinolin-4-amine |
| 64-25 | | 64-25a | | 2-butyl-1-(4-((dodecylamino)methyl)benzyl)-1H-imidazo[4,5-c]quinolin-4-amine |
| 64-26 | | 64-26a | | 2-butyl-1-(4-((tridecylamino)methyl)benzyl)-1H-imidazo[4,5-c]quinolin-4-amine |

TABLE 1-continued

| Compound No. | Formula | Compound No. | Formula | Name[1] |
|---|---|---|---|---|
| 64-27 | | 64-27a | | 2-butyl-1-(4-((tetradecylamino)methyl)benzyl)-1H-imidazo[4,5-c]quinolin-4-amine |
| 64-28 | | 64-28a | | 2-butyl-1-(4-((pentadecylamino)methyl)benzyl)-1H-imidazo[4,5-c]quinolin-4-amine |
| 64-29 | | 64-29a | | 2-butyl-1-(4-((hexadecylamino)methyl)benzyl)-1H-imidazo[4,5-c]quinolin-4-amine |

TABLE 1-continued

| Compound No. | Formula | Compound No. | Formula | Name[1] |
|---|---|---|---|---|
| 64-30 | | 64-30a | | 2-butyl-1-(4-((heptadecylamino)methyl)benzyl)-1H-imidazo[4,5-c]quinolin-4-amine |
| 64-31 | | 64-31a | | 2-butyl-1-(4-((octadecylamino)methyl)benzyl)-1H-imidazo[4,5-c]quinolin-4-amine |
| 64-32 | | 64-32a | | 2-butyl-1-(4-((nonadecylamino)methyl)benzyl)-1H-imidazo[4,5-c]quinolin-4-amine |

[1]The listed chemical names are the chemical names of the corresponding unconjugated compounds having a hydrogen atom at the position indicated by the wave line (i.e., primary or secondary amine).

The TLR7/8 agonist moieties of formula (D-2), (D-2a), and (D-2b) are generated from the corresponding unconjugated compounds, which can be synthesized according to Scheme D-2 and/or using methods known in the art.

Scheme D-2

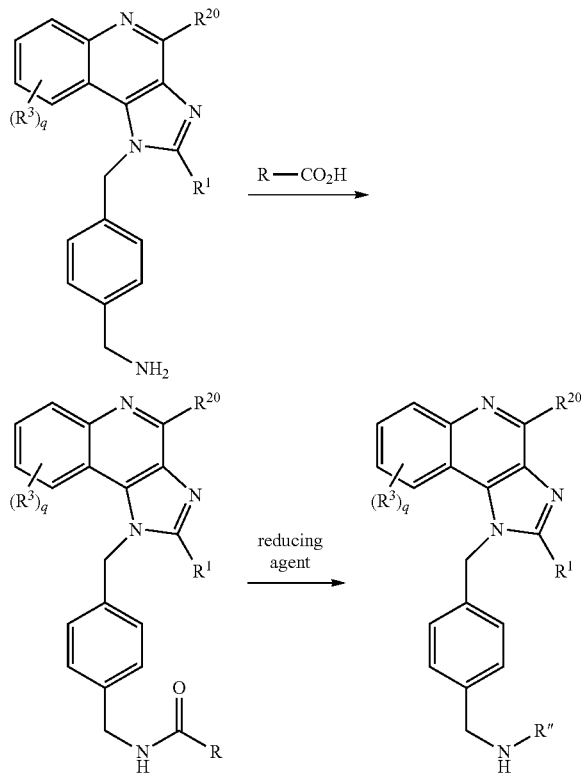

wherein $R^1$, q, and $R^3$ are as defined for formula (D-2), (D-2a), and (D-2b); $R^{20}$ is $NH_2$ or as defined for formula (D-2a) and (D-2b); and R and R" are linear alkyl groups.

In some embodiments, where $R^1$ is $C_3$-$C_6$ alkyl (e.g., n-butyl), O is $NH_2$, and q is 0, the compounds are synthesized according to Scheme D-2-a. For more detailed description of the individual reaction steps useful for preparing the starting compound in Scheme D-2-a (IMDQ), see e.g., U.S. Pat. Nos. 8,728,486 and 9,441,005.

Scheme D-2-a

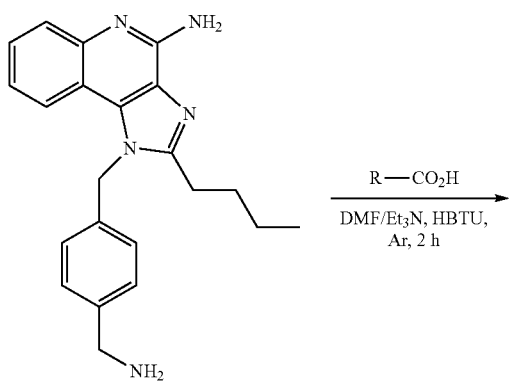

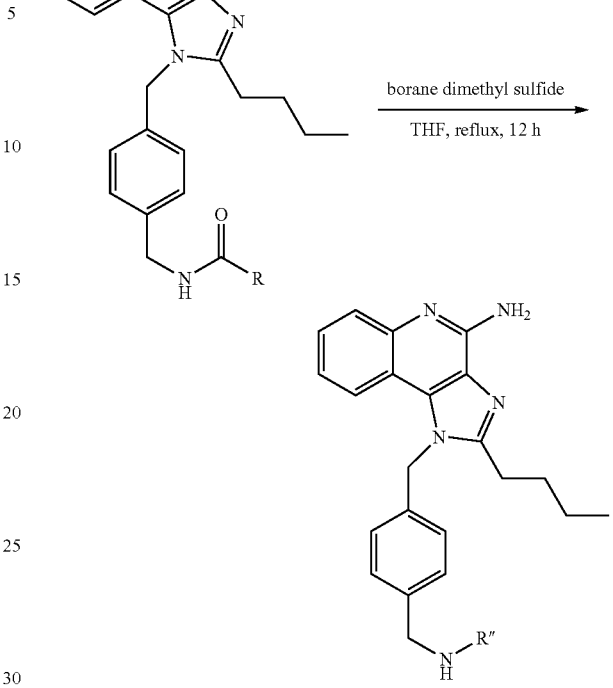

wherein R and R" are linear alkyl groups.

Those skilled in the art will appreciate that other synthetic routes may be employed to synthesize the TLR7/8 agonist moieties of formula (D-2), (D-2a), or (D-2b) described herein including various solvents, catalysts, reducing agents, temperatures, reaction times, and atmospheric conditions.

In some embodiments, the TLR7/8 agonist moiety of D is of the formula (D-3):

(D-3)

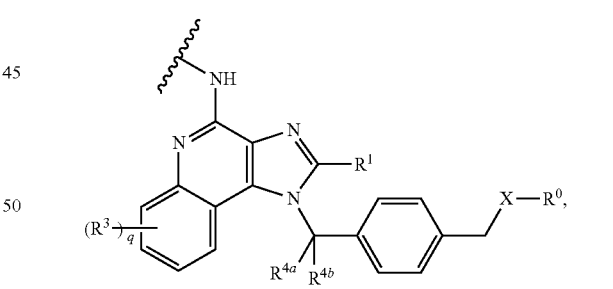

wherein:
$R^0$ is $C_4$-$C_{21}$ hydrocarbyl optionally substituted by 1 to 4 halogen atoms;
X is —NH— or —NH(C=O)—;
$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;
each $R^3$ is independently halogen, $C_1$-$C_8$ alkyl, —($C_1$-$C_7$ alkylene)-$NH_2$, or —$CH_2$-phenylene-$CH_2NH_2$;
q is 0, 1, 2, 3, or 4;
$R^{4a}$ and $R^{4b}$ are independently H or $C_1$-$C_8$ alkyl; and
the wave line represents the point of attachment of D in formula (I).

In some embodiments, $R^O$ is $C_4$-$C_{21}$ hydrocarbyl. In some embodiments, $R^O$ is $C_4$-$C_{14}$ hydrocarbyl. In some embodiments, $R^O$ is $C_5$-$C_{10}$ hydrocarbyl. In some embodiments, $R^O$ is hydrocarbyl. In some embodiments, $R^O$ is $C_5$-$C_7$ hydrocarbyl. In some embodiments, $R^O$ is $C_{15}$-$C_{21}$ hydrocarbyl. In some embodiments, $R^O$ is $C_4$-$C_{21}$ hydrocarbyl substituted by 1 to 4 halogen atoms. In some embodiments, $R^O$ is $C_4$-$C_{14}$ hydrocarbyl substituted by 1 to 4 halogen atoms. In some embodiments, $R^O$ is $C_4$-$C_{10}$ hydrocarbyl substituted by 1 to 2 halogen atoms. In some embodiments, $R^O$ is $C_{10}$-$C_{14}$ hydrocarbyl substituted by 1 to 2 halogen atoms. In some embodiments, $R^O$ is $C_4$-$C_7$ hydrocarbyl substituted by 1 to 2 halogen atoms. In some embodiments, $R^O$ is $C_4$-$C_7$ hydrocarbyl substituted by 1 halogen atom. In some embodiments, $R^O$ is $C_{15}$-$C_{21}$ hydrocarbyl substituted by 1 to 4 halogen atoms.

In some embodiments, X is —NH(C=O)—. In other embodiments, X is —NH—.

In some embodiments, $R^O$ is branched $C_4$-$C_{14}$ alkyl or —$(CH_2)_m R^A$; m is 0, 1, 2, or 3; and $R^A$ is $C_3$-$C_8$ cycloalkyl optionally substituted by 1 to 4 groups independently selected from the group consisting of $C_1$-$C_4$ alkyl and $C_1$-$C_4$ alkylene.

In some embodiments, $R^O$ is branched $C_4$-$C_{14}$ alkyl. In some embodiments, $R^O$ is branched $C_5$-$C_{10}$ alkyl. In some embodiments, $R^O$ is branched $C_{10}$-$C_{14}$ alkyl. In some embodiments, $R^O$ is branched $C_5$-$C_7$ alkyl. In some embodiments, $R^O$ is branched $C_{15}$-$C_{21}$ alkyl.

In some embodiments, $R^O$ is —$(CH_2)_m R^A$. In one variation, m is 1 or 2, and $R^A$ is cyclopropyl, cyclobutyl, or cyclopentyl.

In some embodiments, $R^A$ is $C_3$-$C_8$ cycloalkyl.

In some embodiments, $R^A$ is $C_3$-$C_6$ cycloalkyl optionally substituted by 1 to 3 groups independently selected from the group consisting of methyl and methylene. In one variation, m is 1 or 2. In another variation, m is 0, and $R^A$ is cyclobutyl, cyclopentyl, or cyclohexyl.

In some embodiments, $R^A$ is cyclopropyl optionally substituted by 1 to 3 groups independently selected from the group consisting of methyl and methylene, and m is 1 or 2.

In some embodiments, m is 0 or 1, and $R^A$ is cyclohexyl optionally substituted by 1 to 3 groups independently selected from the group consisting of methyl and methylene.

In some embodiments, $R^A$ is $C_3$-$C_6$ cycloalkyl optionally substituted by 1 to 4 halogen atoms. In some embodiments, $R^A$ is $C_3$-$C_6$ cycloalkyl optionally substituted by 1 to 3 chlorine or fluorine atoms. In some embodiments, $R^A$ is $C_3$-$C_6$ cycloalkyl optionally substituted by 1 to 2 chlorine or fluorine atoms. In some embodiments, $R^A$ is cyclobutyl optionally substituted by 1 to 2 fluorine atoms. In one variation, m is 1.

In some embodiments, $R^O$ is —$(CH_2)_z(C(CH_3)_2)R^A$. In one variation, z is 1 or 2, and $R^A$ is cyclopropyl, cyclobutyl, or cyclopentyl. In one variation, z is 1, and $R^A$ is cyclopropyl, cyclobutyl, or cyclopentyl.

In some embodiments, $R^O$ is selected from the group consisting of:

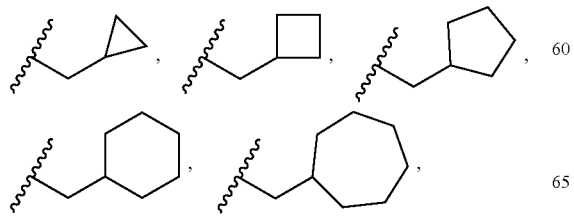

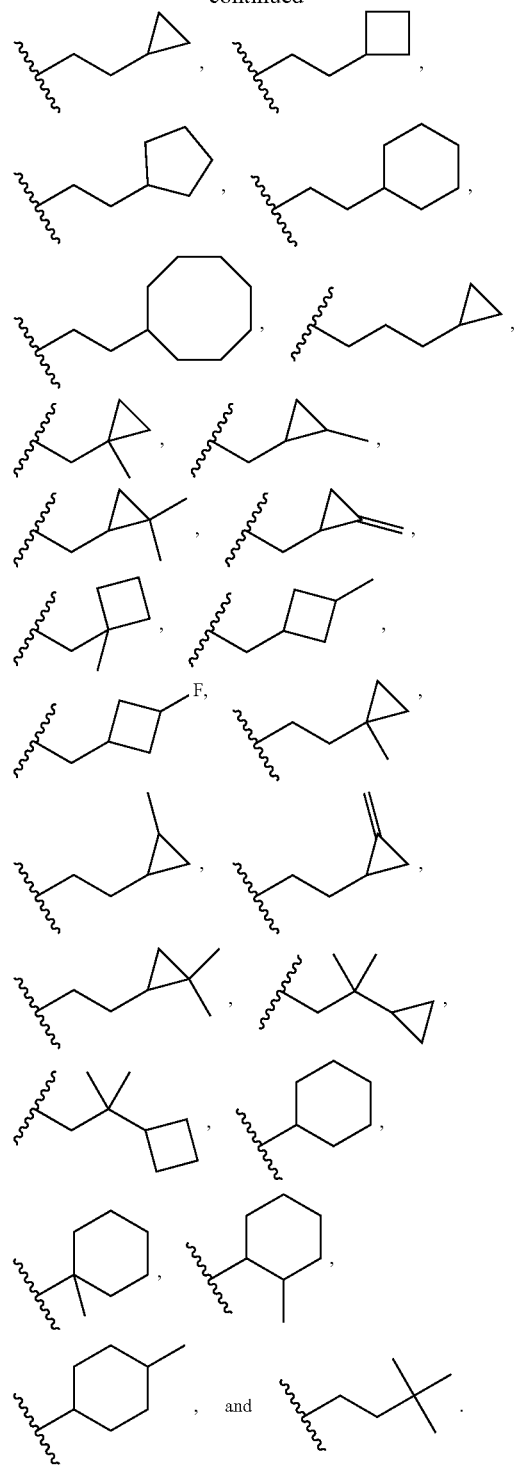

In some embodiments, $R^O$ is selected from the group consisting of:

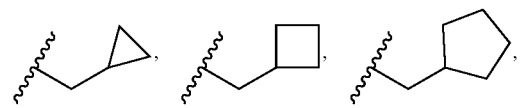

-continued

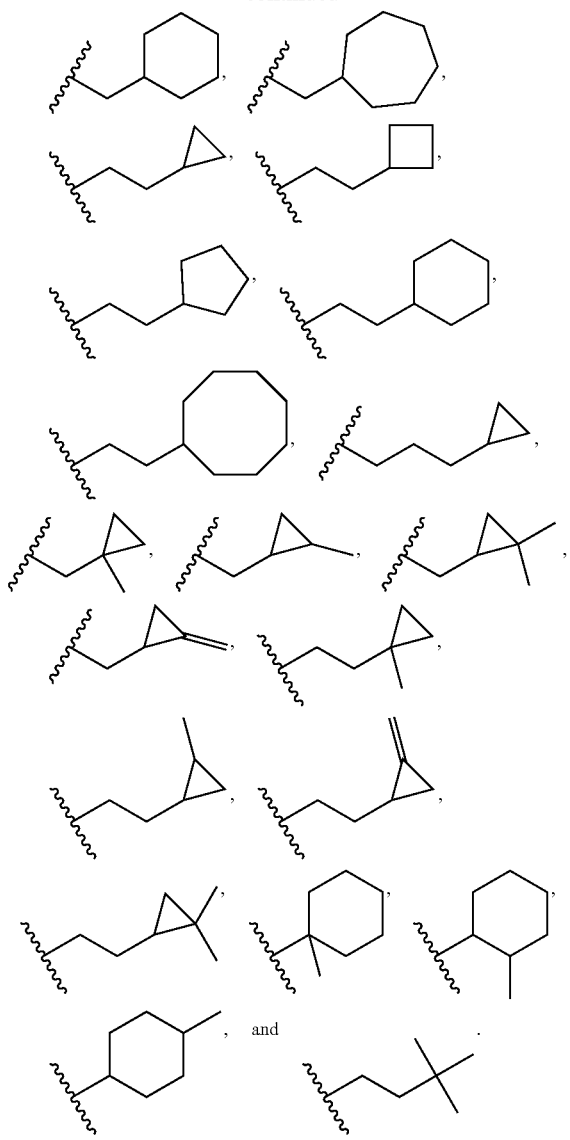

In some embodiments, R⁰ is selected from the group consisting of:

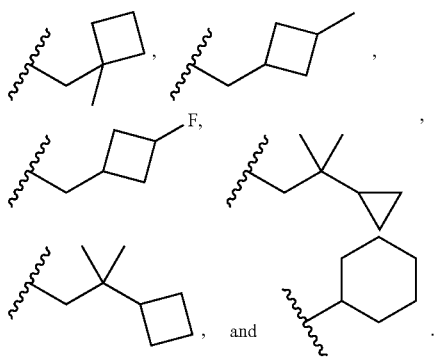

In some embodiments, X is —NH—, R⁰ is —(CH$_2$)$_m$R$^A$, m is 2, and R$^A$ is cyclopropyl, cyclobutyl, or cyclopentyl.

In some embodiments, X is —NH—, R⁰ is —(CH$_2$)$_z$(C(CH$_3$)$_2$)R$^A$, z is 1, and R$^A$ is cyclopropyl, cyclobutyl, or cyclopentyl.

In some embodiments, X is —NH—, R⁰ is —(CH$_2$)$_m$R$^A$, m is 0, and R$^A$ is cyclobutyl, cyclopentyl, or cyclohexyl.

In some embodiments, X is —NH(C=O)—, R⁰ is —(CH$_2$)$_m$R$^A$, m is 1, and R$^A$ is cyclopropyl, cyclobutyl, or cyclopentyl.

In some embodiments, R$^1$ is C$_3$-C$_6$ alkyl (e.g., n-butyl). In some embodiments, R$^1$ is propyl, butyl, pentyl, or hexyl. In some embodiments, R$^1$ is n-butyl. In some embodiments, R$^1$ is n-pentyl. In some embodiments, R$^1$ is —(CH$_2$)$_p$OR$^{1a}$ (e.g., CH$_2$OCH$_2$CH$_3$). In some embodiments, R$^1$ is —(CH$_2$)$_p$NHR$^{1b}$ (e.g., CH$_2$NHCH$_2$CH$_3$). In some embodiments, R$^1$ is —(CH$_2$)$_p$R$^{1c}$. In one variation, R$^{1c}$ is cyclopropyl.

In some embodiments, the phenyl moiety of the 1H-imidazo[4,5-c]quinoline core is unsubstituted (i.e., q is 0). In some embodiments, the phenyl moiety of the 1H-imidazo[4,5-c]quinoline core is substituted by 1, 2, 3, or 4 substituents independently selected from the group consisting of halogen, C$_1$-C$_8$ alkyl, —(C$_1$-C$_7$ alkylene)-NH$_2$, and —CH$_2$-phenylene-CH$_2$NH$_2$. In some embodiments, q is 1 and R$^3$ is C$_1$-C$_8$ alkyl.

In some embodiments, R$^{4a}$ and R$^{4b}$ are independently H or C$_1$-C$_8$ alkyl. In some embodiments, each R$^{4a}$ and R$^{4b}$ is H.

It is intended and understood that where present, each and every variation of X and R⁰ described for formula (D-3) can be combined with each and every variation of R$^1$, R$^{1a}$, R$^{1b}$, R$^{1c}$, p, q, m, R$^A$, R$^3$, R$^{4a}$, and R$^{4b}$ described for formula (D-3) the same as if each and every combination is specifically and individually described.

In some embodiments, the TLR7/8 agonist moiety of D is of the formula (D-3a) or (D-3b):

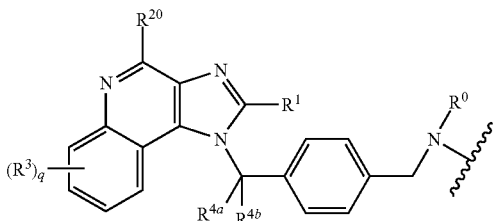

(D-3a)

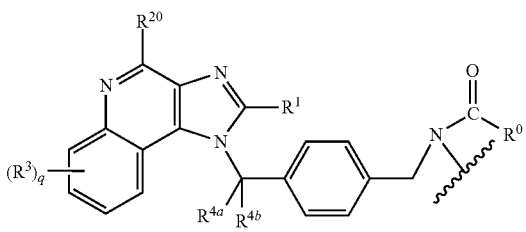

(D-3b)

wherein:
R⁰ is C$_4$-C$_{21}$ hydrocarbyl optionally substituted by 1 to 4 halogen atoms; R$^1$ is C$_3$-C$_6$ alkyl, —(CH$_2$)$_p$OR$^{1a}$, —(CH$_2$)$_p$NHR$^{1b}$, or —(CH$_2$)$_p$R$^{1c}$; where R$^{1a}$ and R$^{1b}$ are independently C$_1$-C$_3$ alkyl; R$^{1c}$ is C$_3$-C$_4$ cycloalkyl; and p is 1 or 2;

R$^{20}$ is NHR$^{20a}$; where R$^{20a}$ is H, OH, NH$_2$, or methyl;
each R$^3$ is independently halogen, C$_1$-C$_8$ alkyl, —(C$_1$-C$_7$ alkylene)-NH$_2$, or —CH$_2$-phenylene-CH$_2$NH$_2$;

q is 0, 1, 2, 3, or 4;

$R^{4a}$ and $R^{4b}$ are independently H or $C_1$-$C_8$ alkyl; and the wave line represents the point of attachment of D in formula (I).

In some embodiments, the TLR7/8 agonist moiety of D is of the formula (D-3a). In other embodiments, the TLR7/8 agonist moiety of D is of the formula (D-3b).

In some embodiments, $R^O$ is $C_4$-$C_{21}$ hydrocarbyl. In some embodiments, $R^O$ is $C_4$-$C_{14}$ hydrocarbyl. In some embodiments, $R^O$ is $C_5$-$C_{10}$ hydrocarbyl. In some embodiments, $R^O$ is $C_{10}$-$C_{14}$ hydrocarbyl. In some embodiments, $R^O$ is $C_5$-$C_7$ hydrocarbyl. In some embodiments, $R^O$ is $C_{15}$-$C_{21}$ hydrocarbyl. In some embodiments, $R^O$ is $C_4$-$C_{21}$ hydrocarbyl substituted by 1 to 4 halogen atoms. In some embodiments, $R^O$ is $C_4$-$C_{14}$ hydrocarbyl substituted by 1 to 4 halogen atoms. In some embodiments, $R^O$ is $C_4$-$C_{10}$ hydrocarbyl substituted by 1 to 2 halogen atoms. In some embodiments, $R^O$ is $C_{10}$-$C_{14}$ hydrocarbyl substituted by 1 to 2 halogen atoms. In some embodiments, $R^O$ is $C_4$-$C_7$ hydrocarbyl substituted by 1 to 2 halogen atoms. In some embodiments, $R^O$ is $C_4$-$C_7$ hydrocarbyl substituted by 1 halogen atom. In some embodiments, $R^O$ is $C_{15}$-$C_{21}$ hydrocarbyl substituted by 1 to 4 halogen atoms.

In some embodiments, $R^O$ is branched $C_4$-$C_{14}$ alkyl or —$(CH_2)_m R^A$; m is 0, 1, 2, or 3; and $R^A$ is $C_3$-$C_8$ cycloalkyl optionally substituted by 1 to 4 groups independently selected from the group consisting of $C_1$-$C_4$ alkyl and $C_1$-$C_4$ alkylene.

In some embodiments, $R^O$ is branched $C_4$-$C_{14}$ alkyl. In some embodiments, $R^O$ is branched $C_5$-$C_{10}$ alkyl. In some embodiments, $R^O$ is branched $C_{10}$-$C_{14}$ alkyl. In some embodiments, $R^O$ is branched $C_5$-$C_7$ alkyl. In some embodiments, $R^O$ is branched $C_{15}$-$C_{21}$ alkyl.

In some embodiments, $R^O$ is —$(CH_2)_m R^A$. In one variation, m is 1 or 2, and $R^A$ is cyclopropyl, cyclobutyl, or cyclopentyl. In another variation, m is 0, and $R^A$ is cyclobutyl, cyclopentyl, or cyclohexyl.

In some embodiments, $R^A$ is $C_3$-$C_8$ cycloalkyl.

In some embodiments, $R^A$ is $C_3$-$C_6$ cycloalkyl optionally substituted by 1 to 3 groups independently selected from the group consisting of methyl and methylene. In one variation, m is 1 or 2.

In some embodiments, $R^A$ is cyclopropyl optionally substituted by 1 to 3 groups independently selected from the group consisting of methyl and methylene, and m is 1 or 2.

In some embodiments, m is 0 or 1, and $R^A$ is cyclohexyl optionally substituted by 1 to 3 groups independently selected from the group consisting of methyl and methylene.

In some embodiments, $R^A$ is $C_3$-$C_6$ cycloalkyl optionally substituted by 1 to 4 halogen atoms. In some embodiments, $R^A$ is $C_3$-$C_6$ cycloalkyl optionally substituted by 1 to 3 chlorine or fluorine atoms. In some embodiments, $R^A$ is $C_3$-$C_6$ cycloalkyl optionally substituted by 1 to 2 chlorine or fluorine atoms. In some embodiments, $R^A$ is cyclobutyl optionally substituted by 1 to 2 fluorine atoms. In one variation, m is 1.

In some embodiments, $R^O$ is —$(CH_2)_z(C(CH_3)_2)R^A$. In one variation, z is 1 or 2, and $R^A$ is cyclopropyl, cyclobutyl, or cyclopentyl. In one variation, z is 1, and $R^A$ is cyclopropyl, cyclobutyl, or cyclopentyl.

In some embodiments, $R^O$ is selected from the group consisting of:

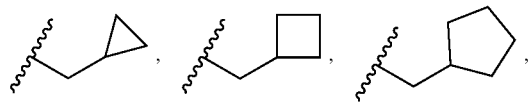

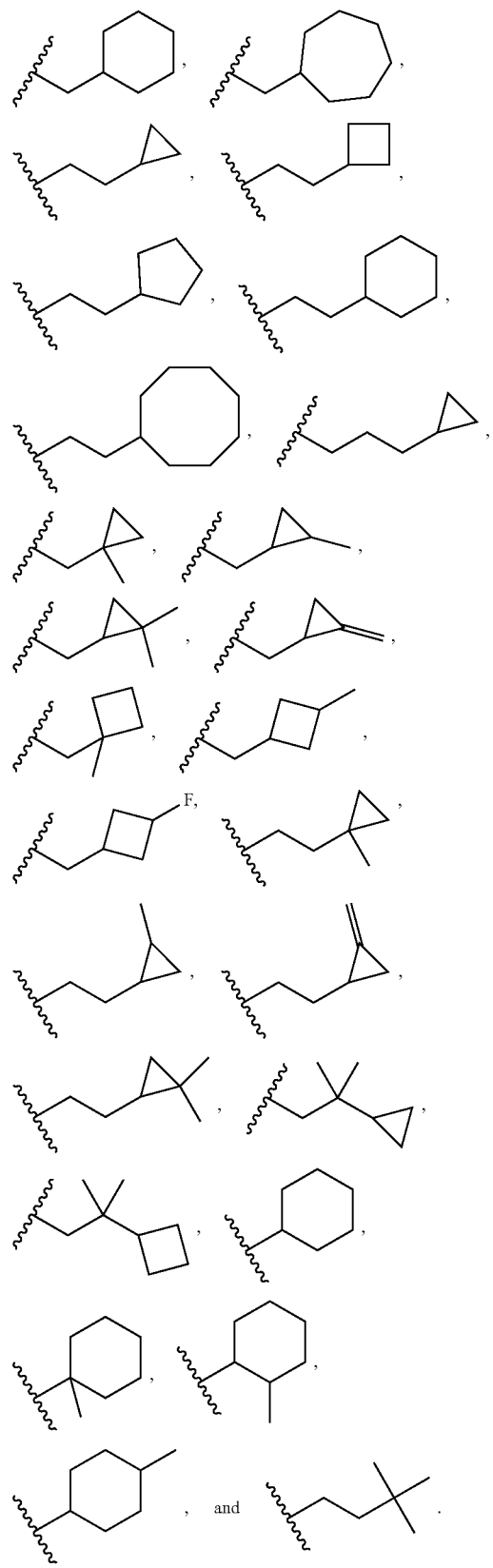

In some embodiments, $R^O$ is selected from the group consisting of:

In some embodiments, $R^0$ is selected from the group consisting of:

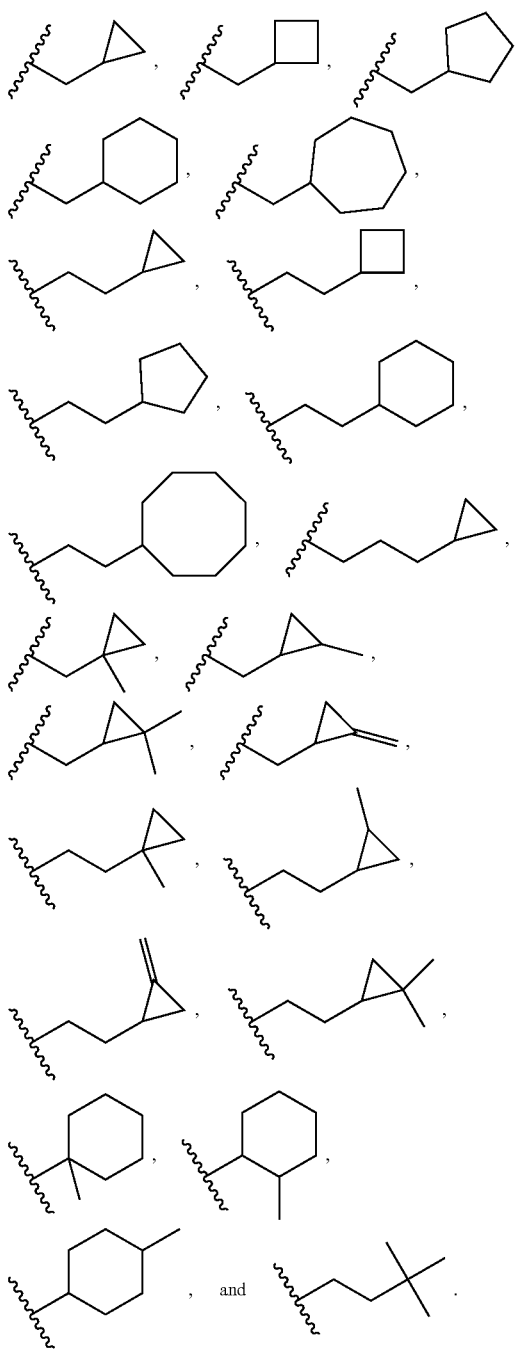

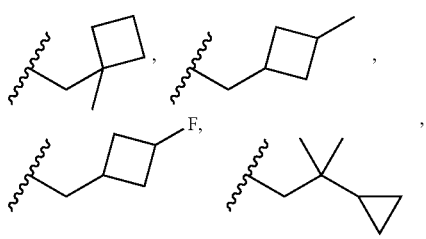

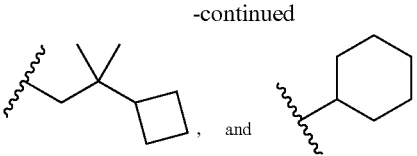

In some embodiments, the TLR7/8 agonist moiety of D is of the formula (D-3a), $R^0$ is $-(CH_2)_m R^A$, m is 2, and $R^A$ is cyclopropyl, cyclobutyl, or cyclopentyl.

In some embodiments, the TLR7/8 agonist moiety of D is of the formula (D-3a), $R^0$ is $-(CH_2)_z(C(CH_3)_2)R^A$, z is 1, and $R^A$ is cyclopropyl, cyclobutyl, or cyclopentyl.

In some embodiments, the TLR7/8 agonist moiety of D is of the formula (D-3a), $R^0$ is $-(CH_2)_m R^A$, m is 0, and $R^A$ is cyclobutyl, cyclopentyl, or cyclohexyl.

In some embodiments, the TLR7/8 agonist moiety of D is of the formula (D-3b), $R^0$ is $-(CH_2)_m R^A$, m is 1, and $R^A$ is cyclopropyl, cyclobutyl, or cyclopentyl.

In some embodiments, $R^1$ is $C_3$-$C_6$ alkyl (e.g., n-butyl). In some embodiments, $R^1$ is propyl, butyl, pentyl, or hexyl. In some embodiments, $R^1$ is n-butyl. In some embodiments, $R^1$ is n-pentyl. In some embodiments, $R^1$ is $-(CH_2)_p OR^{1a}$ (e.g., $CH_2OCH_2CH_3$). In some embodiments, $R^1$ is $-(CH_2)_p NHR^{1b}$ (e.g., $CH_2NHCH_2CH_3$). In some embodiments, $R^1$ is $-(CH_2)_p R^{1c}$. In one variation, $R^{1c}$ is cyclopropyl.

In some embodiments, the phenyl moiety of the 1H-imidazo[4,5-c]quinoline core is unsubstituted (i.e., q is 0). In some embodiments, the phenyl moiety of the 1H-imidazo[4,5-c]quinoline core is substituted by 1, 2, 3, or 4 substituents independently selected from the group consisting of halogen, $C_1$-$C_8$ alkyl, $-(C_1$-$C_7$ alkylene)-$NH_2$, and $-CH_2$-phenylene-$CH_2NH_2$. In some embodiments, q is 1 and $R^3$ is $C_1$-$C_8$ alkyl.

In some embodiments, $R^{20}$ is $NHR^{20a}$, where $R^{20a}$ is H, OH, $NH_2$, or methyl. In some embodiments, $R^{20}$ is $NH_2$. In some embodiments, $R^{20}$ is NHOH, $NHNH_2$, or $NHCH_3$.

In some embodiments, $R^{4a}$ and $R^{4b}$ are independently H or $C_1$-$C_8$ alkyl. In some embodiments, each $R^{4a}$ and $R^{4b}$ is H.

It is intended and understood that where present, each and every variation of $R^0$ described for formula (D-3a) can be combined with each and every variation of $R^1$, $R^{1a}$, $R^{1b}$, $R^{1c}$, $R^{20}$, p, q, m, z, $R^A$, $R^3$, $R^{4a}$, and $R^{4b}$ described for formula (D-3a) the same as if each and every combination is specifically and individually described. Similarly, it is intended and understood that where present, each and every variation of $R^0$ described for formula (D-3b) can be combined with each and every variation of $R^1$, $R^{1a}$, $R^{1b}$, $R^{1c}$, $R^{20}$, p, q, m, z, $R^A$, $R^3$, $R^{4a}$, and $R^{4b}$ described for formula (D-3b) the same as if each and every combination is specifically and individually described.

Representative compounds of formula (D-3), (D-3a), and (D-3b) are listed in Table 2, where the wave line represents the point of attachment of D in formula (I).

TABLE 2

| Compound No. | Formula | Compound No. | Formula | Name |
|---|---|---|---|---|
| 64-33 | | 64-33a | | 2-butyl-1-(4-(((2-cyclopropylethyl)amino)methyl)benzyl)-1H-imidazo[4,5-c]quinolin-4-amine |
| 64-34 | | 64-34a | | N-(4-((4-amino-2-butyl-1H-imidazo[4,5-c]quinolin-1-yl)methyl)benzyl)-2-cyclopropylacetamide |
| 64-35 | | 64-35a | | 2-butyl-1-(4-(((2-cyclobutylethyl)amino)methyl)benzyl)-1H-imidazo[4,5-c]quinolin-4-amine |

TABLE 2-continued

| Compound No. | Formula | Compound No. | Formula | Name[1] |
|---|---|---|---|---|
| 64-36 | | 64-36a | | N-(4-((4-amino-2-butyl-1H-imidazo[4,5-c]quinolin-1-yl)methyl)benzyl)-2-cyclobutylacetamide |
| 64-37 | | 64-37a | | 2-butyl-1-(4-(((2-cyclopentylethyl)amino)methyl)benzyl)-1H-imidazo[4,5-c]quinolin-4-amine |
| 64-58 | | 64-58a | | 2-butyl-1-(4-(((3-cyclopropylpropyl)amino)methyl)benzyl)-1H-imidazo[4,5-c]quinolin-4-amine |

TABLE 2-continued

| Compound No. | Formula | Compound No. | Formula | Name[1] |
|---|---|---|---|---|
| 64-59 | | 64-59a | | 2-butyl-1-(4-(((cyclopropylmethyl)amino)methyl)benzyl)-1H-imidazo[4,5-c]quinolin-4-amine |
| 64-60 | | 64-60a | | 2-butyl-1-(4-((((1-methylcyclobutyl)methyl)amino)methyl)benzyl)-1H-imidazo[4,5-c]quinolin-4-amine |
| 64-61 | | 64-61a | | 2-butyl-1-(4-((((3-methylcyclobutyl)methyl)amino)methyl)benzyl)-1H-imidazo[4,5-c]quinolin-4-amine |

TABLE 2-continued

| Compound No. | Formula | Compound No. | Formula | Name |
|---|---|---|---|---|
| 64-62 | | 64-62a | | 2-butyl-1-(4-(((2-(1-methylcyclopropyl)ethyl)amino)methyl)benzyl)-1H-imidazo[4,5-c]quinolin-4-amine |
| 64-63 | | 64-63a | | 2-butyl-1-(4-(((2-cyclobutyl-2-methylpropyl)amino)methyl)benzyl)-1H-imidazo[4,5-c]quinolin-4-amine |
| 64-64 | | 64-64a | | 2-butyl-1-(4-((((2-methylcyclopropyl)methyl)amino)methyl)benzyl)-1H-imidazo[4,5-c]quinolin-4-amine |

TABLE 2-continued

| Compound No. | Formula | Compound No. | Formula | Name[1] |
|---|---|---|---|---|
| 64-65 | | 64-65a | | 2-butyl-1-(4-((((2,2-dimethylcyclopropyl)methyl)amino)methyl)benzyl)-1H-imidazo[4,5-c]quinolin-4-amine |
| 64-66 | | 64-66a | | 2-butyl-1-(4-(((cyclobutylmethyl)amino)methyl)benzyl)-1H-imidazo[4,5-c]quinolin-4-amine |
| 64-67 | | 64-67a | | 2-butyl-1-(4-(((2-cyclopropyl-2-methylpropyl)amino)methyl)benzyl)-1H-imidazo[4,5-c]quinolin-4-amine |

TABLE 2-continued

| Compound No. | Formula | Compound No. | Formula | Name[1] |
|---|---|---|---|---|
| 64-68 | | 64-68a | | 2-butyl-1-(4-((((3-fluorocyclobutyl)methyl)amino)methyl)benzyl)-1H-imidazo[4,5-c]quinoline-4-amine |
| 64-69 | | 64-69a | | 2-butyl-1-(4-((cyclohexylamino)methyl)benzyl)-1H-imidazo[4,5-c]quinolin-4-amine |

[1]The listed chemical names are the chemical names of the corresponding unconjugated compounds having a hydrogen atom at the position indicated by the wave line (i.e., primary and secondary amine).

The TLR7/8 agonist moieties of formula (D-3), (D-3a), and (D-3b) are generated from the corresponding unconjugated compounds, which can be synthesized according to Scheme D-3 and/or using methods known in the art.

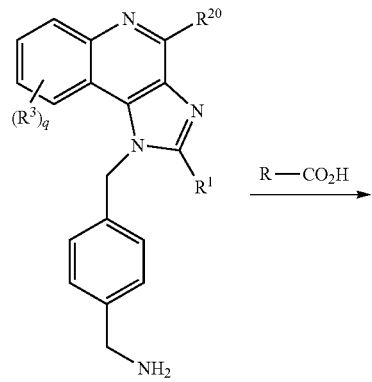

Scheme D-3

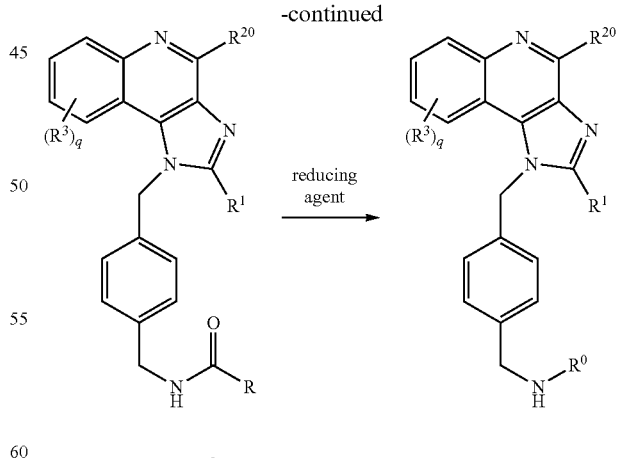

wherein q, and $R^3$ are as defined for formula (D-3), (D-3a), and (D-3b); $R^{20}$ is $NH_2$ or as defined for formula (D-3a) and (D-3b); and R and $R^0$ are optionally substituted hydrocarbyl groups.

In some embodiments, where $R^1$ is $C_3$-$C_6$ alkyl (e.g., n-butyl), $R^{20}$ is $NH_2$, and q is 0, the compounds are synthesized according to Scheme D-3-a. For more detailed description of the individual reaction steps useful for preparing the starting compound (IMDQ) in Scheme D-3-a, see e.g., U.S. Pat. Nos. 8,728,486 and 9,441,005.

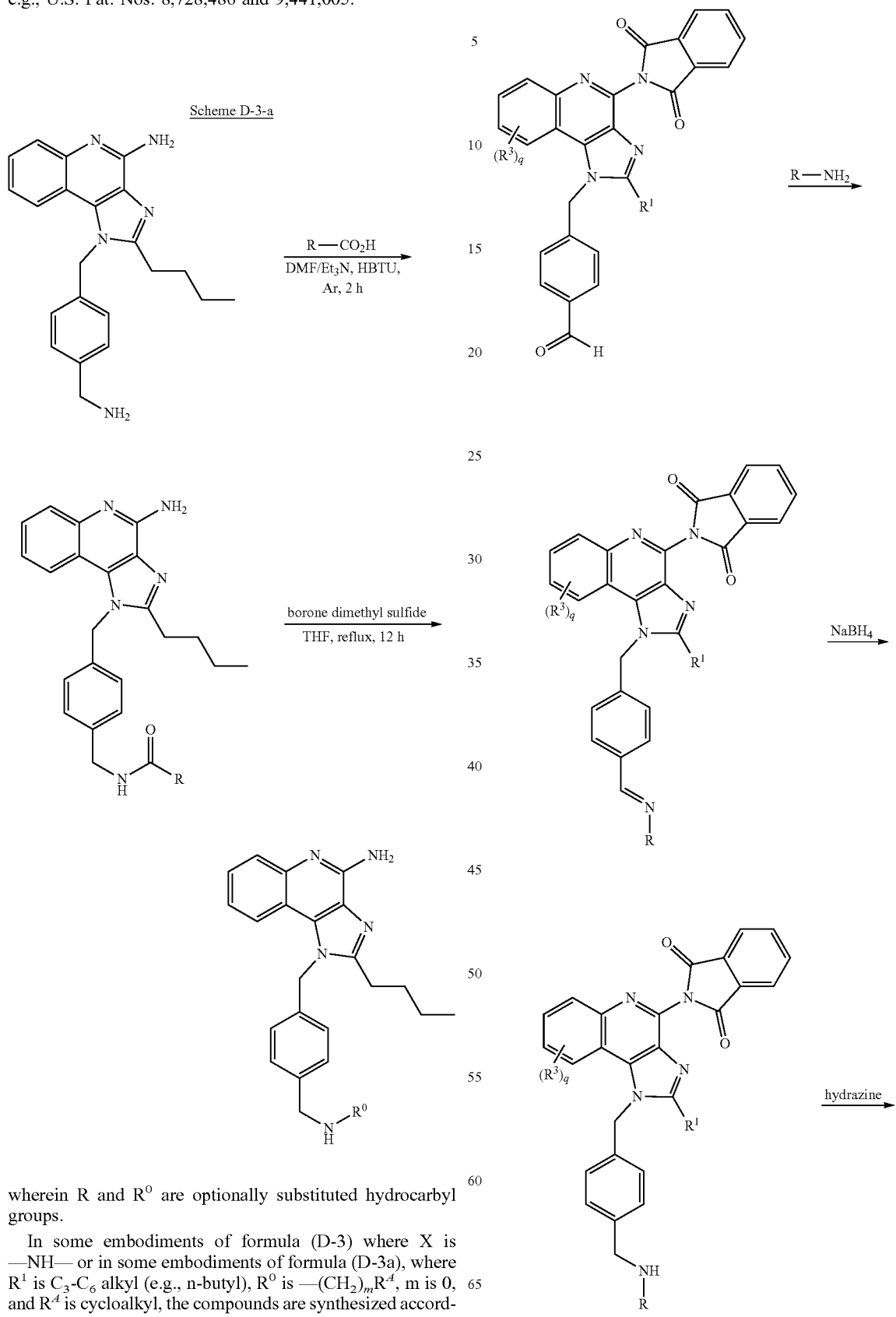

wherein R and $R^0$ are optionally substituted hydrocarbyl groups.

In some embodiments of formula (D-3) where X is —NH— or in some embodiments of formula (D-3a), where $R^1$ is $C_3$-$C_6$ alkyl (e.g., n-butyl), $R^0$ is —$(CH_2)_m R^4$, m is 0, and $R^4$ is cycloalkyl, the compounds are synthesized according to Scheme D-3-b.

-continued

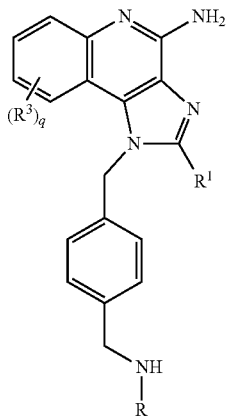

wherein R[1], q, and R[3] are as defined for formula (D-3) and (D-3a), and R is a cycloalkyl group.

Those skilled in the art will appreciate that other synthetic routes may be employed to synthesize the TLR7/8 agonist moieties of formula (D-3), (D-3a), and (D-3b) described herein including various solvents, catalysts, reducing agents, temperatures, reaction times, and atmospheric conditions.

In some embodiments, the TLR7/8 agonist moiety of D is of the formula (D-4):

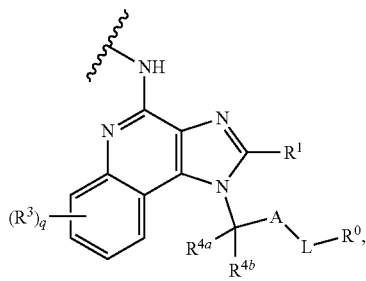

(D-4)

wherein:

R[0] is $C_4$-$C_{21}$ hydrocarbyl optionally substituted with 1 to 4 halogen atoms;

L is X or —CH$_2$—X—;

X is —NH— or —NH(C=O)—;

A is $C_6$-$C_{14}$ arylene optionally substituted by 1 to 4 groups independently selected from the group consisting of halogen and $C_1$-$C_8$ alkyl optionally substituted by 1 to 8 halogen atoms, or 5- to 14-membered heteroarylene optionally substituted by 1 to 4 groups independently selected from the group consisting of halogen and $C_1$-$C_8$ alkyl optionally substituted by 1 to 8 halogen atoms;

R[1] is $C_3$-$C_6$ alkyl, —(CH$_2$)$_p$OR[1a], —(CH$_2$)$_p$NHR[1b], or —(CH$_2$)$_p$R[1c]; where R[1a] and R[1b] are independently $C_1$-$C_3$ alkyl; R[1c] is $C_3$-$C_4$ cycloalkyl; and p is 1 or 2;

each R[3] is independently halogen, $C_1$-$C_8$ alkyl, —($C_1$-$C_7$ alkylene)-NH$_2$, or —CH$_2$-phenylene-CH$_2$NH$_2$;

q is 0, 1, 2, 3, or 4;

R[4a] and R[4b] are independently H or $C_1$-$C_8$ alkyl; and the wave line represents the point of attachment of D in formula (I).

In some embodiments, A is $C_6$-$C_{10}$ arylene optionally substituted by 1 to 4 groups independently selected from the group consisting of halogen and $C_1$-$C_8$ alkyl optionally substituted by 1 to 8 halogen atoms.

In some embodiments, A is phenylene optionally substituted by 1 to 4 groups independently selected from the group consisting of halogen and $C_1$-$C_8$ alkyl optionally substituted by 1 to 8 halogen atoms. In some embodiments, A is 1,4-phenylene optionally substituted by 1 to 4 groups independently selected from the group consisting of halogen and $C_1$-$C_8$ alkyl optionally substituted by 1 to 8 halogen atoms. In some embodiments, A is 1,4-phenylene optionally substituted with 1 to 4 groups independently selected from the group consisting of F, Cl, CF$_3$, and methyl.

In some embodiments, A is 2,6-dimethyl-1,4-phenylene; 2,3-dimethyl-1,4-phenylene; 2,6-difluoro-1,4-phenylene; 2,3-difluoro-1,4-phenylene; 2,6-dichloro-1,4-phenylene; 2,6-dichloro-1,4-phenylene; 2,3,5,6-tetramethyl-1,4-phenylene; or 2,3,5,6-tetrafluoro-1,4-phenylene.

In some embodiments, A is 1,3-phenylene optionally substituted with 1 to 4 groups independently selected from the group consisting of halogen and $C_1$-$C_8$ alkyl optionally substituted by 1 to 8 halogen atoms.

In some embodiments, A is 5- to 10-membered heteroarylene optionally substituted by 1 to 4 groups independently selected from the group consisting of halogen and $C_1$-$C_8$ alkyl optionally substituted by 1 to 8 halogen atoms.

In some embodiments, A is naphthylene optionally substituted by 1 to 4 groups independently selected from the group consisting of halogen and $C_1$-$C_8$ alkyl optionally substituted by 1 to 8 halogen atoms. In some embodiments, A is 1,4-naphthylene, 1,3-naphthylene, or 2,7-naphthylene. In some embodiments, A is 2,6-naphthylene.

In some embodiments, A is 4,7-benzo[b]thiophene. In some embodiments, A is 2,5-1H-benzo[d]imidazole.

In some embodiments, L is X. In other embodiments, L is —CH$_2$—X—.

In some embodiments, X is —NH—. In some embodiments, X is —NH(C=O)—.

In some embodiments, R[0] is $C_4$-$C_{14}$ hydrocarbyl. In some embodiments, R[0] is $C_5$-$C_{10}$ hydrocarbyl. In some embodiments, R[0] is $C_{10}$-$C_{14}$ hydrocarbyl. In some embodiments, R[0] is $C_5$-$C_7$ hydrocarbyl. In some embodiments, R[0] is $C_{15}$-$C_{21}$ hydrocarbyl. In some embodiments, R[0] is $C_4$-$C_{21}$ hydrocarbyl substituted by 1 to 4 halogen atoms. In some embodiments, R[0] is $C_4$-$C_{14}$ hydrocarbyl substituted by 1 to 4 halogen atoms. In some embodiments, R[0] is $C_4$-$C_{10}$ hydrocarbyl substituted by 1 to 2 halogen atoms. In some embodiments, R[0] is $C_{10}$-$C_{14}$ hydrocarbyl substituted by 1 to 2 halogen atoms. In some embodiments, R[0] is $C_4$-$C_7$ hydrocarbyl substituted by 1 to 2 halogen atoms. In some embodiments, R[0] is $C_4$-$C_7$ hydrocarbyl substituted by 1 halogen atom. In some embodiments, R[0] is $C_{15}$-$C_{21}$ hydrocarbyl substituted by 1 to 4 halogen atoms.

In some embodiments, R[0] is —(CH$_2$)$_m$R[4]; m is 0, 1, 2, or 3; and R[4] is $C_3$-$C_8$ cycloalkyl optionally substituted by 1 to 4 groups independently selected from the group consisting of $C_1$-$C_4$ alkyl and $C_1$-$C_4$ alkylene. In one variation, m is 1 or 2, and R[4] is cyclopropyl, cyclobutyl, or cyclopentyl. In some embodiments, R[4] is $C_3$-$C_6$ cycloalkyl optionally substituted by 1 to 3 groups independently selected from the group consisting of methyl and methylene. In one variation, m is 1 or 2. In some embodiments, R[4] is cyclopropyl optionally substituted by 1 to 3 groups independently selected from the group consisting of methyl and methylene, and m is 1 or 2. In some embodiments, m is 0 or 1, and R[4] is cyclohexyl optionally substituted by 1 to 3 groups independently selected from the group consisting of methyl and methylene.

In some embodiments, R[0] is selected from the group consisting of:

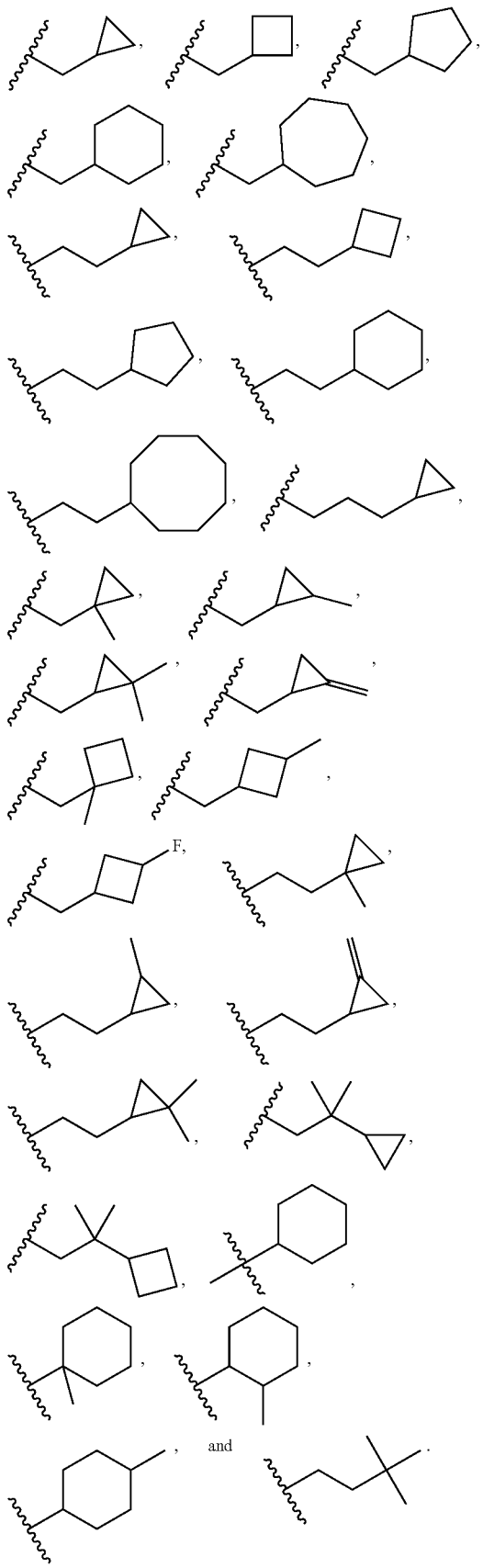

In some embodiments, $R^0$ is (cyclopropyl)methyl, 2-(cyclopropyl)ethyl, 2-(cyclobutyl)ethyl, 2-(cyclopentyl)ethyl, or 2-(cyclohexyl)ethyl.

In some embodiments, $R^0$ is branched $C_4$-$C_{14}$ alkyl. In some embodiments, $R^0$ is branched $C_5$-$C_{10}$ alkyl. In some embodiments, $R^0$ is branched $C_{10}$-$C_{14}$ alkyl. In some embodiments, $R^0$ is branched $C_5$-$C_7$ alkyl. In some embodiments, $R^0$ is branched $C_{15}$-$C_{21}$ alkyl.

In some embodiments, $R^1$ is $C_3$-$C_6$ alkyl (e.g., n-butyl). In some embodiments, $R^1$ is propyl, butyl, pentyl, or hexyl. In some embodiments, $R^1$ is n-butyl. In some embodiments, $R^1$ is n-pentyl. In some embodiments, $R^1$ is —$(CH_2)_pOR^{1a}$ (e.g., $CH_2OCH_2CH_3$). In some embodiments, $R^1$ is —$(CH_2)_pNHR^{1b}$ (e.g., $CH_2NHCH_2CH_3$). In some embodiments, $R^1$ is —$(CH_2)_pR^{1c}$. In one variation, $R^{1c}$ is cyclopropyl.

In some embodiments, $R^{4a}$ and $R^{4b}$ are independently H or $C_1$-$C_8$ alkyl. In some embodiments, each $R^{4a}$ and $R^{4b}$ is H.

In some embodiments, the phenyl moiety of the 1H-imidazo[4,5-c]quinoline core is unsubstituted (i.e., q is 0). In some embodiments, the phenyl moiety of the 1H-imidazo[4,5-c]quinoline core is substituted by 1, 2, 3, or 4 substituents independently selected from the group consisting of halogen, $C_1$-$C_8$ alkyl, —$(C_1$-$C_7$ alkylene$)$-$NH_2$, and —$CH_2$-phenylene-$CH_2NH_2$. In some embodiments, q is 1 and $R^3$ is $C_1$-$C_8$ alkyl.

It is intended and understood that where present, each and every variation of A, L, and $R^0$ described for formula (D-4) can be combined with each and every variation of $R^1$, $R^{1a}$, $R^{1b}$, $R^{1c}$, p, X, $R^4$, m, q, $R^3$, $R^{4a}$, and $R^{4b}$ described for formula (D-4) the same as if each and every combination is specifically and individually described. In some embodiments, $R^1$ is n-butyl, q is 0, each $R^{4a}$ and $R^{4b}$ is H, A is 1,4-napthylene, L is —$CH_2$—X—, X is —NH—, $R^0$ is m is 1 or 2, and $R^4$ is cyclopropyl, cyclobutyl, cyclopentyl, or cyclohexyl.

In some embodiments, the TLR7/8 agonist moiety of D is of the formula (D-4a) or (D-4b):

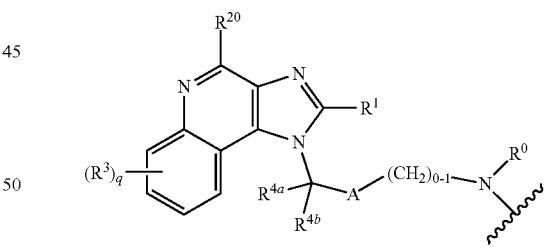

(D-4a)

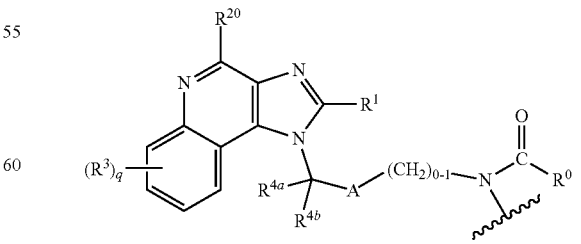

(D-4b)

wherein:
$R^0$ is $C_4$-$C_{21}$ hydrocarbyl optionally substituted by 1 to 4 halogen atoms;

A is $C_6$-$C_{14}$ arylene optionally substituted by 1 to 4 groups independently selected from the group consisting of halogen and $C_1$-$C_8$ alkyl optionally substituted by 1 to 8 halogen atoms, or 5- to 14-membered heteroarylene optionally substituted by 1 to 4 groups independently selected from the group consisting of halogen and $C_1$-$C_8$ alkyl optionally substituted by 1 to 8 halogen atoms;

$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;

$R^{20}$ is $NHR^{20a}$; where $R^{20a}$ is H, OH, $NH_2$, or methyl;

each $R^3$ is independently halogen, $C_1$-$C_8$ alkyl, —$(C_1$-$C_7$ alkylene)-$NH_2$, or —$CH_2$-phenylene-$CH_2NH_2$;

q is 0, 1, 2, 3, or 4;

$R^{4a}$ and $R^{4b}$ are independently H or $C_1$-$C_8$ alkyl; and the wave line represents the point of attachment of D in formula (I).

In some embodiments, the TLR7/8 agonist moiety of D is of the formula (D-4a). In some embodiments, the TLR7/8 agonist moiety of D is of the formula (D-4b).

In some embodiments, A is $C_6$-$C_{10}$ arylene optionally substituted by 1 to 4 groups independently selected from the group consisting of halogen and $C_1$-$C_8$ alkyl optionally substituted by 1 to 8 halogen atoms.

In some embodiments, A is phenylene optionally substituted by 1 to 4 groups independently selected from the group consisting of halogen and $C_1$-$C_8$ alkyl optionally substituted by 1 to 8 halogen atoms. In some embodiments, A is 1,4-phenylene optionally substituted by 1 to 4 groups independently selected from the group consisting of halogen and $C_1$-$C_8$ alkyl optionally substituted by 1 to 8 halogen atoms. In some embodiments, A is 1,4-phenylene optionally substituted with 1 to 4 groups independently selected from the group consisting of F, Cl, $CF_3$, and methyl.

In some embodiments, A is 2,6-dimethyl-1,4-phenylene; 2,3-dimethyl-1,4-phenylene; 2,6-difluoro-1,4-phenylene; 2,3-difluoro-1,4-phenylene; 2,6-dichloro-1,4-phenylene; 2,6-dichloro-1,4-phenylene; 2,3,5,6-tetramethyl-1,4-phenylene; or 2,3,5,6-tetrafluoro-1,4-phenylene.

In some embodiments, A is 1,3-phenylene optionally substituted with 1 to 4 groups independently selected from the group consisting of halogen and $C_1$-$C_8$ alkyl optionally substituted by 1 to 8 halogen atoms.

In some embodiments, A is 5- to 10-membered heteroarylene optionally substituted by 1 to 4 groups independently selected from the group consisting of halogen and $C_1$-$C_8$ alkyl optionally substituted by 1 to 8 halogen atoms.

In some embodiments, A is naphthylene optionally substituted by 1 to 4 groups independently selected from the group consisting of halogen and $C_1$-$C_8$ alkyl optionally substituted by 1 to 8 halogen atoms. In some embodiments, A is 1,4-naphthylene, 1,3-naphthylene, or 2,7-naphthylene. In some embodiments, A is 2,6-naphthylene.

In some embodiments, A is 4,7-benzo[b]thiophene. In some embodiments, A is 2,5-1H-benzo[d]imidazole.

In some embodiments, the TLR7/8 agonist moiety of D is of the formula (D-4a). In some embodiments, the TLR7/8 agonist moiety of D is of the formula (D-4b).

In some embodiments, $R^O$ is $C_4$-$C_{14}$ hydrocarbyl. In some embodiments, $R^O$ is $C_5$-$C_{10}$ hydrocarbyl. In some embodiments, $R^O$ is $C_{10}$-$C_{14}$ hydrocarbyl. In some embodiments, $R^O$ is $C_5$-$C_7$ hydrocarbyl. In some embodiments, $R^O$ is $C_{15}$-$C_{21}$ hydrocarbyl. In some embodiments, $R^O$ is $C_4$-$C_{21}$ hydrocarbyl substituted by 1 to 4 halogen atoms. In some embodiments, $R^O$ is $C_4$-$C_{14}$ hydrocarbyl substituted by 1 to 4 halogen atoms. In some embodiments, $R^O$ is $C_4$-$C_{10}$ hydrocarbyl substituted by 1 to 2 halogen atoms. In some embodiments, $R^O$ is $C_{10}$-$C_{14}$ hydrocarbyl substituted by 1 to 2 halogen atoms. In some embodiments, $R^O$ is $C_4$-$C_7$ hydrocarbyl substituted by 1 to 2 halogen atoms. In some embodiments, $R^O$ is $C_4$-$C_7$ hydrocarbyl substituted by 1 halogen atom. In some embodiments, $R^O$ is $C_{15}$-$C_{21}$ hydrocarbyl substituted by 1 to 4 halogen atoms.

In some embodiments, $R^O$ is —$(CH_2)_mR^4$; m is 0, 1, 2, or 3; and $R^4$ is $C_3$-$C_8$ cycloalkyl optionally substituted by 1 to 4 groups independently selected from the group consisting of $C_1$-$C_4$ alkyl and $C_1$-$C_4$ alkylene. In one variation, m is 1 or 2, and $R^4$ is cyclopropyl, cyclobutyl, or cyclopentyl. In some embodiments, $R^4$ is $C_3$-$C_6$ cycloalkyl optionally substituted by 1 to 3 groups independently selected from the group consisting of methyl and methylene. In one variation, m is 1 or 2. In some embodiments, $R^4$ is cyclopropyl optionally substituted by 1 to 3 groups independently selected from the group consisting of methyl and methylene, and m is 1 or 2. In some embodiments, m is 0 or 1, and $R^4$ is cyclohexyl optionally substituted by 1 to 3 groups independently selected from the group consisting of methyl and methylene.

In some embodiments, $R^O$ is selected from the group consisting of:

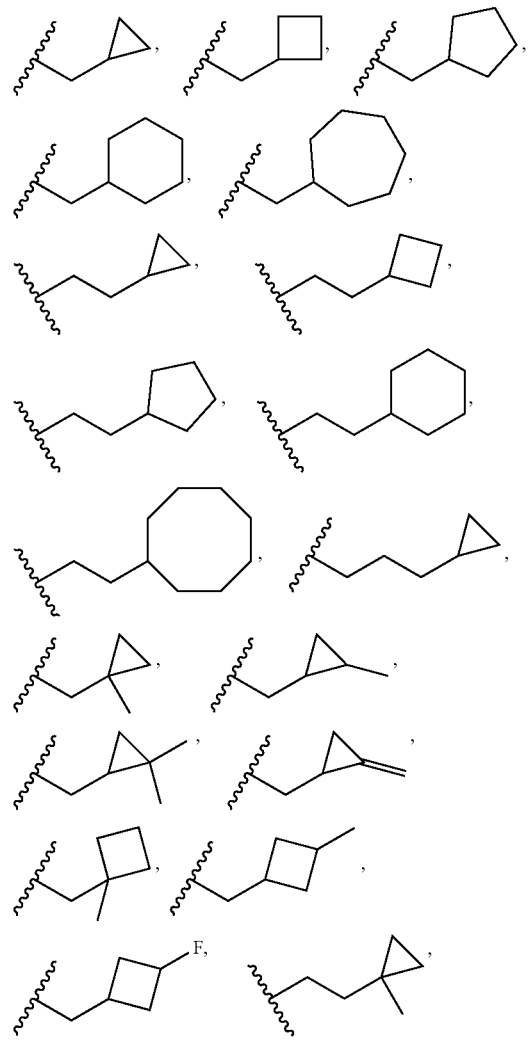

-continued

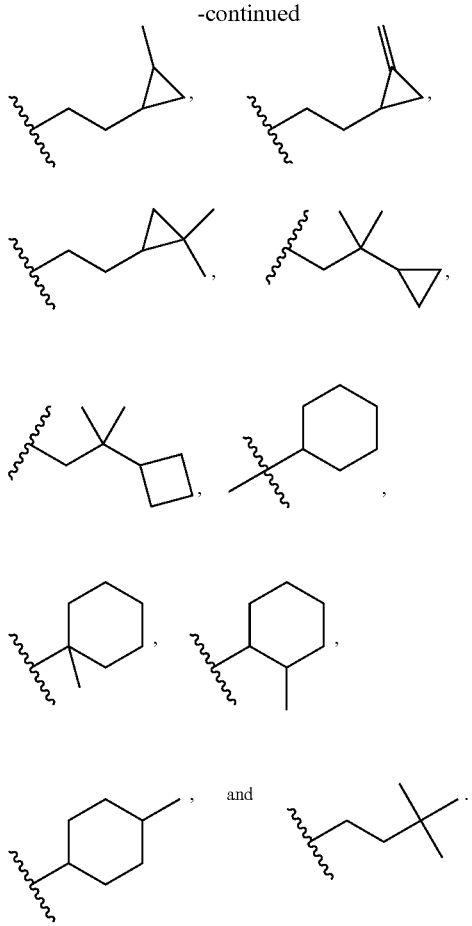

In some embodiments, $R^0$ is (cyclopropyl)methyl, 2-(cyclopropyl)ethyl, 2-(cyclobutyl)ethyl, 2-(cyclopentyl)ethyl, or 2-(cyclohexyl)ethyl.

In some embodiments, $R^0$ is branched $C_4$-$C_{14}$ alkyl. In some embodiments, $R^0$ is branched $C_5$-$C_{10}$ alkyl. In some embodiments, $R^0$ is branched $C_{10}$-$C_{14}$ alkyl. In some embodiments, $R^0$ is branched $C_5$-$C_7$ alkyl. In some embodiments, $R^0$ is branched $C_{15}$-$C_{21}$ alkyl.

In some embodiments, $R^1$ is $C_3$-$C_6$ alkyl (e.g., n-butyl). In some embodiments, $R^1$ is propyl, butyl, pentyl, or hexyl. In some embodiments, $R^1$ is n-butyl. In some embodiments, $R^1$ is n-pentyl. In some embodiments, $R^1$ is —(CH$_2$)$_p$OR$^{1a}$ (e.g., CH$_2$OCH$_2$CH$_3$). In some embodiments, $R^1$ is —(CH$_2$)$_p$NHR$^{1b}$ (e.g., CH$_2$NHCH$_2$CH$_3$). In some embodiments, $R^1$ is —(CH$_2$)$_p$R$^{1c}$. In one variation, $R^{1c}$ is cyclopropyl.

In some embodiments, $R^{20}$ is NHR$^{20a}$, where $R^{20a}$ is H, OH, NH$_2$, or methyl. In some embodiments, $R^{20}$ is NH$_2$. In some embodiments, $R^{20}$ is NHOH, NHNH$_2$, or NHCH$_3$.

In some embodiments, $R^{4a}$ and $R^{4b}$ are independently H or $C_1$-$C_8$ alkyl. In some embodiments, each $R^{4a}$ and $R^{4b}$ is H.

In some embodiments, the phenyl moiety of the 1H-imidazo[4,5-c]quinoline core is unsubstituted (i.e., q is 0). In some embodiments, the phenyl moiety of the 1H-imidazo[4,5-c]quinoline core is substituted by 1, 2, 3, or 4 substituents independently selected from the group consisting of halogen, $C_1$-$C_8$ alkyl, —($C_1$-$C_7$ alkylene)-NH$_2$, and —CH$_2$-phenylene-CH$_2$NH$_2$. In some embodiments, q is 1 and $R^3$ is $C_1$-$C_8$ alkyl.

It is intended and understood that where present, each and every variation of A and $R^0$ described for formula (D-4a) can be combined with each and every variation of $R^1$, $R^{1a}$, $R^{1b}$, $R^{1c}$, $R^{20}$, p, $R^A$, m, q, $R^3$, $R^{4a}$, and $R^{4b}$ described for formula (D-4a) the same as if each and every combination is specifically and individually described. Similarly, it is intended and understood that where present, each and every variation of A and $R^0$ described for formula (D-4b) can be combined with each and every variation of $R^1$, $R^{1a}$, $R^{1b}$, $R^{1c}$, $R^{20}$, p, $R^A$, m, q, $R^3$, $R^{4a}$, and $R^{4b}$ described for formula (D-4b) the same as if each and every combination is specifically and individually described. For example, in some embodiments of the formula (D-4a), $R^1$ is n-butyl, $R^{20}$ is NH$_2$, q is 0, each $R^{4a}$ and $R^{4b}$ is H, A is 1,4-napthylene, $R^0$ is —(CH$_2$)$_m$R$^A$, m is 1 or 2, and $R^A$ is cyclopropyl, cyclobutyl, cyclopentyl, or cyclohexyl.

Representative compounds of formula (D-4), (D-4a), and (D-4b) are listed in Table 3, where the wave line represents the point of attachment of D in formula (I).

TABLE 3

| Compound No. | Formula | Compound No. | Formula | Name[1] |
|---|---|---|---|---|
| 64-38 | | 64-38a | | 2-butyl-1-((4-(((2-cyclopropylethyl)amino)methyl)naphthalen-1-yl)methyl)-1H-imidazo[4,5-c]quinolin-4-amine |

TABLE 3-continued

| Compound No. | Formula | Compound No. | Formula | Name |
|---|---|---|---|---|
| 64-39 | | 64-39a | | 2-butyl-1-((4-(((2-cyclobutylethyl)amino)methyl)naphthalen-1-yl)methyl)-1H-imidazo[4,5-c]quinolin-4-amine |
| 64-40 | | 64-40a | | 2-butyl-1-((4-(((2-cyclopentylethyl)amino)methyl)naphthalen-1-yl)methyl)-1H-imidazo[4,5-c]quinolin-4-amine |
| 64-41 | | 64-41a | | 2-butyl-1-((3-(((2-cyclopropylethyl)amino)methyl)naphthalen-1-yl)methyl)-1H-imidazo[4,5-c]quinolin-4-amine |

TABLE 3-continued

| Compound No. | Formula | Compound No. | Formula | Name |
|---|---|---|---|---|
| 64-42 | | 64-42a | | 2-butyl-1-(7-((2-cyclopropylethyl)amino)naphthalen-2-yl)-1H-imidazo[4,5-c]quinolin-4-amine |
| 64-43 | | 64-43a | | 2-butyl-1-(4-(((2-cyclopropylethyl)amino)methyl)-2,6-bis(trifluoromethyl)benzyl)-1H-imidazo[4,5-c]quinolin-4-amine |
| 64-44 | | 64-44a | | 2-butyl-1-(4-(((2-cyclopropylethyl)amino)methyl)-2,6-dimethylbenzyl)-1H-imidazo[4,5-c]quinolin-4-amine |

TABLE 3-continued

| Compound No. | Formula | Compound No. | Formula | Name |
|---|---|---|---|---|
| 64-45 | | 64-45a | | 2-butyl-1-(4-(((2-cyclopropylethyl)amino)methyl)-2,6-difluorobenzyl)-1H-imidazo[4,5-c]quinolin-4-amine |
| 64-46 | | 64-46a | | 2-butyl-1-(4-(((2-cyclopropylethyl)amino)methyl)-2,3-difluorobenzyl)-1H-imidazo[4,5-c]quinolin-4-amine |
| 64-47 | | 64-47a | | 2-butyl-1-(4-(((2-cyclopropylethyl)amino)methyl)-2,3,5,6-tetrafluorobenzyl)-1H-imidazo[4,5-c]quinolin-4-amine |

TABLE 3-continued

| Compound No. | Formula | Compound No. | Formula | Name[1] |
|---|---|---|---|---|
| 64-48 | 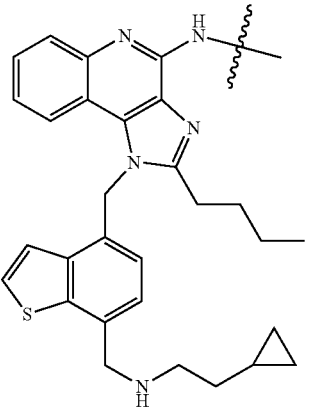 [SMILES: *Nc1nc2ccccc2c2c1nc(CCCC)n2Cc1ccc(CNCCC2CC2)c2sccc12] | 64-48a | 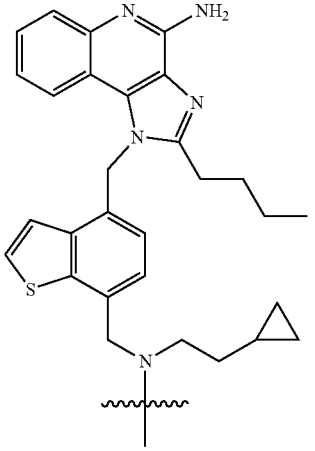 [SMILES: *N(CCC1CC1)Cc1ccc(Cn2c(CCCC)nc3c(N)nc4ccccc4c32)c2ccsc12] | 2-butyl-1-((7-(((2-cyclopropylethyl)amino)methyl)benzo[b]thiophen-4-yl)methyl)-1H-imidazo[4,5-c]quinolin-4-amine |
| 64-49 | 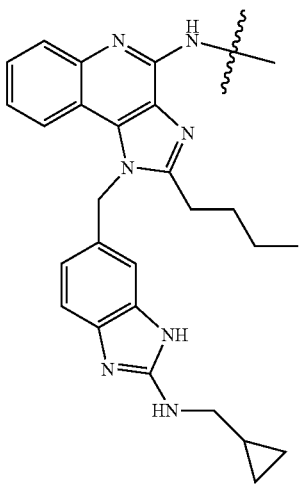 [SMILES: *Nc1nc2ccccc2c2c1nc(CCCC)n2Cc1ccc2nc(NCC3CC3)[nH]c2c1] | 64-49a | 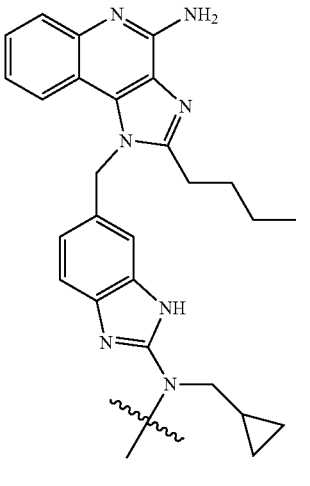 [SMILES: *N(CC1CC1)c1nc2ccc(Cn3c(CCCC)nc4c(N)nc5ccccc5c43)cc2[nH]1] | 2-butyl-1-((2-((cyclopropylmethyl)amino)-1H-benzo[d]imidazol-5-yl)methyl)-1H-imidazo[4,5-c]quinolin-4-amine |
| 64-50 | 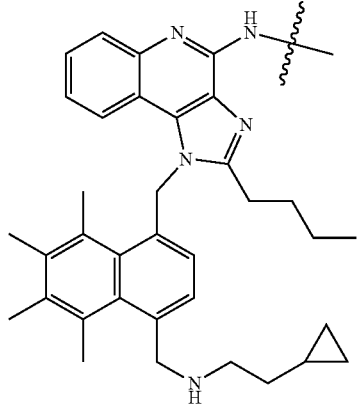 [SMILES: *Nc1nc2ccccc2c2c1nc(CCCC)n2Cc1ccc(CNCCC2CC2)c2c(C)c(C)c(C)c(C)c12] | 64-50a | 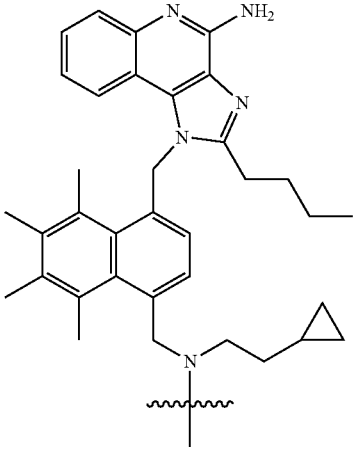 [SMILES: *N(CCC1CC1)Cc1ccc(Cn2c(CCCC)nc3c(N)nc4ccccc4c32)c2c(C)c(C)c(C)c(C)c12] | 2-butyl-1-((4-(((2-cyclopropylethyl)amino)methyl)-5,6,7,8-tetramethylnaphthalen-1-yl)methyl)1H-imidazo[4,5-c]quinolin-4-amine |

[1]The listed chemical names are the chemical names of the corresponding unconjugated compounds having a hydrogen atom at the position indicated by the wave line (i.e., primary and secondary amine).

The TLR7/8 agonist moieties of formula (D-4), (D-4a), and (D-4b) are generated from the corresponding unconjugated compounds, which can be synthesized according to Scheme D-4 and/or using methods known in the art.

linker $L^1$ undergoes a spontaneous chemical rearrangement that causes the moiety to be eliminated from the TLR7/8 agonist conjugate and releases the unconjugated chemical form of the TLR7/8 agonist.

Scheme D-4

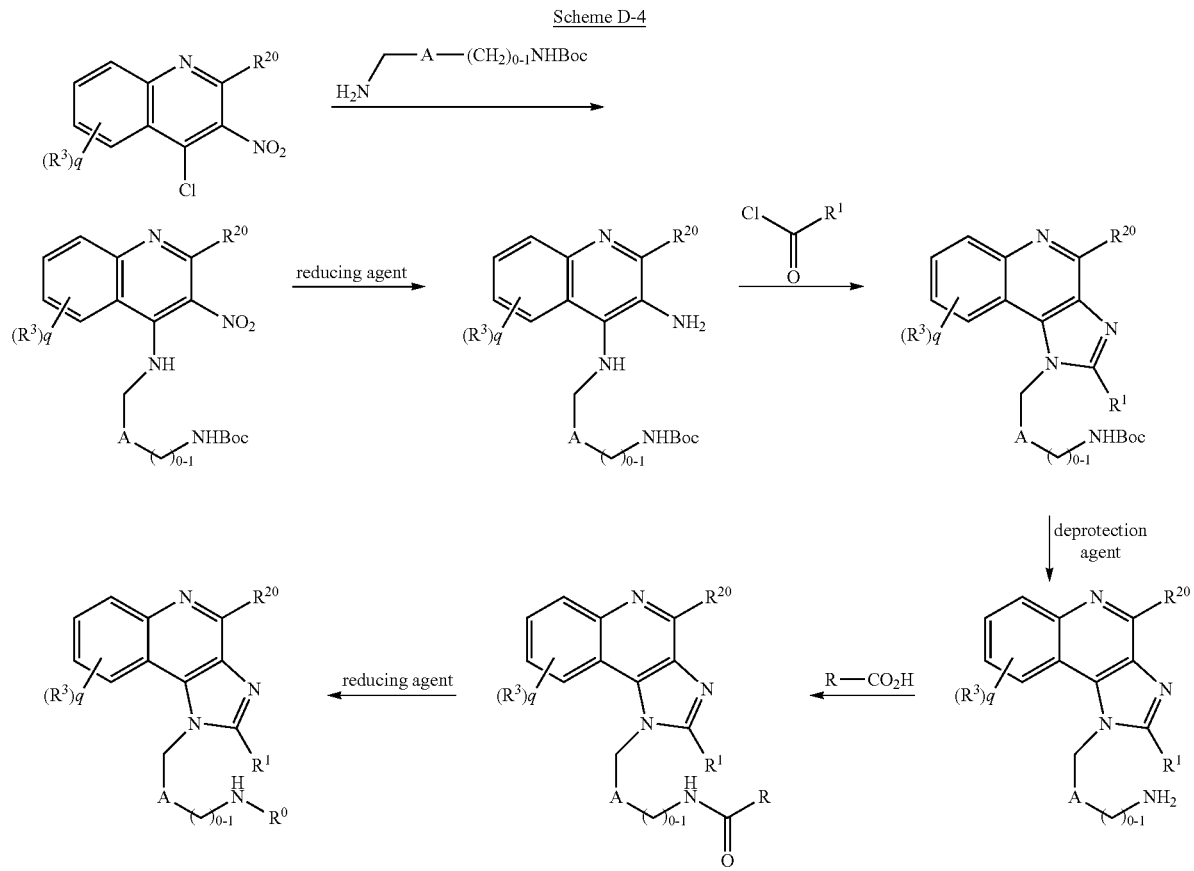

wherein $R^1$, q, $R^3$, and A are as defined for formula (D-4), (D-4a), and (D-4b); $R^{20}$ is $NH_2$ or as defined for formula (D-4a) and (D-4b); and R and $R^0$ are optionally substituted hydrocarbyl groups.

Those skilled in the art will appreciate that other synthetic routes may be employed to synthesize the TLR7/8 agonist moieties of formula (D-4), (D-4a), and (D-4b) described herein including various solvents, catalysts, reducing agents, temperatures, reaction times, and atmospheric conditions.

B. Self-Eliminating Linkers

Those skilled in the art will recognize that, as for ADCs, cleavable conjugates of TLR7/8 agonist compounds, such as those of formula (I) described herein, possess lower bioactivity when stably conjugated and have greater TLR7/8 agonist bioactivity when cleavage occurs in the tumor microenvironment in a manner that releases the original (i.e., unconjugated) chemical form of the TLR7/8 agonist (Beck et al. 2017, Nature Reviews 16:315-337; Dubowchik et al. 2002, Bioconj Chem 13:855-869). In the present disclosure, self-elimating linker moieties ($L^1$ in formula (I)) are used to covalently link the TLR7/8 agonist compound (D in formula (I)) to the cleavable linker moieties ($L^2$ in formula (I)). The presence of the self-eliminating linker $L^1$ in formula (I) maintains the TLR7/8 agonist moiety D in a relatively inactive state; following hydrolysis of the cleavable linker $L^2$ in the tumor microenvironment, the self-eliminating An amino group in a TLR7/8 agonist moiety (D) in formula (I) can serve as a reactive chemical group to enable chemical conjugation to a self-eliminating linker. In some embodiments, the primary amine on the N1-benzyl group of a 1-(aminomethylbenzyl)-1H-imidazo[4,5-c]quinolin-4-amine (see, e.g., compounds of formula (D-1a-1) or (D-1b-1)) can be used for conjugation of $L^1$ to D in formula (I). In some embodiments, the primary amine on the quinoline ring of a modified 1H-imidazo[4,5-c]quinolin-4-amine derivative (see, e.g., Compound Nos. 64-01 to 64-50 and 64-58 to 64-69 in Tables 1-3) can be used for conjugation of $L^1$ to D in formula (I). In some embodiments, the secondary amine (i.e., substituent X in formula (D-2), (D-3), and (D-4)) of a modified 1H-imidazo[4,5-c]quinolin-4-amine derivative (see, e.g., Compound Nos. 64-01a to 64-50a and 64-58a to 64-69a in Tables 1-3) can be used for conjugation of $L^1$ to D in formula (I). However, derivatizing these amino groups can result in decreased TLR7 and/or TLR8 agonist activity. Thus, it is desirable to have a linker that releases the TLR7/8 agonist moiety in its original form (i.e., unconjugated form; that is, as the compound bearing the free primary amine group) once the conjugate is cleaved. The self-eliminating linker of the present disclosure provides a system in which cleavage of a specific bond triggers a series of 1,6- and/or 1,4-elimination reactions that result in self-destruction of the linker and regeneration of the original (i.e., unconjugated) TLR7/8 agonist moiety.

In some embodiments, the self-eliminating linker $L^1$ in formula (I) is a moiety which can be eliminated from the compound of formula (I) upon cleavage of a specific bond by one or more 1,6- and/or 1,4-elimination reactions.

In some embodiments, the self-eliminating linker $L^1$ in the compound of formula (I) is of the formula (L-1):

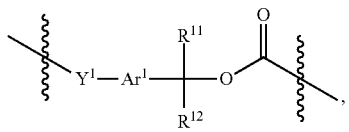
(L-1)

wherein $Y^1$ is S, O or NH; $Ar^1$ is an optionally substituted arylene; and $R^{11}$ and $R^{12}$ are independently H or optionally substituted alkyl.

In some embodiments, $Y^1$ is S or NH. In some embodiments, $Y^1$ is S. In some embodiments, $Y^1$ is NH.

In some embodiments, $R^{11}$ and $R^{12}$ are independently H or optionally substituted $C_1$-$C_8$ alkyl. In some embodiments, $R^{11}$ and $R^{12}$ are each H.

In some embodiments, $Ar^1$ is an optionally substituted phenylene. In some embodiments, $Ar^1$ is an optionally substituted 1,4-phenylene. In some embodiments, $Ar^1$ is an optionally substituted 1,2-phenylene. In some embodiments, $Ar^1$ is an optionally substituted naphthylene. In some embodiments, $Ar^1$ is an optionally substituted 1,4-naphthylene, optionally substituted 1,2-naphthylene, or optionally substituted 2,6-naphthylene. In some embodiments, $Ar^1$ is 1,4-phenylene. In some embodiments, $Ar^1$ is 1,2-phenylene.

In some embodiments, $Ar^1$ is 1,4-phenylene and $R^{11}$ and $R^{12}$ are each H, and $L^1$ is of the formula (L-1a):

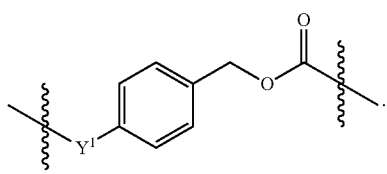
(L-1a)

In some embodiments, $Ar^1$ is 1,2-phenylene and $R^{11}$ and $R^{12}$ are each H, and $L^1$ is of the formula (L-1b):

(L-1b)

In some embodiments, $Y^1$ is NH and $L^1$ is:

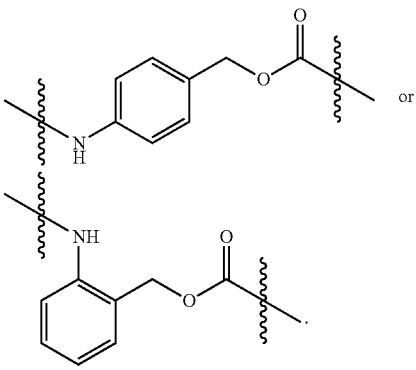
or

In some embodiments, $Y^1$ is S and $L^1$ is:

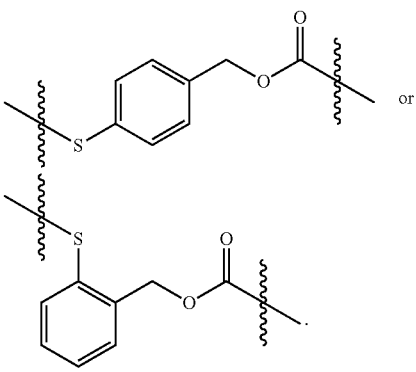
or

Other self-eliminating linkers useful for drug conjugation are known in the art, for example, the self-eliminating linkers described in Blencowe et al. 2011, *Polymer Chem* 2:773-790; and in U.S. Pat. No. 6,180,095, the disclosures of which are incorporated herein by reference. The descriptions of self-eliminating linkers provided herein is not meant to limit the scope of the invention as those skilled in the art will recognize that other self-eliminating linkers can be functionally equivalent.

Self-eliminating linker moieties of the current invention impart two key attributes to the cleavable conjugates of TLR7/8 agonist compounds. First, when self-eliminating linker moieties are connected to the TLR7/8 agonist, they maintain the TLR7/8 agonist in a relatively inactive state. Second, upon hydrolysis of the cleavable linker $L^2$ in formula (I), the eliminating linker moieties self-eliminate to yield the original (i.e., unconjugated) TLR7/8 agonist moiety. Accordingly, in some embodiments, $L^1$-D in formula (I) is of formula (L1-D-1), (L1-D-2), (L1-D-3), or (L1-D-4):

(L1-D-1)

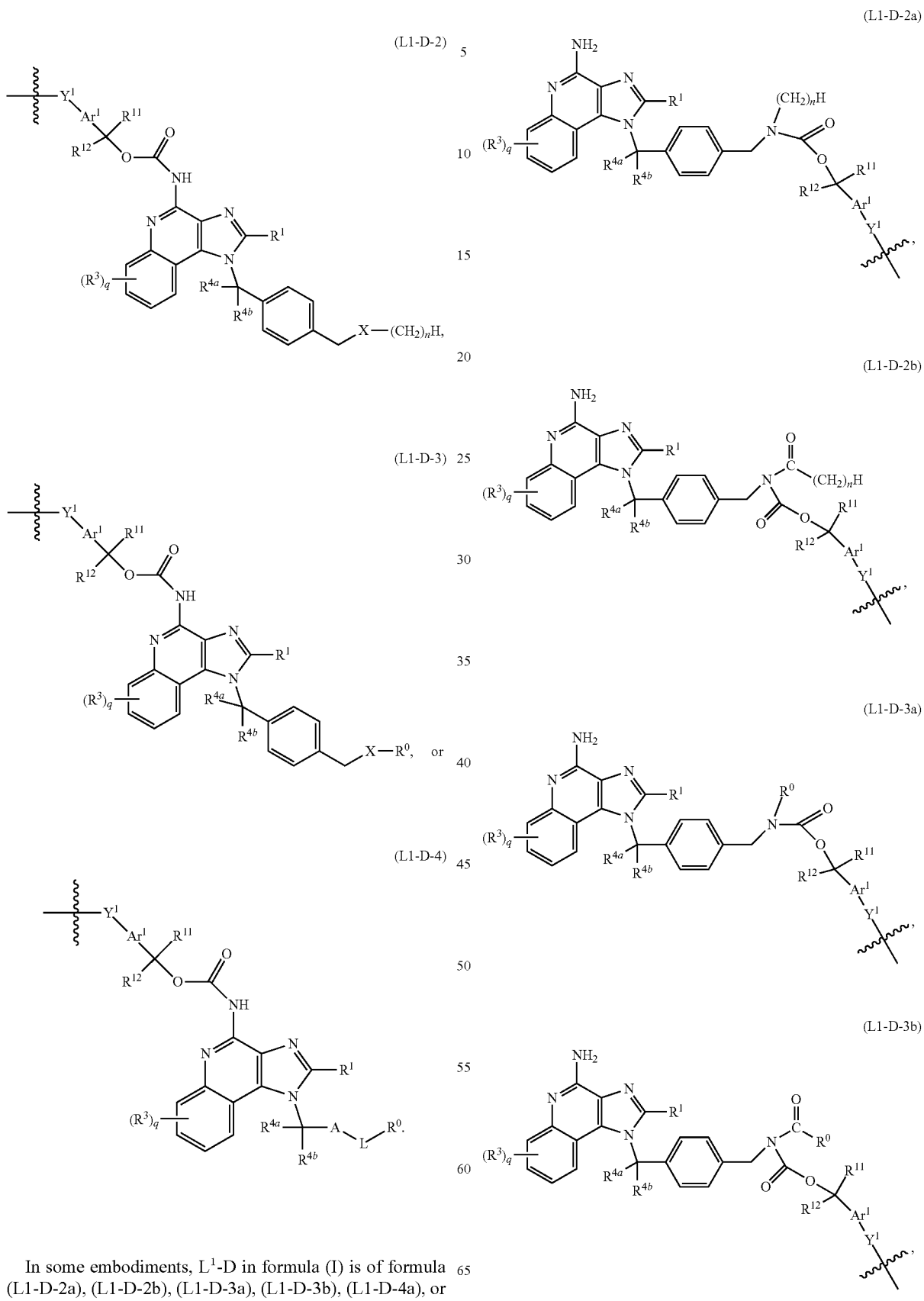
In some embodiments, L¹-D in formula (I) is of formula (L1-D-2a), (L1-D-2b), (L1-D-3a), (L1-D-3b), (L1-D-4a), or (L1-D-4b):

99
-continued
(L1-D-4a)
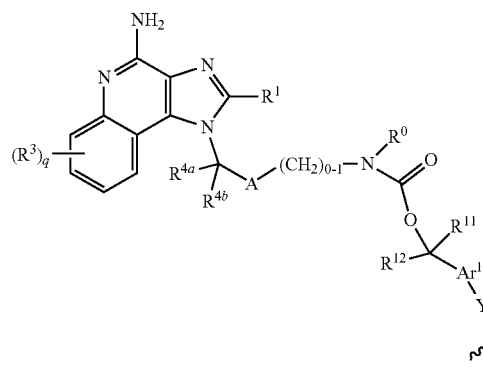
100
-continued
(L1-D-4b)
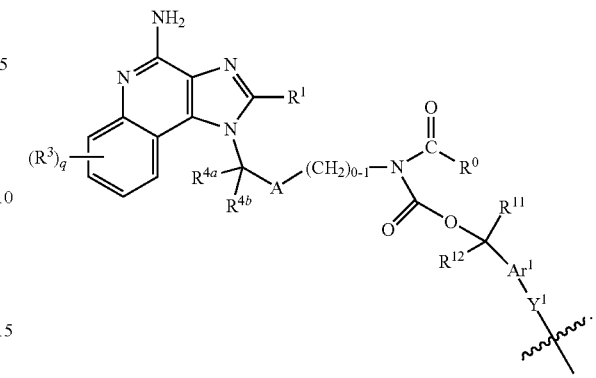
, or
In some embodiments, L¹-D in formula (I) is:
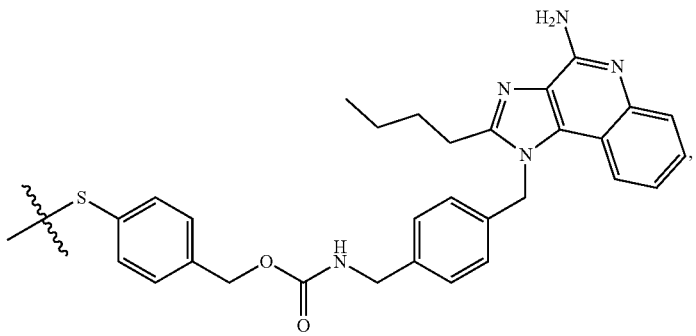
,
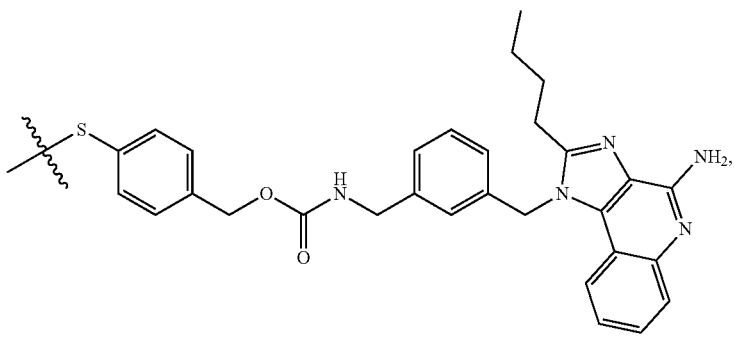
,
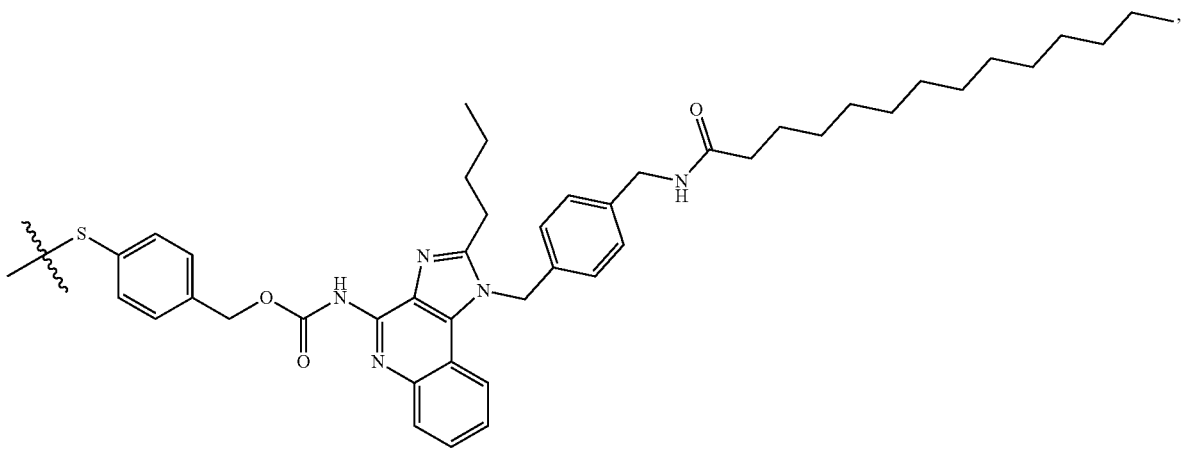

-continued
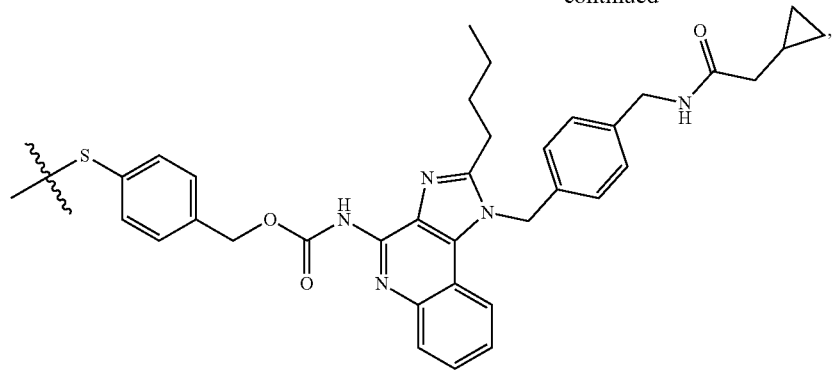
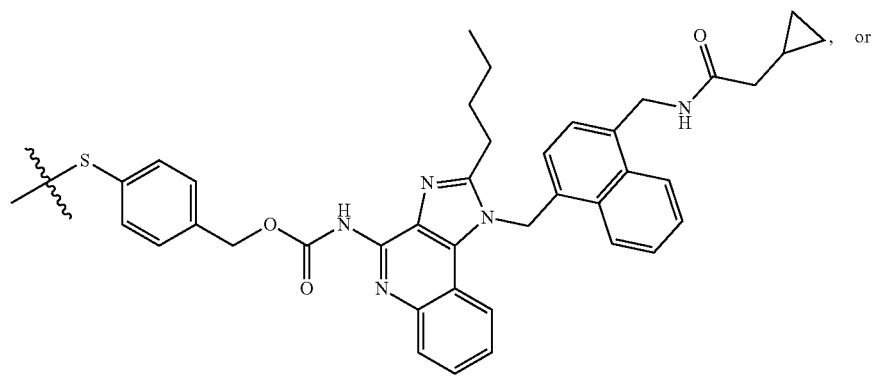
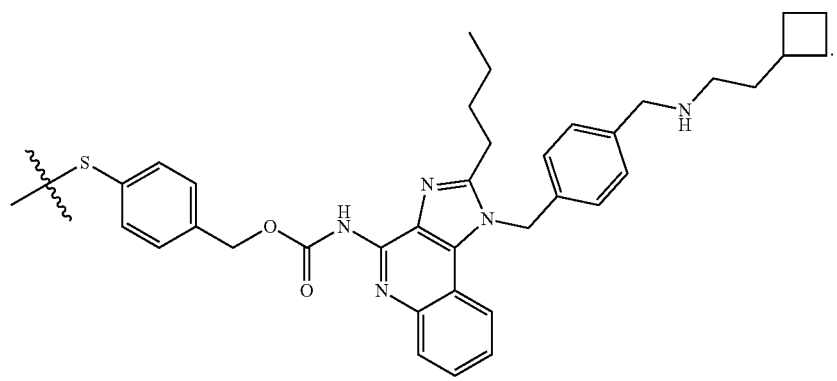
In some embodiments, L$^1$-D in formula (I) is:
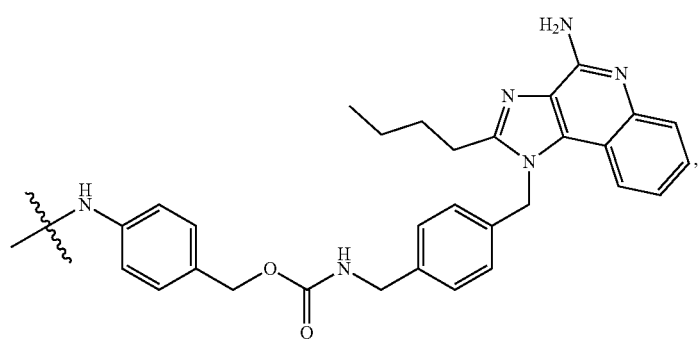

-continued
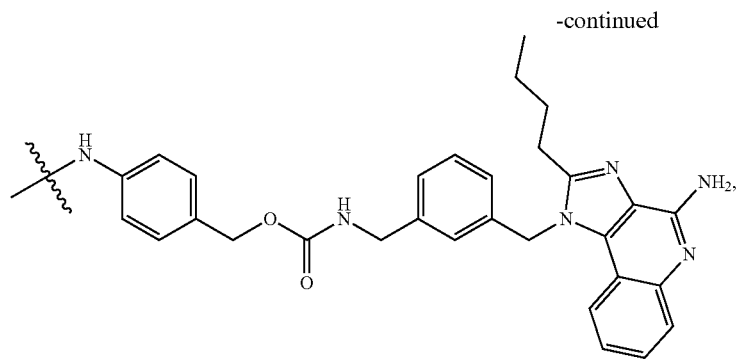
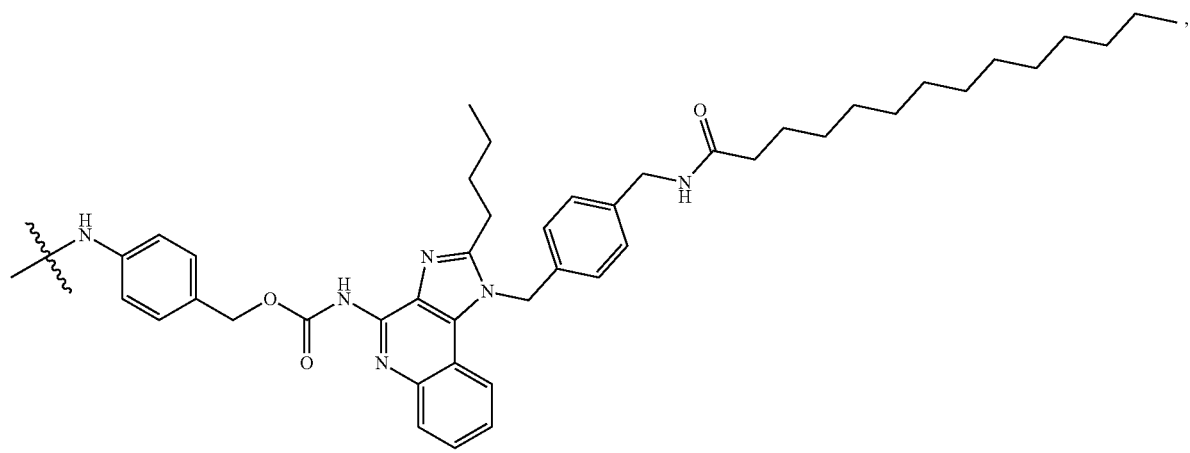
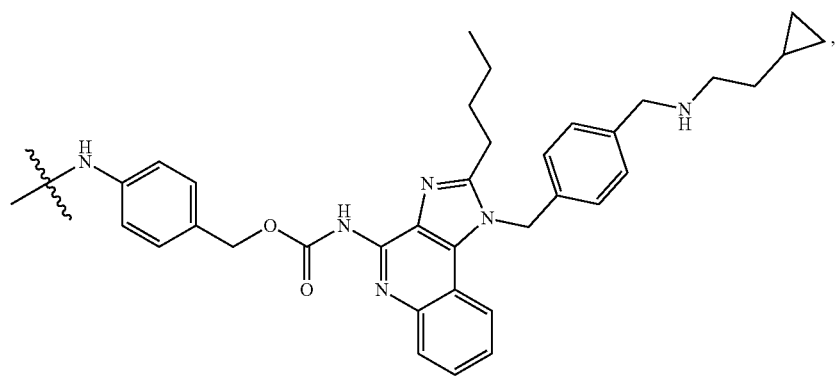
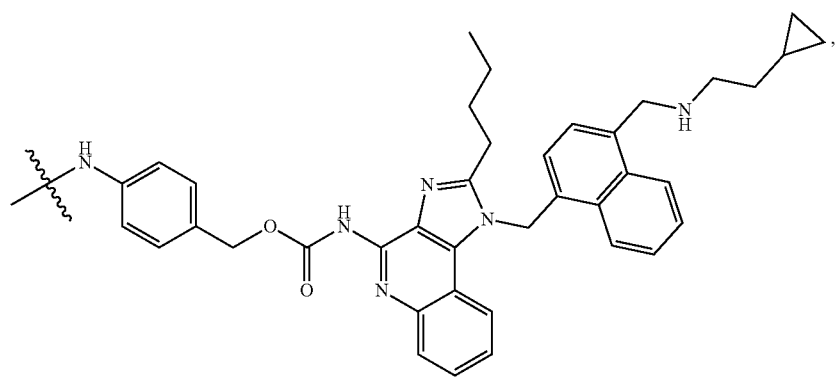

-continued
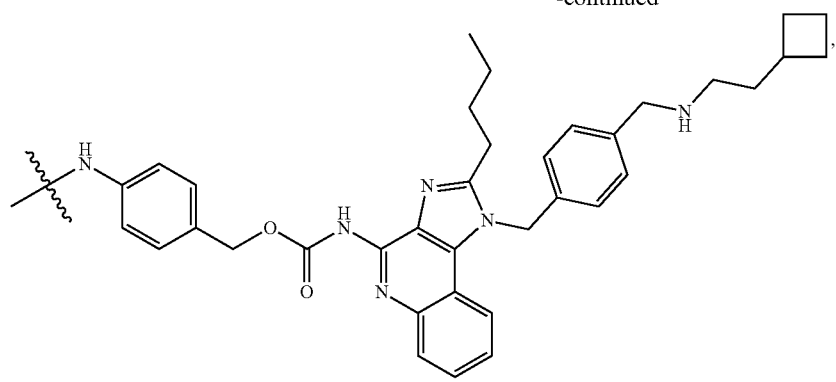
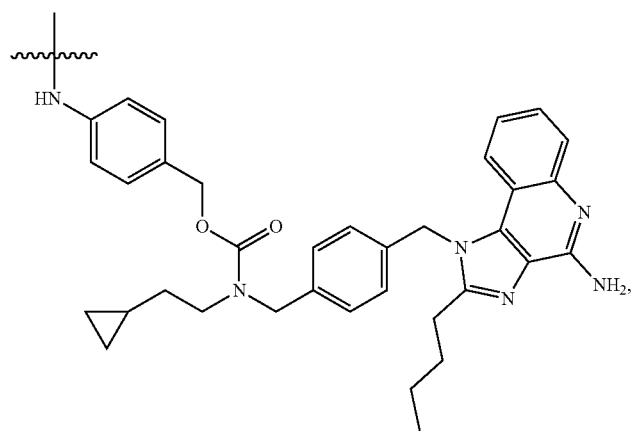
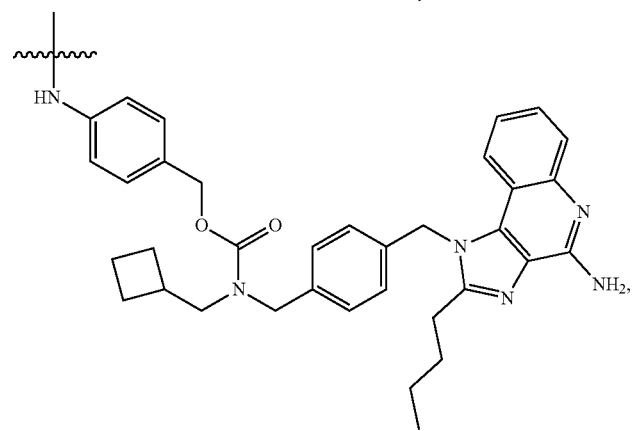
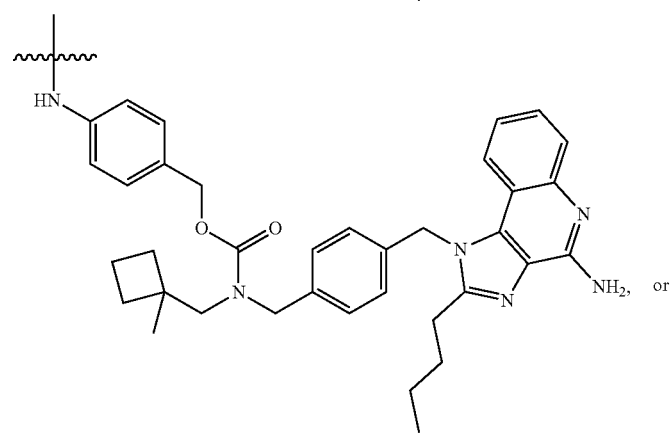

-continued

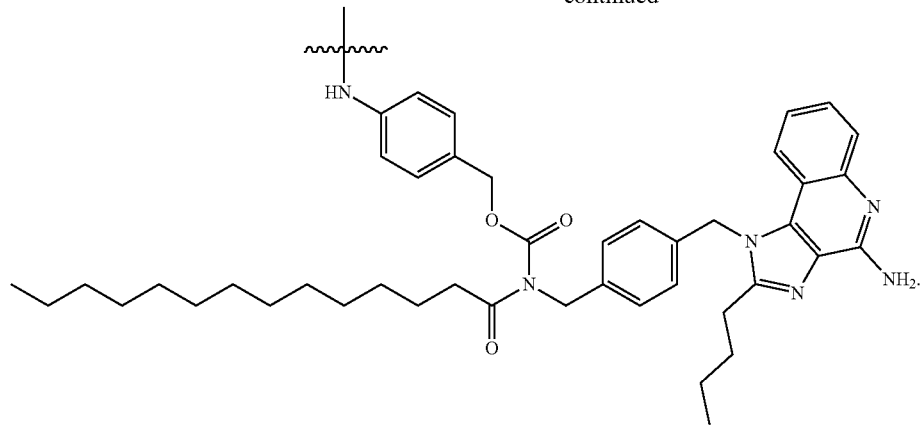

In some embodiments, $L^1$ in the compound of formula (I) is a bond, and the compound of formula (I) is F—[W-$L^3$-$L^2$-D]$_x$. In some embodiments, $L^1$-D in formula (I) is:

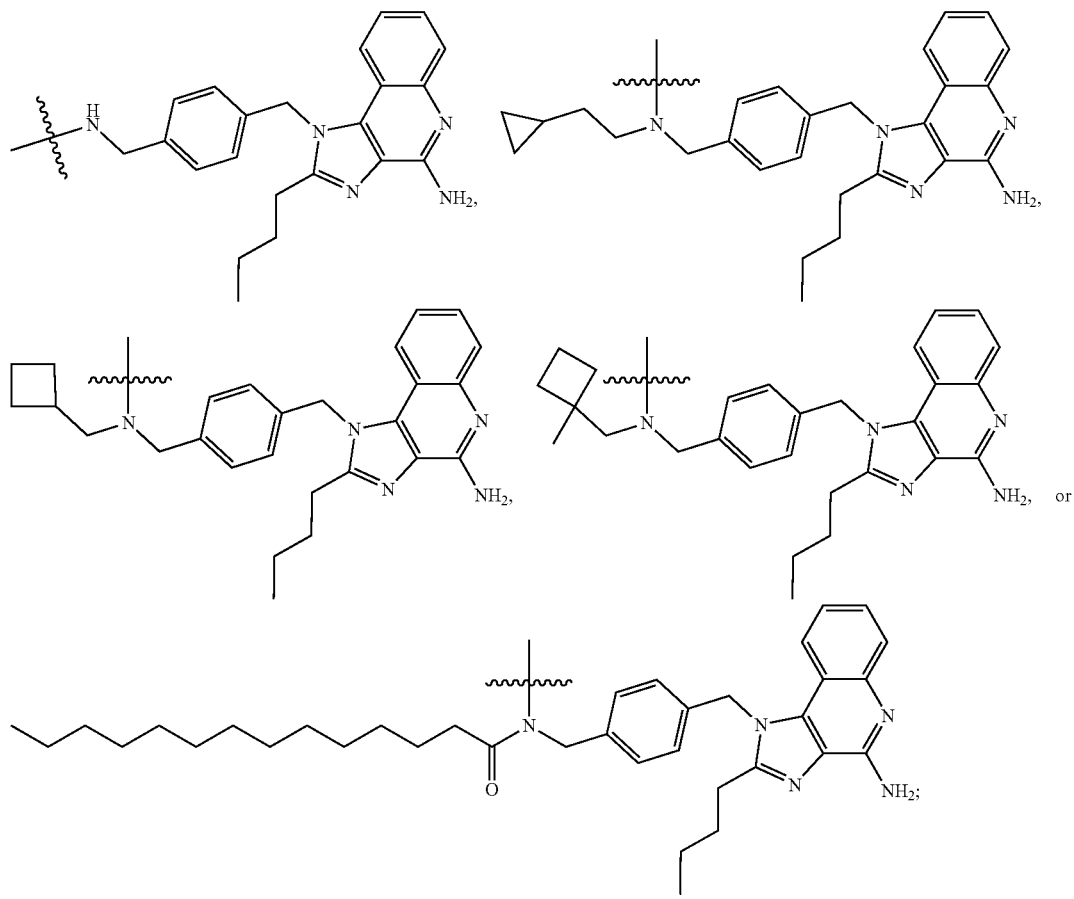

wherein $L^1$ is a bond.

C. Cleavable Linkers

The cleavable linker moiety $L^2$ in formula (I) enables the subsequent release of the original (i.e., unconjugated) form of the TLR7/8 agonist moiety D upon localization or retention of the compound of formula (I) to the tumor microenvironment. In some embodiments, $L^1$ is a self-eliminating linker, and the conjugation moiety F and the conjugation linker moieties W-$L^3$ (i.e., F—W-$L^3$ in formula (I)) are covalently conjugated to the TLR7/8 agonist moiety D and the self-eliminating linker $L^1$ (i.e., -$L^1$-D in formula (I)) via a cleavable linker moiety $L^2$. In some embodiments, $L^1$ is a bond, and the conjugation moiety F and the conjugation linker moieties W-$L^3$ (i.e., F—W-$L^3$ in formula (I)) are covalently conjugated to the TLR7/8 agonist moiety D via a cleavable linker moiety $L^2$, and the compound of formula (I) is F—[W-$L^3$-$L^2$-D]$_x$.

One skilled in the art will recognize that cleavable linker systems have been utilized for antibody targeting of highly potent chemotherapeutic drugs in the development of ADCs (see e.g., Beck et al. 2017, *Nature Reviews* 16:315-337) to address the narrow therapeutic window observed with the use of increasingly potent cytotoxic agents as cancer therapeutics. Cleavable linkers used in the construction of ADCs generally fall into 3 classes: 1) enzymatically labile peptide-based linkers; 2) disulfide linkers cleavable by gluthione reduction; and 3) linkers susceptible to hydrolytic degradation under acidic conditions (Nolting, B. 2013, *Methods Mol Biol* 1045:71-100).

In some embodiments, the cleavable linker moiety $L^2$ in formula (I) is a peptide-based cleavable linker. In some embodiments, the cleavable linker $L^2$ of the present disclosure comprises an amino acid motif that can be cleaved by a proteolytic enzyme, such as Cathepsin B, yielding an unstable intermediate that self-immolates in such a manner to yield the original (i.e., unconjugated) TLR7/8 agonist moiety D (see, e.g., FIG. 2). In such embodiments, $L^2$ is a peptide, such as a peptide cleavable by a proteolytic enzyme (e.g., Cathepsin B). In some embodiments, $L^2$ is a peptide linker of 2 to 10, 2 to 8, 2 to 6, or 2 to 4 amino acid residues. In some embodiments, $L^2$ is a di-peptide. In some embodiments, $L^2$ is a peptide of 2, 3, 4, 5, 6, 7, 8, 9, or 10 amino acid residues.

Amino acid residues of the present disclosure include proteinogenic amino acids such as Ala, Asp, Cys, Glu, Phe, Gly, His, Ile, Lys, Leu, Met, Asn, Pro, Gln, Arg, Ser, Thr, Val, Trp, and Tyr; as well as those not found in proteins, such as homoserine, homoarginine, citrulline ("Cit"), phenylglycine, taurine, iodotyrosine, seleno-cysteine, norleucine ("Nle"), norvaline ("Nva"), beta-alanine, L- or D-naphthalanine, ornithine ("Orn"), and the like.

Peptide-based cleavable linkers rely on the differential expression of certain key enzymes in the the tumor microenvironment and/or specific uptake of the targeted therapeutic into the endolysosomal compartment of tumor cells (see, e.g., Mason, S. D. and Joyce, J. A. 2011, *Trends Cell Biol* 21:228-237; Weidle, U. H. et al. 2014, *Cancer Genomics Proteomics* 11:67-79; Doronina, S. O. et al. 2003, *Nature Biotechol* 21:778-784). In s ome embodiments, $L^2$ is a peptide linker cleavable by one or more endosomal or lysosomal peptidase(s) or protease(s), or one or more pericellular peptidase(s) or protease(s), that are expressed by cells in the tumor microenvironment (see, e.g., Tanabe, L. M. and List, K. 2017, *FEBS J* 284:1421-1436; Ulisse, S. et al. 2009, *Curr Cancer Drug Targets* 9:32-71; Uhland, K. 2006, *Cell Mol Life Sci* 63:2968-2978; LeBeau, A. M. et al. 2013, *Proc Nat Acad Sci USA* 110:93-98; Liu, C. et al. 2003, *Cancer Res* 63:2957-2964).

In some embodiments, $L^2$ is a peptide linker cleavable by endosomal cathepsins, including Cathepsins B, C, D, H, L, Z and/or S. In some embodiments, $L^2$ is a peptide linker cleavable by pericellular proteases, including urokinase-type plasminogen activator (uPA), membrane-type serine protease 1 (matriptase), matriptase-2, and/or legumain.

In some embodiments, $L^2$ is peptide linker cleaved by Cathepsin B. In some embodiments, $L^2$ is peptide linker cleaved by Cathepsin B described by the amino acid sequence $AA_1$-$AA_2$-$AA_3$-$AA_4$, where $AA_1$ is absent, alanine, β-alanine, isoleucine, leucine, valine, or glycine; $AA_2$ is absent, alanine, β-alanine, isoleucine, leucine, or valine; $AA_3$ is alanine, β-alanine, isoleucine, leucine, or valine; and $AA_4$ is arginine, serine, alanine, β-alanine leucine, ornithine or citrulline.

In some embodiments, $L^2$ is:

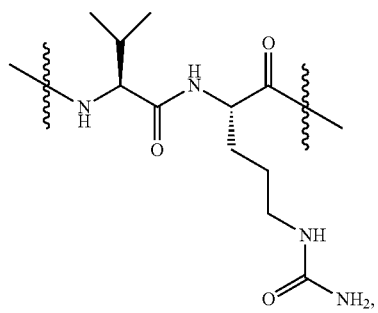

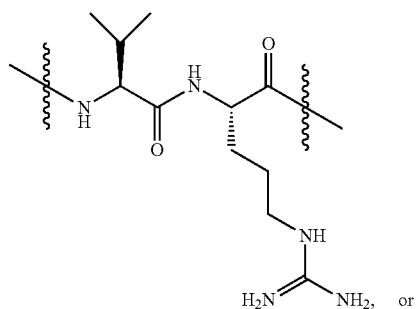

or

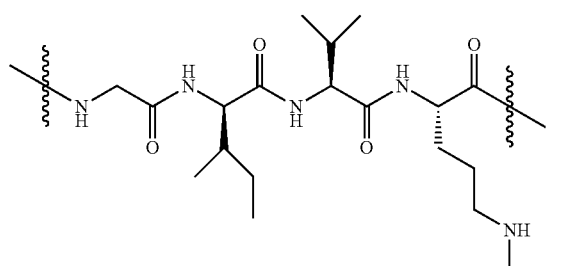

In some embodiments, $L^2$ is peptide linker specifically cleavable by members of the type II transmembrane serine protease family of enzymes including 1) matriptases, 2) hepsin/transmembrane protease/serine, 3) human airway trypsin-like/differentially expressed in squamous cell carcinoma, and 4) corin. In some embodiments, $L^2$ is peptide linker specifically cleavable by urokinase-type plasminogen activator (uPA), matriptases (including membrane-type serine protease 1/ST14 and matriptase-2/TMPRSS6, and/or legumain/LGMN.

In some embodiments, $L^2$ is:

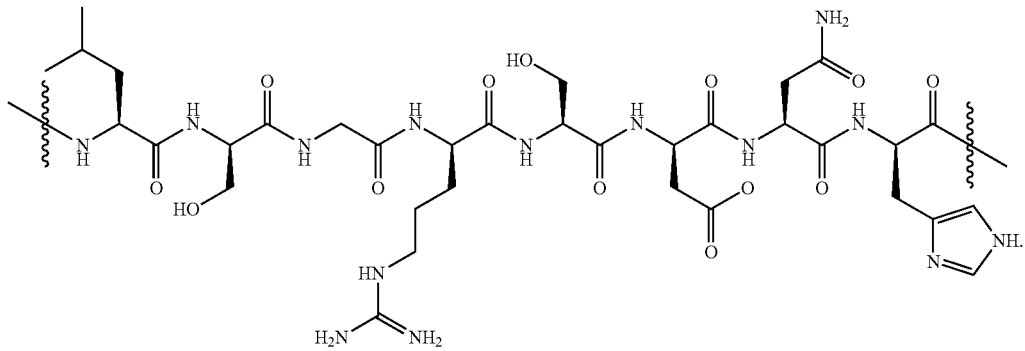

Figure 3:
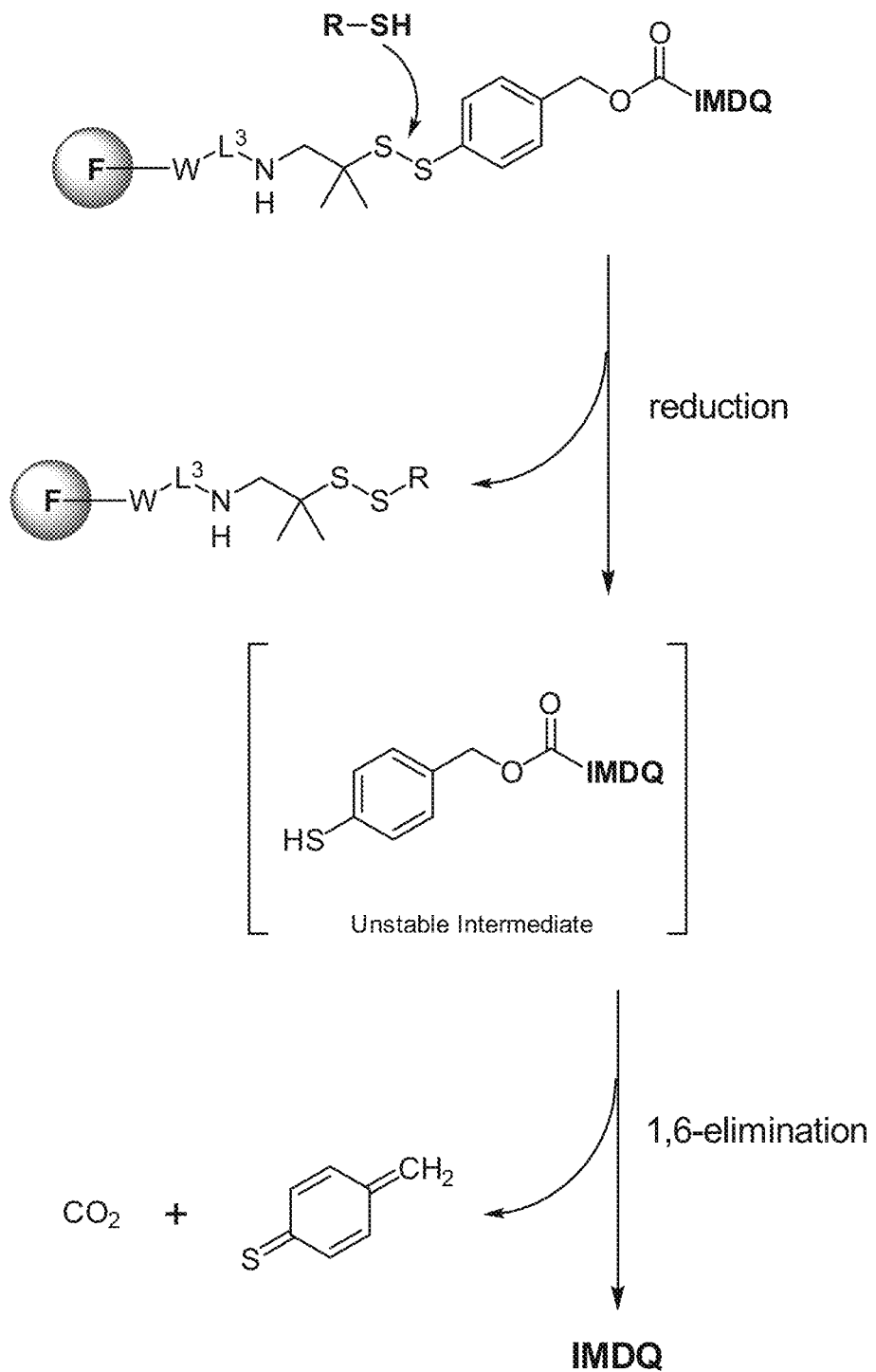
FIG. 3 depicts a mechanism of release of IMDQ from an exemplary compound of formula (I) containing a dimethyl disulfide cleavable linker.

In some embodiments, the cleavable linker moiety $L^2$ in formula (I) forms a disulfide linker (—S—S—) with the self-eliminating linker $L^1$ in formula (I) that can be subject to reductive thiolysis by elevated levels of reducing agents within the tumor microenvironment, to yield an unstable intermediate that self-immolates in such a manner to yield the original (i.e., unconjugated) TLR7/8 agonist moiety D (see, e.g., FIG. 3). Preferential disulfide linker cleavage in the tumor relies on the relatively high levels of reduced glutathione found in the tumor microenvironment and cytosol of tumor cells, relative to the lower levels of free cysteine in the plasma (see, e.g., Brulisauer, L. et al. 2014, *J Controlled Release* 195:147-154; Flygare et al. 2013, *Chem Biol Drug Des* 81:113-121; Yang et al. 2006, *PNAS* 103:13872-13877). It is understood by those skilled in the art that the balance between plasma stability and tumor cleavage of disulfide bonds (relative reductive thiolysis) can be tailored by the absence or presence of adjacent alkyl groups (see. e.g., Hamann, P. R. et al. 2002, *Bioconjugate Chem* 13:40-46; Lambert, J. M. 2013, *Br J Clin Pharmacol* 76:248-262).

In some embodiments, the cleavable linker $L^2$ in formula (I) is of the formula (L-2):

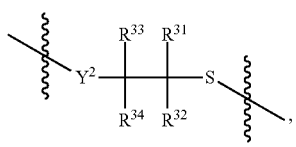
(L-2)

wherein $Y^2$ is $NR^{30}$, O or S; and $R^{30}$, $R^{31}$, $R^{32}$, $R^{33}$ and $R^{34}$ are independently H, optionally substituted alkyl, or optionally substituted cycloalkyl; or two of $R^{30}$, $R^{31}$, $R^{32}$, $R^{33}$ and $R^{34}$ are taken together with the atom(s) to which they are attached to form an optionally substituted cycloalkyl or optionally substituted heterocyclyl. The sulfur atom of formula (L-2) forms a disulfide bond with a sulfur atom of the $L^1$ moiety of formula (I), and $Y^2$ of (L-2) connects to the conjugation linker $L^3$.

In some embodiments, $Y^2$ is $NR^{30}$, O, or S; and $R^{30}$, $R^{31}$, $R^{32}$, $R^{33}$, and $R^{34}$ are independently H, $C_1$-$C_8$ alkyl, or $C_3$-$C_8$ cycloalkyl. In some embodiments, $Y^2$ is NH and $R^{31}$, $R^{32}$, $R^{33}$, and $R^{34}$ are independently H or $C_1$-$C_8$ alkyl. In some embodiments, $Y^2$ is NH, $R^{33}$ and $R^{34}$ are each H, and $R^{31}$ and $R^{32}$ are independently H or $C_1$-$C_8$ alkyl (e.g., methyl). In some embodiments, $Y^2$ is $NR^{30}$, where $R^{30}$ is $C_1$-$C_8$ alkyl (e.g., methyl). In some embodiments, $R^{31}$ and $R^{32}$ are each H. In some embodiments, $R^{31}$ is H and $R^{32}$ is $C_1$-$C_8$ alkyl (e.g., methyl). In some embodiments, $R^{31}$ and $R^{32}$ are independently $C_1$-$C_8$ alkyl (e.g., methyl). In some embodiments, $Y^2$ is NH; $R^{33}$ and $R^{34}$ are each H; and $R^{31}$ and $R^{32}$ are taken together with the carbon atom to which they are attached to form a $C_3$-$C_8$ cycloalkyl or 3- to 8-membered heterocyclyl. In some embodiments, $R^{31}$ and $R^{32}$ are taken together to form a $C_2$-$C_6$ alkylene or a $C_2$-$C_6$ alkylene, where one or more of the carbon atoms is replaced by a heteroatom selected from N, O and S (e.g., —$CH_2CH_2OCH_2CH_2$—).

In a some embodiments, $L^2$ is of the formula (L-2a), (L-2b), (L-2c), or (L-2d):

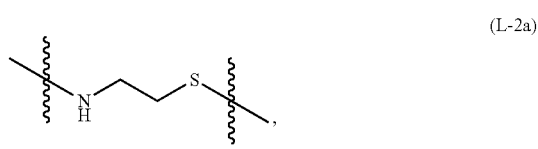
(L-2a)

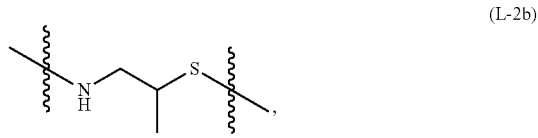
(L-2b)

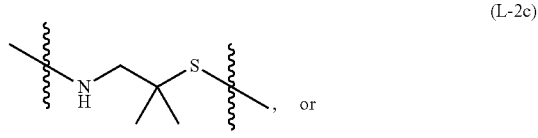
(L-2c)
or

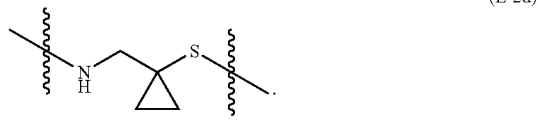
(L-2d)

Other disulfide linkers useful for drug conjugation are known in the art, for example, the disulfide linkers described in U.S. Pat. Nos. 7,276,248 and 7,592,307, the disclosures of which are incorporated herein by reference.

The cleavable linker $L^2$ is covalently conjugated to the self-eliminating linker $L^1$ in formula (I) (i.e., -$L^2$-$L^1$- in formula (I)). In some embodiments, $L^2$ is covalently conjugated to the self-eliminating linker $L^1$, wherein $L^1$ is of the formula (L-1):

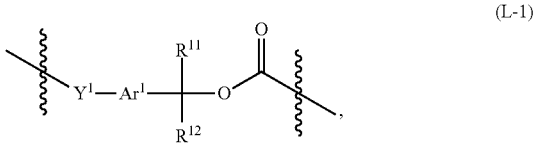

(L-1)

wherein $Y^1$ is S, O, or NH; $Ar^1$ is an optionally substituted arylene; and $R^{11}$ and $R^{12}$ are independently H or optionally substituted $C_1$-$C_8$ alkyl.

In some embodiments, $L^2$ is a peptide linker, $Y^1$ is NH, and the -$L^2$-$L^1$- moiety is of the formula (L-2-L-1):

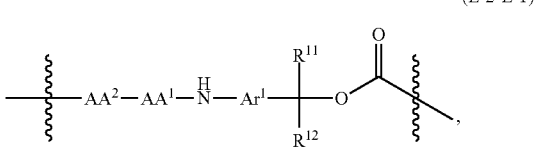

(L-2-L-1)

wherein $Ar^1$, $R^{11}$, and $R^{12}$ are as defined for formula (L-1), or any variations described herein, and $AA^1$ and $AA^2$ are independently amino acid residues. In some embodiments, $AA^1$ comprises a residue of an amino acid selected from the group consisting of lysine, lysine protected with acetyl or formyl, arginine, arginine protected with tosyl or nitro groups, histidine, ornithine, ornithine protected with acetyl or formyl, and citrulline (e.g., lysine or citrulline); and $AA^2$ comprises a residue of an amino acid selected from the group consisting of alanine, valine, leucine, isoleucine, methionine, phenylalanine, tryptophan and proline, (e.g., phenylalanine, leucine or valine). In some embodiments, $AA^1$ is a citrulline residue (Cit) and $AA^2$ is a valine residue (Val).

In some embodiments, $L^2$ forms a disulfide bond with the self-eliminating linker $L^1$ of formula (I). In some embodiments, $Y^1$ is S, and -$L^2$-$L^1$- is of the formula (L-2a-L-1a):

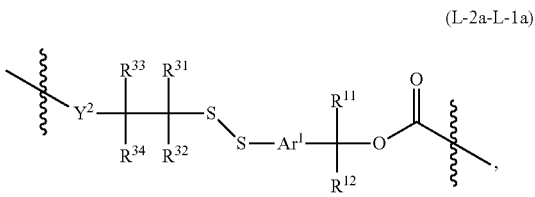

(L-2a-L-1a)

wherein $Ar^1$, $R^{11}$, and $R^{12}$ are as defined for formula (L-1), or any variations described herein, and $Y^2$, $R^{31}$, $R^{32}$, $R^{33}$ and $R^{34}$ are as defined for formula (L-2), or any variations described herein.

The descriptions of cleavable linkers provided herein are not meant to limit the scope of the invention as those skilled in the art will recognize that other cleavable linkers may be functionally equivalent.

In some embodiments, $L^1$ is a bond and the cleavable linker $L^2$ is directly linked to the TLR7/8 agonist moiety D.

D. Conjugation Moieties and Conjugation Linkers

One skilled in the art will recognize that there are several conjugation moieties/linkers (i.e., F—W—$L^3$- in formula (I)) that can be employed to promote either preferential accumulation of the compound of formula (I) in the tumor microenvironment, or to promote retention of the compound of formula (I) at the site of local administration. In some embodiments, the compound of formula (I) is a therapeutic agent. In some embodiments, the compound of formula (I) is a vaccine adjuvant. In some embodiments, the conjugation moiety/linker of the compound of formula (I) is comprised of a nano/microparticle-based conjugation moiety that is directly administered to the tumor by intratumoral injection, or administered to a tissue adjacent to a tumor lesion by subcutaneous or intramuscular injection for localized peritumoral retention. In some embodiments, the conjugation moiety/linker of the compound of formula (I) is comprised of a tumor-targeting antibody conjugation moiety (that is administered by intravenous, intraperitoneal, or subcutaneous injection for preferential accumulation of the compound of formula (I) in the tumor microenvironment. Nano/microparticle-based or antibody-based conjugation moieties (F—W—$L^3$- in formula (I)) can promote the preferential accumulation and/or retention of the compound of formula (I) in the tumor microenvironment or at the site of local administration, which allows for release of the original (i.e., unconjugated) form of the TLR7/8 agonist moiety D in formula (I) in the target tissue upon cleavage of the cleavable linker moiety $L^2$ and self-elimination of the self-eliminating linker $L^1$ in formula (I).

Particle-Based Conjugation Moieties

In some embodiments, the conjugation moiety F in formula (I) is a micro/nanoparticle-based conjugation moiety that can promote 1) preferential accumulation of the compound of formula (I) to the tumor microenvironment, or 2) retention of the compound of formula (I) at the site of local administration. In some embodiments, the conjugation moiety F of formula (I) possesses physical properties (e.g., charge, size, shape, hydrophobicity, etc.), or chemical modifications of the surface (e.g., tumor cell specific binding ligands) that can promote 1) preferential accumulation of the compound of formula (I) to the tumor microenvironment, or 2) retention of the compound of formula (I) at the site of local administration. The preferential accumulation or retention of compound of formula (I) in the target tissue promoted by conjugation moiety F subsequently allows target tissue release of the TLR7/8 agonist moiety D to occur upon subsequent cleavage of the cleavable linker $L^2$ and self-elimination of the self-eliminating linker $L^1$.

In some embodiments, the particle-based conjugation moiety is a nanoparticle polymer (e.g., a branched copolymer of sucrose and epichlorohydrin, more specifically Ficoll®). In some embodiments, the conjugation moiety is a high molecular weight polysaccharide (e.g., a dextran). In some embodiments, the conjugation moiety is a synthetic polymer [e.g., poly(hydroxypropylmethacrylamide)]. In some embodiments, the conjugation moiety is a dendrimer (e.g., a tris(2-aminoethyl)amine derived dendrimer). In some embodiments, the conjugation moiety is a polypeptide (e.g., a cancer antigen). In some embodiments, the conjugation moiety is a protein. In some embodiments, the conjugation moiety is a virus-like particle. In some embodiments, the conjugation moiety moiety is monovalent, that is, each conjugation moiety moiety is attached to one TLR7/8 agonist moiety (for example, a compound of formula (I) where x is 1). In some embodiments, the conjugation moiety moiety is multivalent, that is, each conjugation moiety moiety is capable of attaching multiple TLR7/8 agonist moieties, for example, a compound of formula (I) where x is greater than 1 (e.g., up to 500).

Macromolecules, Supramolecule, Nanoparticles, Microparticles

Macromolecules and supramolecules that preferentially target the TLR7/8 agonist compound to the tumor microenvironment or enhance local retention at desired anatomical sites are useful as conjugation moieties for the cleavable conjugates of the present disclosure, in particular macromolecules and supramolecules having molecular weight of about 5,000 daltons to about 2,000,000 daltons, for example, nanoparticle polymers (e.g., a branched copolymer of sucrose and epichlorohydrin, more specifically Ficoll®), high molecular weight polysaccharides (e.g., a dextran), and synthetic polymers (e.g., poly(hydroxypropylmethacrylamide)).

In some embodiments, the macromolecule or supramolecule conjugation moiety is a nanoparticle polymer of ≥10 nm in diameter. In some embodiments, the nanoparticle polymer is of 10-150 nm in diameter. In some embodiments, the macromolecule or supramolecule is a branched copolymer of sucrose and epichlorohydrin, or an epichlorohydrin-crosslinked sucrose, e.g., branched copolymer of sucrose and epichlorohydrin branded as FICOLL® by GE Healthcare. In some embodiments, the macromolecule or supramolecule conjugation moiety is a high molecular weight polysaccharide. In some embodiments, the macromolecule or supramolecule conjugation moiety is a synthetic polymer (e.g., poly(hydroxypropylmethacrylamide)).

Polysaccharides derivatized to enable linking to TLR7/8 agonist moieties can be used as a conjugation moiety for the cleavable conjugates of the present disclosure. Suitable polysaccharides can be naturally occurring polysaccharides or synthetic polysaccharides. Exemplary polysaccharides include, e.g., dextran, mannin, chitosan, agarose, and starch. In some embodiments, the polysaccharide is cross-linked.

In some embodiments, the present disclosure provides a cleavable conjugate of the formula (I) where the conjugation moiety F is a macromolecule or supramolecule. In some embodiments, the macromolecule or supramolecule is a branched copolymer of sucrose and epichlorohydrin having a molecular weight of about 50,000 to about 1,000,000 daltons, which is connected to $L^3$ via an ether linkage. The ether linkage is derived from a hydroxyl group of the sucrose in the copolymer. In some embodiments, the macromolecule or supramolecule conjugation moiety of F is a branched copolymer of sucrose and epichlorohydrin having a molecular weight greater than (lower limit) about 50,000, 60,000, 70,000, 80,000, 100,000, 200,000, 300,000, 400,000, or 500,000 daltons. In some embodiments, the macromolecule or supramolecule conjugation moiety F is a branched copolymer of sucrose and epichlorohydrin having a molecular weight less than (upper limit) about 1,000,000, 900,000, 800,000, 700,000, 600,000, 500,000, 400,000, 300,000, or 200,000 daltons. That is, the molecular weight of the macromolecule or supramolecule conjugation moiety F can be any of a range of sizes from about 50,000 to about 1,000,000 daltons, in which the lower limit is less than the upper limit. In some embodiments, the macromolecule or supramolecule conjugation moiety of F has a molecular weight of from about 300,000 to 1,000,000 daltons (e.g., FICOLL® PM 400 of GE Healthcare). In some embodiments, the macromolecule or supramolecule conjugation moiety F has a molecular weight of from about 20,000 to 100,000 daltons (e.g., FICOLL® PM 70 of GE Healthcare).

In some embodiments, the conjugation moiety F is a polysaccharide (e.g. a dextran) having a molecular weight of about 5,000 to about 2,000,000 daltons, which is connected to $L^3$ via an ether linkage derived from a hydroxyl group in the polysaccharide. In some embodiments, the conjugation moiety F is a polysaccharide (e.g. a dextran) having a molecular weight greater than (lower limit) about 5,000, 10,000, 25,000, 50,000, 100,000, 200,000, 500,000, or 1,000,000 daltons. In some embodiments, the conjugation moiety F is a polysaccharide having a molecular weight less than (upper limit) about 2,000,000, 1,000,000, 500,000, 200,000, 100,000, 50,000, 20,000, or 10,000 daltons. That is, the molecular weight of the polysaccharide can be any of a range of sizes from about 5,000 to about 2,000,000 daltons, in which the lower limit is less than the upper limit.

For conjugates where the conjugation moiety F is a polysaccharide (e.g., dextran) or a branched copolymer of sucrose and epichlorohydrin (e.g., Ficoll®), the number of TLR7/8 agonists D in the compound of formula (I) can range from 3 to about 500. That is, x is an integer from 3 to 500. In some embodiments, x is an integer greater than (lower limit) 3, 6, 9, 12, 20, 30, 40, 50, 60, 70, 80, 90, 100, 110, 120, 130, 140, 150, 160, 180, 200, 250, or 300. In some embodiments, x is an integer less than (upper limit) 500, 400, 300, 275, 250, 225, 200, 190, 180, 160, 150, 140, 130, 120, 110, 100, 90, 80, 70, 60, 50, 40, or 30. That is, x can be an integer in the range of from about 3 to 500, in which the lower limit is less than the upper limit. For instance, in some embodiments, x is from 20 to 500, from 20 to 200, from 30 to 180, from 30 to 150, from 50 to 100, from 60 to 180, from 90 to 150, from 100 to 140, or from 110 to 130. In some embodiments, x is about 120±30, or about 70±20.

The loading level of the TLR7/8 agonist moieties D in the compound of formula (I) can also be expressed as the number of the TLR7/8 agonist moieties D relative to the molecular weight of the compound of formula (I), for example, the number of TLR7/8 agonist moieties D per 100,000 daltons (or 100 kDa) of the compound of formula (I) ("relative loading ratio"). In some embodiments, the compound of formula (I) contains between about 1 and about 200 of the TLR7/8 agonist moieties D per 100 kDa molecular weight of the conjugation moiety F, that is, a relative loading ratio of between about 1 and about 200 of D per 100 kDa of F. In some embodiments, the relative loading ratio is about 5, 10, 15, 20, 25, 30, 40, 50, 60, 70, 80, 90, 100, 110, 120, 130, 140, 150, 160, 170, 180, 190, or 200 of D per 100 kDa of F. In some embodiments, the relative loading ratio is greater than (lower limit) 3, 6, 9, 12, 20, 30, 40, 50, 60, 70, 80, 90, 100, 110, 120, 130, 140, 150, 160, or 180 of D per 100 kDa of F. In some embodiments, the relative loading ratio is less than (upper limit) 200, 190, 180, 160, 150, 140, 130, 120, 110, 100, 90, 80, 70, 60, 50, 40, or 30 of D per 100 kDa of F. The relative loading ratio can be in the range of from about 1 to 200 of D per 100 kDa of F, in which the lower limit is less than the upper limit. For instance, in some embodiments, the relative loading ratio is between about 5 and about 200 of D per 100 kDa of F, between about 10 and about 180 of D per 100 kDa of F, between about 10 and about 50 of D per 100 kDa of F, between about 10 and about 20 of D per 100 kDa of F, between about 20 and about 200 of D per 100 kDa of F, between about 20 and about 100 of D per 100 kDa of F, between about 20 and about 50 of D per 100 kDa of F, between about 30 and about 150 of D per 100 kDa of F, between about 40 and about 100 of D per 100 kDa of F, between about 50 and about 150 of D per 100 kDa of F, between about 50 and about 100 of D per 100 kDa of F, between about 80 and about 200 of D per 100 kDa of F, between about 80 and about 160 of D per 100 kDa of F, between about 80 and about 120 of D per 100 kDa of F, between about 100 and about 200 of D per 100 kDa of F, between about 100 and about 150 of D per 100 kDa of F, between about 120 and about 200 of D per 100 kDa of F, between about 120 and about 150 of D per 100 kDa of F, or between about 150 and about 200 of D per 100 kDa of F.

Dendrimers

Dendrimers can also be used to target the TLR7/8 agonist compound preferentially to the tumor microenvironment or enhance local retention at desired anatomical sites. In some embodiments, the present disclosure provides a compound of formula (I) where the conjugation moiety F is a dendrimer, and where the TLR7/8 agonist moiety D is covalently linked to the terminal functional group of the dendrimer via a cleavable linker.

In some embodiments, the dendrimer is a tris(2-aminoethyl)amine derived dendrimer, which is connected to the conjugation linker $L^3$ via the terminal amino groups. In some embodiments, provided is a compound of formula (II):

$$\{N(CH_2CH_2N)_3\}[-L^3-L^2-L^1-D]_6 \qquad (II)$$

wherein $L^3$, $L^2$, $L^1$, and D are as defined for formula (I), or any variations thereof detailed herein. )

Other dendrimers can also be used as the conjugation moiety F for the cleavable conjugate of the present disclosure, for example, the 2,2-bismethylolpropionic acid (bis-MPA) based dendrimers described in Carlmark et al. 2013 *Chem. Soc. Rev.*, 42:5858-5879, the disclosures of which are incorporated herein by reference.

Figure 16:
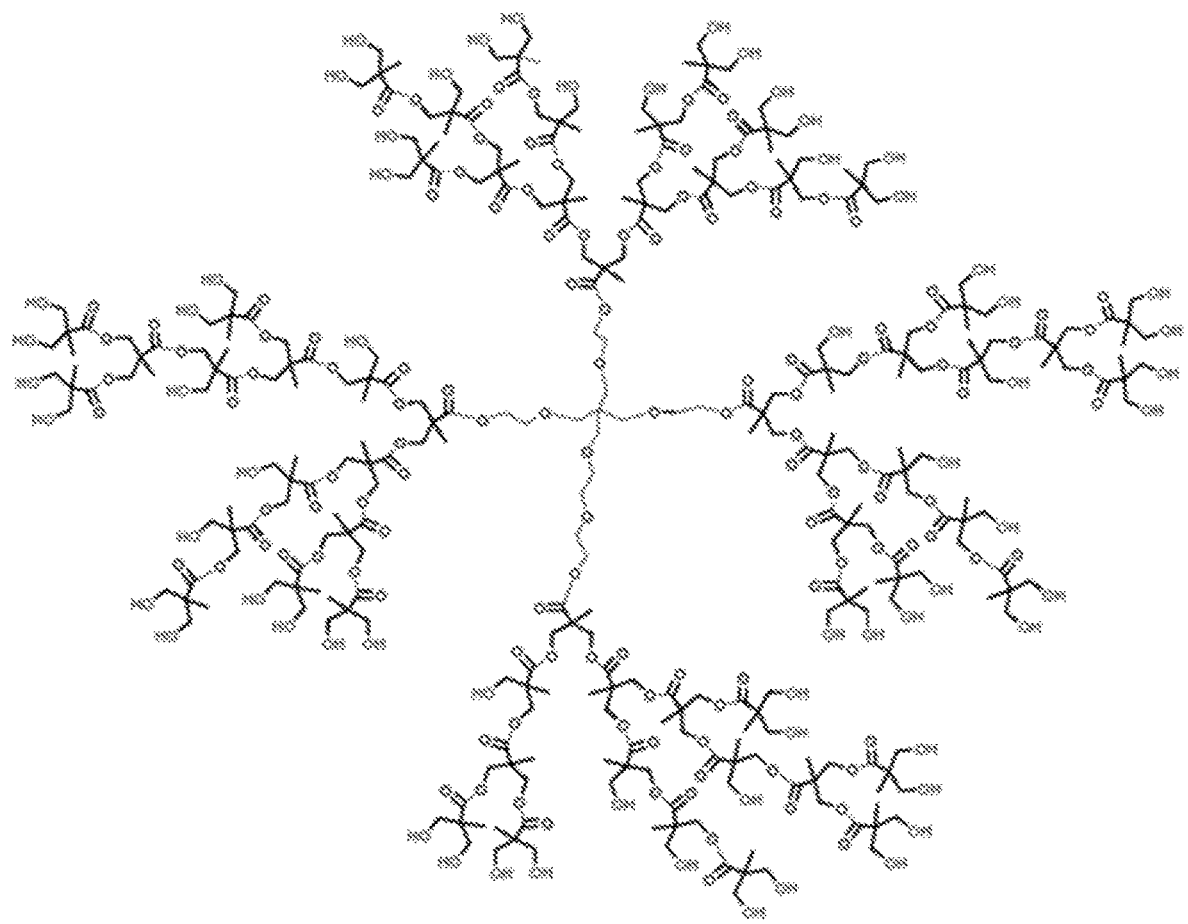
FIG. 16 shows a bis-MPA dendrimer of the formula (F-1), which is linked to the TLR7/8 agonist D via an ether linkage derived from the hydroxyl groups.

In some embodiments, the conjugation moiety F of formula (I) is a bis-MPA dendrimer of the formula (F-1) depicted in FIG. 16, which is linked to the TLR7/8 agonist D via an ether linkage derived from the hydroxyl groups, wherein $L^3$, $L^2$, $L^1$, and D are as defined for formula (I), or any variations thereof detailed herein, and x is 16 to 64.

In some embodiments, the conjugation moiety F of formula (I) is a poly(ethylene glycol)-based bis-MPA dendrimer of the formula (F-2), which is linked to the TLR7/8 agonist D via an ether linkage derived from the hydroxyl groups:

(F-2)

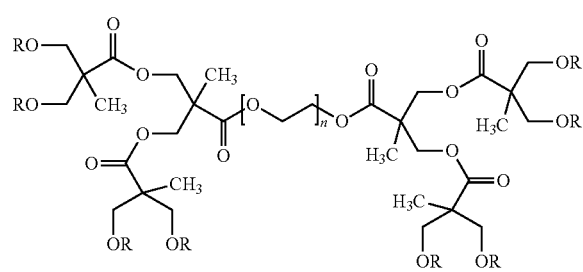

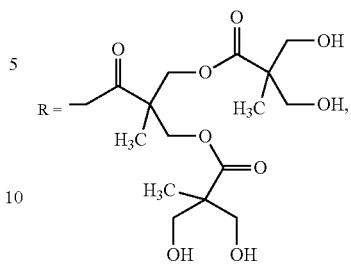

wherein n is 100 to 1000; $L^3$, $L^2$, $L^1$, and D are as defined for formula (I), or any variations thereof detailed herein; and x is 4 to 32. In some embodiments, the poly(ethylene glycol)-based bis-MPA dendrimer has a molecular weight of about 5,000 to about 50,000 daltons (e.g., the PEG-core dendrimers available from Sigma-Aldrich®).

In some embodiments, the conjugation moiety F is a polyamidoamine (PAMAM)-based dendrimer, for example, the core structures as shown in Scheme F-3, which can be linked to the TLR7/8 agonist moiety D, for example, via an ether linkage derived from the surface hydroxyl groups in the PAMAM molecule:

Scheme F-3

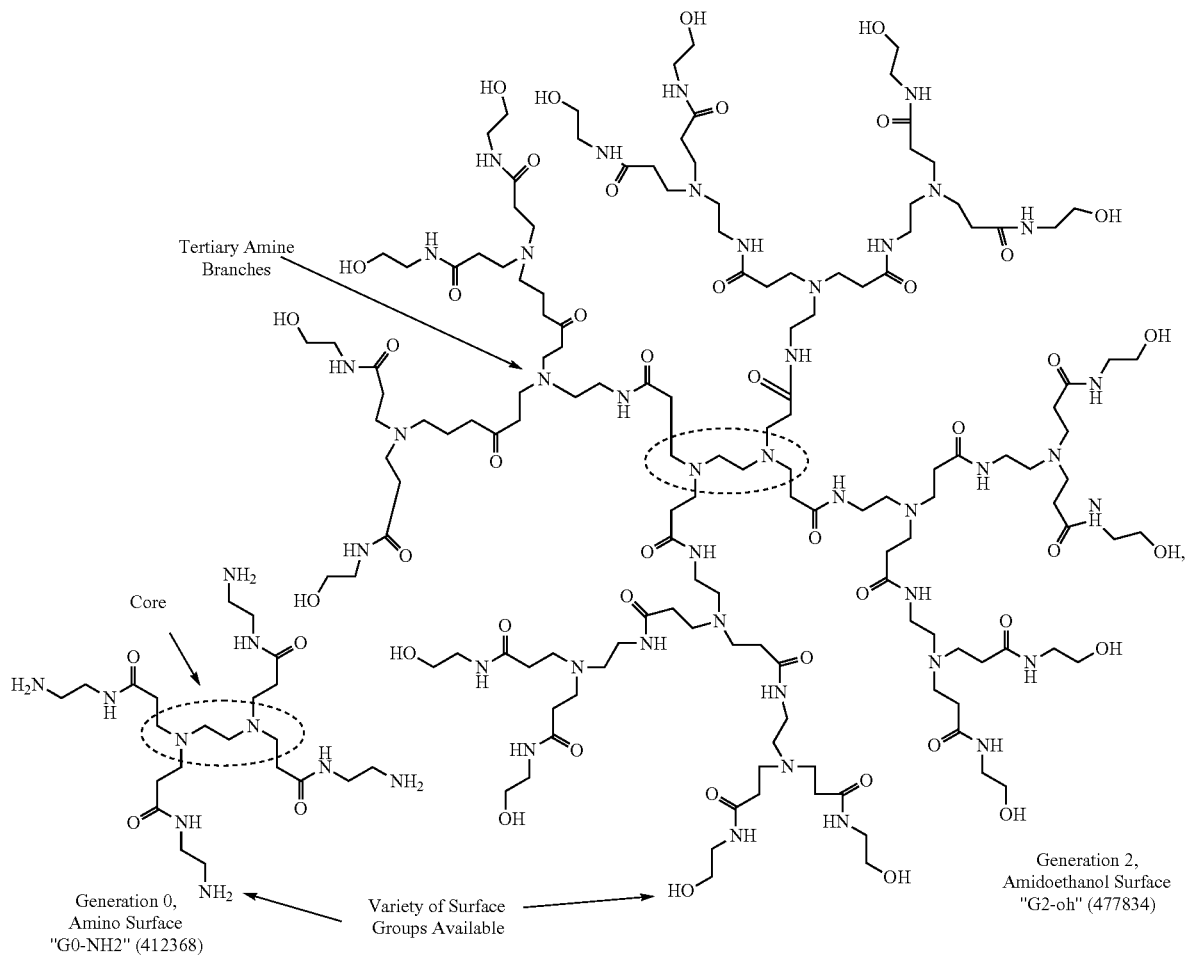

wherein $L^3$, $L^2$, $L^1$, and D are as defined for formula (I), or any variations thereof detailed herein, and x is 16 (or higher, up to 4000, where the core structure is further extended). The compound of formula (I), where the conjugation moiety F is a dendrimer, can be made using methods known in the art and methods described herein. For example, the surface hydroxyl groups on the dendrimers described herein can be converted to propargylamine-carboxymethyl (PACM) groups for reaction with an azide-linked-IMDQ compound using click chemistry (see, e.g., Kolb, H. C. et al. 2001, *Angew Chem Int Ed Engl* 40:2004-2021; Kolb, H. C. and Sharpless, K. B. 2003, *Drug Discov Today* 8:1128-1137), similar to the methods described herein for linking IMDQ to the hydroxyl groups on the surface of a Ficoll®.

Polypeptides

In some embodiments, the present disclosure provides a compound of formula (I), where the conjugation moiety F is a polypeptide, for example, comprising at least 9 amino acid residues. In some embodiments, the polypeptide conjugation moiety of F is a polypeptide antigen. In some embodiments, the polypeptide of F is a cancer antigen. In some embodiments, the polypeptide of F is a viral antigen, a bacterial antigen, or an allergen antigen. In some embodiments, the polypeptide of F comprises a polyalanine. In some embodiments, the polypeptide of F comprises a polyglutamic acid. In some embodiments, the polypeptide of F is not an antigen.

The TLR7/8 agonist D conjugated to an antigen can serve to enhance the immunological response of the antigen (e.g., a cancer antigen). For antigen conjugates, typically 1 to up to 30 TLR7/8 agonist moieties D can be linked to each polypeptide molecule F (via any of the applicable —W-$L^3$-$L^2$-$L^1$-linkers detailed herein), i.e., x is an integer from 1 to 30. In some embodiments, x is 1 to 20, 1 to 10, 1 to 5, 2 to 30, 2 to 20, 2 to 10, 2 to 5, 3 to 30, 3 to 20, 3 to 15, 3 to 10, 5 to 30, 5 to 20, 5 to 15, or 5 to 10. The tumor antigen comprises the amino acid sequence of at least one full length protein or fragment thereof. Suitable tumor antigens have been described in the art (see, e.g., Cheever et al., 2009, *Clinical Cancer Research*, 15:5323-5337; and Caballero and Chen, 2009, *Cancer Science*, 100:2014-2021). For example, suitable tumor antigens include, but are not limited to, WT1, MUC1, LMP2, HPV E6, HPV E7, EGFRvIII, Her-2/neu, idiotype, MAGE A3, p53, NY-ESO-1 (CTAG1B), PSMA, GD2, CEA, MelanA/Mart1, Ras, gp100, proteinase 3, bcr-able, tyrosinase, survivin, PSA, hTERT, sarcoma translocation breakpoints, EphA2, PAP, MP-IAP, AFP, EpCAM, ERG, NA17-A, PAX3, ALK, androgen receptor, cyclin B1, MYCN, PhoC, TRP-2, mesothelin, PSCA, MAGE A1, —CYP1B1, PLAC1, BORIS, ETV6-AML, NY-BR-1, RGSS, SART3, carbonic anhydrase IX, PAX5, OY-TES1, sperm protein 17, LCK, HMWMAA, AKAP-4, SSX2, XAGE 1, B7-H3, legumain, Tie 2, Page4, VEGFR2, MAD-CT-1, FAP, PAP, PDGFR-beta, MAD-CT-2, CEA, TRP-1 (gp75), BAGE1, BAGE2, BAGE3, BAGE4, BAGE5, CAMEL, MAGE-A2, MAGE-A4, MAGE-A5, MAGE-A6, MAGE-A8, MAGE-A9, MAGE-A10, MAGE-A11, MAGE-A12, and Fos-related antigen 1. The amino acid sequences of representative tumor antigens are catalogued in the UniProtKB database under the accessions numbers listed in Table 4, and are incorporated by reference herein.

TABLE 4

Tumor Antigens

| Tumor Antigen | Protein | Gene | UniProtKB Accession No. |
|---|---|---|---|
| WT-1 | Wilms tumor protein | WT1 | P19544 |
| MUC-1 | Mucin-1 | MUC1 | P15941 |
| LMP2 | Latent membrane protein 2 | LMP2 | P13285 |
| HPV E6 | HPV Protein E6 | E6 | P03126 |
| HPV E7 | HPV Protein E7 | E7 | P03129 |
| EGFRvIII | Epidermal growth factor receptor | EGRF | P00533 |
| Her-2/neu | Receptor tyrosine-protein kinase erbB-2 | ERBB2 | P04626 |
| MAGE A1 | Melanoma-associated antigen 1 | MAGEA1 | P43355 |
| MAGE A2 | Melanoma-associated antigen 2 | MAGEA2 | P43356 |
| MAGE A3 | Melanoma-associated antigen 3 | MAGEA3 | P43357 |
| MAGE A4 | Melanoma-associated antigen 4 | MAGEA4 | Q1RN33 |
| MAGE A5 | Melanoma-associated antigen 5 | MAGEA5 | P43359 |
| MAGE A6 | Melanoma-associated antigen 6 | MAGEA6 | P43360 |
| MAGE A8 | Melanoma-associated antigen 8 | MAGEA8 | P43361 |
| MAGE A9 | Melanoma-associated antigen 9 | MAGEA9 | P43362 |
| MAGE A10 | Melanoma-associated antigen 10 | MAGEA10 | P43363 |
| MAGE A11 | Melanoma-associated antigen 11 | MAGEA11 | P43364 |
| MAGE A12 | Melanoma-associated antigen 12 | MAGEA12 | Q6FHH8 |
| p53 | Cellular tumor antigen p53 | TP53 | P04637 |
| NY-ESO-1 | Cancer/testis antigen 1 | CTAG1A | P78358 |
| PSMA | Glutamate carboxypeptidase 2 | FOLH1 | Q04609 |
| CEA | Carcinoembryonic antigen-related cell adhesion molecule 1 | CEACAM1 | P13688 |
| MelanA/Mart1 | Melanoma antigen recognized by T-cells 1 | MLANA | Q16655 |
| Ras | GTPase KRas | KRAS | P01116 |
| gp100 | Melanocyte protein PMEL | PMEL | P40967 |
| Proteinase 3 | Proteinase 3 | PRTN3 | D6CHE9 |
| bcr-able | Tyrosine-protein kinase ABL1 | ABL1 | P00519 |
| tyrosinase | Tyrosinase | TYR | P14679 |
| survivin | Baculoviral IAP repeat-containing protein 5 | BIRC5 | O15392 |
| PSA | Prostate-specific antigen | KLK3 | P07288 |
| hTERT | Telomerase reverse transcriptase | TERT | O14746 |
| sarcoma translocation breakpoints | RNA-binding protein EWS | EWSR1 | Q01844 |

TABLE 4-continued

Tumor Antigens

| Tumor Antigen | Protein | Gene | UniProtKB Accession No. |
|---|---|---|---|
| EphA2 | Ephrin type-A receptor 2 | EPHA2 | P29317 |
| PAP | Prostatic acid phosphatase | ACPP | P15309 |
| MP-IAP | Baculoviral IAP repeat-containing protein 7 | BIRC7 | Q96CA5 |
| AFP | Alpha-fetoprotein | AFP | P02771 |
| EpCAM | Epithelial cell adhesion molecule | EPCAM | P16422 |
| ERG | Transcriptional regulator ERG | ERG | P11308 |
| NA17-A | Alpha-1,6-mannosylglycoprotein 6-beta-N-acetylglucosaminyltransferase A | MGAT5 | Q09328 |
| PAX3 | Paired box protein Pax-3 | PAX3 | P23760 |
| ALK | ALK tyrosine kinase receptor | ALK | Q9UM73 |
| androgen receptor | Androgen receptor | AR | P10275 |
| cyclin B1 | G2/mitotic-specific cyclin-B1 | CCNB1 | P14635 |
| MYCN | N-myc proto-oncogene protein | MYCN | P04198 |
| TRP-2 | L-dopachrome tautomerase | DCT | P40126 |
| mesothelin | Mesothelin | MSLN | Q13421 |
| PSCA | Prostate stem cell antigen | PSCA | O43653 |
| CYP1B1 | Cytochrome P450 1B1 | CYP1B1 | Q16678 |
| PLAC1 | Placenta-specific protein | PLAC1 | Q9HBJ0 |
| BORIS | Transcriptional repressor CTCFL | CTCFL | Q8NI51 |
| ETV6-AML | Transcription factor ETV6 | ETV6 | P41212 |
| NY-BR-1 | Ankyrin repeat domain-containing protein 30A | ANKRD30A | Q9BXX3 |
| RGS5 | Regulator of G-protein signaling 5 | RGS5 | O15539 |
| SART3 | Squamous cell carcinoma antigen recognized by T-cells 3 | SART3 | Q15020 |
| carbonic anhydrase IX | Carbonic anhydrase 9 | CA9 | Q16790 |
| PAX5 | Paired box protein Pax-5 | PAX5 | Q02548 |
| OY-TES1 | Acrosin-binding protein | ACRBP | Q8NEB7 |
| sperm protein 17 | Sperm surface protein Sp17 | SPA17 | Q15506 |
| LCK | Tyrosine-protein kinase Lck | LCK | P06239 |
| HMWMAA | Chondroitin sulfate proteoglycan 4 | CSPG4 | Q6UVK1 |
| AKAP-4 | A-kinase anchor protein 4 | AKAP4 | Q5JQC9 |
| SSX2 | Protein SSX2 | SSX2 | Q16385 |
| XAGE 1 | X antigen family member 1 | XAGE 1 | Q9HD64 |
| B7-H3 | CD276 antigen | CD276 | Q5ZPR3 |
| legumain | Legumain | LGMN | Q99538 |
| Tie 2 | Angiopoietin-1 receptor | TEK | Q02763 |
| Page4 | P antigen family member 4 | PAGE4 | O60829 |
| VEGFR2 | Vascular endothelial growth factor receptor 2 | KDR | P35968 |
| MAD-CT-1 | Sperm protamine P1 | PRM1 | P04553 |
| MAD-CT-2 | Protamine-2 | PRM2 | P04554 |
| FAP | Prolyl endopeptidase FAP | FAP | Q12884 |
| PAP | Prostatic acid phosphatase | ACPP | P15309 |
| PDGFR-beta | Platelet-derived growth factor receptor beta | PDGFRB | P09619 |
| CEA | Carcinoembryonic antigen-related cell adhesion molecule 5 | CEACAM5 | P06731 |
| TRP-1 (gp75) | 5,6-dihydroxyindole-2-carboxylic acid oxidase | TYRP1 | P17643 |
| BAGE1 | B melanoma antigen 1 | BAGE1 | Q13072 |
| BAGE2 | B melanoma antigen 2 | BAGE2 | Q86Y30 |
| BAGE3 | B melanoma antigen 3 | BAGE3 | Q86Y29 |
| BAGE4 | B melanoma antigen 4 | BAGE4 | Q86Y28 |
| BAGE5 | B melanoma antigen 5 | BAGE5 | Q86Y27 |
| CAMEL | CTL-recognized antigen on melanoma | CAMEL | O95987 |
| Fos-related antigen 1 | Fos-related antigen 1 | FOSL1 | P15407 |

In some embodiments, the tumor antigen comprises an amino acid sequence or fragment thereof from one or more of the group consisting of gp100, hTERT, MAGE A1, MAGE A3, MAGE A10, MelanA/Mart1, NY-ESO-1 (CTAG1B), PSA, Ras, survivin, TRP1 (gp75), TRP2, and tyrosinase. In some embodiments, the tumor antigen comprises a mammalian antigen (e.g., Triple peptide) or a viral antigen (e.g., HPV1 E6 and/or HPV E7) expressed by the tumor. In some embodiments, the mammalian antigen is a neoantigen or is encoded by a gene comprising a mutation relative to the gene present in normal cells from the mammalian subject. Neoantigens are thought to be particularly useful in enabling T cells to distinguish between cancer cells and non-cancer cells (see, e.g, Schumacher and Schreiber, 2015, *Science* 348:69-74; Desrichard et al., 2016, *Clinical Cancer Res*, 22:8-7-812; Wang and Wang, 2017, *Cell Research* 27:11-37).

The polypeptide of F can be linked to the TLR7/8 agonist-containing portion of the compound of formula (I) ($-L^3-L^2-L^1-D$) through a cysteine, N-terminal amine, lysine, tyrosine, methionine, arginine, glutamate, or aspartate residue. In some embodiments, W is S and F is a polypeptide moiety (linked to $L^3$ via a cysteine thiol). In some embodiments, W is NH and F is a polypeptide moiety (linked to $L^3$ via an amino group, e.g., of an N-terminal amine or a lysine residue).

In some embodiments, the conjugation moiety F of formula (I) is a virus-like particle (VLP).

The compound of formula (I), where the conjugation moiety F is a polypeptide or a VLP, can be synthesized using methods know in the art and methods described herein. The polypeptide or VLP can be linked to the TLR7/8 agonist-containing portion of the compound of formula (I) ($-L^3-L^2-L^1$-D) by using the hydroxyl, thiol, amino, or carboxy groups present in an amino acid residue of the polypeptide or VLP. For example, a hydroxyl group can be converted to an ether linkage using the methods described herein for conjugating Ficoll® via the hydroxyl group. A thiol group can be converted to a thioether linkage or to a succimide spacer by reacting with a maleimide compound.

It is intended and understood that each and every variation of F detailed herein for the compound of formula (I) can be combined with each and every variation of D detailed herein for the compound of formula (I) as if each and every combination is individually described. For example, in some embodiments, provided is a compound of formula (I):

F—[W-$L^3$-$L^2$-$L^1$-D]$_x$     (I)

wherein:
D is a TLR7/8 agonist moiety;
$L^1$ is a bond or a self-eliminating linker;
$L^2$ is a cleavable linker;
$L^3$ is a conjugation linker;
W is O, S, or $NR^{10}$;
$R^{10}$ is H or $C_1$-$C_8$ alkyl;
x is an integer from 3 to 300; and
F is a branched copolymer of sucrose and epichlorohydrin having a molecular weight of about 50,000 to about 700,000 daltons (e.g., FICOLL® PM 400 of GE Healthcare);
wherein D is a 1H-imidazo[4,5-c]quinoline derivative.

In some embodiments, W is O (i.e., F is connected to $L^3$ via an ether linkage).

In some embodiments, the compound of formula (I) is a polymeric prodrug comprising a TLR7/8 agonist moiety D linked to a conjugation moiety F via a cleavable linker $L^2$, a self-eliminating linker $L^1$, a conjugation linker $L^3$, and a connector W as —W-$L^3$-$L^2$-$L^1$-, wherein $L^1$ is a self-eliminating linker; $L^2$ is cleavable linker; $L^3$ is a conjugation linker; and W is O, S, or $NR^{10}$, where $R^{10}$ is H or $C_1$-$C_8$ alkyl. In some embodiments where $L^1$ is a bond, the compound of formula (I) is a polymeric prodrug comprising a TLR7/8 agonist moiety D linked to a conjugation moiety F via a cleavable linker $L^2$, a conjugation linker $L^3$, and a connector W as —W-$L^3$-$L^2$-, wherein $L^2$ is cleavable linker; $L^3$ is a conjugation linker; and W is O, S, or $NR^{10}$, where $R^{10}$ is H or $C_1$-$C_8$ alkyl.

Antibody-Based Conjugation Moieties

In some embodiments, the conjugation moiety F in formula (I) is a tumor-targeting antibody conjugation moiety that causes preferential accumulation of the compound of formula (I) to the tumor microenvironment by the antibody's ability to preferentially bind to tumor cell surface antigens, unique structural elements of the tumor microenvironment extracellular matrix, or unique structural elements of the tumor vasculature. This allows for local release of the TLR7/8 agonist moiety upon subsequent hydrolysis of the cleavable linker $L^2$ and, where $L^1$ is a self-eliminating linker, self-elimination of the self-eliminating linker $L^1$. In some embodiments, $L^1$ is a bond and local release of the TLR7/8 agonist moiety occurs upon subsequent hydrolysis of the cleavable linker $L^2$.

Antibody drug conjugates (ADCs) consist of 3 main structural units: recombinant antibodies that bind specifically to protein targets in the tumor microenvironment; highly potent cytotoxic agents; and stable synthetic linkers that connect the recombinant antibodies to the cytotoxic agents by covalent conjugation (see, e.g., Beck, A. et al. 2017, *Nature Rev Drug Discovery* 16:315-337; Sau, S. et al. 2017, *Drug Discov Today* 22:1547-1556). Conjugation to tumor-targeted antibodies improves the therapeutic window of these highly potent cytotoxic agents by preferentially accumulating the ADC in the tumor microenviroment, where the original (i.e., unconjugated) cytoxic agent is then released by preferential cleavage of the cleavable linker. There are currently more than 60 ADC therapeutics that are either approved by the U.S. Food and Drug Administration (FDA) or are currently in clinical trials. A key attribute contributing to anti-tumor efficacy of ADCs is the tumor-targeting antibody, and a survey of the field indicates that a wide variety of antibody targets are currently being investigated (see, e.g., Beck, A. et al. 2017, *Nature Rev Drug Discovery* 16:315-337; Sau, S. et al. 2017, *Drug Discov Today* 22:1547-1556; and Wagh, A. et al. 2018, *MABS* 10:222-243).

Another key attribute of ADCs is the extent and uniformity of loading of the cleavable linker/cytotoxic agent on the antibody, commonly referred to as the antibody:drug ratio. Studies have shown that ADCs with a controlled and uniform stoichiometry (generally antibody:drug ratios are between 2 and 6-8 for highly hydrophobic cytotoxic agents) display superior plasma half-life that translates into increased in vivo efficacy (Sun, X. et al. 2017, *Bioconjug Chem* 28:1371-1381; Lyon, R. P. et al. 2015, *Nat Biotechnol* 33:733-735). Control over the extent and uniformity of loading of the cleavable linker/cytotoxic agent on the antibody is imparted by the specific conjugation chemistry employed, including the choice of reactive moieties on the synthetic linker and the antibody. Initial ADC constructs involved conjugation of the cleavable linker-cytotoxic agent to native lysine and cysteine amino acids within the primary sequence of the antibody (see, e.g., Lu, J. et al. 2016, *Int J Mol Sci* 14:561; Jain N. et al. 2015, *Pharma Res* 32:3526-3540). However, more recent developments of cleavable linker-cytotoxic agent conjugation chemistries allow for more precise control over the antibody:drug ratio by creating a more highly defined number of reactive sites on the antibody, together with linker chemistries that are more stable in the plasma (see, e.g., Agarwal, P. et al. 2013, *Bioconjug Chem* 24:846-851; Kato, A. et al. 2017, *Bioconjug Chem* 28:2099-2108; Sadowsky, J. et al. 2017, *Bioconjug Chem* 28:2086-2098; Grunewald, J. et al. 2017, *Bioconjug Chem* 28:1906-1915; Tang, F. et al. 2017, *Nature Protocols* 12:1702-1721).

In some embodiments, the conjugation moiety F in formula (I) is an antibody or an antibody derivative. In some embodiments, F is an antibody with a murine sequence, a 'humanized' murine sequence, or a fully human sequence. In some embodiments, F is an antibody of the IgG1, 2, or 4 class, or a derivative or fragment thereof, including but not limited to bivalent monospecific antibodies, bivalent bispecific antibodies, and the like, or derivatives without Fc regions including single-chain variable fragments (scFv), and derivatives such as tandem divalent-scFvs, diabodies, tandem trivalent-scFvs, triabodies, bispecific tandem divalent-scFvs, and the like (see, e.g., Weidle, U. H. et al. 2014, *Seminars in Oncology* 41:653-660, and the like). In some embodiments, the IgG scaffold is engineered to modulate the effector functions of the molecule (see e.g., Warncke, M. et al. 2012, *J Immunol* 188:4405-4411; Jacobsen, F. W. et al. 2017, *J Biol Chem* 292:1865-1875; and the like).

The descriptions of ADCs provided herein is not meant to limit the scope of the invention as those skilled in the art will recognize that other ADCs can be functionally equivalent.

In some embodiments, the antibody, or a derivative or fragment thereof, specifically binds to a tumor microenvironment specific antigen. In some embodiments, the antibody, or a derivative or fragment thereof, binds to a tumor cell surface marker. In some embodiments, the antibody, or a derivative or fragment thereof, binds HER2, transmembrane glycoprotein NMB (gpNMB), EGFR, EGFRvIII, glutamate carboxypeptidase II (GCPII/PSMA), CD11b, CD16A, CD19, CD22, CD25, CD27L, CD30, CD33, CD37, CD44v6, CD56, CD70, CD71 (transferrin), CD74, CD79b, CD103, CD117 (KIT), CD123, CD138, CD142, CD174 (Lewis Y ag), CD227 (MUC1), CD303, CD352, ectonucleotide pyrophosphatase/phosphodiesterase family member 3 (ENPP3), TIM3, LY6E, LIV1, Nectin 4, SLITRK6, HGFR (cMet), SLAM7, BCMA, AXL, NaPi2B, GCC, STEAP1, mesothelin, ETBR, EphA2, 5T4, FOLR1, CEACAM5 (CD66e), LAMP1, cadherin, FGFR2, FGFR3, EpCAM, CA6, MUC16, integrin αV, criptol (TDGF1), DLL3, TROP2, mesothelin, PTK7, NOTCH3, C4.4A, FLT3, LIV-1, SLC44A4, CA-IX, CanAg, guanylyl cyclase C, B7H3, ROR-1, and the like. In some embodiments, the antibody is a bispecific antibody, or a derivative or fragment thereof, and binds EpCAM×CD3, HER2×CD3, HER2×CD63, CD19× CD3, CEA×CD3, PSMA×CD3, CD123×CD3, CD30× CD16A, CD20×CD3, CD22×CD19, CEACAM5×CD303, CEACAM5×CD103, CEACAM5×CD11b, HER2×CD303, HER2×CD103, HER2×CD11b, and the like.

In some embodiments, the tumor-targeted antibody F in formula (I) is conjugated with a cleavable linker/self-eliminating linker/TLR7/8 agonist moiety (-$L^2$-$L^1$-D) via native lysine residues using a conjugation linker $L^3$ that is well-known to those in the art, including N-succinimidyl-4-(2-pyridyldthio) butanoate (SPDB), N-succinimidyl-4-(2-pyridyldthio)-2-butanoate (sulfo-SPDB), maleimidomethyl cyclohexane-1-carboxylate (MCC), 4-(4-acetylphenoxy)butanoic acid (AcBut), succinimidyl 4-(N-maleimidomethyl) cyclohexane-1-carboxylate (SMCC), N-succinimidyl-4-(2-pyridyldithio)pentanoate (SPP), derivatives thereof, and the like. In some embodiments, $L^1$ is a bond and the tumor-targeted antibody F in formula (I) is conjugated with a cleavable linker/TLR7/8 agonist moiety (-$L^2$-D) via native lysine residues using a conjugation linker $L^3$ that is well-known to those in the art, including N-succinimidyl-4-(2-pyridyldthio) butanoate (SPDB), N-succinimidyl-4-(2-pyridyldthio)-2-butanoate (sulfo-SPDB), maleimidomethyl cyclohexane-1-carboxylate (MCC), 4-(4-acetylphenoxy)butanoic acid (AcBut), succinimidyl 4-(N-maleimidomethyl) cyclohexane-1-carboxylate (SMCC), N-succinimidyl-4-(2-pyridyldithio)pentanoate (SPP), derivatives thereof, and the like.

In some embodiments, the tumor targeted antibody F in formula (I) is conjugated with a cleavable linker/self-eliminating linker/TLR7/8 agonist moiety (-$L^2$-$L^1$-D-) via native or engineered cysteine residues using a conjugation linker $L^3$ that is well-known to those in the art, including maleimidocaproyl (MC), maleimidomethyl cyclohexane-1-carboxylate (MCC), succinimidyl 4-(N-maleimidomethyl)cyclohexane-1-carboxylate (SMCC), N-succinimidyl-4-(2-pyridyldithio)pentanoate (SPP), derivatives thereof, and the like. In some embodiments, $L^1$ is a bond and the tumor targeted antibody F in formula (I) is conjugated with a cleavable linker/TLR7/8 agonist moiety (-$L^2$-D-) via native or engineered cysteine residues using a conjugation linker $L^3$ that is well-known to those in the art, including maleimidocaproyl (MC), maleimidomethyl cyclohexane-1-carboxylate (MCC), succinimidyl 4-(N-maleimidomethyl)cyclohexane-1-carboxylate (SMCC), N-succinimidyl-4-(2-pyridyldithio)pentanoate (SPP), derivatives thereof, and the like. Methods for mild reduction of antibodies with dithiothreitol (DTT) or tris(2-carboxyethyl)phosphine (TCEP) are well known to those in the art; partial reduction of the antibody disulfide bonds allows for conjugation to certain cysteine residues without disrupting the secondary and tertiary structures of the protein, and without causing aggregation (see, e.g., Sun, M. C. et al. 2005, *Bioconjug Chem* 16:1282-1290; Doronina, S. O. et al. 2003, *Nature Biotechnology* 21:778-784; and the like).

In some embodiments, the tumor targeted antibody F in formula (I) is conjugated with a cleavable linker/self-eliminating linker/TLR7/8 agonist moiety (-$L^2$-$L^1$-D) by employing protein engineering technologies that permit controlling the number of position(s) on the antibody that are available for conjugation. In some embodiments, $L^1$ is a bond and the tumor targeted antibody F in formula (I) is conjugated with a cleavable linker/TLR7/8 agonist moiety (-$L^2$-D) by employing protein engineering technologies that permit controlling the number of position(s) on the antibody that are available for conjugation. In some embodiments, the antibody F in formula (I) is engineered to control the number of cysteine residues that are available for conjugation with a maleimide-based reagent as the conjugation linker $L^3$ (see, e.g., Junutula, J. R. et al. 2008, *Nat Biotechnol* 26:925-932; Kung-Sutherland, M. S. et al. 2013, *Blood* 122:1455-1463; Puthenveetil, S. et al. 2017, *PlosOne* 12:e0178452; and the like). In some embodiments, the antibody F in formula (I) has one or more unnatural amino acid(s) engineered into the primary sequence to enable chemical conjugation using an orthogonal conjugation linker ($L^3$ in formula (I)), see, e.g., Tian. F. et al. 2014, *Proc Nat Acad Sci USA* 111:1766-1771; Kato, A. et al. 2017, *Bioconjug Chem* 28:2099-2108; and the like. In some embodiments, the antibody F in formula (I) has a non-native amino acid sequence engineered into the primary sequence to enable enzyme-assisted ligation of the conjugation linker ($L^3$ in formula (I)), see, e.g., Agarwal, P. et al. 2013, *Bioconjug Chem* 24:846-851; Dorywalska, M. et al. 2015, *Bioconjug Chem* 26:650-659; Grunewald, J. et al. 2017, *Bioconjug Chem* 28:1906-1915; and the like. In some embodiments, the antibody F in formula (I) has seen subjected to metabolic engineering, chemical oxidation, or glycoengineering of the N-glycan residue to enable ligation of the conjugation linker ($L^3$ in formula (I)) to the modified glycan residue, see, e.g., Okeley, N. M. et al. 2013, *Bioconjug Chem* 24:1650-1655; Zhou, Q. et al. 2013, *Bioconjug Chem* 25:510-520; Tang, F. et al. 2017, *Nature Protocols* 12:1702-1721; and the like.

In some embodiments, the ratio of the antibody F in formula (I) to TLR7/8 agonist moiety D in formula (I) (x in formula (I)) is an integer, representing the geomean of the population distribution average of D conjugated to F, of between 1 and 10. In some embodiments, x is an integer, representing the geomean of the population distribution average of D conjugated to F, of between 2 and 8, 2 and 7, 2 and 6, 2 and 5, 2 and 4, or 2 and 3. In some embodiments, x is 1, 2, 3, 4, 5, 6, 7, 8, 9, or 10.

III. METHODS OF PREPARATION OF CLEAVABLE CONJUGATES OF TLR7/8 AGONIST COMPOUNDS

This present disclosure further provides methods for preparing the cleavable conjugates of TLR7/8 agonist compounds detailed herein (i.e., the compounds of formula (I) or any variations thereof detailed herein), as well as compositions and intermediates useful therein. The compounds of the present disclosure can be prepared using methods detailed herein, as well as methods well known to those skilled in the art, see, e.g., Dubowchik, G. M. et al. 2002, *Bioconjug. Chem.* 13,855-869; Lyon, R. P. et al. 2014, *Nat Biotechnol* 32:1059-1062.

In one aspect, the disclosure provides a method for preparing cleavable conjugates of TLR7/8 agonist compounds of formula (I) that comprise particle-based (i.e., nanoparticle or microparticle) conjugation moieties F:

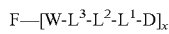  (I), wherein:
D is a TLR7/8 agonist moiety;
$L^1$ is a bond or a self-eliminating linker;
$L^2$ is a cleavable linker;
$L^3$ is a conjugation linker;
W is O, S, or $NR^{10}$;
$R^{10}$ is H or $C_1$-$C_8$ alkyl;
x is an integer from 1 to 500; and
F is a particle-based conjugation moiety;
wherein the method comprises:
reacting a compound of formula (A):

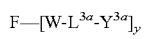  (A)

with a compound of formula (B):

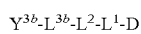  (B)

wherein y is an integer from 1 to 500; F, W, $L^2$, $L^1$, and D are as defined for the compound of formula (I); $L^{3a}$ and $L^{3b}$ are independently optional spacer fragments; $Y^{3a}$ and $Y^{3b}$ are precursor moieties that react with each other to form spacer fragment $Y^3$, and $L^{3a}$, $Y^3$, and $L^{3b}$ are taken together to form the linker $L^3$,
to form the compound of formula (I).

In some embodiments, the TLR7/8 agonist moiety D is IMDQ or meta-IMDQ, or a compound selected from any one of Compound Nos. 64-01 to 64-50, 64-58 to 64-69, 64-01a to 64-50a, and 64-58a to 64-69a. In some embodiments, the particle-based conjugation moiety is a branched copolymer of sucrose and epichlorohydrin (e.g., Ficoll® PM 400 or Ficoll® PM 70) and x is an integer from 3 to 500, 3 to 400, 3 to 300, or 3 to 200. In some preferred embodiments, x is an integer from 3 to 150, 3 to 100, or 3 to 75.

In some embodiments, the conjugation linker is made using "click" chemistry by reaction of an alkyne with an azide to form a [1,2,3]triazole moiety. In some embodiments, $Y^{3a}$ is an alkyne group (—C≡CH), $Y^{3b}$ is an azido group (—$N_3$), and $Y^3$ is a 1,4-[1,2,3]triazolylene moiety.

In some embodiments, $L^{3a}$ is an amide spacer fragment (e.g., —$CH_2$C(O)NH$CH_2$—), and $L^{3b}$ is an acyl spacer fragment (e.g., —$CH_2$C(O)—) or a PEG-acyl spacer fragment (e.g., —$CH_2CH_2$(O$CH_2CH_2$)$_{12}$C(O)—).

In some embodiments, $L^{3a}$ is:

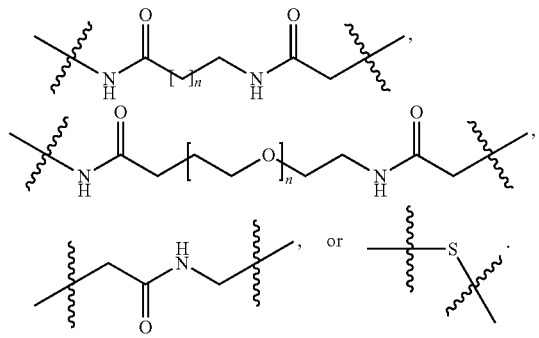

In some embodiments, $L^{3b}$ is an acyl spacer fragment of the formula:

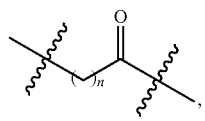

or a PEG-acyl spacer fragment of the formula:

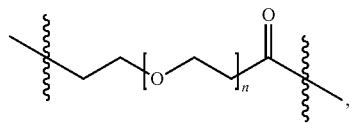

where n is 0 to 200. In some embodiments, $L^{3b}$ is an acyl spacer fragment of the formula:

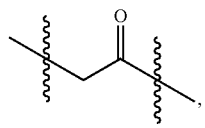 [SMILES: *CC(*)=O]

or a PEG-acyl spacer fragment of the formula:

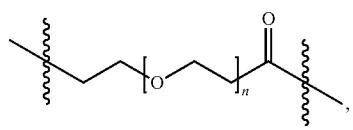

where n is 0 to 200.

In some embodiments, $Y^3$ is:

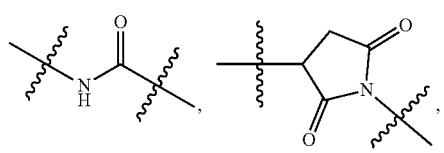

-continued

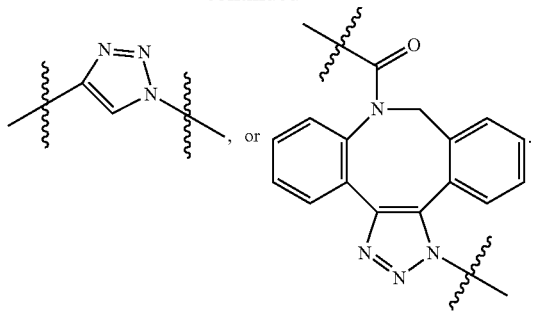, or

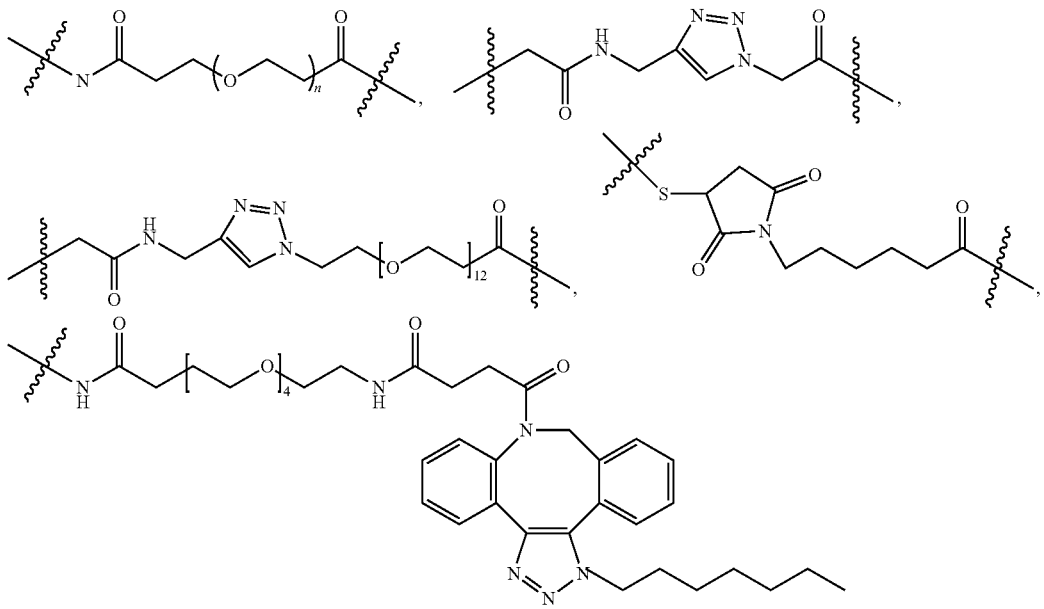

In some embodiments, $L^3$ is:

$R^{10}$ is H or $C_1$-$C_8$ alkyl;
x is an integer from 1 to 50; and
F is an antibody-based conjugation moiety;
wherein the method comprises:
reacting a compound of formula (C):

 (C)

with a compound of formula (D):

 (D)

wherein x is an integer from 1 to 50; and F, $L^3$, $L^2$, $L^1$, and D are as defined for the compound of formula (I), and W' is N, O, S, $N_3$, or alkyne,
to form the compound of formula (I).

In some embodiments, the compound of formula (C) is made by limited reduction of the native cysteine residues in an antibody-based conjugation moiety (F—[W']$_x$), where W' is S, and F is a recombinant antibody that targets the compound to the tumor microenvironment and which has been optionally engineered engineered to add and/or delete cysteine residues. In some embodiments, the compound of formula (C) is an antibody-based conjugation moiety (F—[W']$_x$), where W' is N, O, S, $N_3$, or alkyne, and F is a recombinant antibody that targets the compound of formula (I) to the tumor microenvironment, and that has been engineered with unnatural amino acids or novel amino acid sequences that are subjected to post-translational chemoenzymatic modifications. In some embodiments, the compound of formula (C) is an engineered antibody-based conjugation moiety (F—[W']$_x$), where W' is N on the native lysine residues, and F is a recombinant antibody that targets the compound of formula (I) to the tumor microenvironment. In some embodiments x is an integer from 1 to 50, 1 to 25, 1 to 20, 1 to 15, 1 to 10, 1 to 9, 1 to 8, 1 to 7, 1 to 6, 1 to 5, 1 to 4, 1 to 3, or 1 to 2.

In some embodiments, the compound of formula (D) is made by: (i) covalently attaching $L^2$ to $L^1$; (ii) covalently attaching -$L^2$-$L^1$ to D; and (iii) covalently attaching -$L^2$-$L^1$-D to $L^3$ to synthesize $L^3$-$L^2$-$L^1$-D, an exemplar of the compound of formula (D). In some embodiments, $L^1$ is a bond and the compound of formula (D) is made by: (i)

In some embodiments, W is O and F is a branched copolymer of sucrose and epichlorohydrin having an average molecular weight of about 50,000 to about 700,000 daltons, about 50,000 to about 80,000 daltons, about 200,000 to about 600,000 daltons, or about 300,000 to about 500,000 daltons.

In some embodiments, the TLR7/8 agonist is a derivative of 1-benzyl-2-butyl-1H-imidazo[4,5-c]quinolin-4-amine (e.g., IMDQ or meta-IMDQ). In some embodiments, the TLR7/8 agonist is a compound selected from the group consisting of Compound Nos. 64-01 to 64-50, 64-58 to 64-69, 64-01a to 64-50a, and 64-58a to 64-69a.

In some embodiments, $L^1$ is a bond.

In another aspect, the disclosure provides a method for preparing cleavable conjugates of TLR7/8 agonist compounds of formula (I) that comprise antibody-based conjugation moieties F:

 (I), wherein:
D is a TLR7/8 agonist moiety;
$L^1$ is a bond or a self-eliminating linker;
$L^2$ is a cleavable linker;
$L^3$ is a conjugation linker;
W is O, S, or $NR^{10}$;

covalently attaching $L^2$ to D; and (ii) covalently attaching -$L^2$-D to $L^3$ to synthesize $L^3$-$L^2$-D, an exemplar of the compound of formula (D). In some embodiments, the linker $L^3$ is a maleimidocaproyl conjugation linker, succinimidyl 4-(N-maleimidomethyl)cyclohexane-1-carboxylate linker, N-succinimidyl-4-(2-pyridyldithio)butanoate linker, N-succinimidyl-4-(2-pyridyldithio)pentanoate linker, hydrazone linker, and the like. In some embodiments, the peptide cleavable linker $L^2$ is an amino acid sequence $AA_1$-$AA_2$-$AA_3$-$AA_4$, where $AA_1$ is absent, alanine, β-alanine, isoleucine, leucine, valine, or glycine; $AA_2$ is absent, alanine, β-alanine, isoleucine, leucine, or valine; $AA_3$ is alanine, β-alanine, isoleucine, leucine, or valine; and $AA_4$ is arginine, serine, alanine, β-alanine leucine, ornithine or citrulline, and the like. In some embodiments, the linker $L^1$ is an p-aminobenzylcarbamate self-eliminating linker, and the like. In some embodiments, the TLR7/8 agonist moiety D is IMDQ, meta-IMDQ, or any one of Compound Nos. 64-01 to 64-50, 64-58 to 64-69, 64-01a to 64-50a, and 64-58a to 64-69a.

IV. USES OF CLEAVABLE CONJUGATES OF TLR7/8 AGONIST COMPOUNDS

A. Pharmaceutical Compositions

Pharmaceutical compositions comprising tumor-targeted, cleavable conjugates or locally retained, cleavable conjugates of TLR7/8 agonist compounds of the present disclosure are also provided. The pharmaceutical compositions routinely contain one or more pharmaceutically acceptable excipients. Pharmaceutical compositions of the present disclosure can be in the form of a solution or a freeze-dried solid. The pharmaceutical compositions of the present disclosure are preferably sterile, and preferably essentially endotoxin-free.

Pharmaceutically acceptable excipients of the present disclosure include, for example, solvents, bulking agents, emulsifier/surfactants, buffering agents, tonicity adjusting agents, and preservatives (see, e.g., Pramanick et al. *Pharma Times*, 45:65-77, 2013). In some embodiments, the pharmaceutical compositions comprise an excipient that functions as one or more of a solvent, a bulking agent, a buffering agent, and a tonicity adjusting agent (e.g., sodium chloride in saline can serve as both an aqueous vehicle and a tonicity adjusting agent). The pharmaceutical compositions of the present disclosure are suitable for parenteral administration. In some embodiments, the pharmaceutical compositions of the present disclosure are not intended for enteral administration.

In some embodiments, the pharmaceutical compositions comprise an aqueous vehicle as a solvent. Suitable vehicles include, for example, sterile water, saline solution, phosphate buffered saline, and Ringer's solution. In some embodiments, the composition is isotonic or hypertonic. In some embodiments, the composition is sterile.

The pharmaceutical compositions can comprise a bulking agent. Bulking agents are particularly useful when the pharmaceutical composition is to be lyophilized before administration. In some embodiments, the bulking agent is a lyoprotectant that aids in the stabilization and prevention of degradation of the active agents during freeze-drying and/or during storage. Suitable bulking agents are sugars (mono-, di- and polysaccharides) such as sucrose, lactose, trehalose, mannitol, sorbital, glucose, and raffinose.

The pharmaceutical compositions can comprise a buffering agent. Buffering agents control pH to inhibit degradation of the active agent during processing, storage, and optionally reconstitution. Suitable buffers include, for example, salts comprising acetate, citrate, phosphate, or sulfate. Other suitable buffers include, for example, amino acids such as arginine, glycine, histidine, and lysine. The buffering agent can further comprise hydrochloric acid or sodium hydroxide. In some embodiments, the buffering agent maintains the pH of the composition within a range of 4 to 9. In some embodiments, the pH is greater than (lower limit) 4, 5, 6, 7, or 8. In some embodiments, the pH is less than (upper limit) 9, 8, 7, 6, or 5. That is, the pH is in the range of from about 4 to 9, in which the lower limit is less than the upper limit.

The pharmaceutical compositions can comprise a tonicity adjusting agent. Suitable tonicity adjusting agents include, for example, dextrose, glycerol, sodium chloride, glycerin, and mannitol.

The pharmaceutical composition can comprise a surfactant or an emulsifier agent. Suitable surfactants include, for example, anionic surfactants, cationic surfactants, non-ionic surfactants, and zwitterionic surfactants. In some embodiments, the nonionic surfactant is polyoxyethylene (20) sorbitan monooleate (e.g., Tween 80® or Montanox 80®) or Polyoxyethylene (20) sorbitan monolaurate (e.g., Tween 20® or Montanox 20®).

The pharmaceutical compositions can comprise a preservative. Suitable preservatives include, for example, antioxidants and antimicrobial agents. In some embodiments, the pharmaceutical composition is prepared under sterile conditions and is in a single use container, and thus does not necessitate inclusion of a preservative.

The pharmaceutical compositions of the present disclosure are suitable for a plurality of uses involving stimulating an immune response in a mammalian subject in need thereof. Mammalian subjects include, but are not limited to, humans, nonhuman primates, rodents, pets, and farm animals. In some embodiments, the pharmaceutical compositions are administered to the subject in an amount effective to achieve a specific outcome.

B. Dosage and Mode of Administration

As with all pharmaceutical compositions, the effective amount and mode of administration can vary based on several factors evident to one skilled in the art. Factors to be considered include potency of the modified 1H-imidazo[4,5-c]quinoline TLR7/8 agonist compound (i.e., the compound of formula (I)), the ability of the compound and pharmaceutical composition to promote retention of the agonist compound at the site of administration, the route of administration, and whether the pharmaceutical composition is administered in combination with an antigen or other therapeutic agent for the treatment of cancer. Other factors to be considered include the disease modification outcome to be achieved and the number/frequency of doses to be administered during a therapeutic regimen.

A suitable dosage range is one that provides the desired clinical effect. Dosage can be determined by the amount of the TLR7/8 agonist compound (i.e., the compound of formula (I)) in the pharmaceutical composition that needs to be administered to a subject to yield a desired therapeutic response with minimal adverse events. An exemplary dosage range of the TLR7/8 agonist compound given in amount to be delivered by subject weight is from about 0.0001 to 100 mg/kg, such as about 0.0001 to 75 mg/kg, about 0.0001 to 50 mg/kg, about 0.0001 to 25 mg/kg, about 0.0001 to 10 mg/kg, about 0.0001 to 8 mg/kg, about 0.0001 to 6 mg/kg, about 0.0001 to 5 mg/kg, about 0.0001 to 4 mg/kg, about 0.0010 to 3 mg/kg, about 0.0001 to 2 mg/kg, about 0.0001 to 1 mg/kg, about 0.0001 to 0.5 mg/kg, about 0.001 to 100 mg/kg, about 0.01 to 100 mg/kg, about 0.1 to 100 mg/kg, about 0.5 to 100 mg/kg, about 1 to 100 mg/kg, about 2 to 100 mg/kg, about 3 to 100 mg/kg, about 4 to 100 mg/kg, about 5 to 100 mg/kg, about 6 to 100 mg/kg, about 8 to 100 mg/kg, about 10 to 100 mg/kg, about 25 to 100 mg/kg, about 50 to 100 mg/kg, about 75 to 100 mg/kg, about 0.01 to 10 mg/kg, about 0.05 to 9 mg/kg, about 0.1 to 8 mg/kg, about 0.2 to 7 mg/kg, about 0.3 to 6 mg/kg, about 0.4 to 5 mg/kg, about 0.5 to 4 mg/kg, about 0.6 to 3 mg/kg, about 0.7 to 2.5 mg/kg, about 0.8 to 2.2 mg/kg, about 0.9 to 2.1 mg/kg, or about 1 to 2 mg/kg. In some embodiments, the dosage is greater than about (lower limit) 0.0001, 0.001, 0.01, 0.1, 0.5, 1, 1.5, 2, 5, 10, 25, 50, 75, or 90 mg/kg. In some embodiments, the dosage is less than about (upper limit) 100, 75, 50, 25, 10, 9, 8, 7, 6, 5, 4, 3, 2, 1, 0.1, 0.01, or 0.001 mg/kg. That is, the dosage is anywhere in the range of from about 0.0001 to 100 mg/kg, in which the lower limit is less than the upper limit. An exemplary dosage range of the TLR7/8 agonist given in amount to be delivered to a subject is from about 0.0001 to 100 mg/kg.

In some embodiments, when the pharmaceutical composition further is administered in combination with an antigen, the antigen dosage range given in amount to be delivered to a subject is from about 1 µg to 500 µg. In some embodiments, the antigen dosage is from about 1 µg to 50 µg. In some embodiments, the antigen dosage is greater than about (lower limit) 1, 5, 10, 15, 20, 25, 30, 35, 40, 45, 50, 100, 200, or 400 µg. In some embodiments, the antigen dosage is less than about (upper limit) 500, 400, 300, 200, 100, 50, 45, 40, 35, 30, 25, 20, 15, or 10 µg. That is, the antigen dosage is anywhere in the range of from about 1 to 500 µg, in which the lower limit is less than the upper limit. The optimum antigen dosage can be determined by experimental means for each individual antigen.

Likewise, a suitable route of administration is one that provides the desired effect. In general, the pharmaceutical compositions of the present disclosure are intended for parenteral administration (e.g., not oral or rectal administration). Suitable routes of administration include injection, topical, and inhalation. In particular, the pharmaceutical compositions of the present disclosure can be administered by a route such as intratumoral, intramuscular, subcutaneous, transdermal, and inhalation. Devices suitable for administration by inhalation include, for example, atomizers, vaporizers, nebulizers, and dry powder inhalation delivery devices. In some embodiments, when the pharmaceutical compositions are intended to treat a solid tumor, the compositions are administered intratumorally and/or peritumorally (e.g., in and around the tumor lesion). In some embodiments, the pharmaceutical compositions are administered intravenously.

A suitable dosing regimen of the TLR7/8 agonist compound formulated in the pharmaceutical composition is one that provides the desired effect in a prophylactic or therapeutic context with minimal adverse events. The number of doses administered by a chosen route can be one or more than one. Frequency of dosing can range from weekly, bi-weekly, monthly, bi-monthly, or 3 to 12 months between doses. An exemplary dose frequency of the TLR7/8 agonist compound is from about once per week to once every 8 weeks. In some embodiments, the dose frequency is lower than about (upper limit) once every 8, 6, 5, 4, 3, 2, or 1 weeks. In some embodiments, the dose frequency is greater than about (lower limit) once every 7, 10, or 14 days. In some embodiments, the dose frequency is once every 1, 2, 3, 4, 5, 6, 7, or 8 weeks. In some embodiments, the dose frequency is once every 1, 2, 3, or 4 weeks. In some embodiments, the dose frequency is once every 2, 3, or 4 weeks. An exemplary dose frequency range of the TLR7/8 agonist compound to be delivered to a subject is from about once every week to once every 4 weeks. In some embodiments, 2 doses are administered, with the second dose being administered one to two months after the first dose. In some embodiments, 3 doses are administered, with the second dose being administered one to two months after the first dose and the third dose being administered one to five months after the second dose. In other embodiments, a series of doses can be administered over a 3 to 12 month treatment schedule, where the dose frequency is once every week, every other week, every third week, or monthly. In other embodiments, a shorter or longer period of time can elapse between doses. In certain embodiments, the interval between successive dosages can vary in terms of number of weeks or number of months. In one embodiment, a series of 2, 3, 4, 5, or 6 weekly doses can be administered followed by a second series of weekly doses at a later time point. One skilled in the art will be able to adjust the dosage regimen by measuring biological outcomes such as antigen-specific antibody responses, antigen-specific CD8+ T cell responses, or tumor regression.

In some embodiments, the pharmaceutical compositions are administered to a subject intravenously over about 5 to 120 minutes per infusion. In some embodiments, the infusion time is from about 5 to 120 minutes, about 5 to 90 minutes, about 5 to 60 minutes, about 5 to 45 minutes, about 5 to 30 minutes, about 5 to 15 minutes, about 5 to 10 minutes, about 10 to 120 minutes, about 15 to 120 minutes, about 30 to 120 minutes, about 45 to 120 minutes, about 60 to 120 minutes, about 90 to 120 minutes, about 10 to 45 minutes, or about 15 to 30 minutes.

C. Stimulation of an Immune Response

In one aspect, the present disclosure provides methods of stimulating an immune response in a mammalian subject in need thereof, comprising administering to the mammalian subject a pharmaceutical composition in an amount and frequency sufficient to stimulate an immune response in the mammalian subject. "Stimulating" an immune response means increasing the immune response, which can arise from eliciting a de novo immune response or enhancing an existing immune response. In some embodiments, stimulating an immune response comprises one or more of the group consisting of: stimulating IFNα production, stimulating production of Type 1 and/or Type 2 interferons, stimulating IL-6 production, stimulating TNFα production, stimulating B lymphocyte proliferation, stimulating interferon pathway-associated gene expression, stimulating chemoattractant-associated gene expression, stimulating plasmacytoid dendritic cell (pDC) or myeloid dendritic cell (mDC) maturation and/or antigen presentation, and/or inducing production of tumor antigen specific CD4+ and/or CD8+ T cells. "Inducing" an antigen-specific T cell response means stimulating helper and/or cytotoxic T lymphocytes to enhance their numbers and functional properties, such as providing T cell help for antibody responses or generating cytotoxic T cells with anti-tumor activity. In embodiments in which the pharmaceutical composition further is administered in combination with an antigen, stimulating an immune response comprises inducing an antigen-specific antibody response. "Inducing" an antigen-specific antibody response means increasing titers of antigen-specific antibodies above a threshold level, such as a pre-administration baseline titer or a seroprotective level.

Analysis (both qualitative and quantitative) of the immune response can be by any method known in the art, including, but not limited to, measuring antigen-specific antibody production (including measuring specific antibody subclasses), activation of specific populations of lymphocytes such as B cells and helper T cells, measuring expression of a set of genes specific to a particular immune cell type, production of cytokines such as IFNα, IL-6, IL-12, IL-18, TNFα, and/or release of histamine. Methods for measuring antigen-specific antibody responses include enzyme-linked immunosorbent assay (ELISA). Production of cytokines can also be measured by ELISA. Gene expression analysis can be performed by TaqMan® or nCounter® gene expression assays. Activation of specific populations of lymphocytes can be measured by proliferation assays and with fluorescence-activated cell sorting (FACS). Methods for measuring stimulation of an immune response are described in the biological examples of the present disclosure.

D. Treatment of Cancer

The present disclosure provides a plurality of methods of treating cancer in a mammalian subject in need thereof, comprising administering to the mammalian subject a pharmaceutical composition in an amount sufficient to treat cancer in the mammalian subject. In some embodiments, the present disclosure provides methods of treating cancer in a mammalian subject in need thereof, comprising administering an effective amount of a pharmaceutical composition by intratumoral and/or peritumoral delivery. In some embodiments, intratumoral delivery comprises injection of the pharmaceutical composition into at least one tumor lesion. In some embodiments, treating cancer in a mammalian subject in need thereof comprises inducing accumulation of tumor antigen-specific T cells in the injected tumor, for example, at greater numbers than had the pharmaceutical composition been administered at an extratumoral site. In some embodiments, treating cancer in a mammalian subject in need thereof comprises eliciting a systemic, tumor antigen-specific T cell response including, for example, a systemic, tumor antigen-specific T cell response of a higher magnitude than had the immunogenic composition been administered at an extratumoral site. In some embodiments, treating cancer in a mammalian subject in need thereof comprises eliciting a systemic, tumor antigen-specific T cell response. In some embodiments, treating cancer in a mammalian subject in need thereof comprises reducing numbers of CD4+ FoxP3+ regulatory T cells in the injected tumor. In some embodiments, the subject has one or more uninjected tumors (primary or metastatic lesions) in addition to the injected tumor, and treating cancer in the subject comprises one or more of the following: (a) reducing the number of uninjected tumors; (b) reducing the volume of uninjected tumors; and (c) retarding the growth of uninjected tumors. In some embodiments, treating cancer in a mammalian subject in need thereof comprises one or more of the following: (d) increasing the survival time of the subject; (e) reducing the volume of the injected tumor; and (f) retarding the growth of the injected tumor. In some embodiments, when the cancer is a solid tumor, "treating" cancer comprises shrinking the size of the solid tumor and any metastatic lesions, or otherwise reducing viable cancer cell numbers. In other embodiments, when the cancer is a solid tumor, "treating" cancer comprises delaying growth of the solid tumor and any metastatic lesions. In some aspects, treating cancer comprises increasing progression free survival or increasing time to progression. In other embodiments, the method further comprises administering an effective amount of a second, or additional, therapeutic agent(s) to the subject. "Treating" cancer means to bring about a beneficial clinical result, such as causing remission or otherwise prolonging survival as compared to expected survival in the absence of treatment. In some preferred embodiments, "treating cancer" comprises assessing a patient's response to the immunogenic composition according to the Response Evaluation Criteria in Solid Tumors (RECIST version 1.1) as described (see, e.g., Eisenhauer et al. 2009, *Eur J Cancer* 45:228-247). Response criteria to determine objective anti-tumor responses per RECIST include: complete response, partial response, progressive disease, and stable disease.

In some embodiments, the tumor is a sarcoma, a carcinoma, or an actinic keratosis. In some embodiments, the tumor is a lymphoma. In some embodiments, the cancer is selected from the group consisting of breast cancer, prostate cancer, lung cancer, colorectal cancer, uterine cancer, bladder cancer, melanoma, head and neck cancer, non-Hodgkin lymphoma, kidney cancer, ovarian cancer, pancreatic cancer, and thyroid cancer. In some embodiments, the cancer is breast cancer. In some embodiments, the cancer is ovarian cancer. In some embodiments, the cancer is colorectal cancer. In some embodiments, the cancer is a primary cancer of a site selected from the group consisting of oral cavity, digestive system, respiratory system, skin, breast, genital system, urinary system, ocular system, nervous system, endocrine system, and lymphoma.

In some embodiments, the method further comprises administering an effective amount of a second therapeutic agent to the subject. In some of these embodiments, the second therapeutic agent comprises a chemotherapeutic agent selected from the group consisting of actinomycin, afatinib, alectinib, asparaginase, azacitidine, azathioprine, bicalutamide, binimetinib, bleomycin, bortezomib, camptothecin, carboplatin, capecitabine, carmustine, certinib, cisplatin, chlorambucil, cobimetinib, crizotinib, cyclophosphamide, cytarabine, dabrafenib, dacarbazine, daunorubicin, docetaxel, doxifluridine, doxorubicin, encorafenib, erlotinib, epirubicin, epothilone, etoposide, fludarabine, flutamine, fluorouracil, gefitinib, gemcitabine, hydroxyurea, idarubicin, ifosfamide, imatinib, irinotecan, lapatinib, letrozole, mechlorethamine, mercaptopurine, methotrexate, mitomycin, mitoxantrone, octreotide, oxaliplatin, paclitaxel, pemetrexed, raltitrexed, sorafenib, sunitinib, tamoxifen, temozolomide, teniposide, tioguanine, topotecan, trametinib, valrubicin, vemurafenib, vinblastine, vincristine, vindesine, vinorelbine, and combinations thereof. In some embodiments, the second therapeutic agent comprises one or both of a BRAF inhibitor and a MEK inhibitor. In some embodiments, the second therapeutic agent comprises a epigenetic modulator selected from the group consisting of HDAC inhibitors (see e.g., voronistat [SAHA], romidepsin, entinostat, abexinostat, elinostat [CHR-3996], panobinostat, quisinostat [JNJ-26481585], 4SC-202, resminostat [SB939], pracinostat [CI-9940], and valproate), DNA methyltransferase inhibitors (see e.g., azacytidine, decitabine, zebularine, SGI-1027, RG-108, and sinfungin), and combinations thereof.

In some of these embodiments, the second therapeutic agent is an antagonist of an inhibitory immune checkpoint molecule, for example, an inhibitory immune checkpoint molecule selected from the group consisting of PD-1, PD-L1, PD-L2, CTLA-4 (CD152), LAG-3, TIM-3, TIGIT, IL-10, indoleamine 2,3-dioxygenase (IDO), P-selectin glycoprotein ligand-1 (PSGL-1), and TGF-beta. In some of these embodiments, the second therapeutic agent is an agonist of an immune stimulatory molecule. In some of these embodiments, the immune stimulatory molecule is selected from the group consisting of CD27, CD40, OX40 (CD134), GITR, 4-1BB CD137, CD28, and ICOS (CD278). In some of these embodiments, the second therapeutic agent comprises an antibody, fragment, or derivative thereof. In some of these embodiments, the second therapeutic agent is an antagonist of an inhibitory immune checkpoint molecule and the second therapeutic agent comprises an antibody, fragment, or derivative thereof.

In some embodiments, the method further comprises administering radiation therapy and/or administering an effective amount of a second therapeutic agent to the subject. In some of these embodiments, the effective amount of the immunogenic composition and the effective amount of the second therapeutic agent together result in an additive effect or better against the tumor. In some of these embodiments, the effective amount of the immunogenic composition and the effective amount of the second therapeutic agent together result in a synergistic effect against the tumor.

In some embodiments of the method, treating cancer does not result in development of flu-like symptoms of such severity that repeated administration of the immunogenic composition is contraindicated, wherein the flu-like symptoms comprise one or more of the group consisting of fever, headache, chills, myalgia, and fatigue.

In some embodiments, the present disclosure provides kits that comprise a pharmaceutical composition (e.g., a compound of formula (I), an excipient or excipients, and, optionally, an antigen) and a set of instructions relating to the use of the composition for the methods described herein. The pharmaceutical composition of the kits is packaged appropriately. If the pharmaceutical composition is a liquid, a lyophilized form, or a suspension of nanoparticles, a silicon dioxide vial (e.g., SCHOTT Type I Plus®) with a rubber stopper (e.g., Exxpro halobutyl elastomer) and an aluminum crimp-top is typically used as the container-closure system. In some embodiments, the kits further comprise a device (e.g., syringe and needle) for administration of the pharmaceutical composition. In other embodiments, the kits further comprise a pre-filled syringe/needle system, autoinjectors, or needleless devices. The instructions relating to the use of the pharmaceutical composition generally include information as to dosage, schedule, and route of administration for the intended methods of use.

V. EXAMPLES

List of Abbreviations

CDI: 1,1'-carbonyldiimidazole;
DCM: dichloromethane
DMF: N,N-dimethylformamide;
DIPEA: N,N-Diisopropylethylamine;
DTT: dithiothreitol;
EDC: 1-ethyl-3-(3-dimethylaminopropyl)carbodiimide;
EDTA: ethylenediaminetetraacetic acid;
EMCS: N-ε-malemidocaproyl-oxysuccinimide ester;
Eq: equivalent
Fmoc: 9-Fluorenylmethoxycarbonyl;
HATU: 1-[bis(dimethylamino)methylene]-1H-1,2,3-triazolo[4,5-b]pyridinium 3-oxid hexafluorophosphate;
HCl: hydrochloric acid
$K_2CO_3$: potassium carbonate
LC-MS (LC/MS): liquid chromatography-mass spectrometry;
MALS: multiple angle laser-light scattering;
MeOH: methanol;
$Na_2SO_4$: sodium sulfate;
NMP: N-methyl pyrrolidone;
NMR: Nuclear magnetic resonance (spectroscopy);
PABC: p-aminobenzylcarbamate;
PBS: 10 mM phosphate, 150 mM NaCl, pH 7.4;
RP-HPLC: reverse phase-high pressure liquid chromatography;
SEC: size exclusion chromatography;
TEA: triethylamine;
TFA: trifluoroacetic acid
THF: tetrahydrofuran.

A. Synthetic Examples

Example S1

Preparation of Compound Nos. 64-51 and 64-51a

The procedures and scheme shown in Example S1 and Scheme S1-1 can be used to prepare Azide-Disulfide-PABC-IMDQ compounds (-$L^3$-$L^2$-$L^1$-D in formula (I)) with a variety of alkyl disulfide groups (including, but not limited to, no methyl disulfide (formula (L-2a)), monomethyl disulfide (formula (L-2b)), dimethyl disulfide (formula (L-2c)), and cyclopropyl disulfide (formula (L-2d))) by replacing dimethylcysteamine hydrochloride with other amino-alkyl thiol-containing compounds. This example shows the use of dimethylcysteamine hydrochloride to prepare Compound No. 64-51, an example of the general Azide-Disulfide-PABC-IMDQ structure. This example also describes the preparation of the monomethyl disulfide derivative Compound No. 64-51a. In addition, the TLR7/8 agonist moiety (D in formula (I)) can be either IMDQ or meta-IMDQ (see FIG. 1 for chemical structure representations of IMDQ and meta-IMDQ), as well as any of Compound Nos. 64-01 to 64-50, 64-58 to 64-69, 64-01a to 64-50a, and 64-58a to 64-69a. IMDQ and meta-IMDQ can be prepared as described in U.S. Pat. Nos. 8,728,486 and 9,441,005.

Scheme S1-1

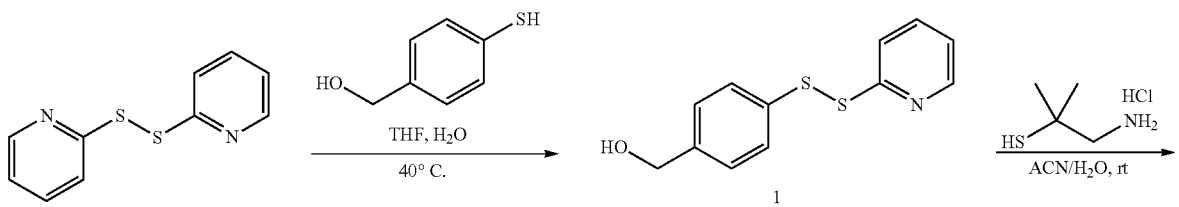

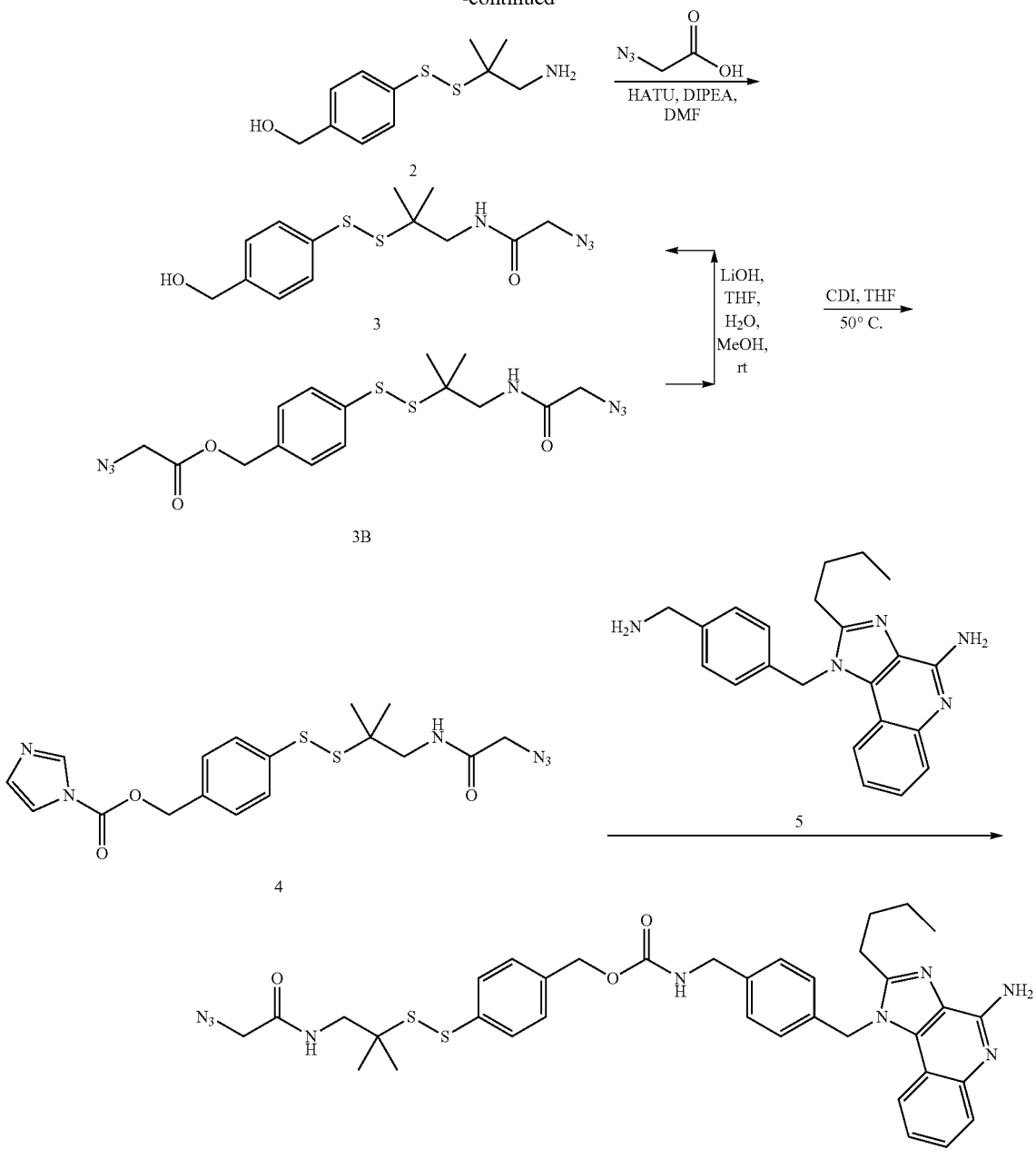

Compound No. 64-51

General Procedure for the Preparation of Compound No. 1.

To a solution of 4-mercaptobenzyl alcohol (700 mg, 5.0 mmol) in H$_2$O/THF (2 mL/20 mL) was added 2,2'-dithiodipyridine (1.65 g, 7.5 mmol). The resulting yellow clear solution was heated to 40° C. and stirred for 4 hours. The reaction solution was diluted with ethyl acetate (100 mL) and washed with 1N HCl (100 mL), followed by water (150 mL). The organic layer was dried over Na$_2$SO$_4$ and concentrated under reduced pressure. The residue was purified by column chromatography (ethyl acetate/hexanes, v/v, 1/2 to 1/1) to give Compound No. 1 (990 mg, 80% yield) as a colorless oil. LC-MS: 250 [M+1]$^+$.

General Procedure for the Preparation of Compound No. 2.

A solution of Compound No. 1 (506 mg, 2.03 mmol) and dimethylcysteamine hydrochloride (375 mg, 2.65 mmol) in acetonitrile/water (6 mL/6 mL) was stirred at room temperature for 18 hours. LC/MS showed the disappearance of Compound No. 1. The reaction mixture was diluted with ethyl acetate (100 mL) and washed with a saturated NaHCO$_3$ aqueous solution (100 mL). The organic layer was dried over Na$_2$SO$_4$ and concentrated under reduced pressure. The residue was purified by column chromatography (ethyl acetate/MeOH/triethylamine, v/v, 1/0/0 to 100/10/3) to give Compound No. 2 (460 mg, 93% yield) as a light yellow solid. LC-MS: 244 [M+1]$^+$.

General Procedure for the Preparation of Compound No. 3.

To a solution of 2-azidoacetic acid (285 mg, 2.82 mmol) in DMF (10 mL) was added HATU (1.14 g, 3.01 mmol) at 0° C. After 10 minutes, a solution of Compound No. 2 (457 mg, 1.88 mmol) and DIPEA (0.66 mL, 3.76 mmol) in DMF (3 mL) was added into above solution. The resulting solution was warmed up to room temperature and stirred for 2 hours. LC/MS indicated the disappearance of Compound No. 2. The reaction mixture was concentrated under reduced pressure and purified by column chromatography (ethyl acetate/hexanes, v/v, 1/1 to 1/0) to give Compound 3 (200 mg) as a colorless oil, together with 505 mg of by-product Compound 3B, which was treated with lithium hydroxide in THF/$H_2O$/MeOH to give Compound No. 3. LC-MS: 325 [M−1]$^-$.

General Procedure for the Preparation of Compound No. 4.

To a solution of Compound No. 3 (310 mg, 0.95 mmol) in THF (5 mL) at 50° C. was added CDI (232 mg, 1.43 mmol) in THF (5 mL) dropwise over 5 minutes. After 2 hours, the reaction mixture was cooled to room temperature and concentrated under reduced pressure. The residue was purified by column chromatography (ethyl acetate/hexanes, v/v, 1/1 to 1/0) to give Compound No. 4 (290 mg, 72% yield) as a white wax-like solid. LC-MS: 325 [M−1]$^-$.

General Procedure for the Preparation of Compound No. 64-51.

A solution of Compound No. 4 (183 mg, 0.435 mmol) and Compound No. 5 (IMDQ; 148 mg, 0.412 mmol) in DMF/THF (5 mL/2 mL) was stirred at 50° C. for 18 hours. LC/MS showed most of Compound No. 5 was consumed. The reaction mixture was cooled down and concentrated under reduced pressure. The residue was purified by column chromatography (dichloromethane/MeOH, v/v, 15/1 to 8/1) to give Compound No. 64-51 (210 mg, 68% yield) as a white solid. LC-MS: 712 [M+1]$^+$. $^1$H NMR (300 MHz, CDCl$_3$) δ 7.79 (d, 1H), 7.68 (d, 1H), 7.56 (d, 2H), 7.43 (td, 1H), 7.30 (d, 2H), 7.23 (d, 2H), 7.11 (td, 1H), 7.01 (d, 2H), 6.24 (t, 1H), 5.71 (s, 2H), 5.63 (bs, 2H), 5.14 (t, 1H), 5.08 (s, 2H), 4.34, (d, 2H), 3.86 (s, 2H), 3.32 (d, 2H), 2.86 (dd, 2H), 1.79 (p, 2H), 1.43 (h, 2H), 1.25 (s, 6H), 0.92 (t, 3H).

General Procedure for the Preparation of Compound No. 64-51a.

Compound No. 64-51a was prepared as shown in Scheme S1-1 for Compound No. 64-51, using HS(CH(CH$_3$))CH$_2$NH$_2$ hydrochloride (i.e., 2-propanethiol, 1-amino, hydrochloride) in place of dimethylcysteamine hydrochloride (i.e., 2-propanethiol, 1-amino-2-methyl-, hydrochloride). The chemical structure of Compound No. 64-51a is shown in Scheme S4-1a.

Example S1a

Preparation of Compound No. 64-70

The procedures and scheme shown in Example S1a and Scheme S1a-1 can be used to prepare an Azide-thiol-PABC-IMDQ compound as a non-cleavable conjugate control. This example shows the use of 4-mercaptobenzyl alcohol to prepare Compound No. 64-70, an example of the general Azide-thiol-PABC-IMDQ structure. The TLR7/8 agonist moiety (D in formula (I)) can be either IMDQ or meta-IMDQ (see FIG. 1 for chemical structure representations of IMDQ and meta-IMDQ), as well as any of Compound Nos. 64-01 to 64-50, 64-58 to 64-69, 64-01a to 64-50a, and 64-58a to 64-69a.

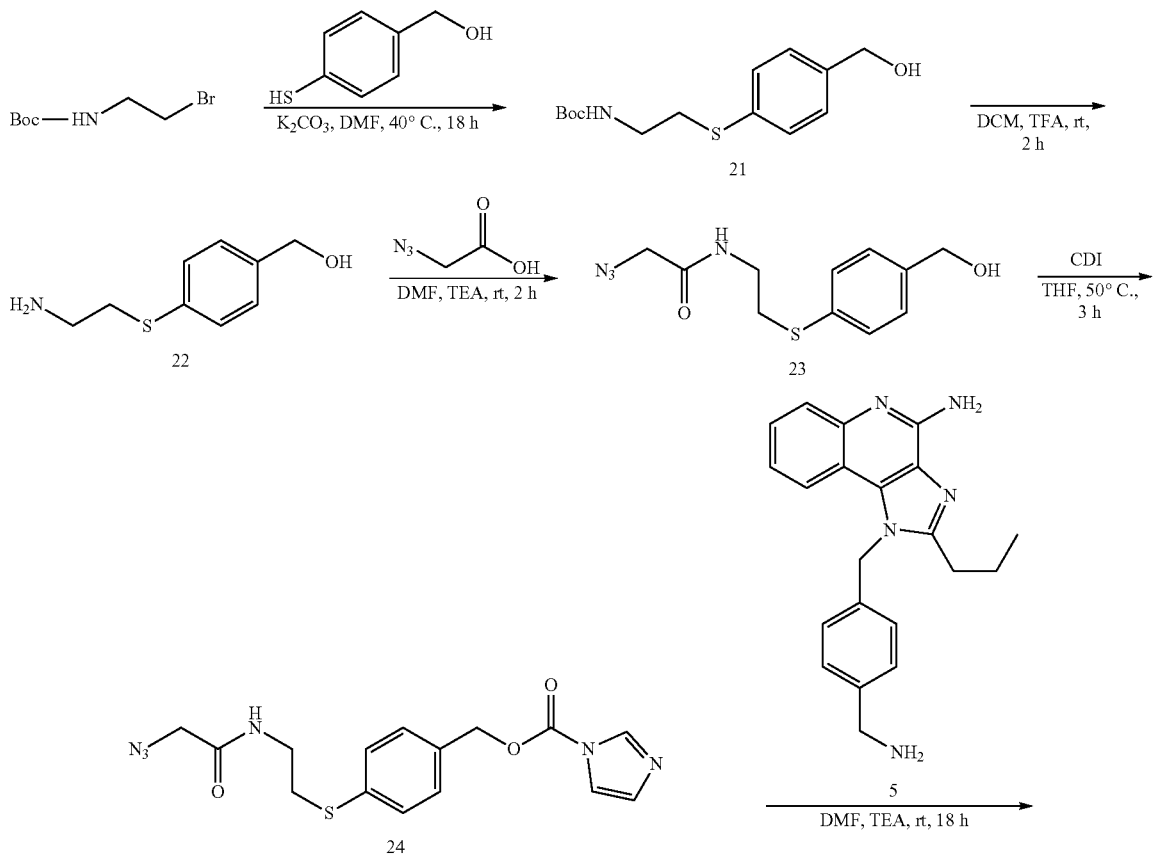

Scheme S1a-1

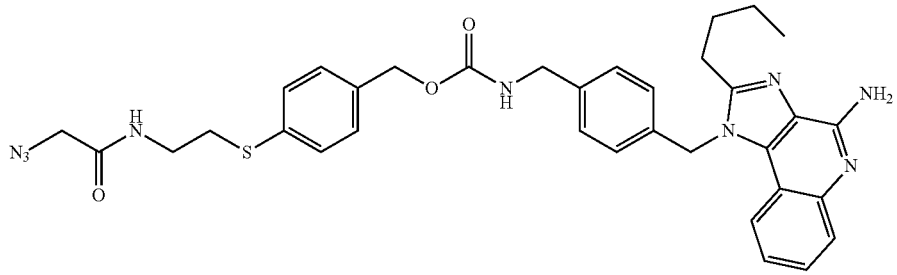

Compound No. 64-70

Procedure for the Preparation of Compound 21.

To a solution of 2-(Boc-amino)ethyl bromide (2.0 g, 8.9 mmol) in DMF (20 mL) was added 4-mercaptobenzyl alcohol (1.04 g, 7.4 mmol) and potassium carbonate (2.24 g, 16.2 mmol). The resulting cloudy solution was stirred at 40° C. for 18 hours. The reaction solution was diluted with ethyl acetate (100 mL) and washed with 0.1 N HCl (100 mL), followed by water (100 mL). The organic layer was dried over $Na_2SO_4$ and concentrated under reduced pressure. The residue was purified by flash column chromatography, eluting with 1/2 to 1/1 (v/v) ethyl acetate/hexanes, to yield 1.72 g of Compound 21 as a colorless oil. Purity was 82% by RP-HPLC at 254 nm and the intended synthetic mass of 549 Daltons was confirmed by LC-MS.

Procedure for the Preparation of Compound 22.

To a solution of Compound 21 (1.72 g, 6.0 mmol) in DCM (100 mL) was added TFA (8 mL). The resulting light yellow solution was stirred at room temperature for 2 hours. After concentration under reduced pressure, the mixture was co-evaporated with DCM (100 mL) three times. The resulting residue was purified by silica gel flash column chromatography, eluting with 1/0/0 to 100/10/2 (v/v) DCM/MeOH/trimethylamine, to yield 0.94 g of Compound 22 as light yellow oil. Purity was 85% by RP-HPLC at 254 nm and the intended synthetic mass of 183 Daltons was confirmed by LC-MS.

Procedure for the Preparation of Compound 23.

To a solution of 2-azidoacetic acid (625 mg, 6.18 mmol) in DMF (5 mL) was added O—(N-Succinimidyl)-N,N,N',N'-tetramethyluronium tetrafluoroborate (680 mg, 6.67 mmol) at room temperature. After 15 minutes, a solution of Compound 22 (945 mg, 5.16 mmol) in DMF (5 mL) was added, followed by the addition of triethylamine (1.6 mL, 11.4 mmol). The resulting solution was stirred at room temperature for 2 hours. The reaction mixture was then diluted with ethyl acetate (100 mL) and extrated with water (100 mL). The organic layer was dried over sodium sulfate and concentrated under reduced pressure. The residue was purified by column chromatography, eluting with 1/1 to 1/0 (v/v) ethyl acetate/hexanes, to yield 0.5 g of Compound 23 as colorless oil. Purity was 36% by RP-HPLC at 254 nm and the intended synthetic mass of 249 Daltons was confirmed by LC-MS.

Procedure for the Preparation of Compound 24.

To a solution of CDI (456 mg, 2.81 mmol) in THF (10 mL) at 50° C. was added Compound 23 (500 mg, 1.87 mmol) in THF (3 mL) dropwise. After 3 hours, the reaction mixture was cooled to room temperature and concentrated under reduced pressure. The residue was purified by column chromatography, eluting with 1/1 to 1/0 (v/v) ethyl acetate/hexanes, to yield 325 mg of Compound 24 as colorless oil. Purity was 48% by RP-HPLC at 254 nm and the intended synthetic mass of 360 Daltons was confirmed by LC-MS.

General Procedure for the Preparation of Compound No. 64-70.

To a solution of Compound 24 (195 mg, 0.54 mmol) and IMDQ (Compound 5, 97 mg, 0.27 mmol) in DMF (6 mL) was added TEA (6 drops). The resulting solution was stirred at room temperature overnight and the reaction mixture was concentrated under reduced pressure. The residue was purified by column chromatography, eluted with 10/1 (v/v) dichloromethane/MeOH, to yield 52 mg of Compound No. 64-70 as a white solid. Purity was 99% by RP-HPLC at 254 nm, the intended synthetic mass of 651.8 Daltons was confirmed by LC-MS, and the intended synthetic structure was confirmed by 300 MHz $^1$H NMR (CD$_3$OD+CDCl$_3$) δ 7.67 (td, 2H), 7.57 (s, 1H), 7.40 (td, 1H), 7.33-7.19 (m, 4H), 7.08 (td, 1H), 6.97-6.94 (m, 3H), 5.69 (s, 2H), 4.99 (s, 2H), 4.26 (s, 2H), 3.81 (s, 2H), 3.40 (t, 2H), 3.01 (t, 2H), 2.84 (t, 2H), 1.74 (m, 2H), 1.39 (m, 2H), 0.88 (t, 3H).

Example S2

Preparation of Compound Nos. 64-52, 64-52a, 64-52b, 64-52c, 64-52d, 64-52e, 64-52f and 64-52g The procedures and schemes shown in Example S2 and Schemes S2-1 thru S2g-1 can be used to prepare a variety of compounds of the invention, -L$^3$-L$^2$-L$^1$-D in formula (I), with a variety of conjugation linkers L$^3$ in formula (I), cleavable peptide sequences L$^2$ in formula (I), self-eliminating linkers L$^1$ in formula (I) and where the TLR7/8 agonist compounds D in formula (I) can be either IMDQ or meta-IMDQ (see FIG. 1 for chemical structure representations of IMDQ and meta-IMDQ), as well as any of Compound Nos. 64-01 to 64-50, 64-58 to 64-69, 64-01a to 64-50a, and 64-58a to 64-69a.

Compound No. 64-52.

Compound No. 64-52 was prepared as shown in Scheme S2-1, to exemplify an embodiment of the invention where the TLR7/8 agonist D in formula (I) is IMDQ, the self-eliminating linker L$^1$ in formula (I) is a para-amino benzyl carbamate moiety, the cleavable linker L$^2$ in formula (I) is valine-citrulline, and the conjugation linker L$^3$ in formula (I) is an azido-PEG$_4$ moiety.

145 146
Scheme S2-1
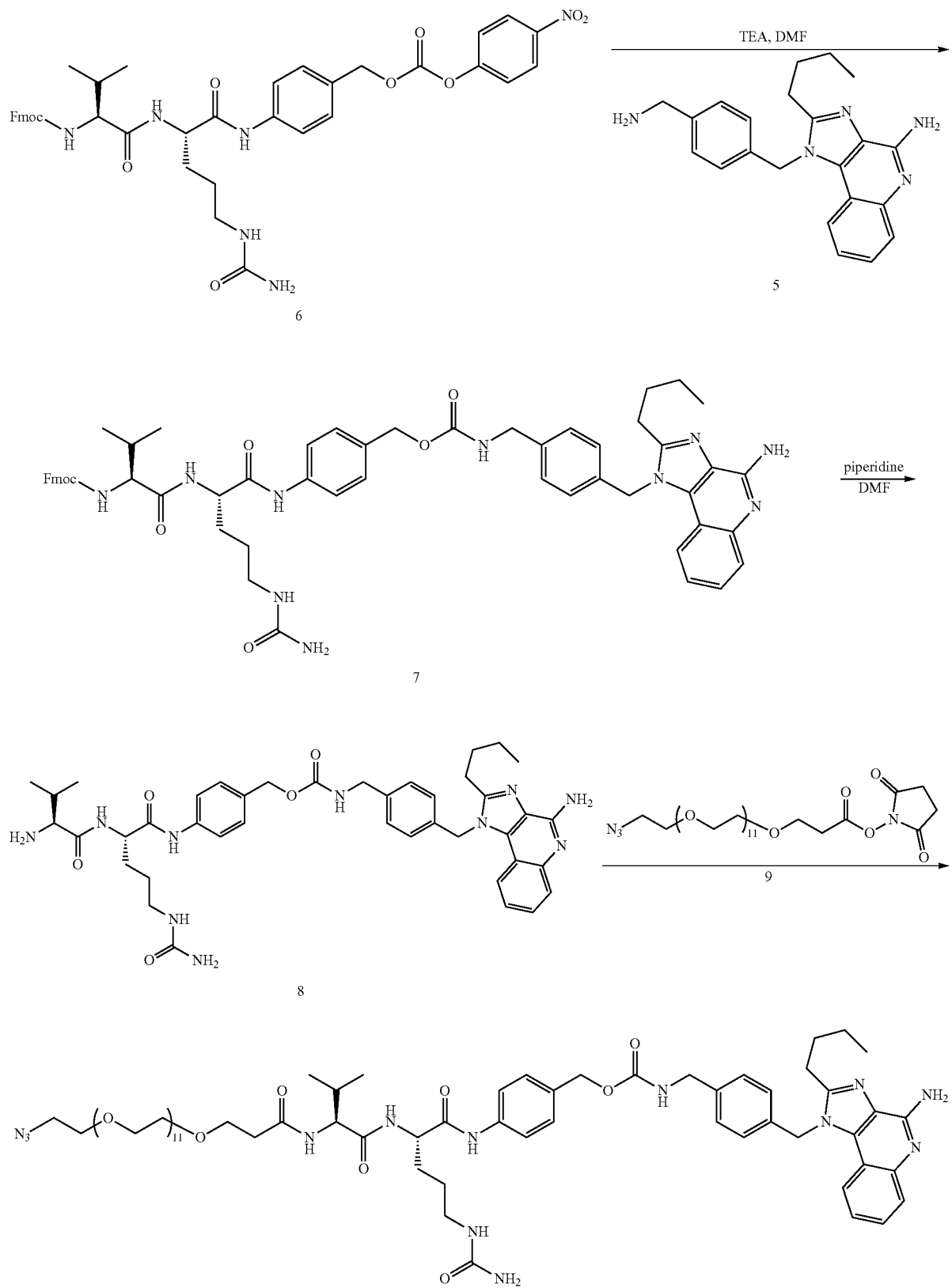
Compound No. 64-52

General Procedure for the Preparation of Compound No. 7.

To a solution of Compound No. 6 (465 mg, 0.61 mmol) and Compound No. 5 (IMDQ; 190 mg, 0.53 mmol) in DMF (15 mL) was added triethylamine (0.13 mL, 0.94 mmol). The resulting yellow clear solution was stirred at room temperature for 15 hours. LC/MS showed mostly the desired product Compound No. 7, and that all of Compound No. 5 was consumed. The reaction mixture was directly used for next step. LC-MS: 987 $[M+1]^+$.

General Procedure for the Preparation of Compound No. 8.

To a crude solution of Compound No. 7 (~0.528 mmol) in DMF (15 mL) was added piperidine (460 mg, 5.41 mmol), and the solution was stirred at room temperature for 6 hours. LC/MS showed the disappearance of the starting material Compound No. 7. The reaction mixture was diluted with 10% MeOH in dichloromethane (200 mL) and washed with water (200 mL×2). The aqueous layers were extracted with ethyl acetate (150 mL). The combined organic layers were dried over $Na_2SO_4$ and concentrated under reduced pressure. The residue was purified by column chromatography (dichloromethane/MeOH, v/v, 100/10 to 100/15) to give Compound No. 8 (304 mg, 65% yield over two steps) as a yellow solid. LC-MS: 765 $[M+1]^+$.

General Procedure for the Preparation of Compound No. 64-52.

To a solution of Compound No. 8 (173 mg, 0.224 mmol) and Compound No. 9 (181 mg, 0.244 mmol) in DMF (5 mL) was added DIPEA (0.08 mL, 0.44 mmol). The resulting solution was stirred at room temperature for 16 hours. LC/MS showed mostly conversion to the desired product. The reaction mixture was concentrated under reduced pressure. The residue was purified by column chromatography (dichloromethane/MeOH, v/v, 100/10 to 100/15) to give Compound No. 64-52 (170 mg, 55% yield) as a white solid. LC-MS: 1390 $[M+1]^+$. $^1$H NMR (300 MHz, $CDCl_3$) δ 7.68 (d, 1H), 6.62 (d, 1H), 7.52 (d, 2H), 7.38 (t, 1H), 7.20 (d, 2H), 7.18 (d, 2H), 7.07 (t, 1H), 6.92 (d, 2H), 5.66 (s, 2H), 4.95 (s, 2H), 4.46 (dd, 1H), 4.23 (s, 2H), 4.09 (d, 1H), 3.61-3.45 (m, 44H), 3.35-3.26 (m, 4H), 3.10 (t, 2H), 2.81 (t, 2H), 2.56-2.45 (m, 2H), 2.12-2.20 (1, 1H), 1.91-1.80 (m, 1H), 1.80-1.55 (m, 3H), 1.55-1.40 (m, 2H), 1.40-1.28 (m, 4H), 0.93-0.82 (m, 9H).

Compound No. 64-52a.

Compound No. 64-52a was prepared as shown in Scheme S2a-1, to exemplify an embodiment of the invention where the TLR7/8 agonist D in formula (I) is IMDQ, the self-eliminating linker $L^1$ in formula (I) is a para-amino benzyl carbamate moiety, the cleavable linker $L^2$ in formula (I) is valine-citrulline, and the conjugation linker $L^3$ in formula (I) is an azido-$PEG_4$ moiety.

Scheme S2a-1

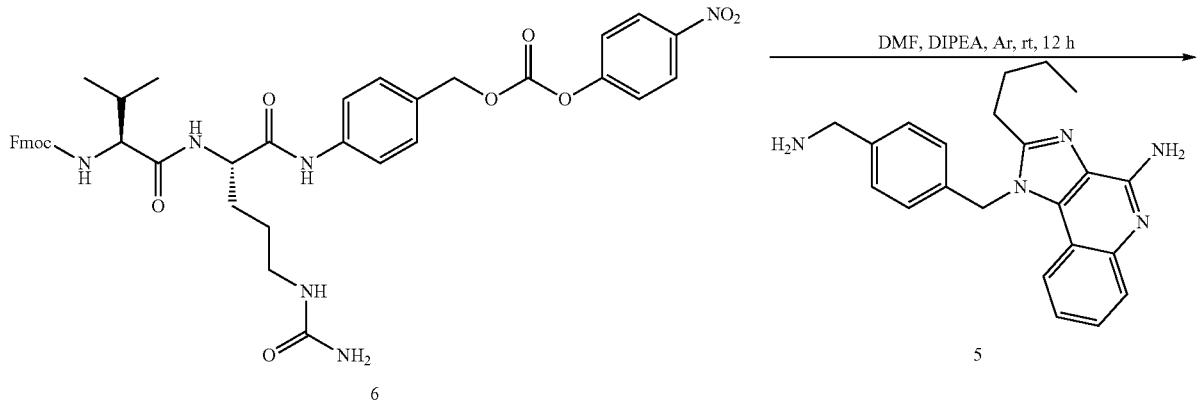

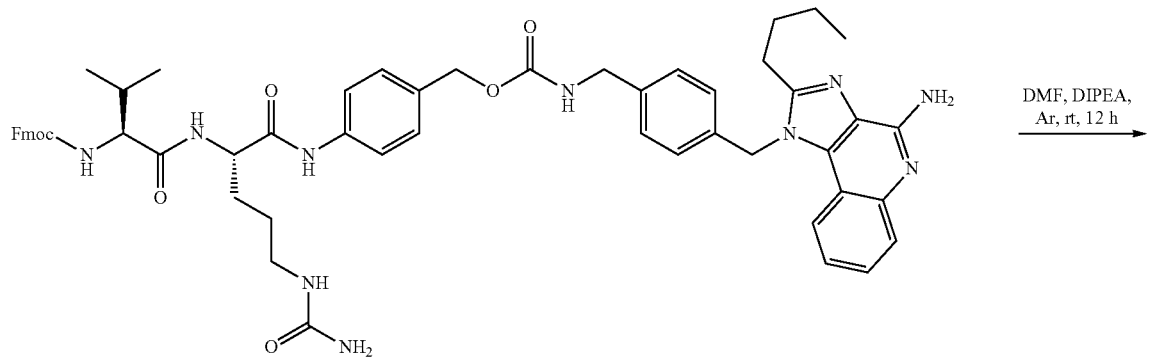

-continued

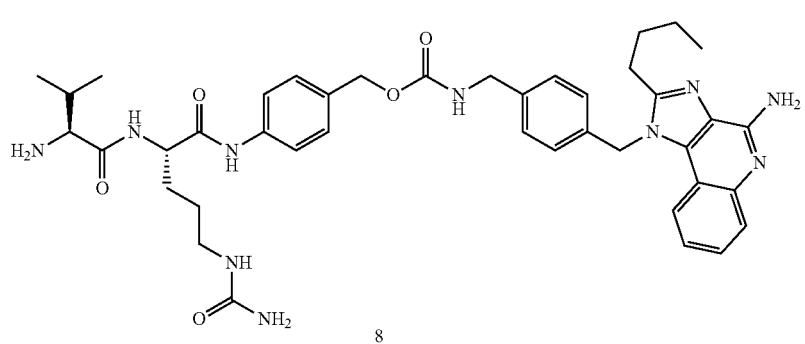

8

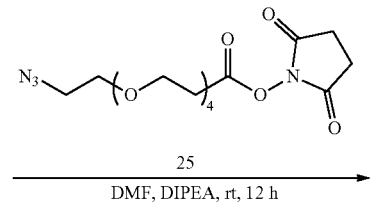

$\xrightarrow{25}$
DMF, DIPEA, rt, 12 h

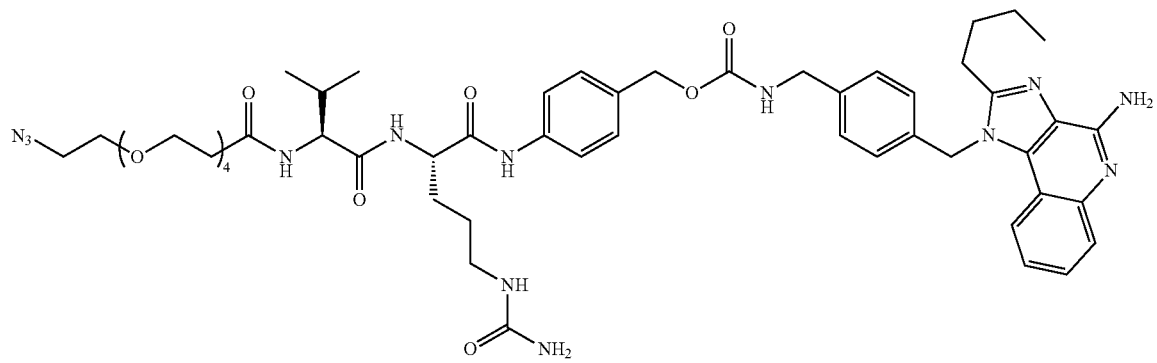

Compound No. 64-52a

Procedure for the Preparation of Compound 7.

To an ice cold solution of IMDQ (Compound 5; 36 mg, 1 eq.) in DMF (1.5 mL) was added DIPEA (0.1 mL), and the solution was stirred for 10 minutes under an argon atmosphere. Compound 6 (77 mg, 1 eq.) was added in two portions and the resulting clear-yellow solution stirred at 0° C. for 2 hours, the solution was slowly warmed to room temperature and then stirring was continued for an additional 12 hours. Thin layer chromatography analysis, developed with 10% (v/v) MeOH in DCM containing 1% (v/v) TEA, indicted that all IMDQ starting material had been consumed. The DMF was removed under reduced pressure, ethyl acetate (3 mL) added to the solid yellow residue, the mixture was triturated, the pale-yellow solid that formed allowed to settle, and the supernatant was decanted. This process was repeated an additional two times. The off-white solid product was dried under reduced pressure to yield 84 mg of Compound 7.

Procedure for the Preparation of Compound 8.

To an ice cold solution of Compound 7 (71 mg, 1 eq.) in DMF (1.5 mL) was added DIPEA (0.1 mL), the mixture was stirred overnight under an argon atmosphere and then slowly warmed to room temperature and stirred for an additional 12 hours. Reverse phase HPLC analysis of the reaction indicated that it had proceeded to completion. The DMF was removed under reduced pressure, ethyl acetate (3 mL) was added to the yellow residue, the mixture triturated, the pale-yellow solid allowed to settle, and the supernatant was decanted. This process was repeated an additional two times, and the off-white solid was dried under reduced pressure to yield 50 mg of Compound 8.

Procedure for the Preparation of Compound No. 64-52a.

Compound 8 (50 mg, 1.0 eq.) and Compound 25 (20.3 mg, 1.2 eq.) were dissolved in DMF (1 mL), DIPEA was added (100 uL), and the solution was stirred for 1.5 hours at room temperature. RP-HPLC analysis of the reaction indicted that Compound 12 had been completely consumed. The DMF was removed under reduced pressure and the solid yellow residue was subjected to silica gel column chromatography, eluting with 1-8% (v/v) MeOH in DCM containing 0.5% (v/v) ammonia, to yield 34 mg of Compound No. 64-52a as a white solid. Product purity was assessed to be 95% by RP-HPLC at 254 nm, the intended synthetic mass of 1,035.5 Daltons was confirmed by LC-MS, and the intended synthetic structure confirmed by 300 MHz $^1$H NMR (CD$_3$OD): δ 7.83 (d, J=8.1 Hz, 1H), 7.68 (d, J=8.4 Hz, 1H), 7.58 (d, J=8.1 Hz, 2H), 7.46 (t, J=7.5, 15.0 Hz, 1H), 7.25-7.31 (m, 1H), 7.14 (t, J=7.5, 15.0 Hz, 1H), 7.03 (d, J=8.4 Hz, 2H), 5.88 (s, 2H), 5.03 (s, 2H), 4.48-4.55 (m, 1H), 4.20-4.26 (m, 3H), 3.73-3.76 (m, 2H), 3.55-3.68 (m, 14H), 3.28, 3.38 (m, 4H), 3.0-3.28 (m, 2H), 2.97 (t, J=7.5, 15.3 Hz, 2H), 2.55 (t, J=6, 12 Hz, 2H), 1.72-2.18 (m, 5H), 1.58-1.70 (m, 2H), 1.43-1.55 (m, 2H), 0.88-1.01 (m, 9H).

Compound No. 64-52b.

Compound No. 64-52b was prepared as shown in Scheme S2b-1, to exemplify an embodiment of the invention where the TLR7/8 agonist D in formula (I) is IMDQ, the self-eliminating linker L$^1$ in formula (I) is a para-amino benzyl carbamate moiety, the cleavable linker L$^2$ in formula (I) is valine-citrulline, and the conjugation linker L$^3$ in formula (I) is an azido moiety.

Scheme S2b-1

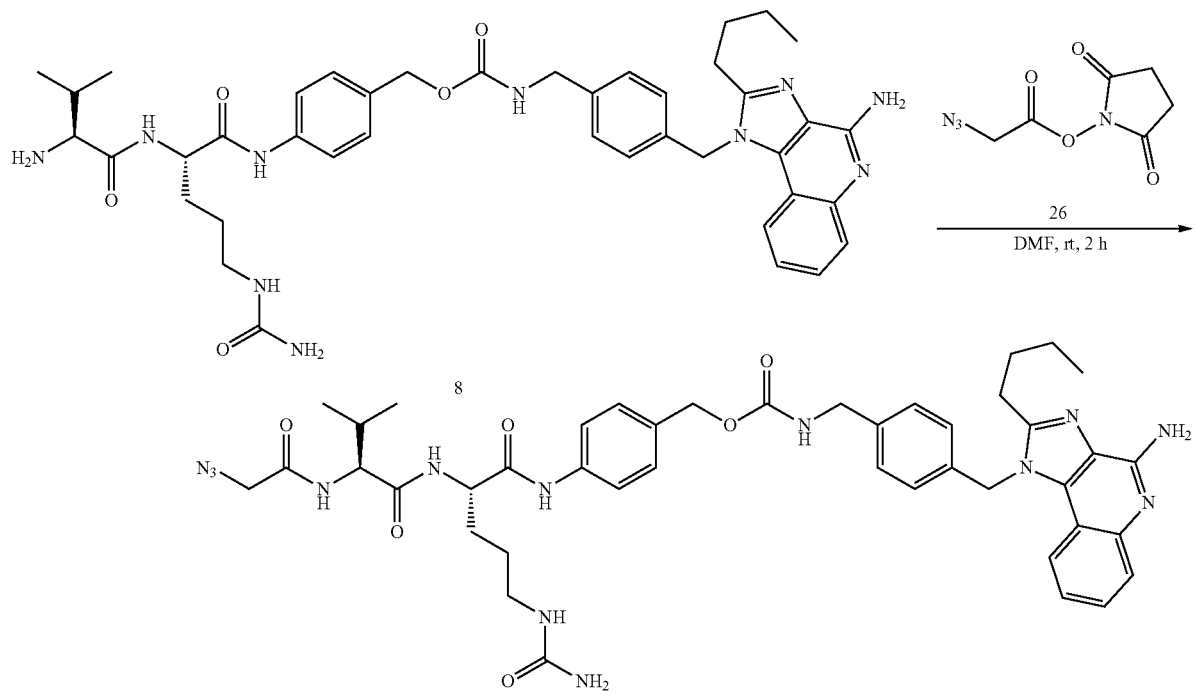

Compound No. 64-52b

Procedure for the Preparation of Compound No. 64-52b.

Compound 8 was prepared as described in Scheme S2a-1. To a solution of Compound 8 (135 mg, 0.176 mmol, 1.0 eq.) in DMF (1.0 mL) was added a DMF solution containing Compound 26 (1.7 mL, 0.265 mmol, 1.5 eq.). The resulting solution was stirred at room temperature for 2 hours, by that time LC-MS analysis showed that Compound 8 had been comsumed. The reaction was then diluted with MeOH (3 mL), further with water (3 mL), and 1N NaOH (0.5 mL) was added. The resulting solution was stirred at room temperature for 24 hours, then was directly purified by preparative RP-HPLC to yield 62 mg of Compound No. 64-52b as a white solid. Product purity was assessed to be 96% by RP-HPLC at 254 nm, the intended synthetic mass of 847.4 Daltons was confirmed by LC-MS, and the intended synthetic structure confirmed by 300 MHz $^1$H NMR (acetone-d6): δ 8.49 (s, 1H), 7.89 (d, J=8.4 Hz, 1H), 7.77 (d, J=8.4 Hz, 1H), 7.64-7.56 (m, 3H), 7.36-7.26 (m, 5H), 7.08 (d, J=6.0 Hz, 2H), 5.88 (s, 2H), 5.05 (s, 2H), 4.50 (dd, J=5.1 and 9.0 Hz, 1H), 4.29-4.25 (m, 3H), 4.05 (s, 2H), 3.19-3.13 (m, 1H), 3.01 (t, J=7.8 Hz, 2H).

Compound No. 64-52c.

Compound No. 64-52c was prepared as shown in Scheme S2c-1, to exemplify an embodiment of the invention where the TLR7/8 agonist D in formula (I) is IMDQ, $L^1$ in formula (I) is a bond, the cleavable linker $L^2$ in formula (I) is valine-citrulline, and the conjugation linker $L^3$ in formula (I) is an azido-PEG$_{12}$ moiety.

Scheme S2c-1

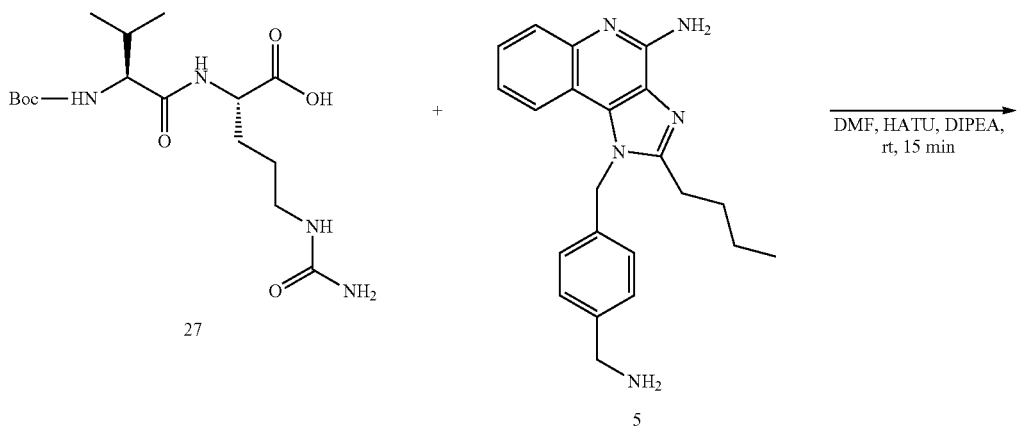

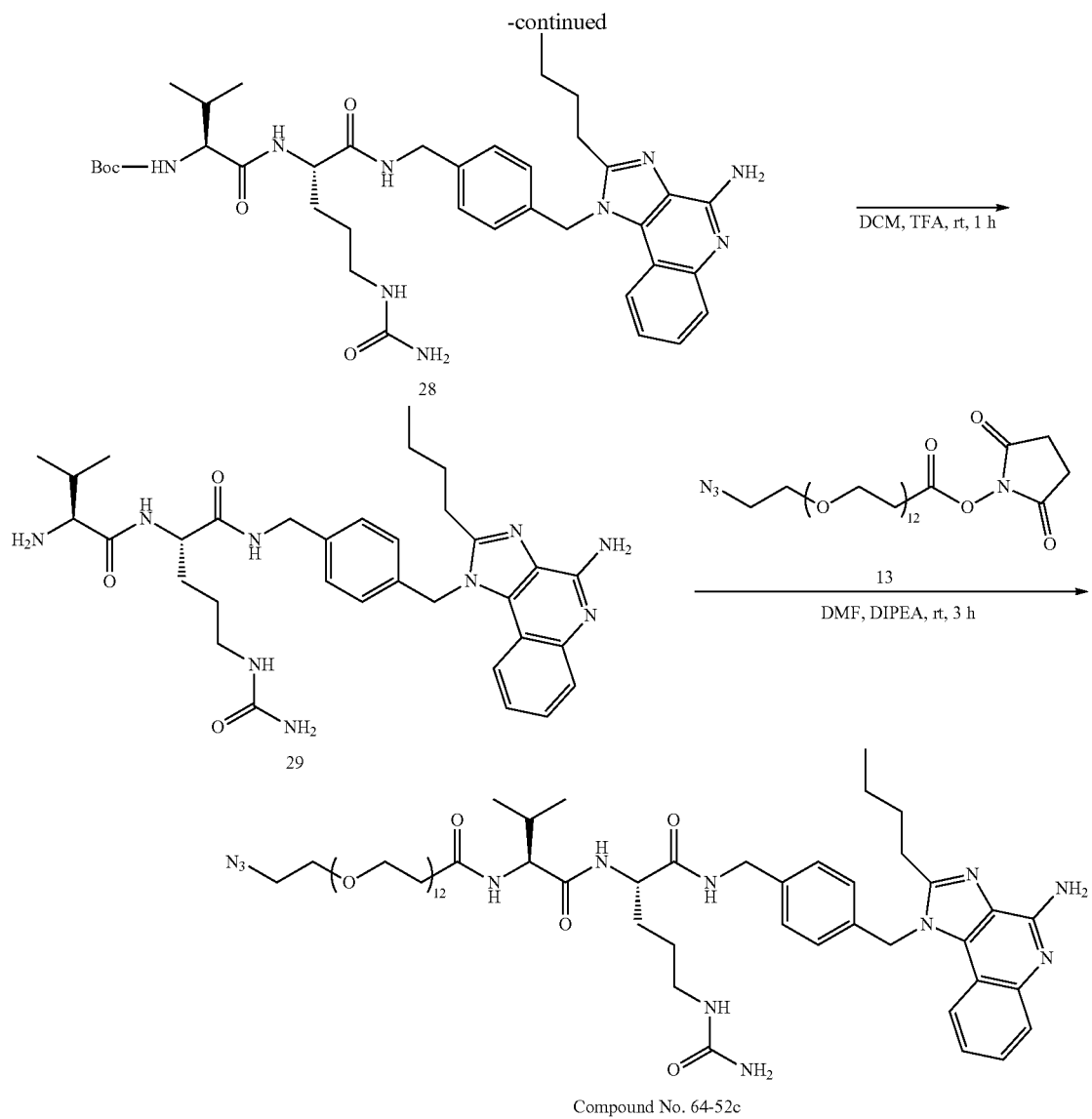

Compound No. 64-52c

Procedure for the Preparation of Compound 28.

To a solution of Compound 27 (100 mg, 0.401 mmol, 1.0 eq.) and IMDQ (Compound 5; 96 mg, 0.40 mmol, 1.0 eq.) in DMF (3 mL) was added HATU (154 mg, 0.602 mmol, 1.5 eq.) followed by the addition of DIPEA (89 μL, 0.80 mmol, 2.0 eq.). The reaction was stirred at room temperature for 15 minutes, and then purified by preparative RP-HPLC (95:5% (v/v) H$_2$O/acetonitrile+0.1% (v/v) acetic acid, 95/5 to 0/100 gradient within 30 min). Fractions containing the main peak with the expected 322 nm adsorbance were collected and dried under reduced pressure to yield 141 mg of the Compound 28 as a white solid.

Procedure for the Preparation of Compound 29.

A solution of Compound 28 (141 mg, 0.197 mmol, 1.0 eq.) in DCM (4 mL) was treated with TFA (1 mL) at room temperature for 1 hour. The reaction was concentrated to dryness under reduced pressure and the residue, containing Compound 29, used without further purification.

Procedure for the Preparation of Compound No. 64-52c.

To a solution of Compound 29 (73 mg, 0.10 mmol, 1.0 eq.) and Compound 13 (74 mg, 0.10 mmol, 1.0 eq) in DMF (2 mL) was added DIPEA (0.1 mL), and the reaction was stirred at room temperature for 3 hours. The mixture was purified by preparative RP-HPLC (95:5% (v/v) H$_2$O/acetonitrile+0.1% (v/v) acetic acid, 95/5 to 0/100 gradient within 30 min). Fractions containing the main peak with the expected 322 nm adsorbance were colleacted and dried under reduced pressure to yield 79 mg of Compound 64-52c as white solid. Product purity was assessed to be 97% by RP-HPLC at 254 nm, the intended synthetic mass of 1,241.5 Daltons was confirmed by LC-MS, and the intended synthetic structure confirmed by 300 MHz $^1$H NMR (CDCl$_3$): δ 8.40 (t, 1H), 8.15 (d, 1H), 7.98 (d, 2H), 7.74 (d, 1H), 7.65 (t, 1H), 7.38 (t, 1H), 7.28 (d, 2H), 7.03 (d, 2H), 5.94 (s, 2H), 4.40-4.25 (m, 3H), 4.11 (t, 1H), 3.67-3.54 (m, 52H), 3.10-3.00 (m, 6H), 2.75-2.68 (m, 1H), 2.50-2.46 (m, 2H), 2.03-1.81 (m, 4H), 1.48-1.41 (m, 4H), 0.98-0.86 (m, 9H).

Compound No. 64-52d.

Compound No. 64-52d was prepared as shown in Scheme S2d-1, to exemplify an embodiment of the invention where the TLR7/8 agonist D in formula (I) is IMDQ, L$^1$ in formula (I) is a bond, the cleavable linker L$^2$ in formula (I) is valine-citrulline, and the conjugation linker L$^3$ in formula (I) is an azido-PEG$_4$ moiety.

Scheme S2d-1

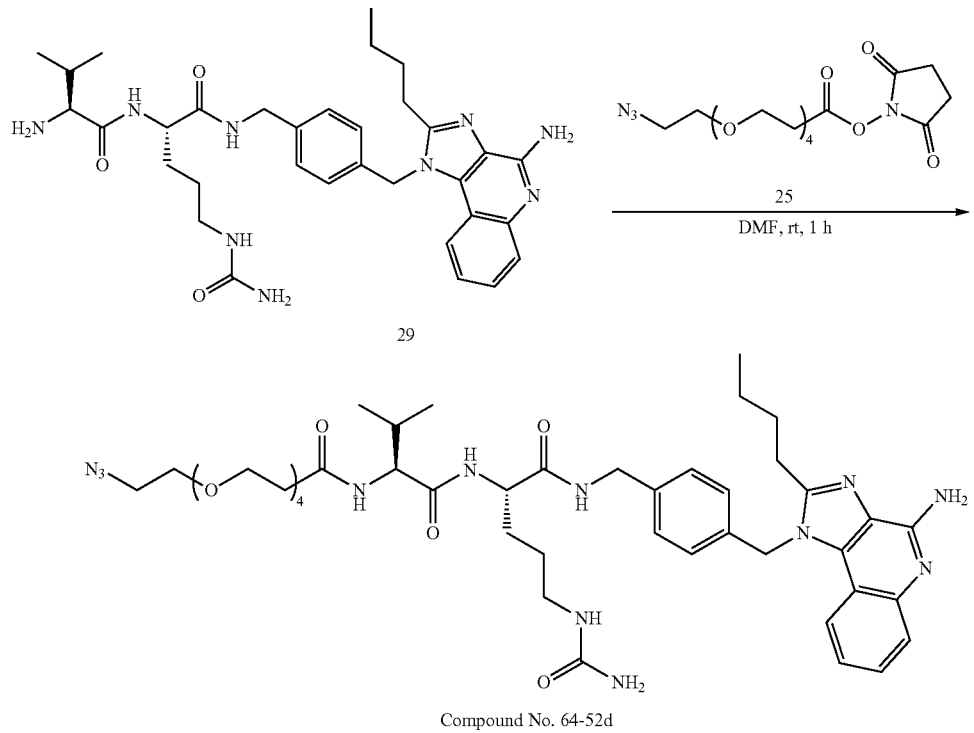

Compound No. 64-52d

Procedure for the Preparation of Compound No. 64-52d.

Compound 29 (1.0 g, 1.0 eq.) was added to a solution of Compound 25 (1.1 eq.) in DMF (10 mL) and the reaction was stirred at room temperature. The reaction progress was monitored by LC-MS, after 1 hour Compound 29 had been fully consumed so the solvent was removed under reduced pressure. The crude product was purified using flash chromatography on a Biotage Selekt, eluting with MeOH in DCM (0-25%) to afford 600 mg of Compound 64-52d as a white solid. Product purity was assessed to be 95% by RP-HPLC at 254 nm, the intended synthetic mass of 889.1 Daltons was confirmed by LC-MS, and the intended synthetic structure confirmed by 300 MHz $^1$H NMR (DMSO-$d_6$): δ 9.10 (s, 1H), 8.36-8.30 (m, 1H), 7.95 (dd, J=16.1, 8.0 Hz, 2H), 7.84 (d, J=8.4 Hz, 1H), 7.75 (d, J=8.3 Hz, 1H), 7.60 (t, J=7.8 Hz, 1H), 7.34 (t, J=7.7 Hz, 1H), 7.16 (d, J=7.8 Hz, 2H), 6.97 (d, J=7.8 Hz, 2H), 5.91 (bs, 3H), 5.36 (bs, 1H), 4.24-4.11 (m, 4H), 3.71-3.40 (m, 16H), 2.96-2.78 (m, 6H), 2.40-2.28 (m, 4H), 1.86-1.81 (m, 2H), 1.74-1.65 (m, 2H), 1.42-1.29 (m, 5H), 0.84 (t, J=7.5 Hz, 3H), 0.71 (d, J=6.8 Hz, 6H).

Compound No. 64-52e.

Compound No. 64-52e was prepared as shown in Scheme S2e-1, to exemplify an embodiment of the invention where the TLR7/8 agonist D in formula (I) is IMDQ, the self-eliminating linker $L^1$ in formula (I) is a para-amino benzyl carbamate moiety, the cleavable linker $L^2$ in formula (I) is phenylalanine-citrulline, and the conjugation linker $L^3$ in formula (I) is an azido-PEG$_{12}$ moiety.

Scheme S2e-1

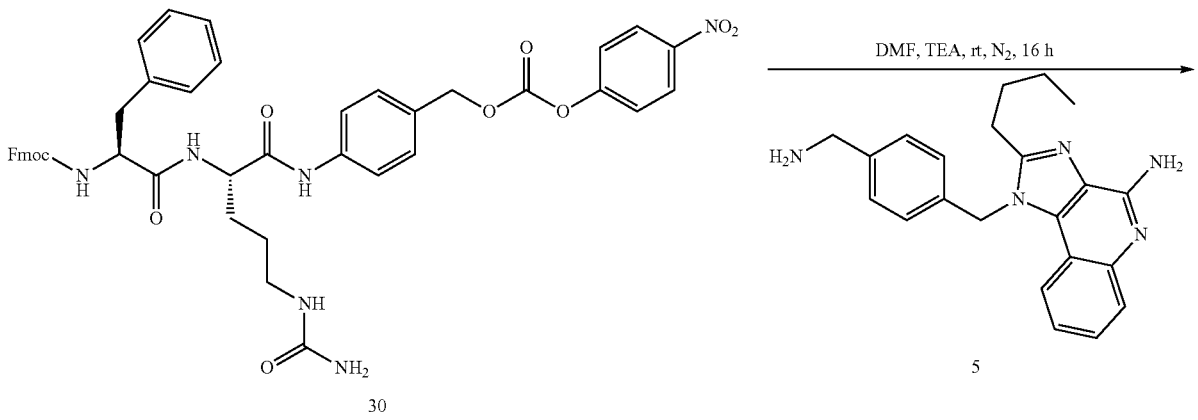

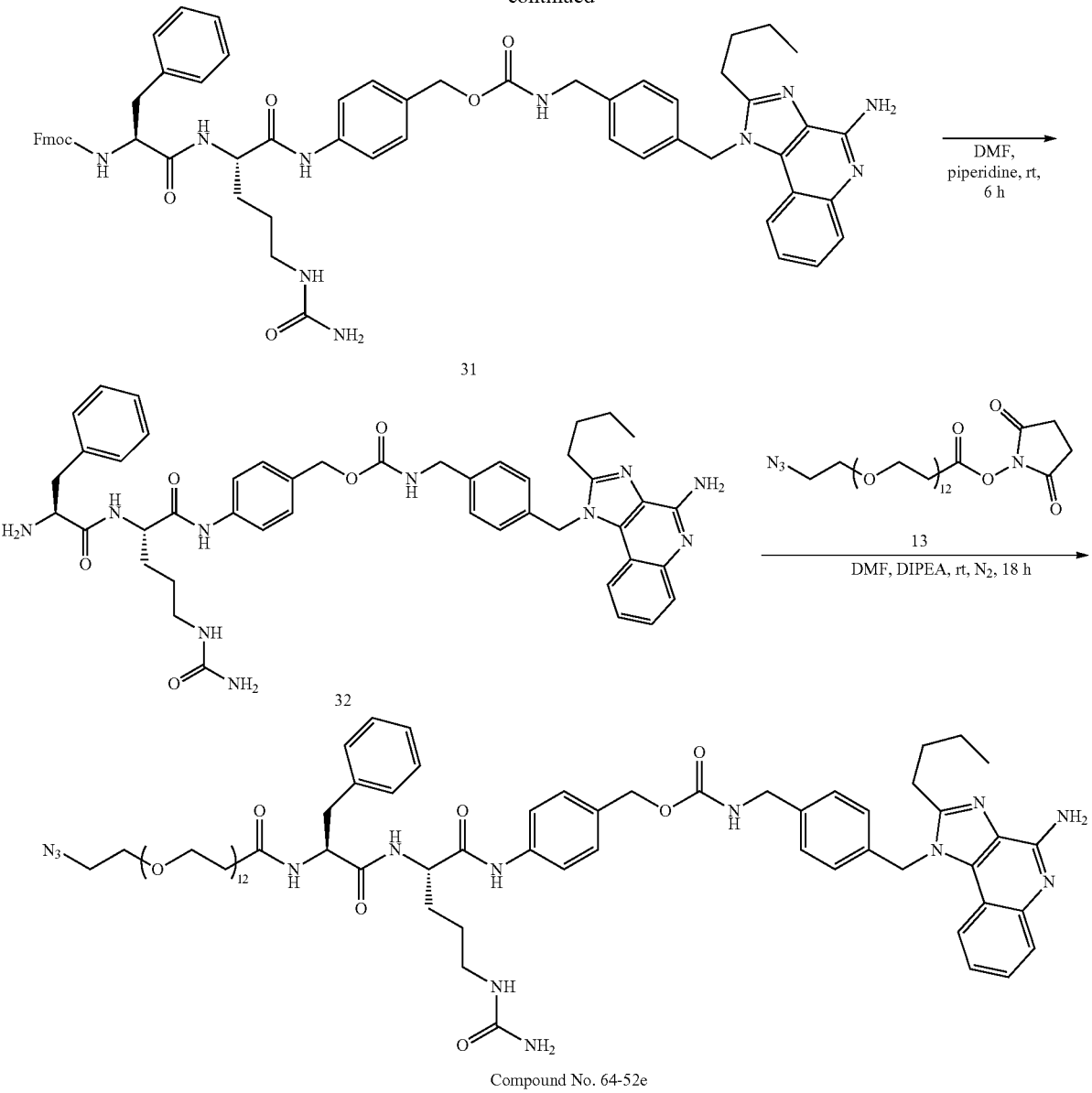

Compound No. 64-52e

Procedure for the Preparation of Compound 30.

To a solution of Compound 30 (0.27 g, 0.33 mmol, 1.2 eq.) in DMF (10.0 mL) was added IMDQ (Compound 5; 0.10 g, 0.28 mmol, 1.0 eq.) and TEA (58 mg, 0.57 mmol, 2.0 eq.). The mixture was stirred at room temperature for 16 hours under nitrogen, at which point LC-MS analysis showed that all the IMDQ was consumed. The reaction mixture was used in the next step reaction directly without further purification.

Procedure for the Preparation of Compound 31.

To the reaction mixture prepared above (~0.28 mmol in DMF) was added piperidine (0.24 g, 2.8 mmol, 10.0 eq.). The resulting mixture was stirred at room temperature for 6 hours, poured into diethyl ether (75 mL), and stirred. The yellow precipitate was collected by filtration and washed with ether. The crude product was purified by flash chromatography on a Biotage Selekt, eluting with 20% MeOH in DCM with 2% (v/v) TEA, to yield 140 mg of Compound 31 as a yellow solid.

Procedure for the Preparation of Compound No. 64-52e.

To a solution of Compound 31 (73.4 mg, 0.09 mmol, 1.2 eq.) in DMF (3.0 mL) was added Compound 13 (73.6 mg, 0.10 mmol, 1.1 eq.) in DMF (0.3 mL) and DIPEA (23.3 mg, 0.18 mmol, 2.0 eq.). The mixture was stirred at room temperature for 18 hours under nitrogen, at which point LC-MS analysis showed that all the Compound 32 was consumed. The reaction mixture was purified by preperative RP-HPLC to yield 54 mg of Compound No. 64-52e as a white solid. Product purity was assessed to be 98% by RP-HPLC at 254 nm, the intended synthetic mass of 1,438.7 Daltons was confirmed by LC-MS, and the intended synthetic structure confirmed by 300 MHz $^1$H NMR (DMSO-$d_6$): δ 10.05 (s, 1H), 8.25 (d, 1H), 8.06 (d, 1H), 7.81-7.85 (m, 2H), 7.59-7.56 (m, 4H), 7.40-7.34 (m, 1H), 7.30-7.04 (m, 14H), 6.98-6.95 (m, 3H), 5.98 (t, 1H), 5.84 (s, 2H), 5.43 (s, 2H), 4.92 (s, 2H), 4.57 (bs, 1H), 4.40 (bs, 1H), 4.11 (d, 2H), 3.60-3.30 (m, 46H), 3.08-2.8 (m, 8H), 2.78-2.70 (m, 1H), 2.28 (t, 2H), 1.75-1.65 (m, 4H), 1.50-1.30 (m, 4H), 0.84 (t, 3H).

Compound No. 64-52f.

Compound No. 64-52f was prepared as shown in Scheme S2f-1, to exemplify an embodiment of the invention where the TLR7/8 agonist D in formula (I) is IMDQ, the self-eliminating linker $L^1$ in formula (I) is a para-amino benzyl carbamate moiety, the cleavable linker $L^2$ in formula (I) is glycine-isoleucine-valine-arginine, and the conjugation linker $L^3$ in formula (I) is an azido-PEG$_4$ moiety.

General Procedure for the Preparation of Compound 33.

To an ice cold solution of IMDQ (Compound 5; 1 eq.) in DMF is added DIPEA (0.1 mL), and the solution is stirred for 10 minutes under an argon atmosphere. Compound 33 (1 eq.) is added in two portions and the resulting clear-yellow solution stirred at 0° C. for 2 hours. The solution is slowly warmed to room temperature and then stirring continued for an additional 12 hours or until thin layer chromatography

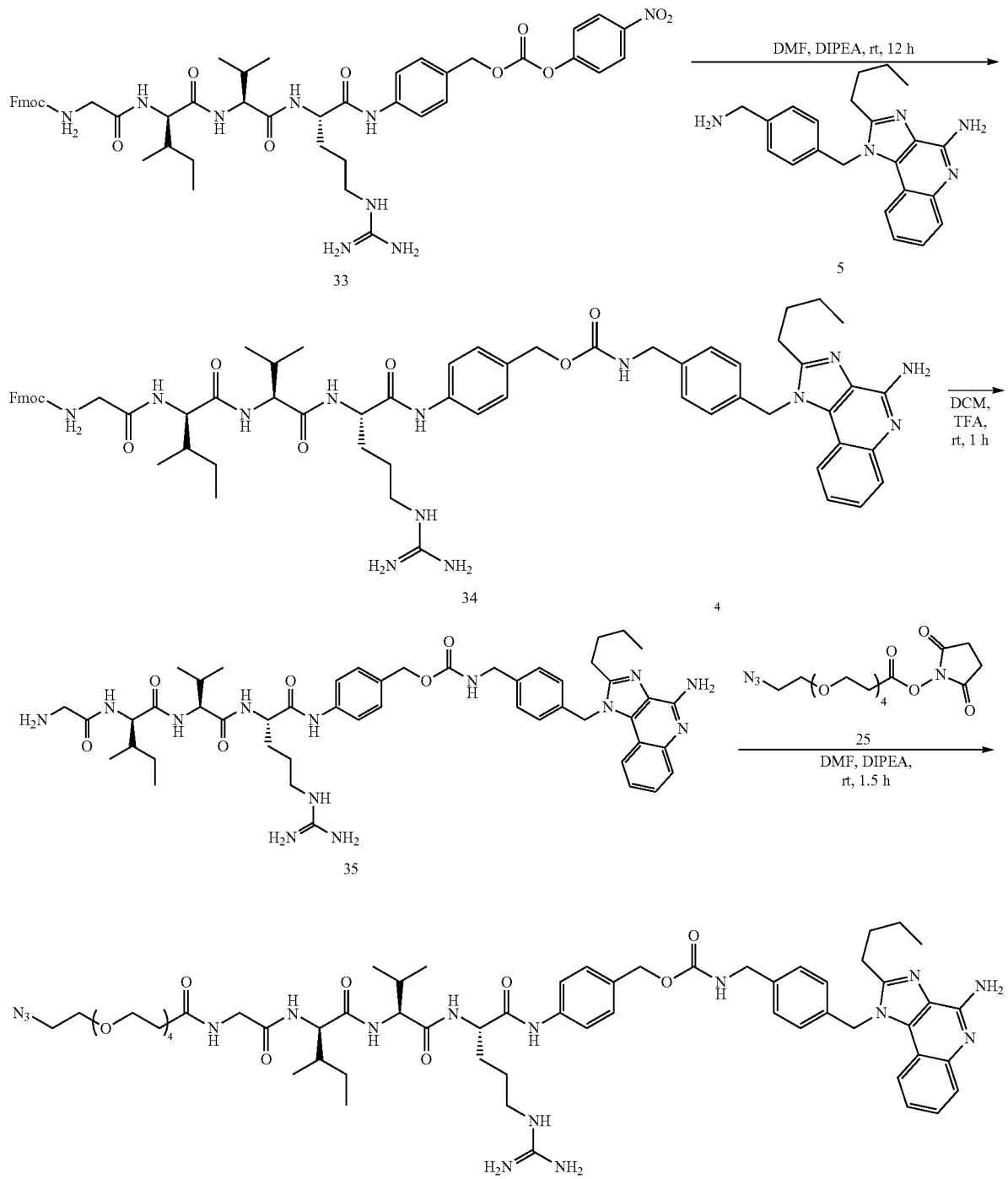

Scheme S2f-1

Compound No. 64-52f analysis, developed with 10% (v/v) MeOH in DCM containing 1% (v/v) TEA, indicates that all IMDQ starting material has been consumed. The DMF is removed under reduced pressure, ethyl acetate added to the solid yellow residue, the mixture is triturated, the pale-yellow solid that forms is allowed to settle, and the supernatant is decanted. This process is repeated an additional two times. The off-white solid product is dried under reduced pressure to yield Compound 34.

General Procedure for the Preparation of Compound 35.

A solution of Compound 34 (1.0 eq.) in DCM is treated with TFA (1.0 mL) at room temperature for 1 hour. The reaction was concentrated to dryness under reduced pressure and the residue, containing Compound 35, used without further purification.

General Procedure for the Preparation of Compound No. 64-52f.

Compound 35 (1.0 eq.) and Compound 25 (1.2 eq.) are dissolved in DMF, DIPEA added (0.1 mL), and the solution is stirred for 1.5 hours at room temperature. When RP-HPLC analysis of the reaction indicates that Compound 35 has been completely consumed the DMF is removed under reduced pressure and the solid yellow residue subjected to silica gel column chromatography, eluting with 1-8% (v/v) MeOH in DCM containing 0.5% (v/v) ammonia, to yield Compound No. 64-52f as a white solid. Product purity is assessed by RP-HPLC at 254 nm, the intended synthetic mass confirmed by LC-MS, and the intended synthetic structure confirmed by $^1$H NMR.

Compound No. 64-52g.

Compound No. 64-52g was prepared as shown in Scheme S2g-1, to exemplify an embodiment of the invention where the TLR7/8 agonist D in formula (I) is IMDQ, the self-eliminating linker $L^1$ in formula (I) is a para-amino benzyl carbamate moiety, the cleavable linker $L^2$ in formula (I) is leucine-serine-glycine-arginine-serine-aspartic, and the conjugation linker $L^3$ in formula (I) is an azido-PEG$_4$ moiety.

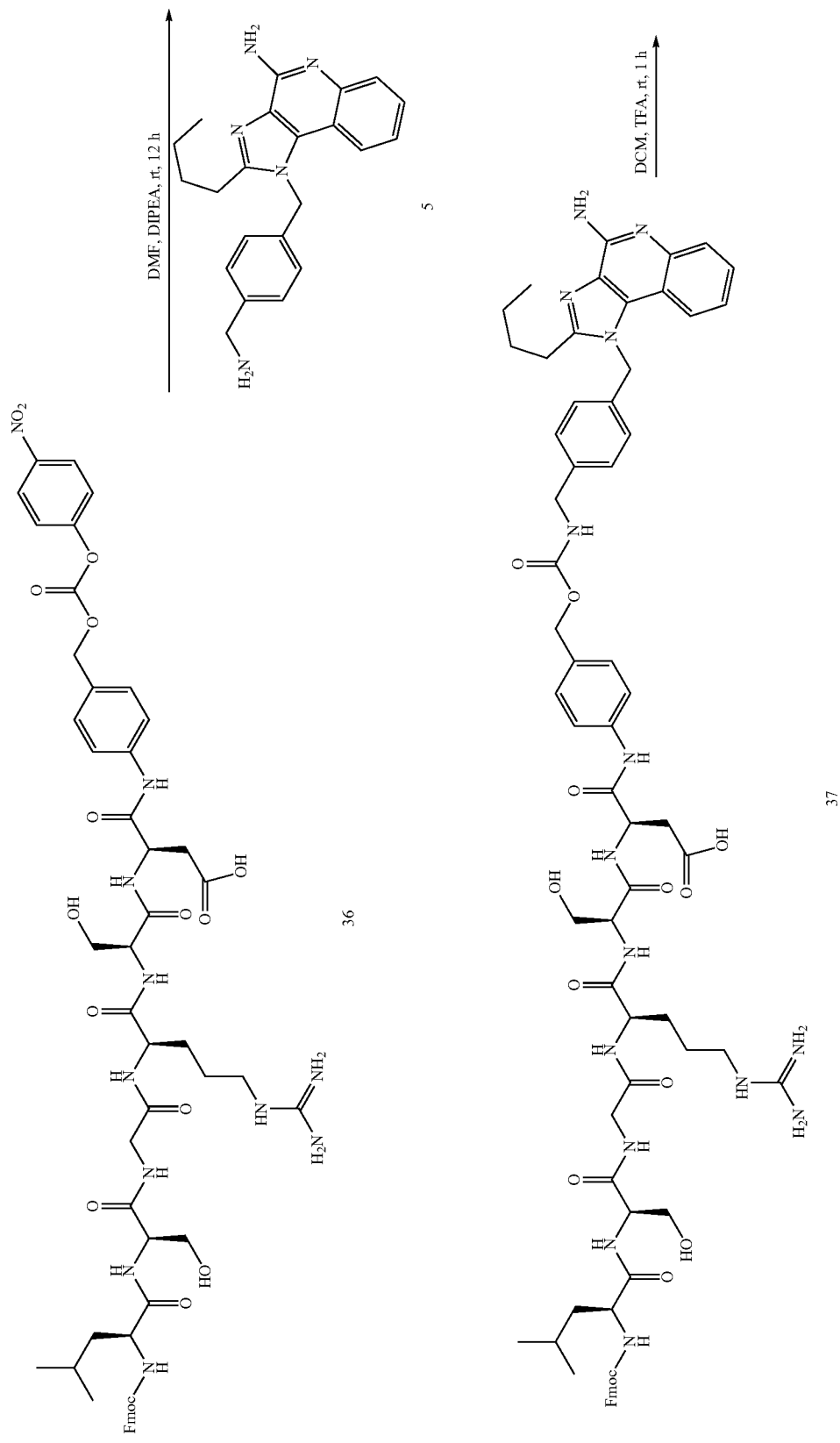

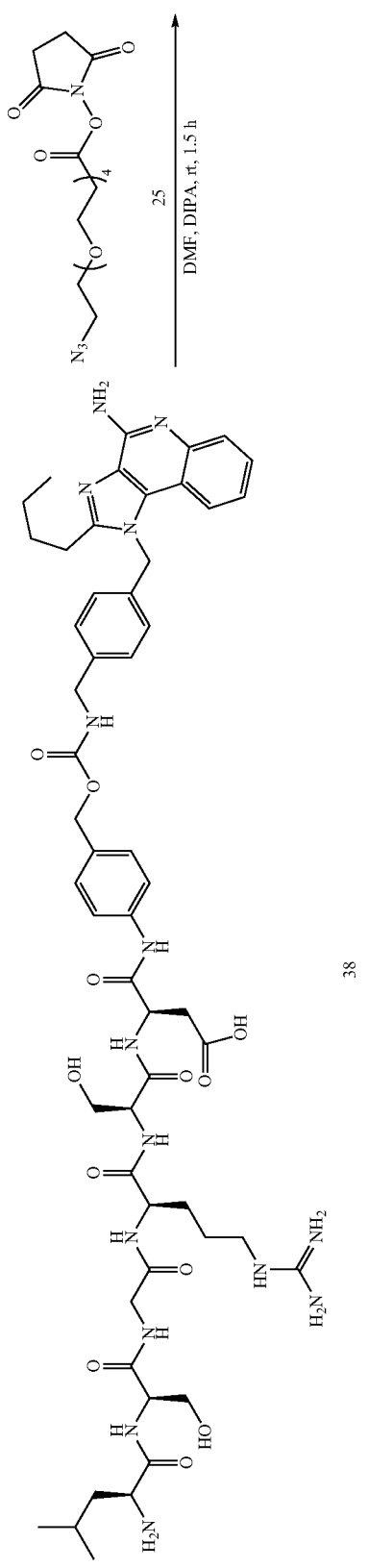

General Procedure for the Preparation of Compound 37.

To an ice cold solution of IMDQ (Compound 5; 1 eq.) in DMF is added DIPEA (0.1 mL), and the solution is stirred for 10 minutes under an argon atmosphere. Compound 36 (1 eq.) is added in two portions and the resulting clear-yellow solution stirred at 0° C. for 2 hours. The solution is slowly warmed to room temperature and then stirring continued for an additional 12 hours or until thin layer chromatography analysis, developed with 10% (v/v) MeOH in DCM containing 1% (v/v) TEA, indicates that all IMDQ starting material has been consumed. The DMF is removed under reduced pressure, ethyl acetate added to the solid yellow residue, the mixture is triturated, the pale-yellow solid that forms is allowed to settle, and the supernatant is decanted. This process is repeated an additional two times. The off-white solid product is dried under reduced pressure to yield Compound 37.

General Procedure for the Preparation of Compound 38.

A solution of Compound 37 (1.0 eq.) in DCM is treated with TFA (1.0 mL) at room temperature for 1 hour. The reaction was concentrated to dryness under reduced pressure and the residue, containing Compound 38, used without further purification.

General Procedure for the Preparation of Compound No. 64-52g.

Compound 38 (1.0 eq.) and Compound 25 (1.2 eq.) are dissolved in DMF, DIPEA added (0.1 mL), and the solution is stirred for 1.5 hours at room temperature. When RP-HPLC analysis of the reaction indicates that Compound 38 has been completely consumed the DMF is removed under reduced pressure and the solid yellow residue subjected to silica gel column chromatography, eluting with 1-8% (v/v) MeOH in DCM containing 0.5% (v/v) ammonia, to yield Compound No. 64-52g as a white solid. Product purity is assessed by RP-HPLC at 254 nm, the intended synthetic mass confirmed by LC-MS, and the intended synthetic structure confirmed by $^1$H NMR.

Compound No. 64-52h.

Compound No. 64-52h was prepared as shown in Scheme S2h-1, to exemplify an embodiment of the invention where the TLR7/8 agonist D in formula (I) is 64-33, the self-eliminating linker $L^1$ in formula (I) is a para-amino benzyl carbamate moiety conjugated to the primary amine in the 4 position of the imidazoquinoline ring of the TLR7/8 agonist (see FIG. 1), the cleavable linker $L^2$ in formula (I) is valine-citrulline, and the conjugation linker $L^3$ in formula (I) is an azido-PEG$_4$ moiety.

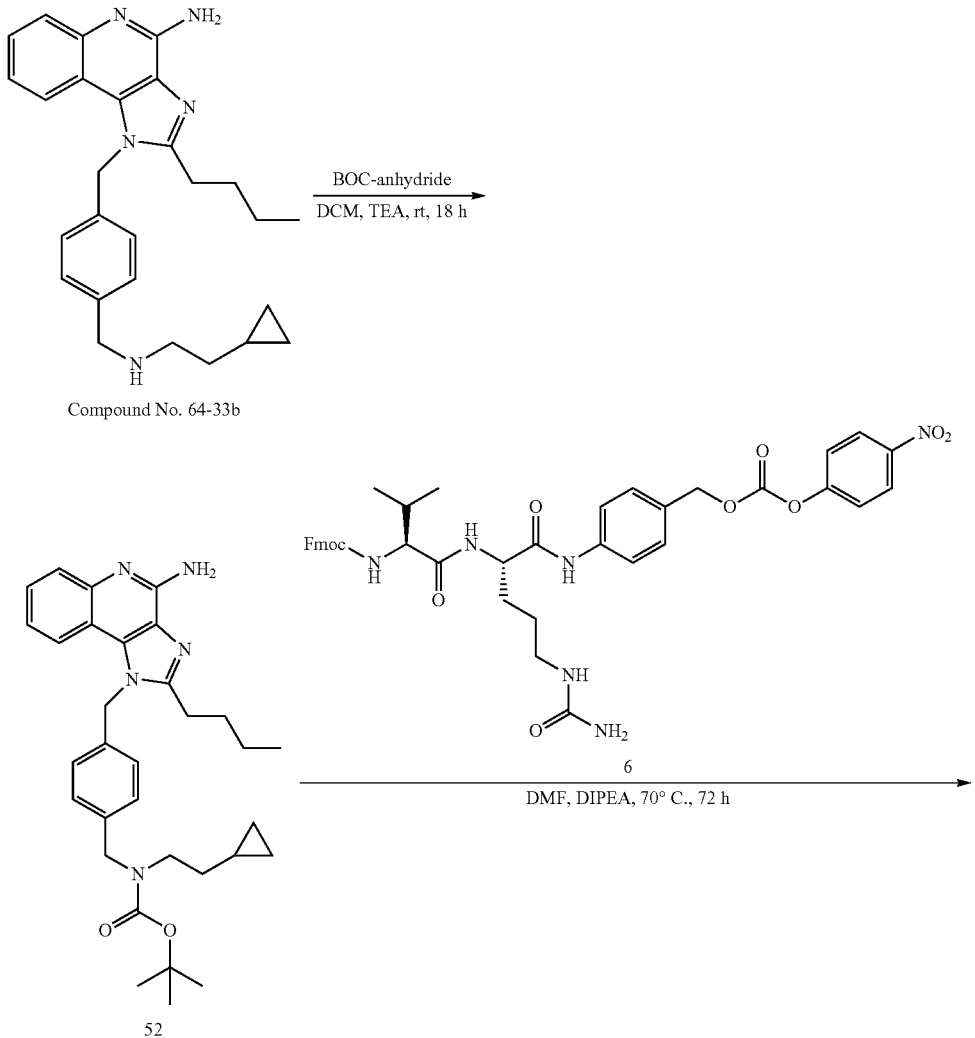

Scheme S2h-1

-continued
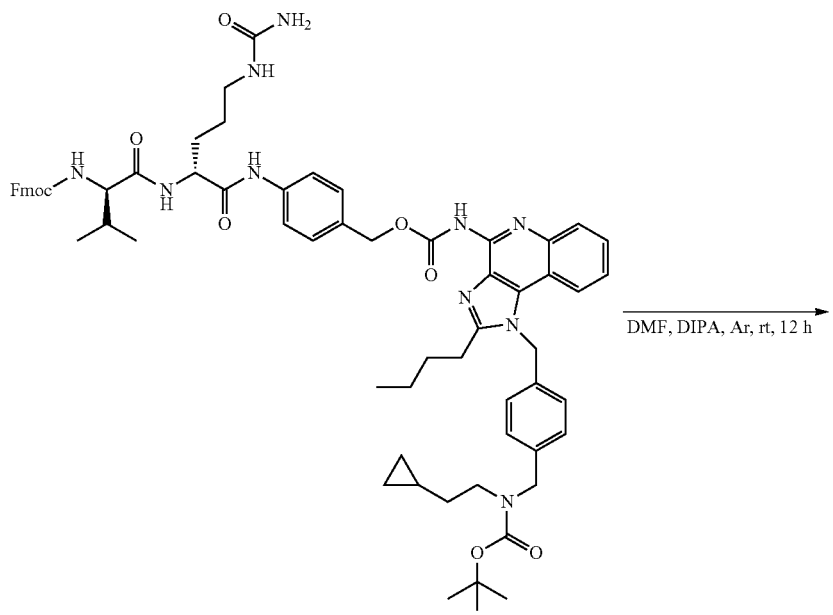
53
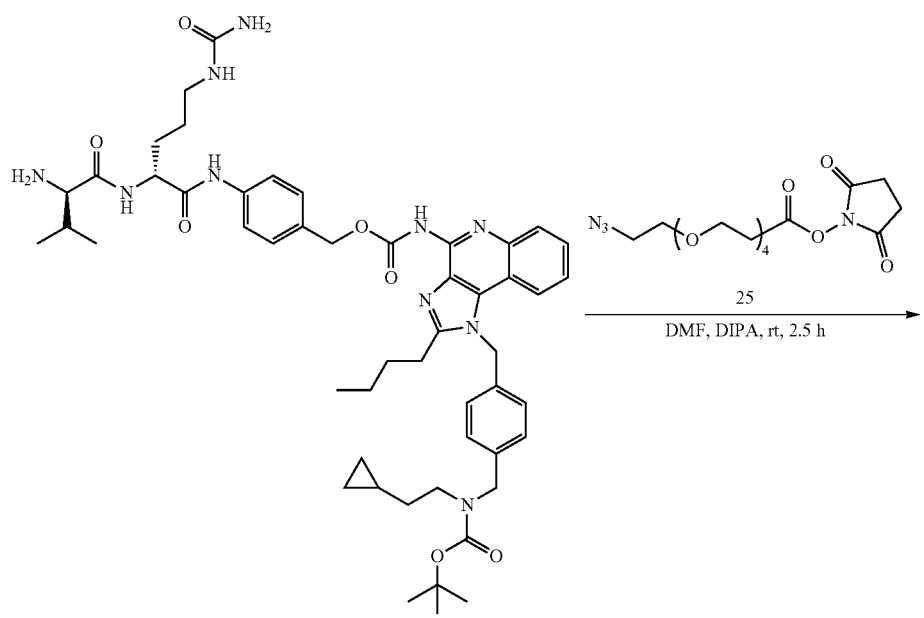
54

-continued

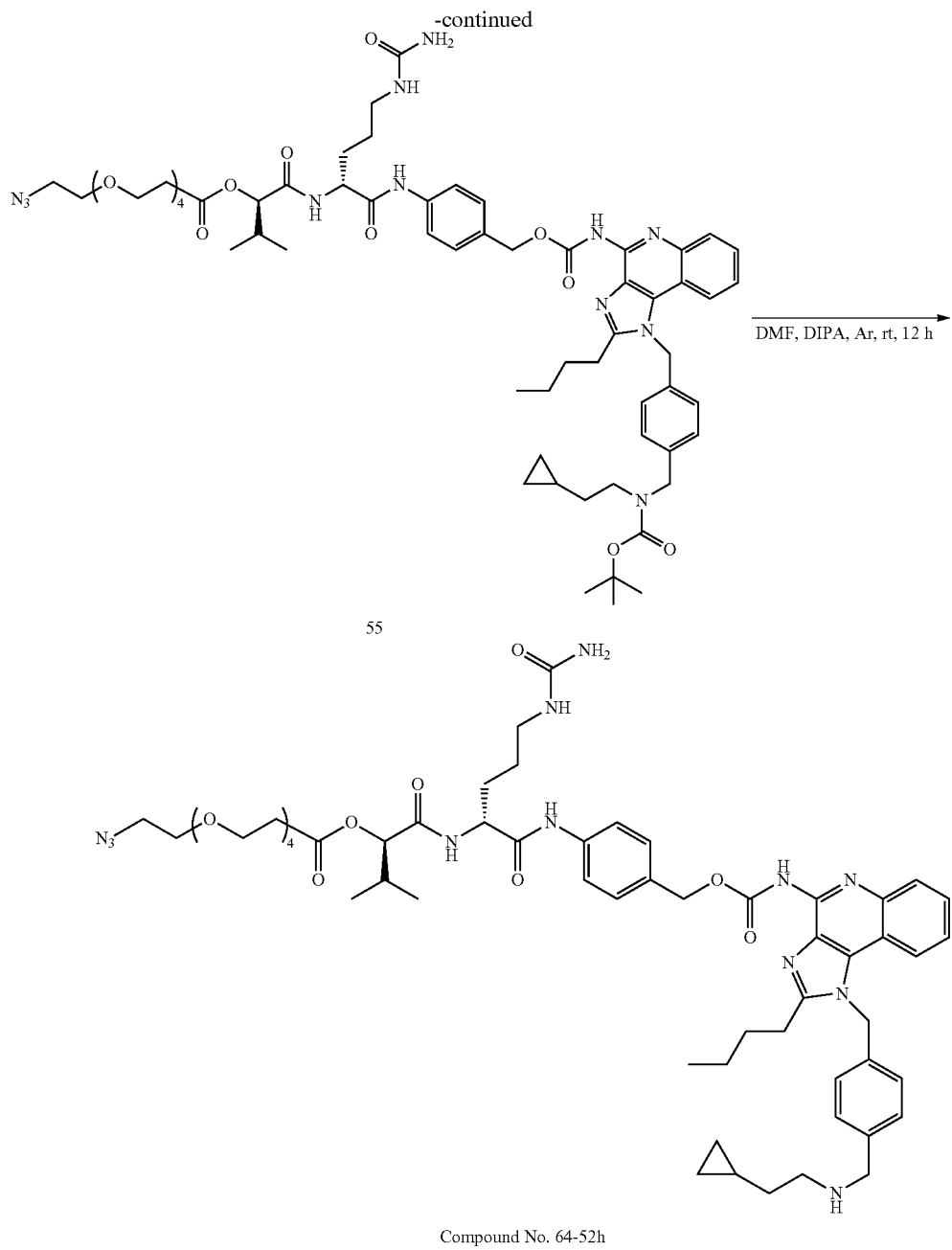

Compound No. 64-52h

Procedure for the Preparation of Compound 52.

To an ice cold solution of Compound 64-33b (96 mg, 0.224 mmol, 1.0 eq.) in DMF (5.0 mL) was added TEA (91 mg, 0.9 mmol), and then di-tert-butyl dicarbonate (54 mg, 0.250 mmol, 1.1 eq.). The solution was slowly warmed to room temperature and stirred overnight. The mixture was concentrated under reduced pressure, and the residue purified on a silica gel column chromatography, eluting with 3-5% (v/v) MeOH containing 1% aqueous ammonia/DCM to yield 94 mg of Compound 52.

Procedure for the Preparation of Compound 53.

To an ice cold solution of Compound 52 (94 mg, 0.178 mmol, 1 eq.) in DMF (1.5 mL) was added DIPEA (0.2 mL) and the solution was stirred for 10 minutes under an argon atmosphere. To this was added Compound 6 (135 mg, 0.178 mmol, 1 eq.) in one portion. The resulting clear yellow solution was stirred at 0° C. for 1 hour, then slowly warmed to room temperature and stirring was continued for 12 hours. Thin layer chromatography analysis, 10% (v/v) MeOH in DCM containing 1% TEA, indicted that only very little reaction had occurred; the mixture was then warmed to 70° C., stirring was continued, and the progress of the reaction was monitored by RP-HPLC. After 3 days the DMF was removed under reduced pressure, ethyl acetate (3 mL) was added to the yellow residue, the mixture triturated, the pale-yellow solid formed allowed to settle, and the supernatant was decanted. This process was repeated an additional two times, and the off-white solid was dried under reduced pressure to yield 84 mg of Compound 53 that was used for the next reaction without further purification.

Procedure for the Preparation of Compound 54.

To an ice cold solution of Compound 53 (84 mg, 0.072 mmol) in DMF (1.5 mL) was added diisopropyl amine (0.1 mL) with stirring under an argon atmosphere. The resulting solution was then slowly warmed to room temperature and stirring continued for 12 hours. The DMF was removed under reduced pressure, ethyl acetate (3 mL) was added to the yellow residue, the mixture triturated, the pale-yellow solid formed allowed to settle, and the supernatant decanted. This process was repeated additional two times and the off-white solid was dried under reduced pressure yield 54 mg of crude Compound 54.

Procedure for the Preparation of Compound 55.

Compound 54 (54 mg, 0.057 mmol) and Compound 25 (22 mg, 0.063 mmol) were dissolved in DMF (1.0 mL), DIPEA (0.1 mL) added, and the solution was stirred for 2.5 hours. The DMF was removed under reduced pressure, and the yellow residue was subjected to silica gel column chromatography, eluting with 1-8% (v/v) MeOH in DCM containing 0.5% ammonia, to yield 14 mg of Compound 55 as an off-white solid.

Procedure for the Preparation of Compound No. 64-52h.

To an ice cold solution of Compound 55 (12 mg, 1.0 eq.) in DMF (1.5 mL) was added diisopropyl amine (0.1 mL) with stirring under an argon atmosphere. The resulting solution was then slowly warmed to room temperature and stirring continued for 12 hours. The DMF was removed under reduced pressure, ethyl acetate (3 mL) was added to the yellow residue, the mixture triturated, the pale-yellow solid formed allowed to settle, and the supernatant decanted. This process was repeated additional two times and the off-white solid was dried under reduced pressure yield 10 mg of crude Compound No. 64-52a as an off-white solid. Product purity was assessed to be 30-40% by RP-HPLC at 254 nm and the intended synthetic mass of 1,120.4 Daltons was present by LC-MS.

Compound No. 64-52i.

Compound No. 64-52i was prepared as shown in Scheme S2i-1, to exemplify an embodiment of the invention where the TLR7/8 agonist D in formula (I) is 64-10b, the self-eliminating linker $L^1$ in formula (I) is a para-amino benzyl carbamate moiety conjugated to the secondary amine at the benzyl methyl amine of the TLR7/8 agonist (see FIG. 1), the cleavable linker $L^2$ in formula (I) is valine-citrulline, and the conjugation linker $L^3$ in formula (I) is an azido-PEG$_4$ moiety. In addition, the TLR7/8 agonist (D in formula (I)) can be either IMDQ or meta-IMDQ (see FIG. 1 for chemical structure representations of IMDQ and meta-IMDQ), as well as any of Compound Nos. 64-01 to 64-50, 64-58 to 64-69, 64-01a to 64-50a, and 64-58a to 64-69a.

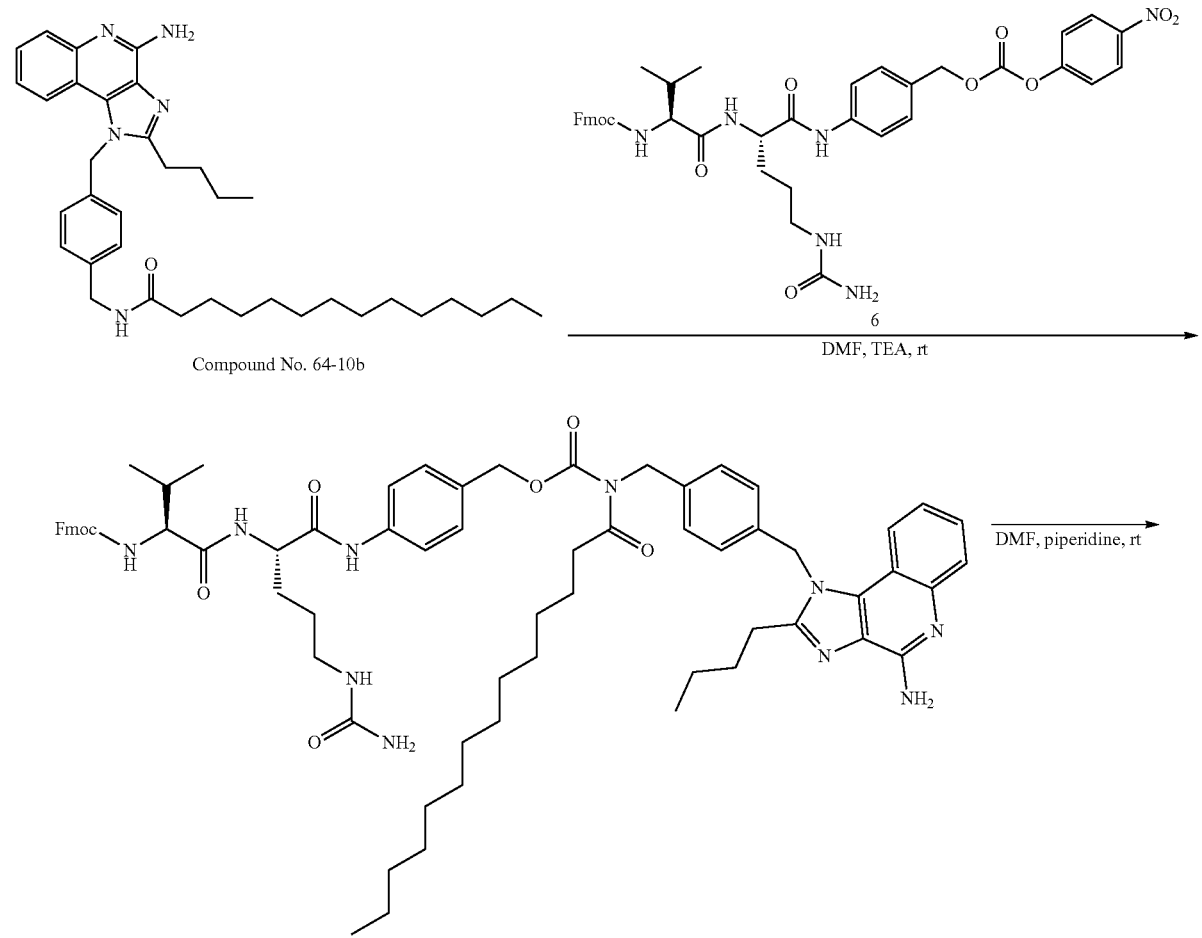

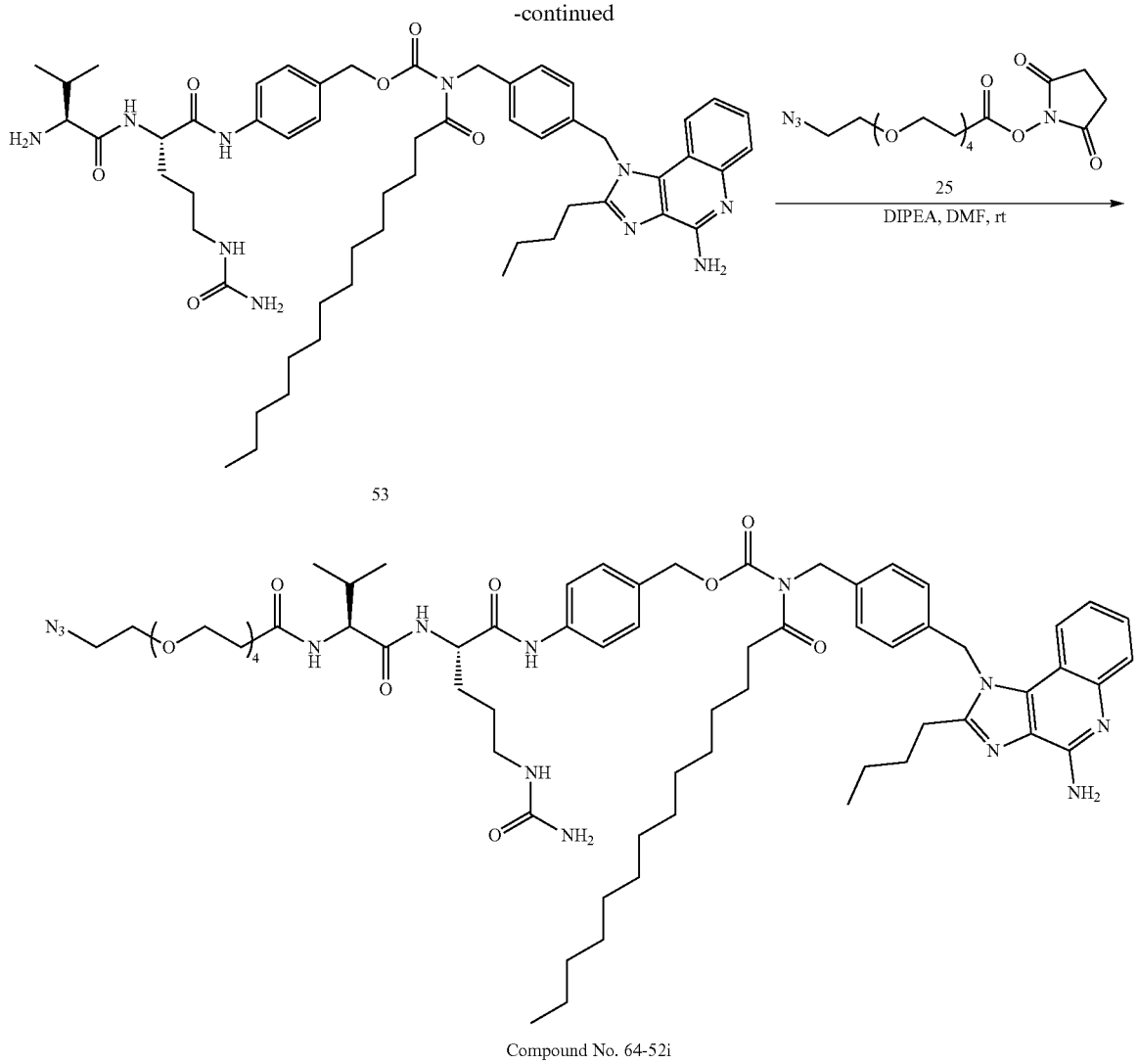

Compound No. 64-52i

General Procedure for the Preparation of Compound No. 52.

To a solution of Compound No. 6 (1.1 eq.) and Compound No. 64-10b (1.0 eq.) in DMF is added TEA (2.0 eq.), and the resulting solution is stirred at room temperature. Once LC/MS shows mostly the desired product Compound No. 52, and that all of Compound No. 64-10b is consumed the reaction mixture is directly used for the next step.

General Procedure for the Preparation of Compound No. 53.

To a crude solution of Compound No. 52 (1.0 eq.) in DMF is added piperidine (~10 eq.), and the solution is stirred at room temperature. Once LC/MS shows the disappearance of the starting material Compound No. 52 the reaction mixture is diluted with 10% MeOH in DCM and washed twice with water. The aqueous layers are extracted with ethyl acetate, the combined organic layers dried over $Na_2SO_4$, and concentrated under reduced pressure. The residue is purified by column chromatography (100/10 to 100/15 (v/v) DCM/MeOH) to yield Compound No. 53 as a yellow solid.

General Procedure for the Preparation of Compound No. 64-52i.

To a solution of Compound No. 53 (1.0 eq.) and Compound No. 25 (1.1 eq.) in DMF is added DIPEA (0.2 mL), and the resulting solution is stirred at room temperature.

Once LC/MS shows mostly conversion to the desired product the reaction mixture is concentrated under reduced pressure. The residue is purified by column chromatography (100/10 to 100/15 (v/v) DCM/MeOH) to yield Compound No. 64-52i as a white solid.

Example S3

Preparation of Propargylamine-Carboxymethylated Ficoll

Carboxymethylated Ficoll (CM-Ficoll) was prepared as described elsewhere (see, e.g., Inman, J. K. 1975, *J Immunol* 114:704-709) at 37.9 mg/mL in 0.2 M sodium chloride. Propargylamine-carboxymethylated Ficoll (PACM-Ficoll) was prepared as shown in Scheme S3-1. Briefly, 1.2 g of propargylamine hydrochloride was dissolved in 10 mL of CM-Ficoll, then 150 mg of EDC was added to the mixture in 25 mg increments over 10 minutes with mixing. The pH of the resulting solution was adjusted to 4.7 with 1 N HCl, and the reaction was allowed to proceed for 3.5 hours at ambient temperature (22-24° C.) with mixing. The pH of the solution was checked periodically during that time, and adjusted to 4.7 with 1 N HCl when necessary. The resulting product was purified by tangential flow filtration using a molecular weight cut-off membrane of 100 kDa, in PBS pH 7.5. The final PACM-Ficoll contained 22.2 mg/mL of Ficoll and was stored at −80° C. The content of propargyl groups in the PACM-Ficoll was determined by conjugation of a fluorophore (Alexa Fluor™ 594 Azide, Thermo Scientific, Rockford Ill., Cat. No. A10270), with subsequent quantitation of fluorescence compared to a standard curve. The batch of PACM-Ficoll was shown to have approximately 250 moles of propargyl groups/mole Ficoll.

Example S4

Preparation of Compound Nos. 64-53, 64-53a, 64-54, 54-54a, 64-54b, and 64-54c

Azide-Disulfide-PABC-IMDQ (Compound Nos. 64-51 and 64-51a) and Azide-Dipeptide-PABC-IMDQ (Compound Nos. 64-52, 54-54a, 64-54b, and 64-52c), corresponding to -L$^3$-L$^2$-L$^1$-D in formula (I), were covalently conjugated to PACM-Ficoll according to Scheme S4-1, Scheme S4-1a, Scheme S4-2, Scheme S4-2a, Scheme S4-2b, and Scheme S4-2c to yield a Ficoll-Azide-Disulfide-PABC-IMDQ compound (Compound Nos. 64-53 and 64-53a) or Ficoll-Azide-Dipeptide-PABC-IMDQ compound (Compound No. 64-54, 64-54a, 64-54b, and 64-54c). Compound Nos. 64-53, 64-53a, 64-54, 64-54a, 64-54b, and 64-54c are representative examples of the compounds of formula (I), i.e., F—[W-L$^3$-L$^2$-L$^1$-D]$_x$.

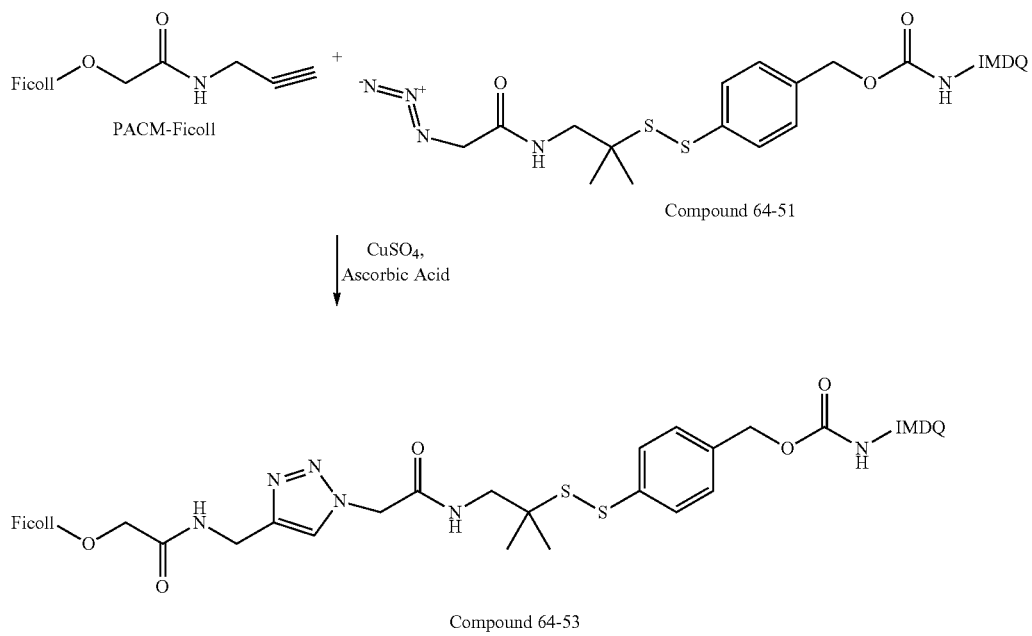

Preparation of Compound No. 64-53.

Compound No. 64-51 was dissolved in DMF at 5 mg/mL. PACM-Ficoll was prepared at 22.2 mg/mL in PBS pH 7.5 buffer. Copper (II) sulfate pentahydrate (CuSO$_4$) and L-ascorbic acid were each prepared at 5 mg/mL in pure water. PACM-Ficoll (0.79 mL, 0.044 µmole) was mixed with 0.97 mL of ascorbic acid solution, 0.27 mL of CuSO$_4$ solution, 1.65 mL of 400 mM sodium acetate pH 5.5 buffer, and 0.95 mL of DMF. Then Compound No. 64-51 (0.62 mL, 4.4 micromoles) was added in 0.2 mL increments while mixing. The reaction proceeded for 18 hours at ambient temperature (22-24° C.), while mixing. The following day, the reaction mixture was dialyzed with a 10,000 Dalton molecular weight cut-off dialysis cassette in 8 liters of PBS pH 7.5. The purified Compound No. 64-53 was aliquoted and stored at −80° C.

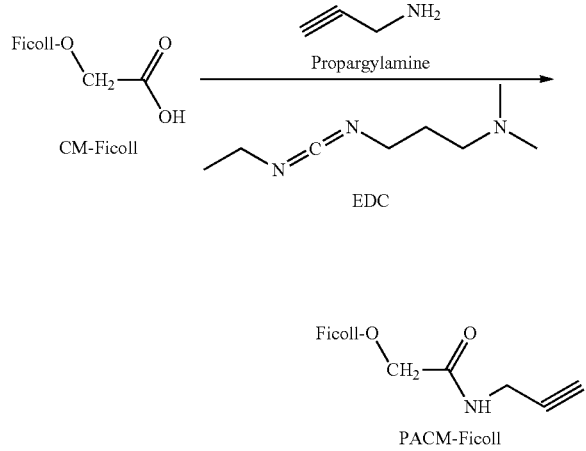

Scheme S4-1a

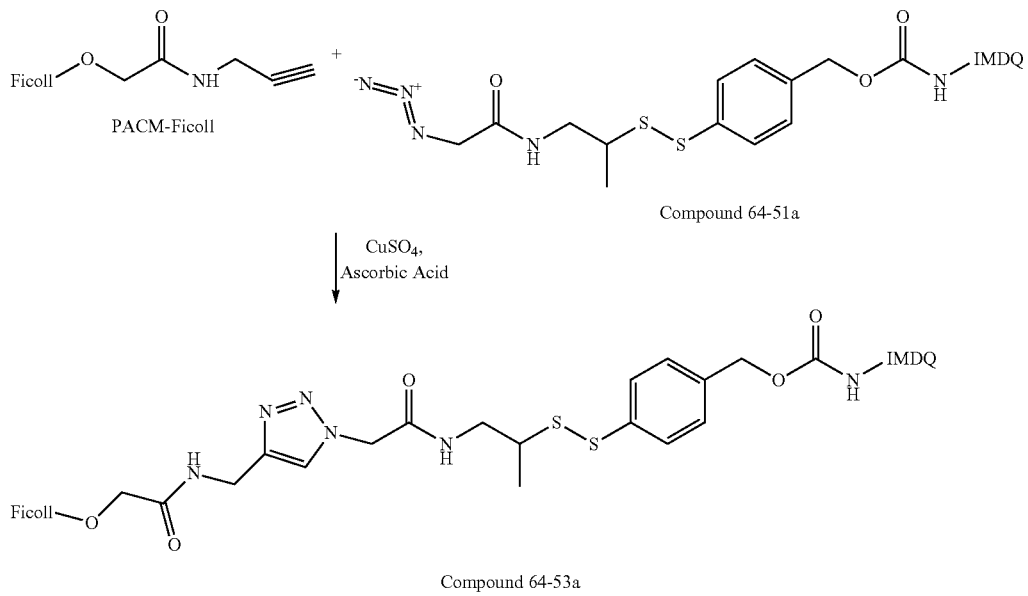

Preparation of Compound No. 64-53a.

Compound No. 64-53a was prepared in a similar manner to that described above for Compound No. 64-53, using Compound No. 64-51a in place of Compound No. 64-51. The synthesis of Compound No. 64-53a is outlined in Scheme S4-1a.

Preparation of Compound No. 64-54.

Compound No. 64-52 was dissolved in DMF at 5 mg/mL. PACM-Ficoll was prepared at 22.2 mg/mL in PBS pH 7.5. Copper (II) sulfate pentahydrate (CuSO$_4$) and L-ascorbic acid were each prepared at 5 mg/mL in pure water. PACM-Ficoll (0.79 mL, 0.044 micromole) was mixed with 0.97 mL Scheme S4-2

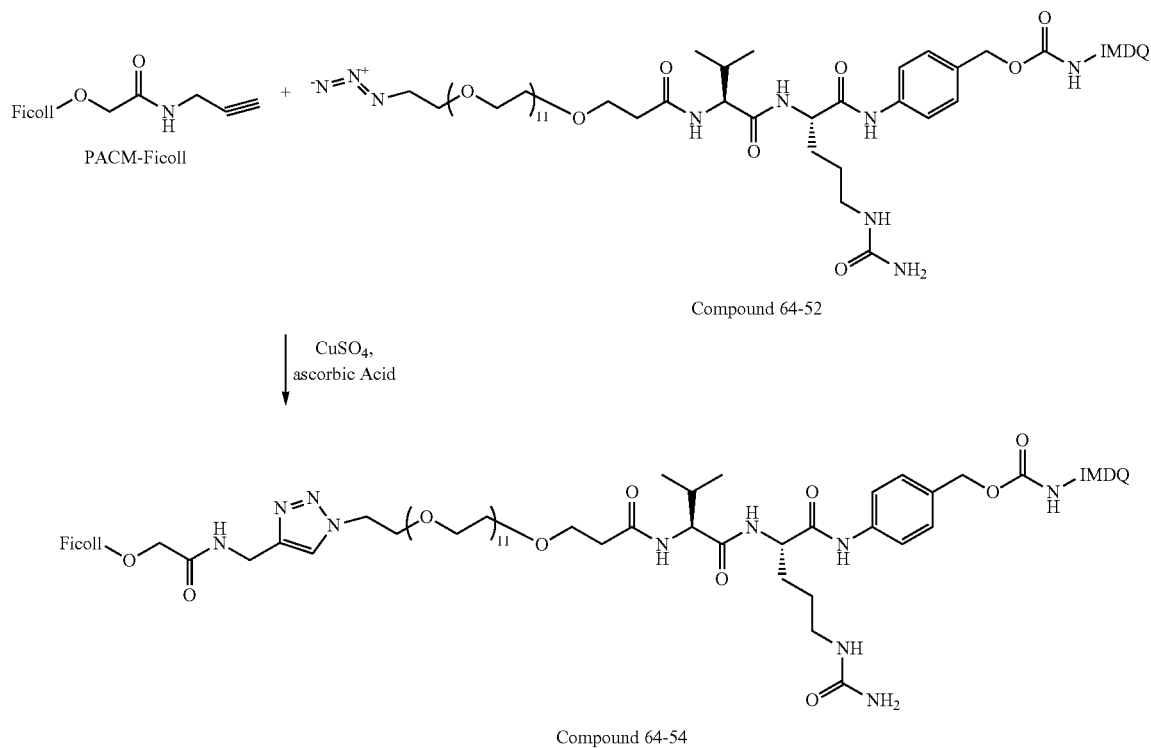

of ascorbic acid solution, 0.27 mL of CuSO₄ solution, 2.6 mL of 400 mM sodium acetate pH 5.5 buffer, and 0.22 mL of DMF. Then Compound No. 64-52 (0.61 mL, 4.4 micromoles) was added in 0.2 mL increments while mixing. The reaction proceeded for 18 hours at ambient temperature (22-24° C.), while mixing. The following day, the reaction mixture (about 4.9 mL) was dialyzed with a 10,000 Dalton molecular weight cut-off dialysis cassette in 8 liters of PBS pH 7.5. The purified Compound No. 64-54 was aliquoted and stored at −80° C.

Preparation of Compound No. 64-54a.

Compound No. 64-54a was prepared in a similar manner to that described above for Compound No. 64-54, using Compound No. 64-52a in place of Compound No. 64-52. The synthesis of Compound No. 64-54a is outlined in Scheme S4-2a.

Preparation of Compound No. 64-54b.

Compound No. 64-54b was prepared in a similar manner to that described above for Compound No. 64-54, using

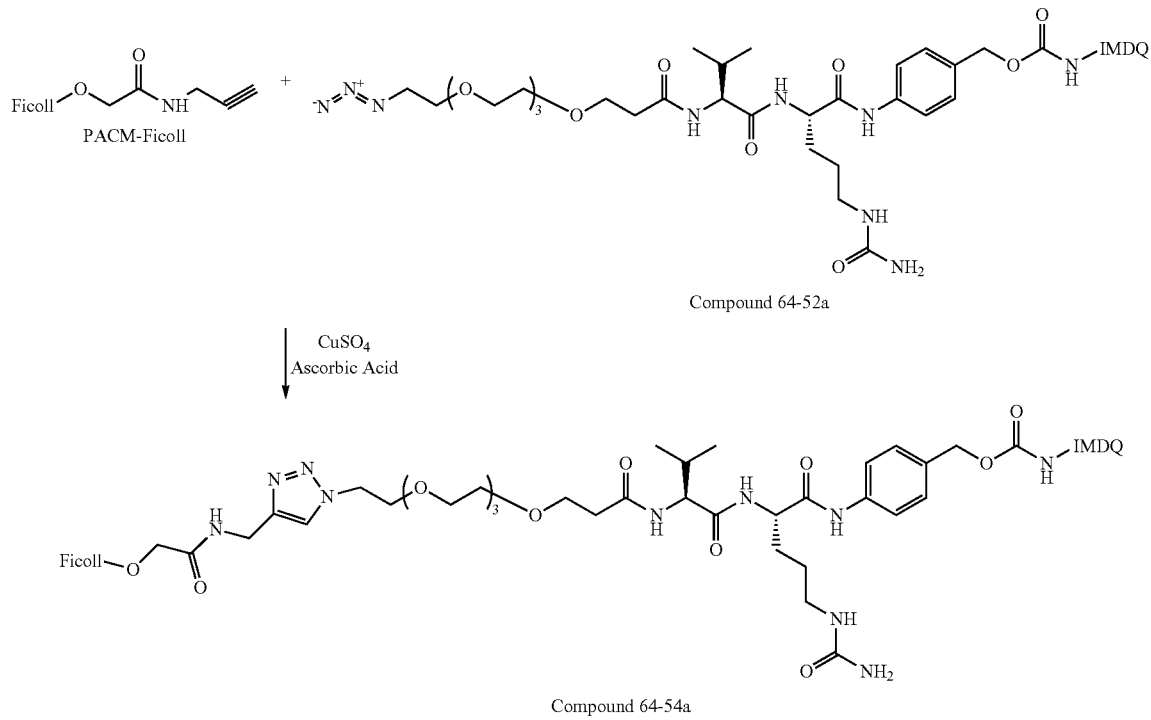

Compound No. 64-52c in place of Compound No. 64-52. The synthesis of Compound No. 64-54b is outlined in Scheme S4-2b.

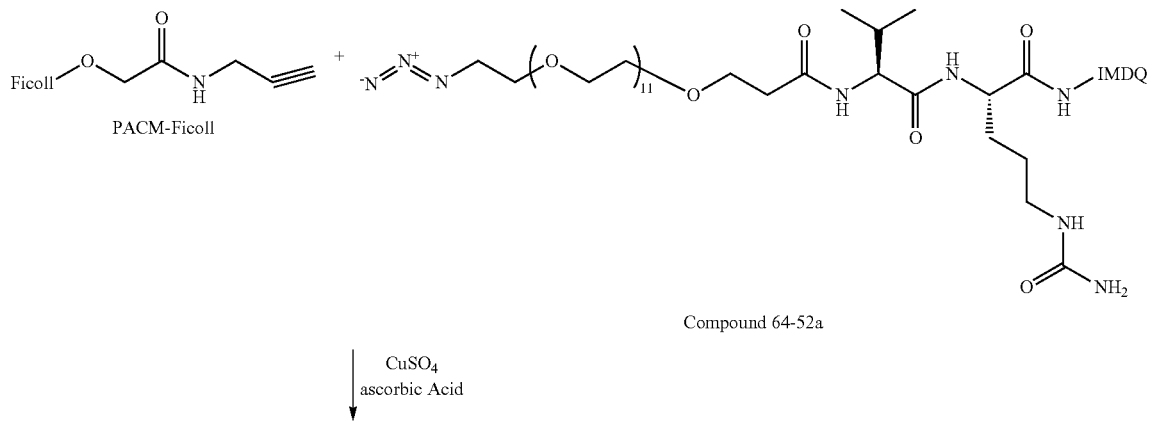

-continued

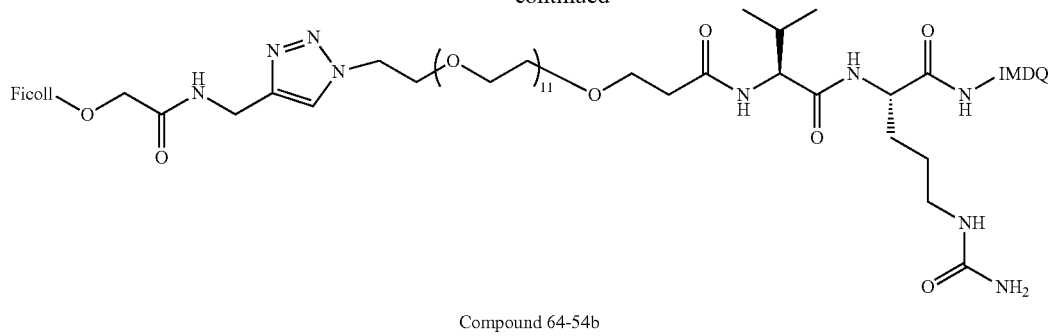

Compound 64-54b

Preparation of Compound No. 64-54c.

Compound No. 64-54c was prepared in a similar manner to that described above for Compound No. 64-54, using Compound No. 64-52b in place of Compound No. 64-52. The synthesis of Compound No. 64-54c is outlined in Scheme S4-2c.

and the reaction mixture was heated to 65° C. for three hours. The mixture was then cooled to 5-10° C. and the solid material collected by filtration, washed with cold water, and air dried. The resulting solid was then recrystallized from methanol and dried under vacuum to yield 58 g of 3-nitro-2,4-quinolinediol as a yellow solid.

Scheme S4-2c

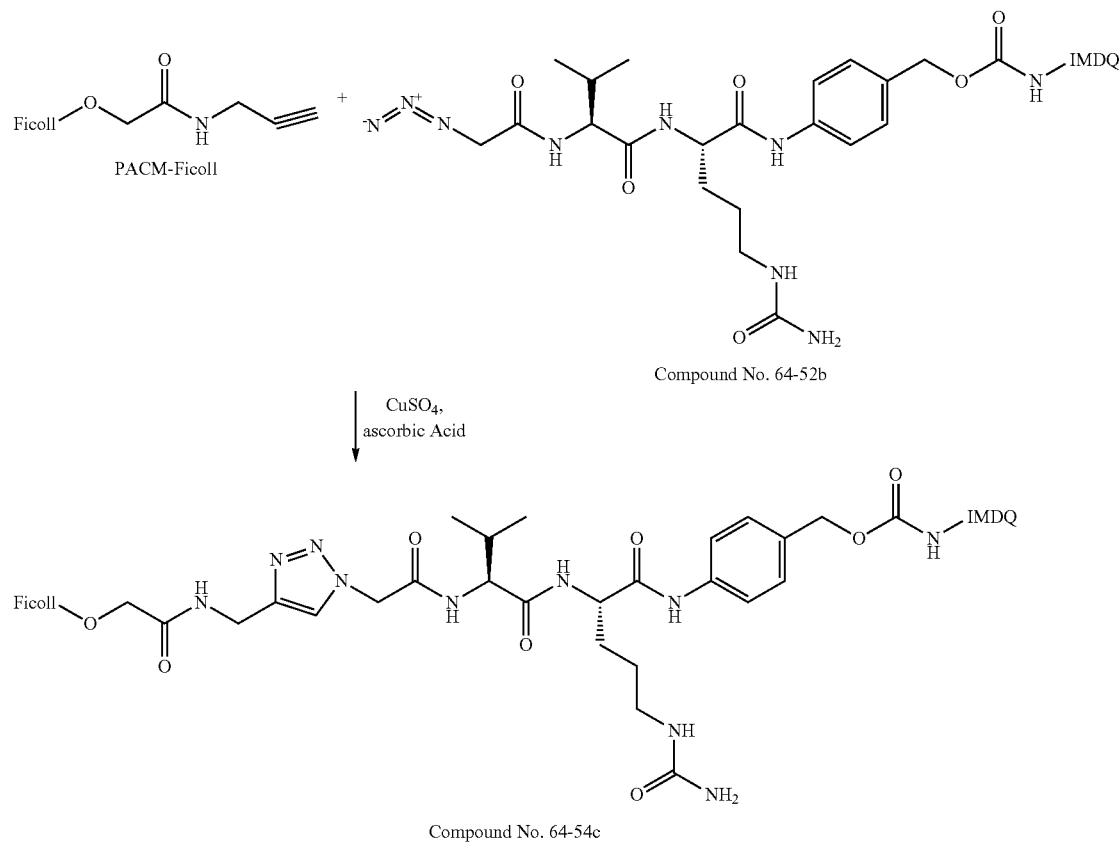

Compound No. 64-54c

Example S4-a

Preparation of N-(4-((4-amino-2-butyl-1H-imidazo[4,5-c]quinolin-1-yl)methyl)benzyl)tetradecanamide (Compound No. 64-10b)

Part A. Nitric acid (125 mL) was added to a slurry of quinoline-2,4-diol (50 g, 0.3 mole) in acetic acid (500 mL), Part B. Phosphorus oxychloride (150 mL) was added to 3-nitro-2,4-quinolinediol (58 g) under an argon atmosphere and heated to 95° C. for 4 hours. The mixture was then cooled to room temperature and poured onto crushed ice with constant stirring. The precipitated product was collected by filtration, washed with water, and dried under vacuum. The crude solid was purified by flash chromatography over silica gel using hexane/ethyl acetate to yield 35 g of 2,4-dichloro-3-nitroquinoline.

Part C. Tert-butyl (4-(aminomethyl)benzyl)carbamate (37.3 g, 0.16 mole, 1.1 eq) was added to a solution of 2,4-dichloro-3-nitroquinoline (35 g, 0.15 mole, 1.0 eq) in anhydrous dichloromethane (400 mL) and trimethylamine (16.0 g, 0.16 mole, 1.1 eq), and stirred overnight at room temperature. The solvents were removed under reduced pressure and the crude product was purified by flash chromatography over silica gel using hexane/ethyl acetate to yield 52 g of tert-butyl (4-(((2-chloro-3-nitroquinolin-4-yl)amino)methyl)benzyl)carbamate.

Part D. A solution of tert-butyl (4-(((2-chloro-3-nitroquinolin-4-yl)amino)methyl)benzyl)carbamate (52 g, 0.12 mole) in ethyl acetate (250 mL) was hydrogenated in the presence of 5% platinum on carbon (2.0 g) and sodium sulfate (52 g) using a Parr hydrogenation apparatus at 60 psi for 12 hours. The platinum catalyst and sodium sulfate were removed by filtering through a pad of Celite®, and the filtrate concentrated under reduced pressure. The product was further purified by flash chromatography over silica gel eluting with hexane/ethyl acetate to yield 32 g of tert-butyl (4-(((3-amino-2-chloroquinolin-4-yl)amino)methyl)benzyl)carbamate.

Part E. Pentanoyl chloride (9.7 mL, 81.5 mmol, 1.05 eq) was added slowly to a solution of tert-butyl (4-(((3-amino-2-chloroquinolin-4-yl)amino)methyl)benzyl)carbamate (32 g, 77.6 mmol, 1.0 eq) in anhydrous tetrahydrofuran (350 mL) and pyridine (30 mL) at 0-5° C. The reaction mixture was then warmed to room temperature and stirred for 12 hours. The solvents were removed under reduced pressure and then the solids were re-dissolved in ethyl acetate (400 mL), washed successively with water and saturated sodium bicarbonate (150 mL), and finally dried over anhydrous magnesium sulfate. The product was further purified by flash chromatography over silica gel, eluting with hexane/ethyl acetate to yield 22 g of tert-butyl (4-(((3-butyramido-2-chloroquinolin-4-yl)amino)methyl)benzyl)carbamate.

Part F. Water (80 mL) was added to a solution of tert-butyl (4-(((3-butyramido-2-chloroquinolin-4-yl)amino)methyl)benzyl)carbamate (22 g, 44.2 mmol, 1.0 eq) in ethanol (320 mL), followed by the addition of potassium carbonate (12.2 g, 88.4 mmol, 2.0 eq), and the mixture was heated with vigorous stirring to 55° C. for 16 hours. This reaction mixture was concentrated and the residue was partitioned between ethyl acetate (500 mL) and water (250 mL). The ethyl acetate layer was then washed with water (100 mL), dried over anhydrous magnesium sulfate, and concentrated under reduced pressure. The product was further purified by flash chromatography over silica gel, eluting with hexane/ethyl acetate to yield 15.4 g of tert-butyl (4-((2-butyl-4-chloro-1H-imidazo[4,5-c]quinolin-1-yl)methyl)benzyl)carbamate.

Part G. Tert-butyl (4-((2-butyl-4-chloro-1H-imidazo[4,5-c]quinolin-1-yl)methyl)benzyl)carbamate (15.4 g, 32.2 mmol, 1 eq) was dissolved in anhydrous dimethyl formamide (125 mL), and then sodium azide (8.4 g, 128.6 mmol, 4 eq) was added to this solution. The resulting suspension was degassed and stirred under argon atmosphere at 110-115° C., with the reaction progress being monitored by reverse-phase HPLC analysis. After 18 hours, the reaction mixture was cooled to room temperature, poured into cold water (500 mL), and extracted with ethyl acetate (3×100 mL). The combined extract was washed with water (2×75 mL), dried over magnesium sulfate, filtered through Celite, and concentrated under reduced pressure to yield an off-white solid. This solid was further worked up by re-crystallization with 1:1 ethyl/hexane to yield 12.5 g of tert-butyl (4-((4-azido-2-butyl-1H-imidazo[4,5-c]quinolin-1-yl)methyl)benzyl)carbamate.

Part H. Tert-butyl (4-((4-azido-2-butyl-1H-imidazo[4,5-c]quinolin-1-yl)methyl)benzyl)carbamate (12.5 g, 25.7 mmol) was added to concentrated hydrochloric acid (65 mL), and 10% platinum on carbon (3.0 g) was added to this suspension. This reaction mixture was subjected to hydrogenation at 65 psi, with the reaction progress being monitored by reverse-phase HPLC analysis. After 6 days, the catalyst was filtered off and the filtered cake was washed with water (2×25 mL). The cake was cooled in an ice bath, ice cold 1N sodium hydroxide was added drop wise while stirring vigorously until the pH reached 8.5, and the material was extracted with dichloromethane containing 5% methanol (4×75 mL). The combined extract was dried over magnesium sulfate, filtered, and concentrated under reduced pressure. The residue was purified on a silica gel column using 8% methanol/dichloromethane containing 1% aqueous ammonia to yield 5.3 g of 1-(4-(aminomethyl)benzyl)-2-butyl-1H-imidazo[4,5-c]quinolin-4-amine.

Part I. Myristic acid (27.4 mg, 0.12 mmol, 1.2 eq) and trimethylamine (0.2 mL) were added to a solution of 1-(4-(aminomethyl)benzyl)-2-butyl-1H-imidazo[4,5-c]quinolin-4-amine (34 mg, 0.1 mmol, 1.0 eq) in anhydrous dimethylformamide (2 mL), and the slurry was mixed for 5 minutes followed by the addition of HBTU (47.4 mg, 0.125 mmol, 1.25 eq). This reaction mixture was further stirred for 2 hours under argon atmosphere. The solvent was removed under reduced pressure, the residue dissolved in ethyl acetate (30 mL) and washed with water (2×10 mL), then dried using magnesium sulfate and concentrated under vacuum. This product was purified using column chromatography (6% methanol/dichloromethane) to yield 35 mg of N-(4-((4-amino-2-butyl-1H-imidazo[4,5-c]quinolin-1-yl)methyl)benzyl)tetradecanamide (Compound No. 64-10a). Product purity was assessed to be ~98% by reverse-phase HPLC, the intended synthetic mass of 569.8 was confirmed by LC/MS, and the intended synthetic structure confirmed by 300 MHz proton NMR (CDCl$_3$): δ 7.98 (d, J=8.1 Hz, 1H), 7.75 (d, J=8.4 Hz, 1H), 7.67 (t, J=8.4 Hz, 1H), 7.40 (t, J=7.5 Hz, 1H), 7.30 (d, J=8.1 Hz, 2H), 7.06 (d, J=8.1 Hz, 2H), 5.95 (s, 2H), 4.33 (s, 2H), 3.74 (s, 2H), 3.01 (t, J=7.8 Hz, 2H), 2.20 (t, J=7.5 Hz, 2H), 1.82-1.9 (m, 2H), 1.42-1.70 (m, 4H), 1.26-1.48 (m, 20H), 0.85-1.05 (m, 6H).

Example S4-b

Preparation of 2-butyl-1-(4-(((2-cyclopropylethyl)amino)methyl)benzyl)-1H-imidazo[4,5-c]quinolin-4-amine (Compound No. 64-33b)

Parts A-H were the same as in Example S4-a.

Part I. Cyclopropylacetic acid (33 mg, 0.33 mmol, 1.2 eq) and trimethylamine (140 mg, 1.39 mmol, 5.0 eq) were added to a solution of 1-(4-(aminomethyl)benzyl)-2-butyl-1H-imidazo[4,5-c]quinolin-4-amine (100 mg, 0.28 mmol, 1.0 eq) in anhydrous dimethylformamide (2 mL), and the slurry was mixed for 5 minutes followed by the addition of HBTU (131 mg, 0.34 mmol, 1.25 eq). This reaction mixture was further stirred for 2 hours under an argon atmosphere. The reaction was diluted with ethyl acetate (100 mL) and washed with water (3×30 mL), then dried using magnesium sulfate and concentrated under vacuum. The crude residue was taken up in ethyl acetate and methanol, and purified using column chromatography (6% methanol/dichloromethane) to yield 140 mg of N-(4-((4-amino-2-butyl-1H-imidazo[4,5-c]quinolin-1-yl)methyl)benzyl)-2-cyclopropylacetamide.

Part J. A solution of borane-dimethyl sulfide complex (2.0 M, 1.5 mL, excess) was added to solution of N-(4-((4-amino-2-butyl-1H-imidazo[4,5-c]quinolin-1-yl)methyl)benzyl)-2-cyclopropylacetamide (123 mg, 0.28 mmol, 1.0 eq) in anhydrous tetrahydrofuran (5 mL) at room temperature, and the reaction mixture was heated to reflux for 12 hours. The mixture was cooled to ambient temperature, quenched with 3N HCl (1 mL), and stirred for 4 hours. The pH of the reaction mixture was made alkaline by the addition 2N sodium hydroxide and the product was extracted with dichloromethane (20 mL×10). The combined organic layers were concentrated under reduced pressure and the residue purified by flash chromatography with 6% methanol/dichloromethane as an eluent to yield 28 mg of 2-butyl-1-(4-(((2-cyclopropylethyl)amino)methyl)benzyl)-1H-imidazo[4,5-c]quinolin-4-amine (Compound No. 64-33b). Product purity was assessed to be 97% by reverse-phase HPLC, the intended synthetic mass of 427.6 was confirmed by LC/MS, and the intended synthetic structure confirmed by 400 MHz $^1$H NMR (CDCl$_3$): δ 7.80 (dd, J=8.5, 1.0 Hz, 1H), 7.70 (dd, J=8.3, 1.1 Hz, 1H), 7.42 (m, J=8.4. 7.0, 1.4 Hz, 1H), 7.29 (as, 1H), 7.25 (as, 1H), 7.10 (m, J=8.2, 7.1, 1.3 Hz, 1H), 7.00 (d, J=8.4 Hz, 2H), 5.92 (bs, 2H), 5.69 (s, 2H), 3.75 (s, 2H), 2.86 (dd, J=8.0 Hz, 2H), 2.68 (dd, J=8.0 Hz, 2H), 1.82-1.74 (m, 2H), 1.45-1.36 (m, 4H), 0.91 (t, J=7.8 Hz, 3H), 0.91-0.85 (m, 1H), 0.68-0.60 (m, 1H), 0.42-0.37 (m, 2H), 0.04-0.00 (m, 2H).

Example S4-c

Preparation of 2-butyl-1-(4-((((1-methylcyclobutyl)methyl)amino)methyl) benzyl)-1H-imidazo [4,5-c]quinoline-4-amine (Compound No. 64-60b)

Part A. N,N-diisopropylcarbodiimide (76 mg, 0.6 mmol) was added to a solution of 1-methylcyclobutane carboxylic acid (57 mg, 0.5 mmol) and pentafluorophenol (94 mg, 0.52 mmol) in dichloromethane (3 mL), in presence of catalytic amount of N,N-dimethylaminopyridine (6 mg), and stirred overnight at room temperature. This mixture was then diluted with ether (20 mL), the precipitated urea removed by filtration, and the filtrate concentrated to obtain crude product. This crude product was suspended in 1% ethyl acetate/hexane and any residual precipitated urea was again removed by filtration. The resultant filtrate was concentrated under reduced pressure to yield 126 mg of the desired (2,3,4,5,6-pentafluorophenyl)-1-methylcyclobutane carboxylate product.

Part B. IMDQ (84 mg, 0.23 mmol) was added to a solution of (2,3,4,5,6-pentafluorophenyl)-1-methylcyclobutane carboxylate (72 mg, 0.26 mmol) in dichloromethane (3 mL) in presence of triethylamine (48 mg, 0.47 mmol), and stirred for 2 hours at room temperature. The reaction mixture was then concentrated under reduced pressure and the residue washed with 5% ethyl acetate/hexane. The residue was dissolved in dichloromethane (15 mL), washed with 1M HCl followed by water (20 mL), dried over magnesium sulfate, filtered and concentrated under reduced pressure to yield 88 mg of N-(4-((4-amino-2-butyl-1H-imidazo[4,5-c]quinolin-1-yl)methyl)benzyl)-1-methylcyclobutane-1-carboxamide as off white solid.

Part C. N-(4-((4-amino-2-butyl-1H-imidazo[4,5-c]quinolin-1-yl)methyl)benzyl)-1-methylcyclobutane-1-carboxamide (88 mg) was reduced with borane dimethyl sulfide complex (3.5 eq) at 55° C. for 12 hours. The reaction was then cooled to room temperature, carefully quenched with 2 M HCl (excess), and stirred for an additional 3 hours at 55° C. The reaction was cooled to room temperature and diluted with water (10 mL), then extracted with dichloromethane (10 mL) to remove impurities. The pH of the reaction mixture was adjusted to 8.0 by adding an ice-cold 1M NaOH solution, extracted with dichloromethane (3×10 mL), dried over MgSO$_4$, and concentrated under reduced pressure to yield an off-white solid. Upon recrystallization with 9:1 ethyl acetate/hexane the reaction yielded 32 mg of 2-butyl-1-(4-((((1-methylcyclobutyl)methyl)amino)methyl)benzyl)-1H-imidazo[4,5-c]quinolin-4-amine (Compound No. 64-60b). Product purity was assessed to be 96% pure by reverse-phase HPLC at 254 nm, the intended synthetic mass of 441.3 Daltons was confirmed by LC/MS, and the intended synthetic structure confirmed by 300 MHz 1H NMR (CDCl3): δ 7.80 (d, J=8.1 Hz, 1H), 7.71 (d, J=8.4 Hz, 1H), 7.43 (t, J=7.5, 15.0 Hz, 1H), 7.31 (d, J=8.4 Hz, 2H), 7.14 (t, J=7.5, 15.0 Hz, 1H), 7.01 (d, J=8.4 Hz, 2H), 5.71 (s, 2H), 5.52 (s, 2H), 3.78 (s, 2H), 2.89 (t, J=7.5, 15.6 Hz, 2H), 2.52 (s, 2H), 1.6-1.88 (m, 8H), 1.35-1.60 (m, 2H), 1.12 (s, 3H), 0.94 (t, J=7.5, 14.7 Hz, 3H).

Example S4-d

Preparation of 2-butyl-1-(4-(((cyclobutylmethyl)amino)methyl)benzyl)-1H-imidazo[4,5-c]quinoline-4-amine (Compound No. 64-66b)

Part A. N,N-diisopropylcarbodiimide (127 mg, 1.0 mmol) was added to a solution of cyclobutane carboxylic acid (106 mg, 0.93 mmol) and pentafluorophenol (175 mg, 0.97 mmol) in dichloromethane (3 mL), in presence of catalytic amount of N,N-dimethylaminopyridine (12 mg), and stirred overnight at room temperature. This mixture was then diluted with ether (20 mL), the precipitated urea removed by filtration, and the filtrate concentrated to obtain crude product. This crude product was suspended in 1% ethyl acetate/hexane and any residual precipitated urea was again removed by filtration. The resultant filtrate was concentrated under reduced pressure to yield 126 mg of the desired (2,3,4,5,6-pentafluorophenyl)cyclobutane carboxylate product.

Part B. IMDQ (62 mg, 0.17 mmol) was added to a solution of (2,3,4,5,6-pentafluorophenyl)cyclobutane carboxylate (50 mg, 0.18 mmol) in dichloromethane (3 mL), in presence of triethylamine (35 mg, 0.34 mmol), and stirred for 2 hours at room temperature. The reaction mixture was then concentrated under reduced pressure and the residue washed with 5% ethyl acetate/hexane. The residue was dissolved in dichloromethane (15 mL), washed with 1M HCl followed by water (20 mL), dried over magnesium sulfate, filtered and concentrated under reduced pressure to yield 85 mg of N-(4-((4-amino-2-butyl-1H-imidazo[4,5-c]quinolin-1-yl)methyl)benzyl)cyclobutanecarboxamide as an off-white solid.

Part C. N-(4-((4-amino-2-butyl-1H-imidazo[4,5-c]quinolin-1-yl)methyl)benzyl)cyclobutanecarboxamide (85 mg) was reduced with borane dimethyl sulfide complex (3.5 eq) at 55° C. for 12 hours. The reaction was then cooled to room temperature, carefully quenched with 2 M HCl (excess), and stirred for an additional 3 hours at 55° C. The reaction was cooled to room temperature and diluted with water (10 mL), then extracted with dichloromethane (10 mL) to remove impurities. The pH of the reaction mixture was adjusted to 8.0 by adding an ice-cold 1M NaOH solution, extracted with dichloromethane (3×10 mL), dried over MgSO4, and concentrated under reduced pressure to yield an off-white solid. Upon recrystallization with 9:1 ethyl acetate/hexane the reaction yielded 21 mg of 2-butyl-1-(4-(((cyclobutylmethyl)amino)methyl)benzyl)-1H-imidazo[4,5-c]quinolin-4-amine (Compound No. 64-66b). Product purity was assessed to be 95% pure by reverse-phase HPLC at 254 nm, the intended synthetic mass of 427.3 Daltons was confirmed by LC/MS, and the intended synthetic structure confirmed by 300 MHz 1H NMR (CDCl3): δ 7.80 (d, J=8.1 Hz, 1H), 7.73 (d, J=8.4 Hz, 1H), 7.45 (t, J=7.5, 15.0 Hz, 1H), 7.29 (d, J=8.4 Hz, 2H), 7.15 (t, J=7.5, 15.0 Hz, 1H), 7.03 (d, J=8.4 Hz, 2H), 5.72 (s, 2H), 5.51 (s, 2H), 3.74 (s, 2H), 2.89 (t, J=7.5, 15.6 Hz, 2H), 2.62 (d, J=7.2 Hz, 2H), 2.40-2.58 (m, 1H), 1.75-2.15 (m, 7H), 1.60-1.70 (m, 2H), 1.35-1.50 (m, 2H), 0.94 (t, J=7.5, 14.7 Hz, 3H).

Example S5

Determination of Percent Free IMDQ in Compound Nos. 64-53, 64-53a, 64-54, 64-54a, 64-54b, and 64-54c Compound Nos. 64-53, 64-53a, 64-54, 64-54a, 64-54b, and 64-54c were analyzed by RP-HPLC for detection of free (i.e., unconjugated) IMDQ. An aliquot of Compound Nos. 64-53, 64-53a, 64-54, 64-54a, 64-54b, or 64-54c was loaded onto a Zobrax Eclipse C18 column (column size: 1.4 mL; temperature: 23° C.; detection wavelength: 322 nm) and eluted with a water/acetonitrile gradient (5 to 95% acetonitrile). The free IMDQ peak (4.5 minutes retention time) was integrated and the area response was compared against an IMDQ standard curve for quantification. The percent free IMDQ was calculated using the following equation:

% free IMDQ=(unconjugated IMDQ concentration)×100/(total IMDQ concentration), where the total IMDQ concentration is determined as described in Example S6 for Compound Nos. 64-53 and 54-53a, or as described in Example S8 for Compound Nos. 64-54, 64-54a, 64-54b, and 64-54c.

Example S6

Determination of Total IMDQ Concentration in Compound No. 64-53 and 64-53a

The total IMDQ concentration in Compound No. 64-53 and 64-53a was determined by quantitation of the released IMDQ following complete thiolysis. Briefly Compound No. 64-53 or 64-53a was incubated with 10 mM of dithiothreitol (DTT) in PBS pH7.5/EDTA buffer for 18 hours at room temperature. The resulting sample was analyzed by RP-HPLC, as described in Example S5, and the released IMDQ peak area was quantitated against an IMDQ standard curve.

Example S7

Determination of Ficoll Concentration in Compound Nos. 64-53, 64-53a, 64-54a and 64-54

Ficoll concentrations in Compound Nos. 64-53, 64-53a, 64-54, 64-54a, 64-54b, or 64-54c were determined using the sodium periodate method as described by the manufacturer (Glycoprotein carbohydrate estimation kit, Thermo Scientific, Rockford Ill., Cat. No. 23260), except that Ficoll PM400 (GE Healthcare, Pittsburgh Pa., Cat. No. 17-0300-50) was used to create the standard curve.

Example S8

Determination of Total IMDQ Concentration in Compound No. 64-54, 64-54a, 64-54b, and 64-54c The total IMDQ concentration in Compound No. 64-54, 64-54a, 64-54b, and 64-54c was determined by quantitation of the released IMDQ following complete proteolysis. Briefly, Compound No. 64-54, 64-54a, 64-54b, or 64-54c was incubated with 3.7 µM of Cathepsin B in the presence of 3.9 mM DTT, in Acetate/EDTA pH 5.5 buffer for 18 hours at 37° C. The resulting sample was analyzed by RP-HPLC, as described in Example S5, and the released IMDQ peak area was quantitated against an IMDQ standard curve.

Example S9

Determination of Particle Size for Compound Nos. 64-53, 64-53a, 64-54, 64-54a, 64-54b, or 64-54c The average particle sizes (Z-average) of Compound Nos. 64-53, 64-53a, 64-54, 64-54a, 64-54b, or 64-54c were measured by dynamic light scattering using a Malvern Zetasizer (Malvern Instruments, Malvern UK). Samples were diluted to a Ficoll concentration of 0.5 mg/mL in PBS pH 7.5 buffer and measured under defined instrument settings. A 50 nm polystyrene nanosphere (Thermo Scientific, Rockford Ill., Cat. No. 3050A) was included in the analysis as a reference standard control, and had a defined particle size of 49±6 nm.

Example S10

Chemical Reaction Conditions and Characterization Data for the Synthesis of Compound Nos. 64-53, 64-53a, 64-54, and 64-54a A summary of the reaction conditions used in the synthesis of Compound Nos. 64-53, 64-53a, 64-54, and 64-54a are provided in Table S10-1. Assays to determine unconjugated IMDQ, total IMDQ, and Ficoll concentrations are as described in Examples S5 to S9. The total IMDQ amount was calculated by multiplication of the total IMDQ concentration by the volume of solution.

TABLE S10-1

Chemical Reaction Conditions and Characterization Data for the Synthesis of Compound Nos. 64-53, 64-53a, 64-54, and 64-54a.

| | Compound No. 64-53 | Compound No. 64-54 | Compound No. 64-53a | Compound No. 64-54a |
|---|---|---|---|---|
| | Chemical Reaction Conditions | | | |
| Starting [PACM-Ficoll] | 3.34 mg/ml (17.5 mg) | 3.21 mg/ml (17.5 mg) | 4.64 mg/ml (55.6 mg) | 5.56 mg/ml (44.5 mg) |

TABLE S10-1-continued

Chemical Reaction Conditions and Characterization Data for the Synthesis of Compound Nos. 64-53, 64-53a, 64-54, and 64-54a.

|  | Compound No. 64-53 | Compound No. 64-54 | Compound No. 64-53a | Compound No. 64-54a |
|---|---|---|---|---|
| Starting [IMDQ] | 0.83 mM (3.1 mg of Compound No. 64-51 = 1.6 mg free IMDQ) | 0.80 mM (6.1 mg of Compound No. 64-52 = 1.6 mg free IMDQ) | 1.66 mM (9.7 mg of Compound No. 64-51a = 5.0 mg free IMDQ) | 1.39 mM (11.6 mg of Compound No. 64-52a = 4.0 mg free IMDQ) |
| IMDQ/Ficoll Molar Equivalents | 100 | 100 | 100 | 100 |
| Purification | Dialysis in PBS pH 7.2 | Dialysis in PBS pH 7.2 | Dialysis in PBS pH 7.2 | Dialysis in PBS pH 7.2 |
| Characterization Data | | | | |
| [Ficoll] | 1.73 mg/ml | 1.77 mg/ml | 3.09 mg/ml | 3.69 mg/ml |
| [Total IMDQ] | 296 µM | 343 µM | 531 µM | 904 µM |
| IMDQ/Ficoll Molar Ratio | 69 | 77 | 69 | 98 |
| Total IMDQ Amount | 0.8 mg | 0.74 mg | 3.3 mg | 4.0 mg |
| Yield (IMDQ) | 50% | 46% | 66% | 100% |
| Appearance | Clear solution, no sign of precipitation | Slightly hazy solution, no sign of precipitation | Yellowish, no haze | Yellowish, slightly hazy |
| Percent Free IMDQ | 0.06% | 0.03% | 0.00% | 0.00% |
| Particle Size | 36 nm | 122 nm | 36 nm | 112 nm |

Example S11

Preparation of Compound Nos. 64-55 and 64-56

The procedures and synthesis schemes shown in Example S11 and Schemes S11-1 and S11-2 can be used to prepare Maleimidocaproyl-Dipeptide-PABC-TLR7/8 agonist compounds ($-L^3-L^2-L^1-D$ in formula (I)) with a variety of TLR7/8 agonist moieties. These examples show the use of the TLR7/8 agonist Compound Nos. 64-10a and 64-33a to prepare Compound Nos. 64-55 (Scheme S11-1) and 64-56 (Scheme S11-2), as exemplars of the general Maleimidocaproyl-Dipeptide-PABC-TLR7/8 agonist structure. In addition, the TLR7/8 agonist (D in formula (I)) can be either IMDQ or meta-IMDQ (see FIG. 1 for chemical structure representations of IMDQ and meta-IMDQ), as well as any of Compound Nos. 64-01 to 64-50, 64-58 to 64-69, 64-01a to 64-50a, and 64-58a to 64-69a.

Scheme S11-1
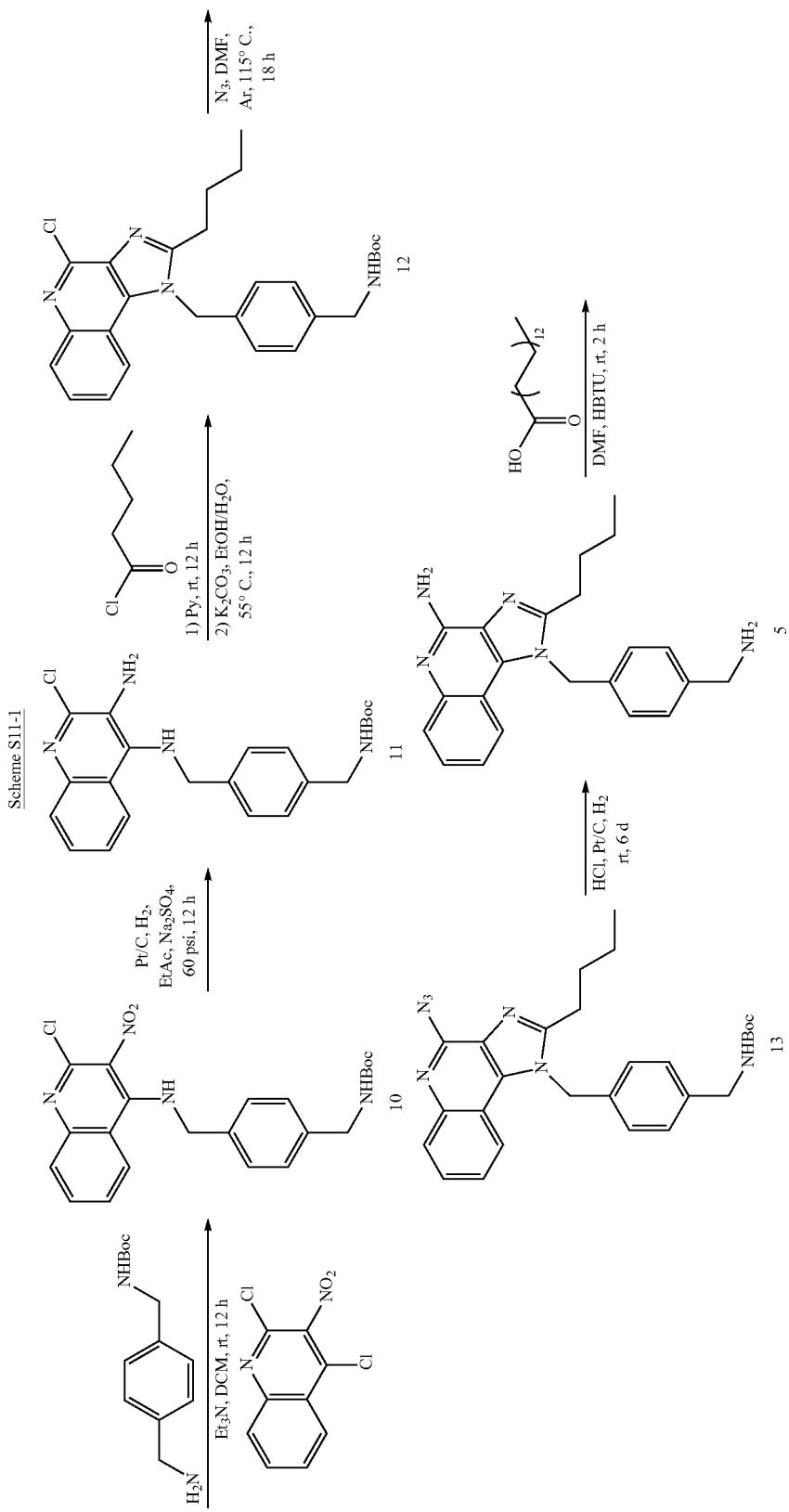

-continued
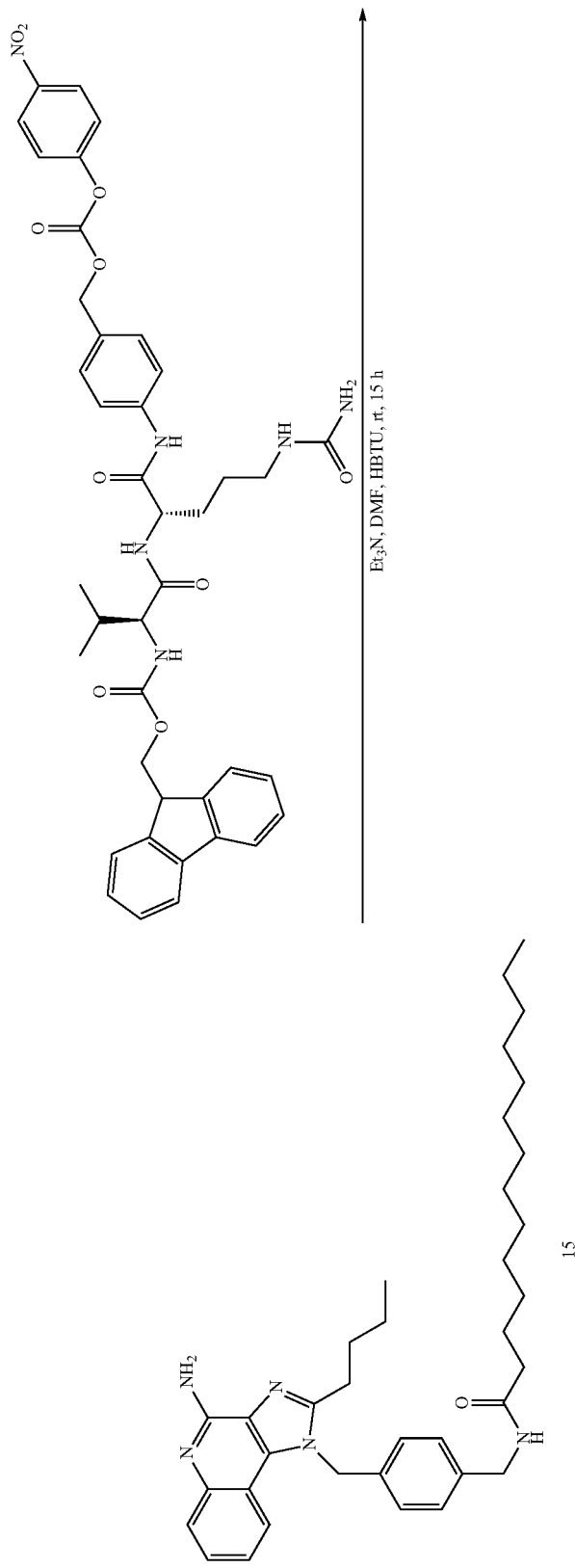

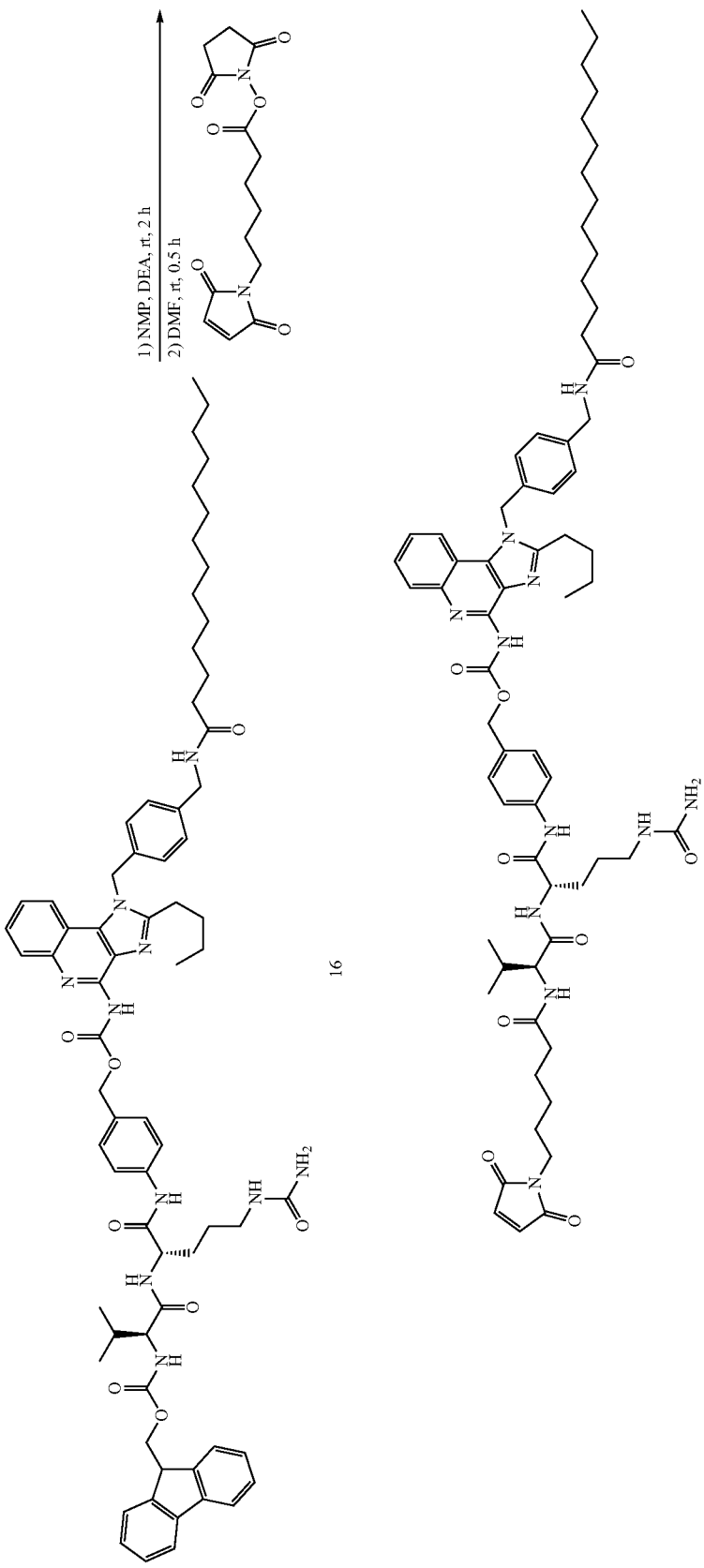

General Procedure for the Preparation of Compound No. 10.

Tert-butyl (4-(aminomethyl)benzyl)carbamate (1.1 eq) is added to a solution of 2,4-dichloro-3-nitroquinoline (1.0 eq) in anhydrous dichloromethane (400 mL) and trimethylamine (1.1 eq), followed by stirring overnight at room temperature. The solvents are removed under reduced pressure and the crude product purified by flash chromatography over silica gel using hexane/ethyl acetate to yield Compound No. 10 (tert-butyl (4-(((2-chloro-3-nitroquinolin-4-yl)amino) methyl)benzyl)carbamate).

General Procedure for the Preparation of Compound No. 11.

A solution of Compound No. 10 (0.12 mole) in ethyl acetate (250 mL) is hydrogenated in the presence of 5% platinum on carbon (2.0 g) and sodium sulfate (52 g) using a Parr hydrogenation apparatus at 60 psi for 12 hours. The platinum catalyst and sodium sulfate are removed by filtering through a pad of Celite®, and the filtrate concentrated under reduced pressure. The product is further purified by flash chromatography over silica gel eluting with hexane/ ethyl acetate to yield Compound No. 11 (tert-butyl (4-(((3-amino-2-chloroquinolin-4-yl)amino)methyl)benzyl)carbamate).

General Procedure for the Preparation of Compound No. 12.

Pentanoyl chloride (1.05 eq) is added slowly to a solution of Compound No. 11 (1.0 eq) in anhydrous tetrahydrofuran (350 mL) and pyridine (30 mL) at 0-5° C. The reaction mixture is then warmed to room temperature and stirred for 12 hours. The solvents are removed under reduced pressure and then the solids are re-dissolved in ethyl acetate (400 mL), washed successively with water and saturated sodium bicarbonate (150 mL), and finally dried over anhydrous magnesium sulfate. The product is further purified by flash chromatography over silica gel, eluting with hexane/ethyl acetate to yield the intermediate tert-butyl (4-(((3-butyramido-2-chloroquinolin-4-yl)amino)methyl)benzyl)carbamate. Water is added to a solution of the intermediate (1.0 eq) in a 4× volume of ethanol, followed by the addition of potassium carbonate (2.0 eq), and the mixture is heated with vigorous stirring to 55° C. for 16 hours. This reaction mixture is then concentrated and the residue is partitioned between ethyl acetate and water. The ethyl acetate layer is then washed with water, dried over anhydrous magnesium sulfate, and concentrated under reduced pressure. The product is further purified by flash chromatography over silica gel, eluting with hexane/ethyl acetate to yield Compound No. 12 (tert-butyl (4-((2-butyl-4-chloro-1H-imidazo[4,5-c] quinolin-1-yl)methyl)benzyl)carbamate).

General Procedure for the Preparation of Compound No. 13.

Compound No. 12 (1.0 eq) is dissolved in anhydrous dimethyl formamide, and then sodium azide (4.0 eq) is added to this solution. The resulting suspension is degassed and stirred under argon atmosphere at 110-115° C., with the reaction progress being monitored by reverse-phase HPLC analysis. After 18 hours, the reaction mixture is cooled to room temperature, poured into cold water, and extracted with ethyl acetate. The combined extract is washed with water, dried over magnesium sulfate, filtered through Celite, and concentrated under reduced pressure to yield an off-white solid. This solid is further worked up by re-crystallization with 1:1 ethyl/hexane to yield Compound No. 13 (tert-butyl (4-((4-azido-2-butyl-1H-imidazo[4,5-c]quinolin-1-yl)methyl)benzyl)carbamate).

General Procedure for the Preparation of Compound No. 5 (IMDQ).

Compound No. 13 (25.7 mmol) is added to concentrated hydrochloric acid, and 10% platinum on carbon (3.0 g) was added to this suspension. This reaction mixture is subjected to hydrogenation at 65 psi, with the reaction progress being monitored by reverse-phase HPLC analysis. After 6 days, the catalyst is filtered off and the filtered cake is washed with water. The cake is cooled in an ice bath, ice cold 1N sodium hydroxide is added drop wise while stirring vigorously until the pH reached 8.5, and the material is extracted with dichloromethane containing 5% methanol. The combined extract is dried over magnesium sulfate, filtered, and concentrated under reduced pressure. The residue is purified on a silica gel column using 8% methanol/dichloromethane containing 1% aqueous ammonia to yield Compound No. 5 (1-(4-(aminomethyl)benzyl)-2-butyl-1H-imidazo[4,5-c]quinolin-4-amine).

General Procedure for the Preparation of Compound No. 15.

Myristic acid (1.2 eq) and trimethylamine are added to a solution of Compound No. 5 (1.0 eq) in anhydrous dimethylformamide, and the slurry is mixed for 5 minutes followed by the addition of HBTU (1.25 eq). This reaction mixture is further stirred for 2 hours under argon atmosphere. The solvent is removed under reduced pressure, the residue dissolved in ethyl acetate and washed with water, then dried using magnesium sulfate and concentrated under vacuum. This product is purified using column chromatography (6% methanol/dichloromethane) to yield Compound No. 15 (N-(4-((4-amino-2-butyl-1H-imidazo[4,5-c]quinolin-1-yl) methyl)benzyl)tetradecanamide).

General Procedure for the Preparation of Compound No. 16.

9-Fluorenylmethyloxycarbonyl-valyl-citrullyl-(4-aminobenzyl)-(4-nitrophenyl)carbonate (1.2 eq) and trimethylamine are added to a solution of Compound No. 15 (1.0 eq) in anhydrous DMF, and and the slurry is mixed for 5 minutes followed by the addition of HBTU (1.25 eq). This reaction mixture is further stirred for 15 hours at room termperature. The solvent is removed under reduced pressure, the residue dissolved in ethyl acetate and washed with water, then dried using magnesium sulfate and concentrated under vacuum. This product is purified using column chromatography (6% methanol/dichloromethane) to yield Compound No. 16 ((9H-fluoren-9-yl)methyl ((S)-1-(((S)-1-((4-((((2-butyl-1-(4-(tetradecanamidomethyl)benzyl)-1H-imidazo[4,5-c]quinolin-4-yl)carbamoyl)oxy)methyl)phenyl)amino)-1-oxo-5-ureidopentan-2-yl)amino)-3-methyl-1-oxobutan-2-yl) carbamate).

General Procedure for the Preparation of Compound No. 64-55.

Compound No. 16 (1.2 eq) is dissolved NMP, and then treated with diethylamine at room temperature for 2 hours. The solvent is removed under reduced pressure, the residue dissolved in ethyl acetate and washed with water, then dried using magnesium sulfate and concentrated under vacuum. The intermediate 4-((S)-2-((S)-2-(12-azanyl)-3-methylbutanamido)-5-ureidopentanamido)benzyl (2-butyl-1-(4-(tetradecanamidomethyl)benzyl)-1H-imidazo[4,5-c]quinolin-4-yl)carbamate (1.0 eq) and N-(e-maleimidocaproyloxy) succinide ester (1.1 eq) are dissolved in NMP and then stirred for 0.5 hour at room temperature. The solvent is removed under reduced pressure, the residue dissolved in ethyl acetate and washed with water, then dried using magnesium sulfate and concentrated under vacuum. This product is purified using column chromatography (6% methanol/dichloromethane) to yield Compound No. 64-55 (4-((S)-2-((S)-2-(6-(2,5-dioxo-2,5-dihydro-1H-pyrrol-1-yl) hexanamido)-3-methylbutanamido)-5-ureidopentanamido) benzyl (2-butyl-1-(4-(tetradecanamidomethyl)benzyl)-1H-imidazo[4,5-c]quinolin-4-yl)carbamate).

Scheme S11-2
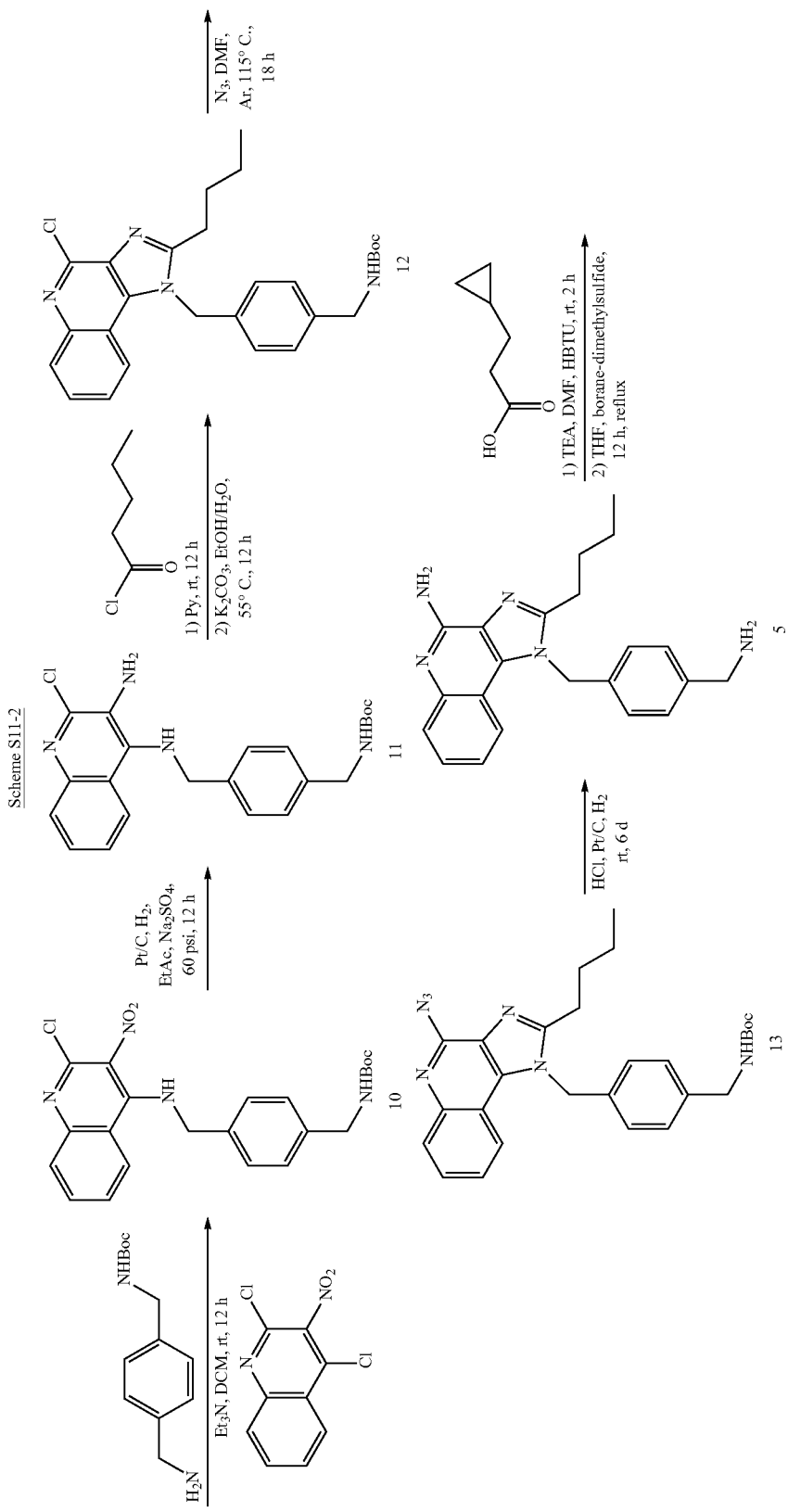

-continued
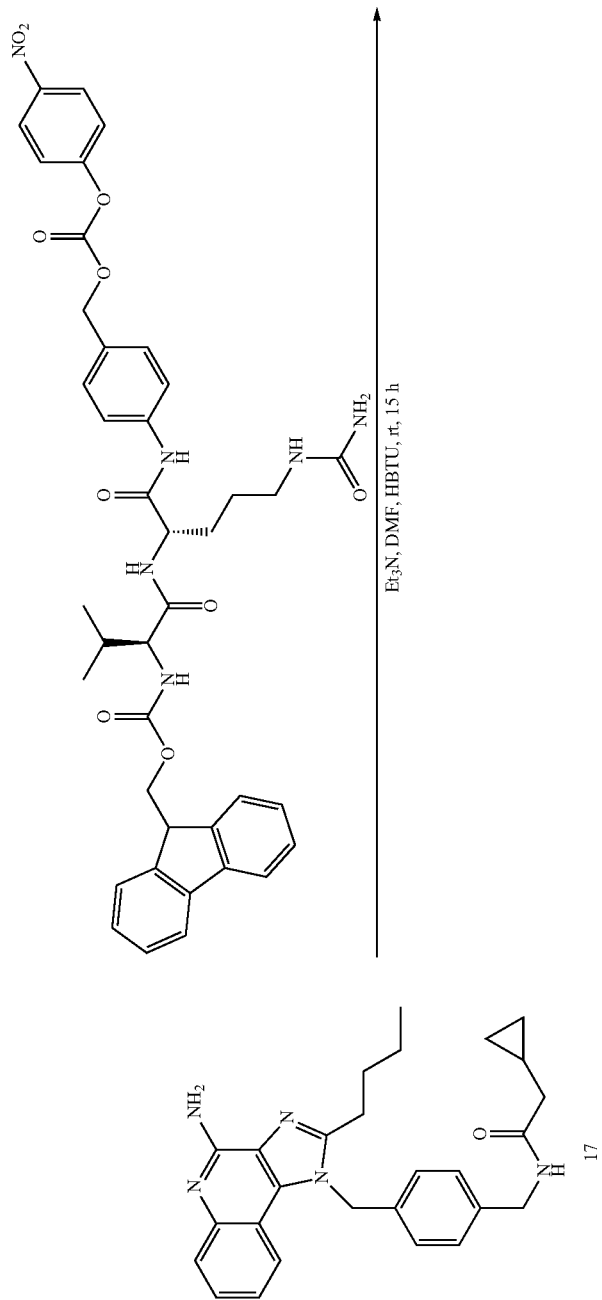

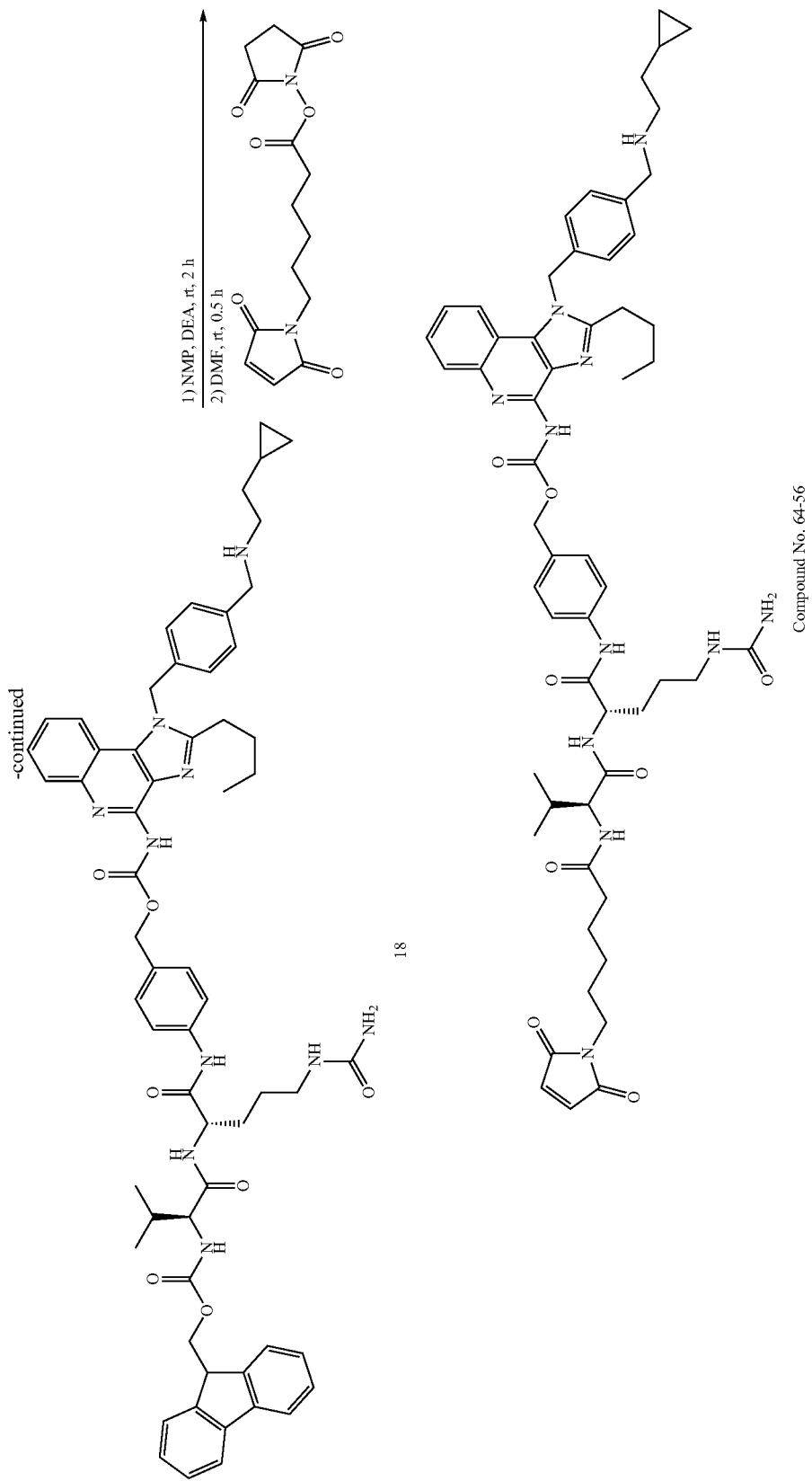

General Procedure for the Preparation of Compound No. 17.

Cyclopropyl acetic acid (1.2 eq) and trimethylamine are added to a solution of Compound No. 5 (IMDQ; 1.0 eq) in anhydrous DMF, and the slurry is mixed for 5 minutes followed by the addition of HBTU (1.25 eq). This reaction mixture is further stirred for 2 hours under argon atmosphere. The reaction is diluted with ethyl acetate and washed with water, then dried using magnesium sulfate and concentrated under vacuum. The crude residue is taken up in ethyl acetate and MeOH, and purified using column chromatography (6% methanol/dichloromethane) to yield the intermediate N-(4-((4-amino-2-butyl-1H-imidazo[4,5-c] quinolin-1-yl)methyl)benzyl)-2-cyclopropylacetamide. A solution of excess borane-dimethyl sulfide complex is added to a solution of the intermediate (1.0 eq) in anhydrous tetrahydrofuran at room temperature, and the reaction mixture is heated to reflux for 12 hours. The mixture is cooled to ambient temperature, quenched with 3N HCl, and stirred for an additional 4 hours. The pH of the reaction mixture was made alkaline by the addition 2N sodium hydroxide and the product is extracted with dichloromethane. The combined organic layers are concentrated under reduced pressure and the residue purified by flash chromatography with 6% methanol/dichloromethane as an eluent to yield Compound No. 17 (2-butyl-1-(4-(((2-cyclopropylethyl)amino)methyl) benzyl)-1H-imidazo[4,5-c]quinolin-4-amine).

General Procedure for the Preparation of Compound No. 18.

9-Fluorenylmethyloxycarbonyl-valyl-citrullyl-(4-aminobenzyl)-(4-nitrophenyl)carbonate (1.2 eq) and trimethylamine are added to a solution of Compound No. 17 (1.0 eq) in anhydrous DMF, and and the slurry is mixed for 5 minutes followed by the addition of HBTU (1.25 eq). This reaction mixture is further stirred for 15 hours at room termperature. The solvent is removed under reduced pressure, the residue dissolved in ethyl acetate and washed with water, then dried using magnesium sulfate and concentrated under vacuum. This product is purified using column chromatography (6% MeOH/dichloromethane) to yield Compound No. 18 ((9H-fluoren-9-yl)methyl ((S)-1-(((S)-1-((4-((((2-butyl-1-(4-(((2-cyclopropylethyl)amino)methyl)benzyl)-1H-imidazo[4,5-c] quinolin-4-yl)carbamoyl)oxy)methyl)phenyl)amino)-1-oxo-5-ureidopentan-2-yl)amino)-3-methyl-1-oxobutan-2-yl) carbamate). General Procedure for the Preparation of Compound No. 64-56.

Compound No. 18 (1.2 eq) is dissolved NMP, and then treated with diethylamine at room temperature for 2 hours. The solvent is removed under reduced pressure, the residue dissolved in ethyl acetate and washed with water, then dried using magnesium sulfate and concentrated under vacuum. The intermediate 4-((S)-2-((S)-2-amino-3-methylbutanamido)-5-ureidopentanamido)benzyl (2-butyl-1-(4-(((2-cyclopropylethyl)amino)methyl)benzyl)-1H-imidazo[4,5-c] quinolin-4-yl)carbamate (1.0 eq) and N-(e-maleimidocaproyloxy) succinide ester (1.1 eq) are dissolved in DMF, and then stirred for 0.5 hour at room temperature. The solvent is removed under reduced pressure, the residue dissolved in ethyl acetate and washed with water, then dried using magnesium sulfate and concentrated under vacuum. This product is purified using column chromatography (6% methanol/dichloromethane) to yield Compound No. 64-56 (4-((S)-2-((S)-2-(6-(2,5-dioxo-2,5-dihydro-1H-pyrrol-1-yl) hexanamido)-3-methylbutanamido)-5-ureidopentanamido) benzyl (2-butyl-1-(4-(((2-cyclopropylethyl)amino)methyl) benzyl)-1H-imidazo[4,5-c]quinolin-4-yl)carbamate).

Example S11a

Preparation of Compound Nos. 64-71, 64-72, 64-73, and 64-74

The procedures and synthesis schemes shown in Example S11a and Schemes S11a-1, S11a-2, S11a-3 and S11a-4 can be used to prepare AzidoPEG$_4$-Dipeptide-PABC-TLR7/8 agonist compounds (-L$^3$-L$^2$-L$^1$-D in formula (I)) with a variety of TLR7/8 agonist moieties. These examples show the use of the TLR7/8 agonist Compound Nos. 64-33b, meta-IMDQ, 64-60b, and 64-66b to prepare Compound Nos. 64-71 (Scheme S11a-1), 64-72 (Scheme S11b-2), 64-73 (Scheme S11c-3), and 64-74 (Scheme S11d-4), as exemplars of the general AzidoPEG$_4$-Dipeptide-PABC-TLR7/8 agonist structure. In addition, the TLR7/8 agonist (D in formula (I)) can be either IMDQ or meta-IMDQ (see FIG. 1 for chemical structure representations of IMDQ and meta-IMDQ), as well as any of Compound Nos. 64-01 to 64-50, 64-58 to 64-69, 64-01a to 64-50a, and 64-58a to 64-69a.

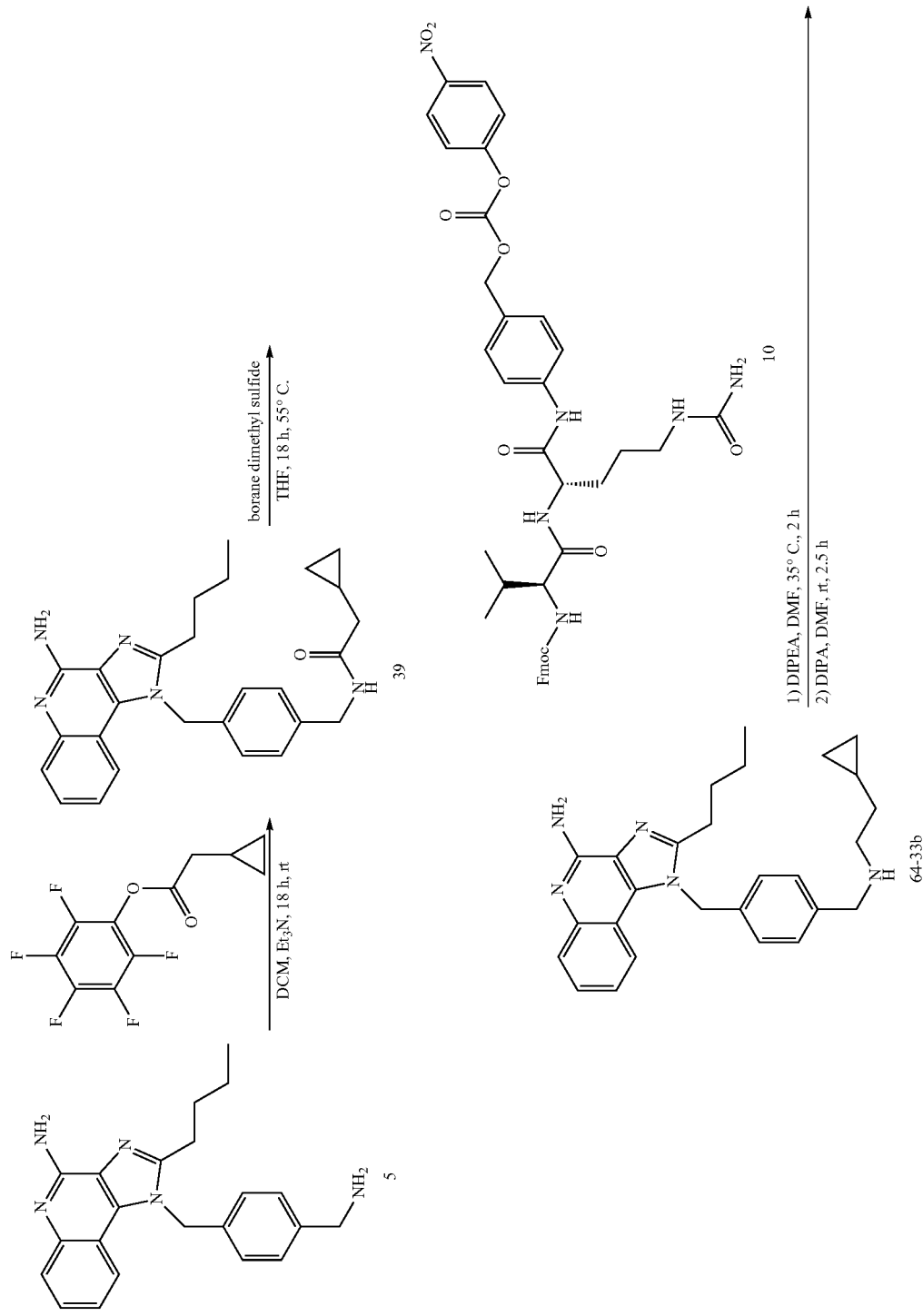

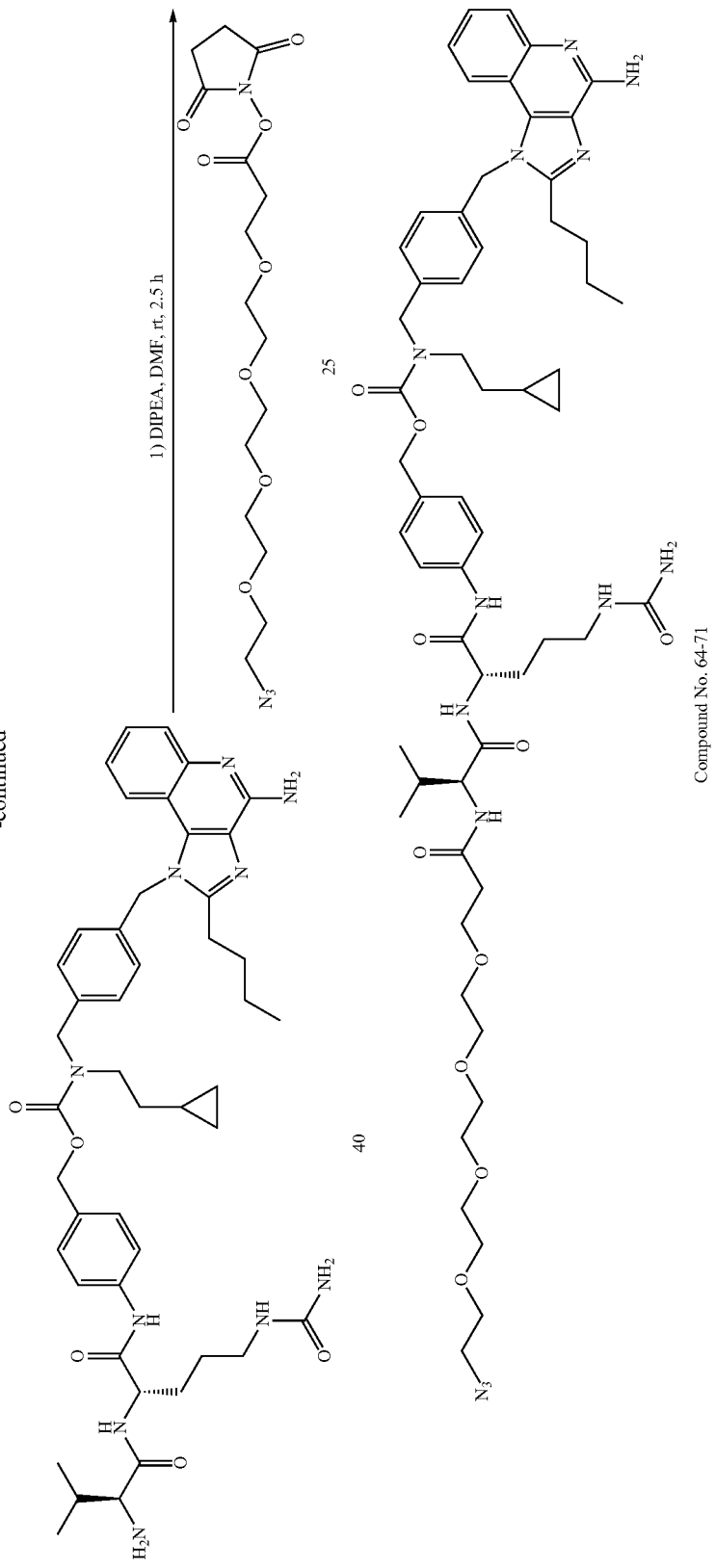

Procedure for the Preparation of Compound 21.

IMDQ (Compound 5; 350 mg; 1.0 eq) was added to a solution of the pentafluoro phenolic ester of cyclopropane carboxylic acid (280 mg; 1.2 eq) in dichloromethane (14 mL) in the presence of triethylamine (105 mg; 0.3 mmol) and stirred overnight at room temperature. After 18 hrs reverse-phase HPLC analysis of the solution the reaction had gone to completion. The solution was concentrated under reduced pressure and purified by flash chromatography, with 5-10% methanol containing 1% aqueous ammonia/dichloromethane, to yield 350 mg of Compound 39.

Procedure for the Preparation of Compound No. 64-33b.

Compound 39 (300 mg, 1 eq.) in THF (5.0 mL) was reduced with borane dimethyl sulfide complex (3.5 eq) at 55° C. for 12 hours. The reaction was cooled to room temperature, carefully quenched with 2 M hydrochloric acid (excess), and stirred for an additional 6 hours at 55° C. The reaction was then cooled to room temperature, diluted with water (15 mL), and extracted with dichloromethane (15 mL) to remove impurities. The pH was adjusted to 8.0 by adding cold 1M NaOH solution, re-extracted with dichloromethane (3×10 mL), dried over $MgSO_4$, and concentrated under reduced pressure to yield an off-white solid. Upon recrystallization with ethyl acetate the solid yielded 114 mg of Compound No. 64-33b as a white solid.

Procedure for the Preparation of Compound 40.

To a solution of Compound No. 64-33b (33 mg, 1.0 eq) in DMF (1.5 mL) was added diisopropylethyl amine (0.1 mL) and the solution was stirred for 10 minutes under an argon atmosphere. Compound 10 (59 mg, 1 eq.) was added to the solution in two portions and the resulting clear yellow solution was stirred at 35° C. for 2 hours. Thin layer chromatography analysis, with 10% methanol in dichloromethane containing 1% trimethylamine, indicted that all of the Compound No. 64-33b had been consumed. The DMF was removed under reduced pressure, ethyl acetate (3 mL) was added to the yellow residue, the mixture triturated, the pale yellow solid formed allowed to settle and the supernatant was decanted. This process was repeated additional two times, and the product was dried under reduced pressure to yield 73 mg of an off-white solid. The off-white solid (70 mg, 0.066 mmol) was dissolved in ice-cold DMF (1.5 mL) and diisopropyl amine was added (0.1 mL). The resulting solution was stirred under an argon atmosphere, slowly warmed to room temperature and stirring was continued for 12 hours. Reverse-phase HPLC analysis of the reaction mixture indicated that removal of the Fmoc moiety was complete. The DMF was removed under reduced pressure, ethyl acetate (3 mL) was added to the yellow residue, the mixture triturated, the pale yellow solid formed allowed to settle and the supernatant was decanted. This process was repeated additional two times, and the product was dried under reduced pressure to yield 47 mg of Compound 40.

Procedure for the Preparation of Compound No. 64-71.

Compound 40 (47 mg, 1.0 eq.) and Compound 25 (24 mg, 1.2 eq.) were dissolved in DMF (1 mL). Diisopropylethyl amine (0.1 mL) was added and the the solution was stirred for 2.5 hours at room temperature. Reverse-phase HPLC analysis indicted that the reaction was complete. The DMF was removed under reduced pressure, and the yellow residue was subjected to a silica gel column chromatography, eluting with 4-10% methanol in dichloromethane containing 0.5% ammonia, to yield 22.2 mg of CompoundNo. 64-71 as a white solid. Purity was assessed to be 72% pure by reverse-phase HPLC at 254 nm, the intended synthetic mass of 1,105.6 Daltons was confirmed by HRMS, and the intended synthetic structure confirmed by 300 MHz $^1$H NMR (CD3OD): δ 7.83 (d, J=8.1 Hz, 1H), 7.68 (d, J=8.4 Hz, 1H), 7.50-7.65 (m, 3H), 6.95-7.50 (m, 7H), 5.89 (s, 2H), 5.05 (brs, 2H), 4.42-4.60 (m, 3H), 4.20 (d, 1H), 3.73-3.76 (m, 2H), 3.55-3.68 (m, 14H), 3.28, 3.38 (m, 4H), 3.0-3.28 (m, 2H), 2.97 (t, J=7.5, 15.3 Hz, 2H), 2.55 (t, J=6, 12 Hz, 2H), 1.72-2.18 (m, 7H), 1.58-1.70 (m, 2H), 1.43-1.55 (m, 2H), 0.88-1.01 (m, 9H), 0.30-0.50 (m, 3H), 0.10-0.08 (m, 2H).

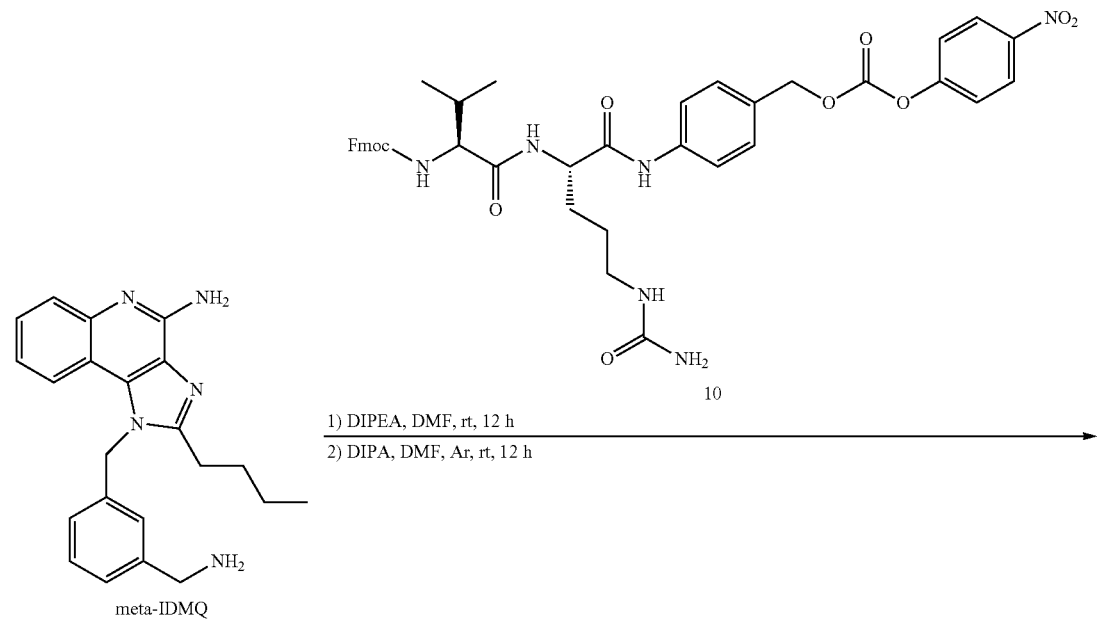

Scheme S11a-2

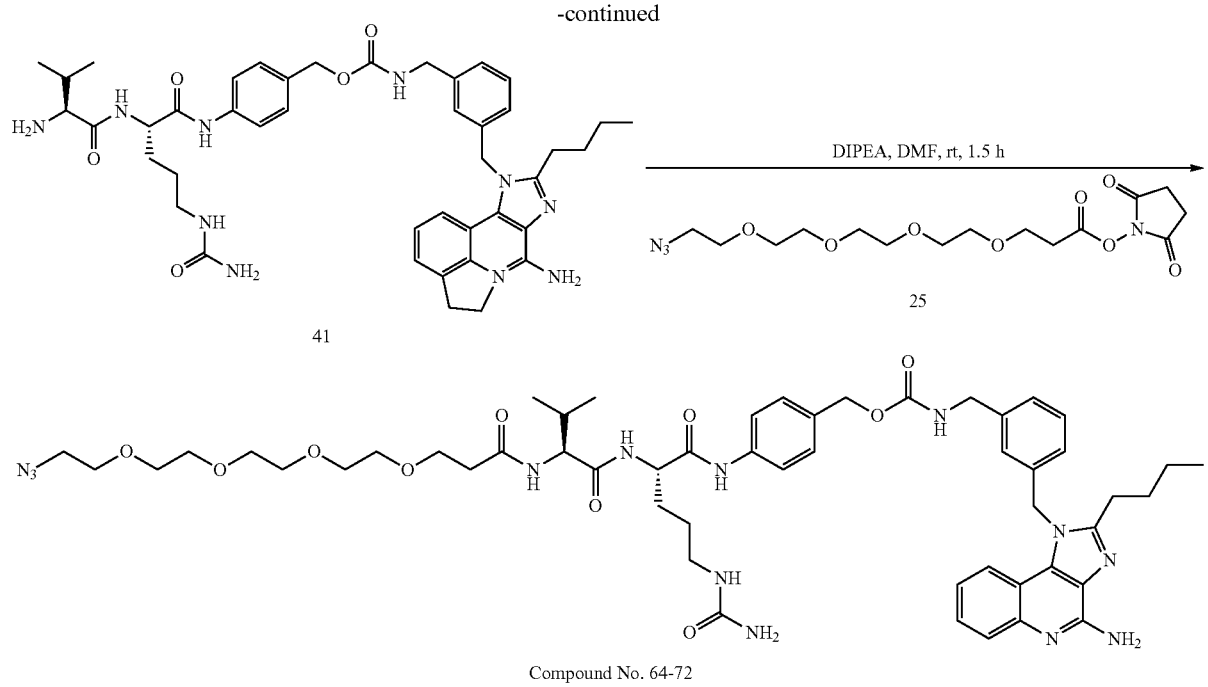

Compound No. 64-72

Procedure for the Preparation of Compound 41.

To a solution of meta-IMDQ (46 mg, 1.0 eq.) in DMF (1.5 mL) was added diisopropylethyl amine (0.2 mL) and the solution was stirred for 10 minutes under an argon atmosphere. Compound 10 (98 mg, 1.0 eq.) was added to the solution in two portions. The resulting clear yellow solution was stirred at 0° C. for 2 hours, then slowly warmed to room temperature and stirring was continued for 12 hours. Thin layer chromatography analysis, with 10% methanol in dichloromethane containing 1% trimethylamine, indicted that all of the meta-IMDQ had been consumed. The DMF was removed under reduced pressure, ethyl acetate (3 mL) was added to the yellow residue, the mixture triturated, the pale yellow solid formed allowed to settle and the supernatant was decanted. This process was repeated additional two times, and the product was dried under reduced pressure to yield 102 mg of an off-white solid. The off-white solid (99 mg, 0.1 mmol) was dissolved in ice-cold DMF (1.5 mL) and diisopropyl amine was added (0.1 mL). The resulting solution was stirred under an argon atmosphere, slowly warmed to room temperature and stirring was continued for 12 hours. Reverse-phase HPLC analysis of the reaction mixture indicated that removal of the Fmoc moiety was complete. The DMF was distilled off under reduced pressure, ethyl acetate (3 mL) was added to the yellow residue, the mixture triturated, the pale yellow solid formed allowed to settle and the supernatant was decanted. This process was repeated additional two times, and the product was dried under reduced pressure to yield 68 mg of Compound 41.

Procedure for the Preparation of Compound No. 64-72.

Compound 41 (68 mg, 1.0 eq.) and Compound 25 (38 mg, 1.2 eq.) were dissolved in DMF (1 mL). Diisopropylethyl amine (0.1 mL) was added to this solution and it was stirred for 1.5 hours at room temperature. Reverse-phase HPLC analysis indicted that the reaction was complete. The DMF was removed under reduced pressure, and the yellow residue was subjected to a silica gel column chromatography, eluting with 1-8% methanol in dichloromethane containing 0.5% ammonia, to yield 47 mg of Compound No. 64-72 as a white solid. Purity was assessed to be 96% pure by reverse-phase HPLC at 254 nm, the intended synthetic mass of 1,037.8 Daltons was confirmed by HRMS, and the intended synthetic structure confirmed by 300 MHz $^1$H NMR (CD3OD): δ 7.79 (d, J=8.1 Hz, 1H), 7.66 (d, J=8.4 Hz, 1H), 7.61 (d, J=8.1 Hz, 2H), 7.41 (t, J=7.5, 15.0 Hz, 1H), 7.21-7.37 (m, 3H), 7.05-7.29 (m, 2H), 7.03 (s, 1H), 6.93 (d, J=7.5 Hz, 1H), 5.82 (s, 2H), 4.96 (s, 2H), 4.48-4.55 (m, 1H), 4.20-4.26 (m, 3H), 3.73-3.76 (m, 2H), 3.55-3.68 (m, 14H), 3.28, 3.38 (m, 4H), 3.0-3.28 (m, 2H), 2.97 (t, J=7.5, 15.3 Hz, 2H), 2.55 (t, J=6, 12 Hz, 2H), 1.72-2.18 (m, 5H), 1.58-1.70 (m, 2H), 1.43-1.55 (m, 2H), 0.88-1.01 (m, 9H).

Scheme S11a-3
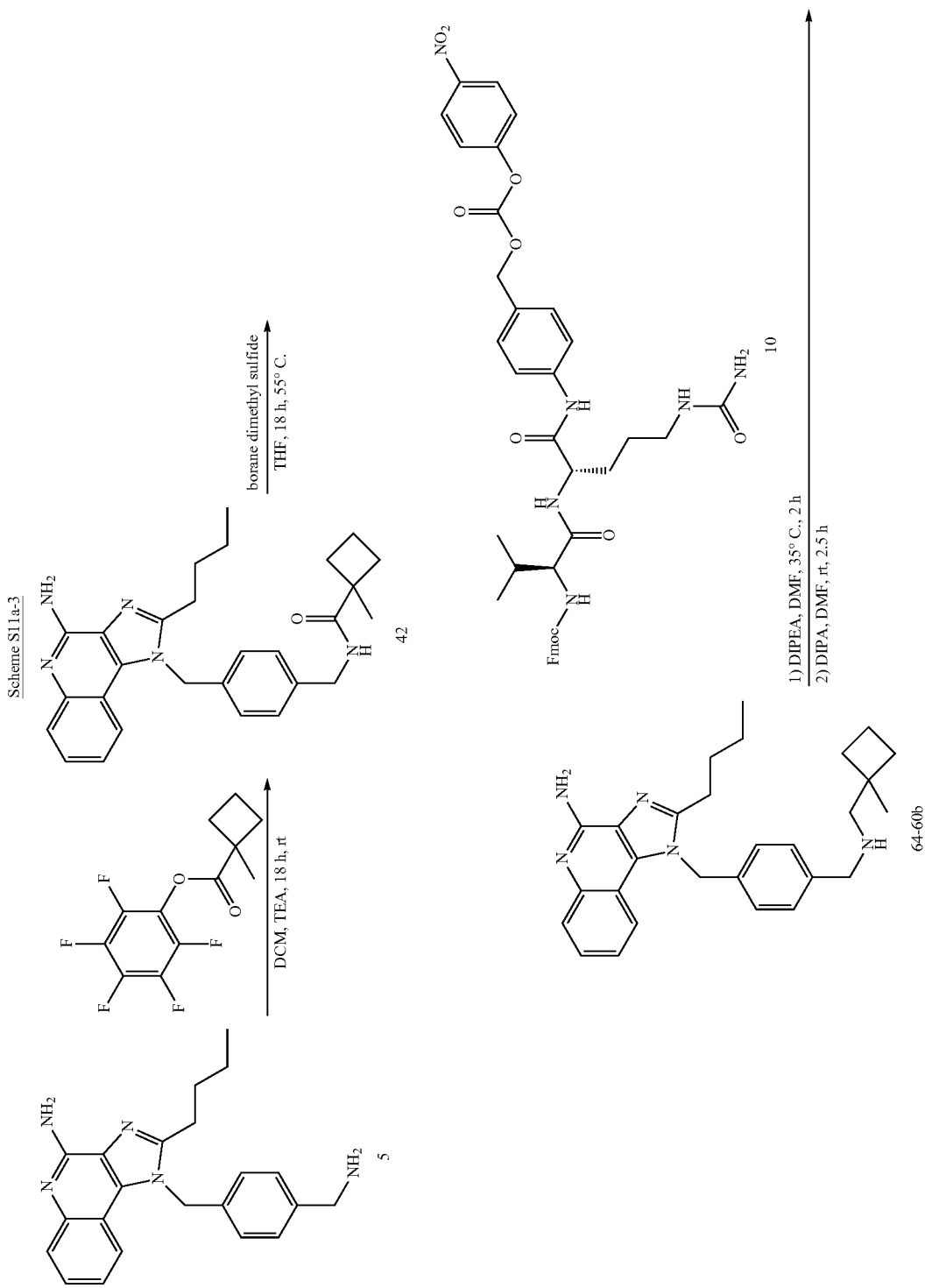

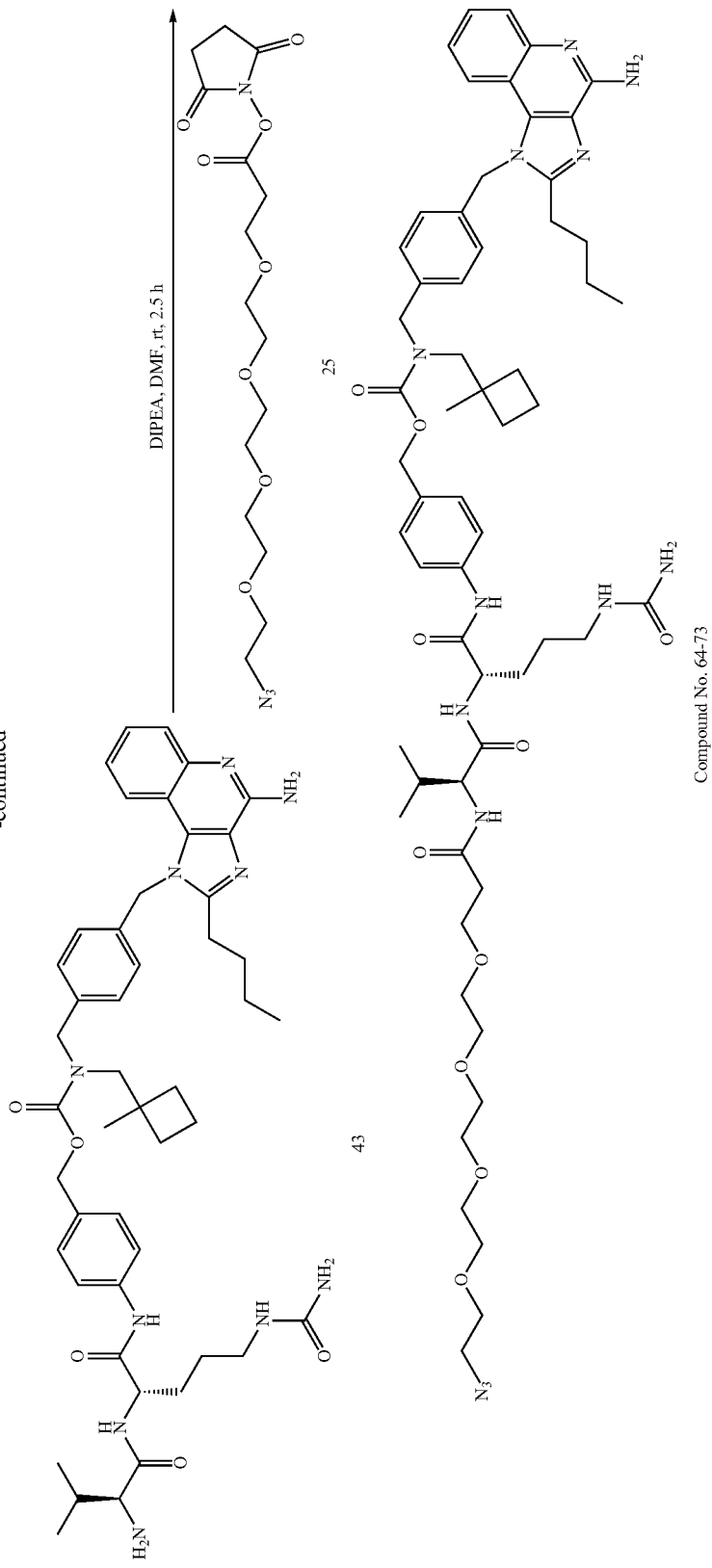

General Procedure for the Preparation of Compound 42.

IMDQ (Compound 5; 1.0 eq.) is added to a solution of the pentafluoro phenolic ester of 1-methylcyclobutane carboxylic acid (1.2 eq.) in DCM, in the presence of TEA, and stirred overnight at room temperature. After 18 hours reverse-phase HPLC analysis of the solution demonstrates the reaction has gone to completion. The solution is concentrated under reduced pressure and purified by flash chromatography, eluting with 5-10% methanol containing 1% (v/v) aqueous ammonia in DCM, to yield Compound 42.

General Procedure for the Preparation of Compound No. 64-60b.

Compound 42 (1 eq.) in THF is reduced with borane-dimethyl sulfide complex (3.5 eq) at 55° C. for 12 hours. The reaction is cooled to room temperature, carefully quenched with 2 M hydrochloric acid (excess), and stirred for an additional 6 hours at 55° C. The reaction is then cooled to room temperature, diluted with water, and extracted with DCM to remove impurities. The pH is adjusted to 8.0 by adding cold 1M NaOH solution, re-extracted with DCM, and the solution is dried over $MgSO_4$ and concentrated under reduced pressure to yield an off-white solid. Upon recrystallization with ethyl acetate the reaction yields Compound No. 64-60b as a white solid.

General Procedure for the Preparation of Compound 43.

To a solution of Compound No. 64-60b (1.0 eq.) in DMF is added DIPEA, and the solution is stirred for 10 minutes under an argon atmosphere. Compound 10 (1.0 eq.) is added to the solution in two portions and the resulting clear yellow solution is stirred at 35° C. for 2 hours. Thin layer chromatography analysis, developed with 10% (v/v) methanol in DCM, containing 1% (v/v) TEA, indicates that all of the Compound No. 64-60b has been consumed. The DMF is removed under reduced pressure, ethyl acetate is added to the yellow residue, the mixture triturated, and the pale yellow solid formed allowed to settle and the supernatant is decanted. This process is repeated additional two times, and the product is dried under reduced pressure to yield an off-white solid. The off-white solid is dissolved in ice-cold DMF and diisopropyl amine is added. The resulting solution is stirred under an argon atmosphere, slowly warmed to room temperature, with stirring continued for 12 hours. Reverse-phase HPLC analysis of the reaction mixture indicates that removal of the Fmoc moiety is complete. The DMF is then removed under reduced pressure, ethyl acetate is added to the yellow residue, the mixture triturated, and the pale yellow solid formed is allowed to settle and the supernatant is decanted. This process is repeated an additional two times, and the product is dried under reduced pressure to yield Compound 43.

General Procedure for the Preparation of Compound No. 64-73.

Compound 43 (1.0 eq.) and Compound 25 (1.2 eq.) are dissolved in DMF. DIPEA is added and the the solution stirred for 2.5 hours at room temperature. Reverse-phase HPLC analysis indicates that the reaction is complete. The DMF is removed under reduced pressure, and the yellow residue subjected to a silica gel column chromatography, eluting with 4-10% (v/v) methanol in dichloromethane, containing 0.5% (v/v) ammonia, to yield Compound No. 64-73 as a white solid. Product purity is assessed by RP-HPLC at 254 nm, the intended synthetic mass confirmed by LC-MS, and the intended synthetic structure confirmed by $^1$H NMR.

Scheme S11a-4
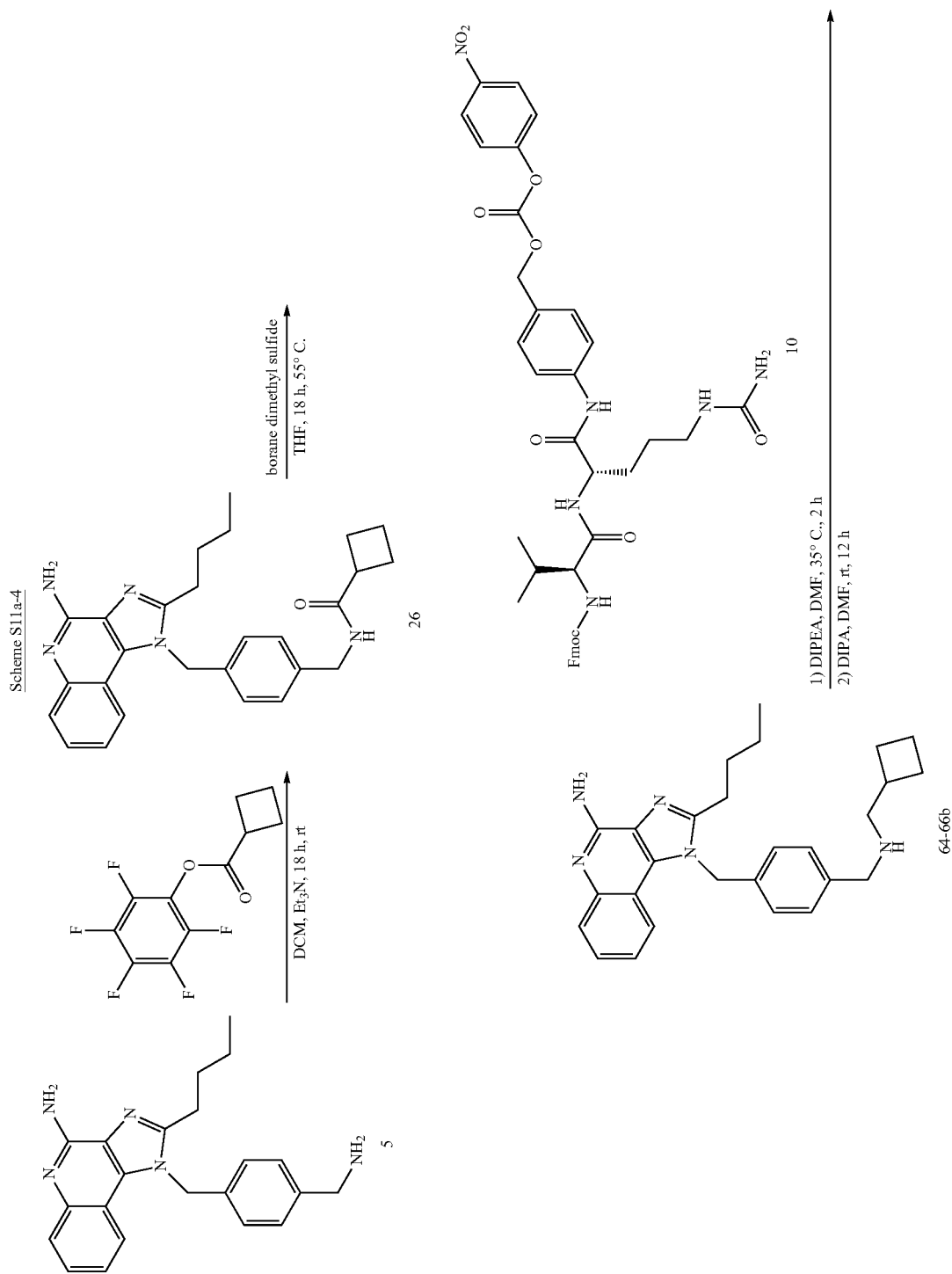

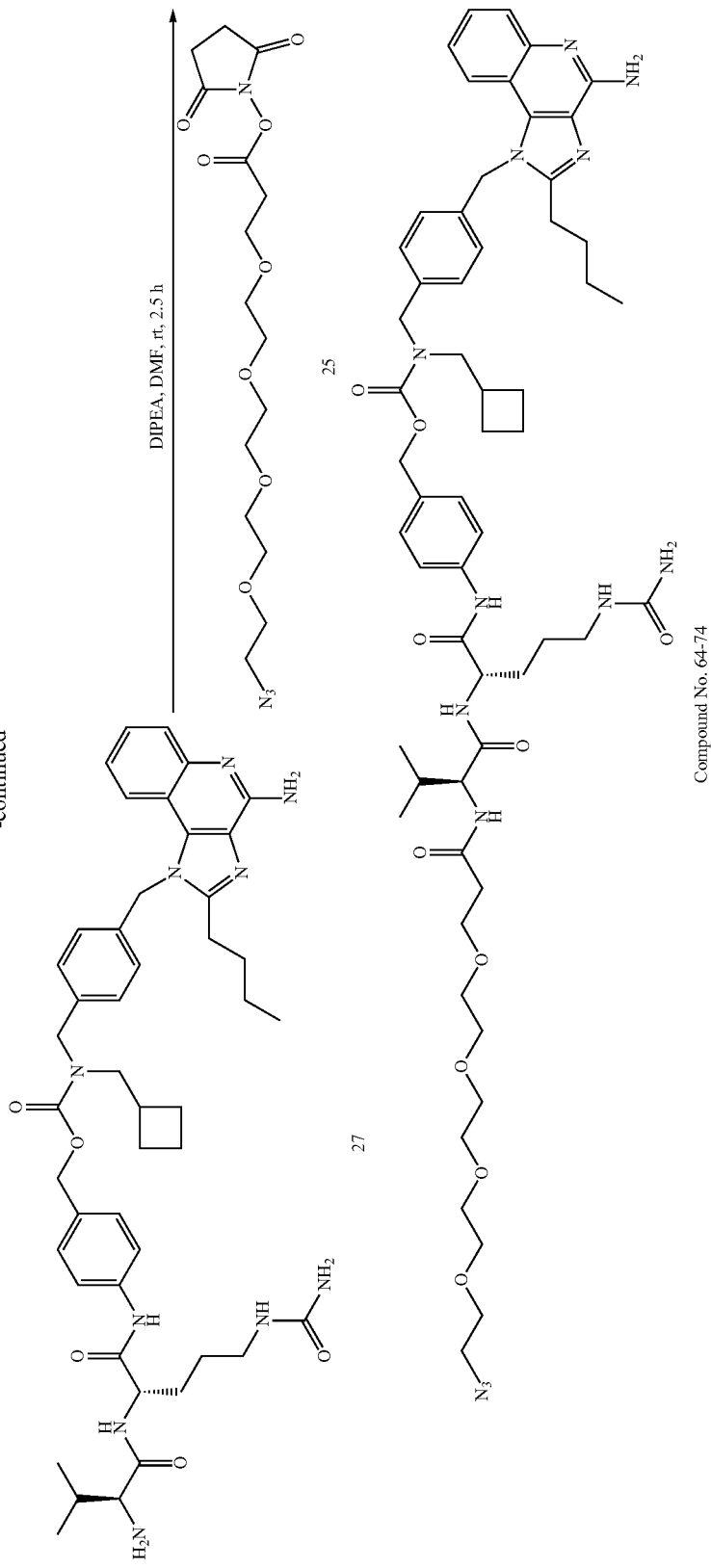

General Procedure for the Preparation of Compound 44.

IMDQ (Compound 5; 1.0 eq.) is added to a solution of the pentafluoro phenolic ester of cyclobutane carboxylic acid (1.2 eq.) in DCM, in the presence of TEA, and stirred overnight at room temperature. After 18 hours reverse-phase HPLC analysis of the solution demonstrates the reaction has gone to completion. The solution is concentrated under reduced pressure and purified by flash chromatography, eluting with 5-10% methanol containing 1% (v/v) aqueous ammonia in DCM, to yield Compound 44.

General Procedure for the Preparation of Compound No. 64-66b.

Compound 44 (1 eq.) in THF is reduced with borane-dimethyl sulfide complex (3.5 eq) at 55° C. for 12 hours. The reaction is cooled to room temperature, carefully quenched with 2 M hydrochloric acid (excess), and stirred for an additional 6 hours at 55° C. The reaction is then cooled to room temperature, diluted with water, and extracted with DCM to remove impurities. The pH is adjusted to 8.0 by adding cold 1M NaOH solution, re-extracted with DCM, and the solution is dried over $MgSO_4$ and concentrated under reduced pressure to yield an off-white solid. Upon recrystallization with ethyl acetate the reaction yields Compound No. 64-66b as a white solid.

General Procedure for the Preparation of Compound 45.

To a solution of Compound No. 64-66b (1.0 eq.) in DMF is added DIPEA, and the solution is stirred for 10 minutes under an argon atmosphere. Compound 10 (1.0 eq.) is added to the solution in two portions and the resulting clear yellow solution is stirred at 35° C. for 2 hours. Thin layer chromatography analysis, developed with 10% (v/v) methanol in DCM, containing 1% (v/v) TEA, indicates that all of the Compound No. 64-66b has been consumed. The DMF is removed under reduced pressure, ethyl acetate is added to the yellow residue, the mixture triturated, and the pale yellow solid formed allowed to settle and the supernatant is decanted. This process is repeated additional two times, and the product is dried under reduced pressure to yield an off-white solid. The off-white solid is dissolved in ice-cold DMF and diisopropyl amine is added. The resulting solution is stirred under an argon atmosphere, slowly warmed to room temperature, with stirring continued for 12 hours. Reverse-phase HPLC analysis of the reaction mixture indicates that removal of the Fmoc moiety is complete. The DMF is then removed under reduced pressure, ethyl acetate is added to the yellow residue, the mixture triturated, and the pale yellow solid formed is allowed to settle and the supernatant is decanted. This process is repeated an additional two times, and the product is dried under reduced pressure to yield Compound 45.

General Procedure for the Preparation of Compound No. 64-74.

Compound 45 (1.0 eq.) and Compound 25 (1.2 eq.) are dissolved in DMF. DIPEA is added and the the solution stirred for 2.5 hours at room temperature. Reverse-phase HPLC analysis indicates that the reaction is complete. The DMF is removed under reduced pressure, and the yellow residue subjected to a silica gel column chromatography, eluting with 4-10% (v/v) methanol in dichloromethane, containing 0.5% (v/v) ammonia, to yield Compound No. 64-74 as a white solid. Product purity is assessed by RP-HPLC at 254 nm, the intended synthetic mass confirmed by LC-MS, and the intended synthetic structure confirmed by $^1$H NMR.

Example S12

Preparation of Compound Nos. 64-57, 64-75, 64-76 and 64-77

The general procedures and schemes described in Example S12, S12a, S12b and S12c and Schemes S12-1, S12a-1, S12b-1 and S12c-1 can be used to prepare the compounds of formula (I). These examples uses the anti-HER2 antibody Trastuzumab with a maleimidocaproyl or NHS-PEG$_4$-trizole-PEG$_4$ conjugation linker, a valine-citrulline cleavable linker, a PABC self-eliminating linker, and Compound Nos. 64-10a and 64-66a, or IMDQ, as the TLR7/8 agonist moiety, where the agonist:antibody ratio is an average of 4 (i.e., 4 TLR7/8 agonist compounds per antibody), to prepare Compound No. 64-57, 64-75, 64-76 and 64-77 as exemplars of compounds of formula (I), wherein the conjugation moiety F is an antibody. In addition, the TLR7/8 agonist moiety (D in formula (I)) can be either IMDQ or meta-IMDQ (see FIG. 1 for chemical structure representations of IMDQ and meta-IMDQ), as well as Compound Nos. 64-01 to 64-50, 64-58 to 64-69, 64-01a to 64-50a, and 64-58a to 64-69a. A skilled artisan will understand that the general procedures described herein using Trastuzumab also apply to other recombinant antibodies, and derivatives thereof.

General Procedure for the Limited Reduction of an Anti-HER2 Antibody and Preparation of Compound No. 19.

Trastuzumab is a humanized IgG1 monoclonal antibody that targets the HER2 receptor (human epidermal growth factor receptor 2, also known as HER2/neu) that is found on the cell membrane of epithelial cells, and heavily over-expressed in certain breast cancer cells. A humanized IgG4 variant, with the S228P mutation engineered into the hinge region, of the anti-HER2 antibody Trastuzumab is obtained from commercial sources (InvivoGen, San Diego Calif., Cat. No. her2tra-mab14 or MedChem Express, Monmouth Junction N.J., Cat. No. HY-P9907); this antibody is generated by recombinant DNA technology and purified by affinity chromatography using methods well known to those skilled in the art (see, e.g., Kuner, R. and Reinhart, D. 2016, *Appl Microbiol Biotechnol* 100:3451-3461). The Trastuzumab antibody is subjected to limited reduction with 2.5 molar equivalents of tris-2-carboxyethylphosphine in PBS pH 7.5, 1 mM diethylenetriaminepentaacetic acid for 2 hours at 37° C. to produce Compound No. 19.

General Procedure for the Preparation of Compound No. 20.

Compound No. 19 (1.0 eq.) in PBS pH 7.5, 1 mM diethylenetriaminepentaacetic acid is reacted with Compound No. 64-56 (8-10 eq.) in PBS pH 7.5 containing 10% (v/v) dimethylacetamide for 0.5 hours at 0° C., and the reaction is quenched with 1 mM cysteine. Compound No. 20 is then purified/buffer exchanged into PBS pH 7.5 using G-25 size exclusion chromatography equilibrated in PBS pH 7.5 (GE Healthcare, Pisquataway N.J.).

General Procedure for the Preparation of Compound No. 64-57.

Figure 12:
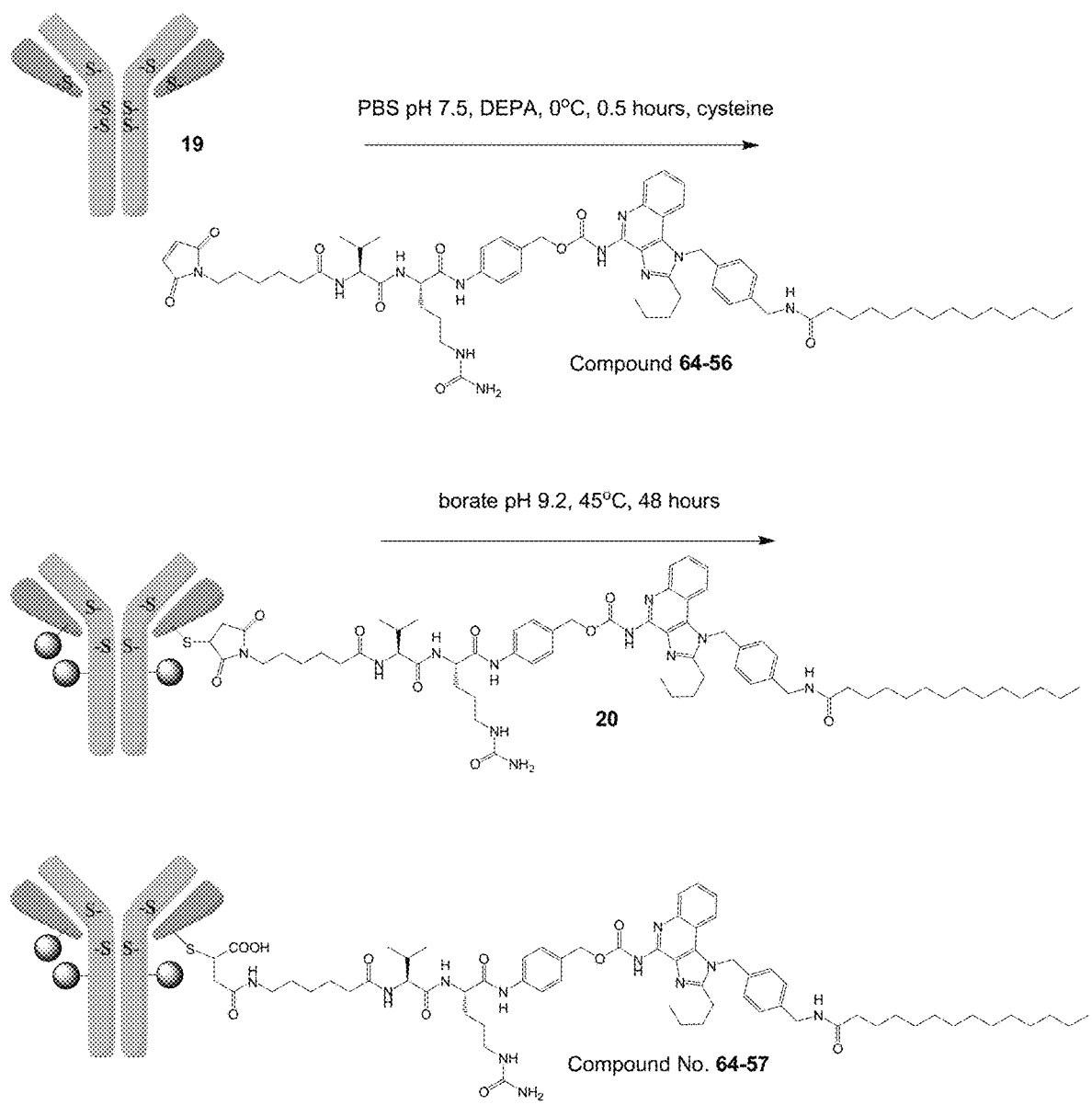
FIG. 12 shows a synthetic scheme for preparing Compound No. 64-57.

Succinimide-thioether ring hydrolysis creates a linkage with greater plasma stability, thus Compound No. 20 is buffer exchanged into 50 mM borate pH 9.2 using tangential flow filtration, heated to 45° C. for 48 hours, then cooled to room temperature and buffer exchanged into PBS pH 7.5. Compound No. 64-57 is subjected to size exclusion chromatography equilibrated in PBS pH 7.5 to remove any residual impurities, aggregated material, and to ensure complete buffer exchange. The synthetic scheme for preparing Compound No. 64-57 is shown in FIG. 12.

General Procedure for the Preparation of Compound No. 46.

Compound No. 45 (1.0 eq.) and N-(ε-maleimidocaproyloxy) succinide ester (1.1 eq.) are dissolved in DMF, DIPEA added, and the reaction is stirred for 2.5 hour at room temperature. The solvent is removed under reduced pressure, the residue dissolved in ethyl acetate and washed with water, then dried using $MgSO_4$ and concentrated under vacuum. This product is purified using column chromatography (6% methanol/dichloromethane) to yield Compound No. 46.

General Procedure for the Preparation of Compound No. 47.

Compound No. 19 (1.0 eq.) in PBS pH 7.5, 1 mM diethylenetriaminepentaacetic acid is reacted with Compound No. 46 (8-10 eq.) in PBS pH 7.5 containing 10% (v/v) dimethylacetamide for 0.5 hours at 0° C., and the reaction is quenched with 1 mM cysteine. Compound No. 47 is then purified/buffer exchanged into PBS pH 7.5 using G-25 size exclusion chromatography equilibrated in PBS pH 7.5 (GE Healthcare, Pisquataway N.J.).

General Procedure for the Preparation of Compound No. 64-75.

Figure 13:
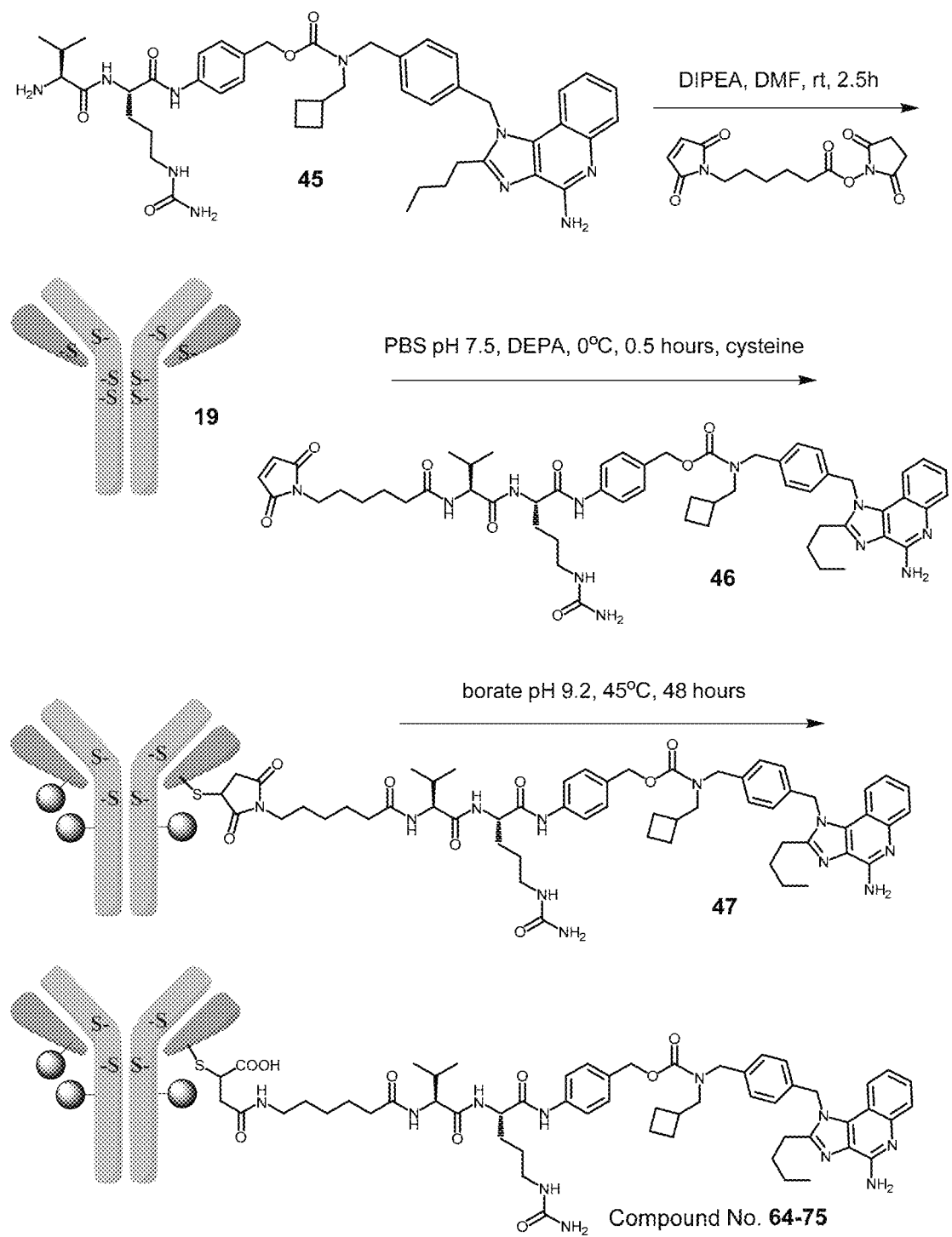
FIG. 13 shows a synthetic scheme for preparing Compound No. 64-75.

Succinimide-thioether ring hydrolysis creates a linkage with greater plasma stability, thus Compound No. 47 is buffer exchanged into 50 mM borate pH 9.2 using tangential flow filtration, heated to 45° C. for 48 hours, then cooled to room temperature and buffer exchanged into PBS pH 7.5. Compound No. 64-75 is subjected to size exclusion chromatography equilibrated in PBS pH 7.5 to remove any residual impurities, aggregrated material, and to ensure complete buffer exchange. The synthetic scheme for preparing Compound No. 64-75 is shown in FIG. 13.

General Procedure for the Preparation of Compound No. 48.

Compound No. 12 (1.0 eq.) and N-(c-maleimidocaproyloxy) succinide ester (1.1 eq.) are dissolved in DMF, DIPEA added, and the reaction is stirred for 2.5 hour at room temperature. The solvent is removed under reduced pressure, the residue dissolved in ethyl acetate and washed with water, then dried using magnesium sulfate and concentrated under vacuum. This product is purified using column chromatography (6% methanol/dichloromethane) to yield Compound No. 48.

General Procedure for the Preparation of Compound No. 49.

Compound No. 19 (1.0 eq.) in PBS pH 7.5, 1 mM diethylenetriaminepentaacetic acid is reacted with Compound No. 48 (8-10 eq.) in PBS pH 7.5 containing 10% (v/v) dimethylacetamide for 0.5 hours at 0° C., and the reaction is quenched with 1 mM cysteine. Compound No. 49 is then purified/buffer exchanged into PBS pH 7.5 using G-25 size exclusion chromatography equilibrated in PBS pH 7.5 (GE Healthcare, Pisquataway N.J.).

General Procedure for the Preparation of Compound No. 64-76.

Figure 14:
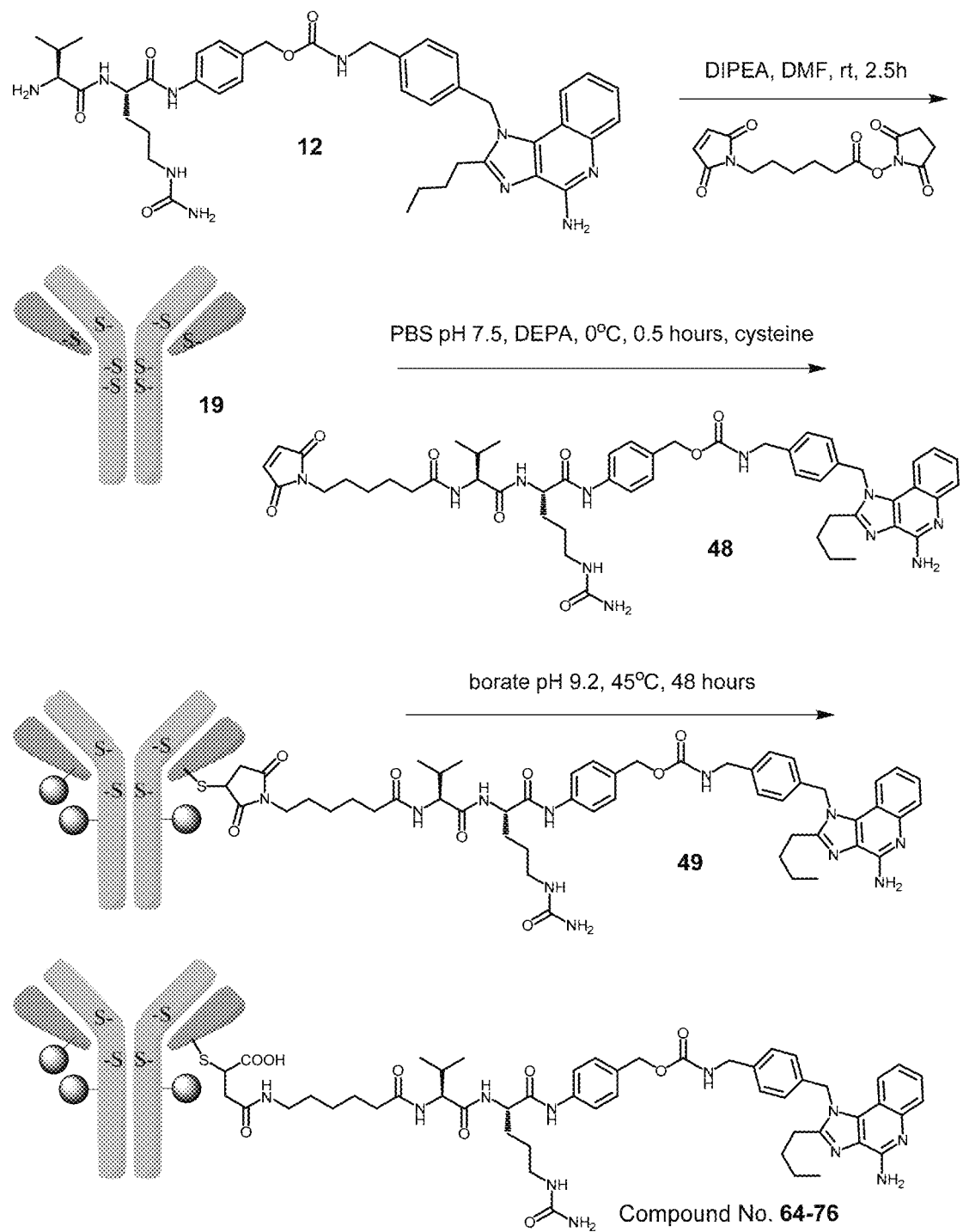
FIG. 14 shows a synthetic scheme for preparing Compound No. 64-76.

Succinimide-thioether ring hydrolysis creates a linkage with greater plasma stability, thus Compound No. 49 is buffer exchanged into 50 mM borate pH 9.2 using tangential flow filtration, heated to 45° C. for 48 hours, then cooled to room temperature and buffer exchanged into PBS pH 7.5. Compound No. 64-76 is subjected to size exclusion chromatography equilibrated in PBS pH 7.5 to remove any residual impurities, aggregrated material, and to ensure complete buffer exchange. The synthetic scheme for preparing Compound No. 64-76 is shown in FIG. 14.

Procedure for the Preparation of Compound No. 51.

To a solution of Trastuzumab antibody (Compound 50; 10 mg, 1 eq.) in PBS pH 7.4 (1 mL) was added dibenzocyclooctyne-$PEG_4$-N-hydroxysuccinimidyl ester (4.0 mg, 10 eq.) in PBS pH 7.4, 1.5% (v/v) DMSO (1 mL), and the reaction was allow to proceed for 2 hours at room temperature. The resulting derivatized antibody was purified by size exclusion chromatography using a Sephadex G-25 column equilibrated with PBS pH 7.2, 0.05% (v/v) Tween 80. Protein concentration of the purified Compound 51 was determined by spectrophotometry at 280 nm, using Compound 50 as a calibration standard.

Procedure for the Preparation of Compound No. 64-77.

Figure 15:
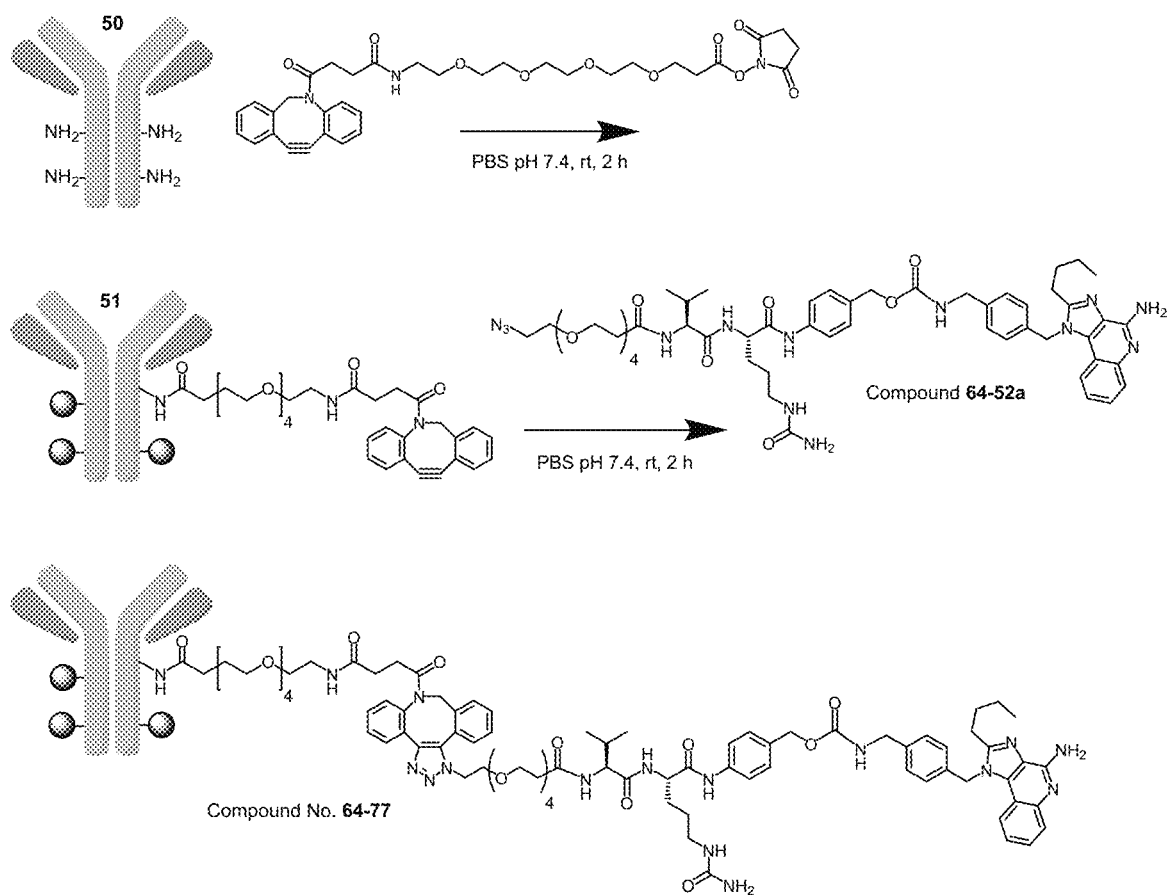
FIG. 15 shows a synthetic scheme for preparing Compound No. 64-77.

Compound 51 (0.5 mg, 1 eq.) in PBS pH 7.4 (1.0 mL) was reacted with Compound 64-52a (0.013 mg, 4 eq.) in PBS pH 7.5, 5% (v/v) DMSO (0.5 mL), and the reaction was allowed to proceed for 2 hours at room temperature and then for an additional 3 hours at 4° C. Compound 64-77 was purified by size exclusion chromatography using Sephadex G-25 Fine column equilibrated with PBS pH 7.2. Purity of Compound No. 64-77 was assessed to by 96% by analytical SEC analysis, and the drug-to-antibody ratio was calculated to be 3.7 using UV/Vis absorbance spectroscopy. The synthetic scheme for preparing Compound No. 64-77 is shown in FIG. 15.

General Procedure for the Characterization of Compound Nos. 64-57, 64-75, 64-76, and 64-77.

The concentration of Compound Nos. 64-57, 64-75, 64-76, and 64-77 are determined by UV absorbance at 280 nm and/or amino acid analysis; polypeptide backbone integriety by SDS-PAGE and N-terminal sequencing; purity by analytical SEC with separate monitoring of the wavelength at the adsorption maxima of both the antibody and the TLR7/8 agonist; aggregation status by analytical SEC-UPLC-MALS; and TLR7/8 agonist-to-antibody ratio using UV/Vis absorbance spectroscopy (see e.g., Examples S5 and S8) and/or by TOF-LC-MS analysis (plus or minus proteolytic degradation). These analytical methods are well known for characterization of antibody drug conjugates to those skilled in the art (see e.g., Doronina, S. O. et al. 2003, *Nature Biotechnol* 21:778-784; Kim, M. T., et al. 2014, *Bioconjugate Chem* 25:123-1232).

B. Biological Examples

The functionality of the cleavable linker in Compound Nos. 64-53, 64-53a, 64-54, 64-54a, 64-53b, and 64-54c was confirmed by incubation in vitro with glutathione or purified human Cathepsin B, as appropriate, followed by assessing the release of the original (i.e., unconjugated) TRL7/8 agonist moiety IMDQ from the compounds over time. In vivo biological activity (pharmacodynamic response) was assessed following single subcutaneous (footpad) injection of Compound Nos. 64-53 and 64-54 in wild type mice, with evaluation of local immune responses measured as TLR7-induced gene expression in draining lymph node tissues and induction of maturation marker expression on antigen-presenting cells (APCs), and evaluation of systemic responses measured as TLR7-induced gene expression in splenic tissues. In vivo biological activity (pharmacodynamic response) was also assessed in tumors following a single intratumoral injection of Compounds Nos. 64-54a and 64-54b, with evaluation of local immune responses measured as TLR7-induced gene expression. Anti-tumor efficacy of Compound Nos. 64-53a, 64-54a, and 64-54b was assessed by measuring tumor growth inhibition over time following repeat-dose intratumoral administration in syngeneic CT26 tumor-bearing Balb/c mice.

Example B1

In Vitro Cleavage of Compound Nos. 64-53, 64-52a, 64-54, and 64-54a by Cathepsin B and Glutathione Methods Compound 64-53 and 64-53a (80 μM) and a non-cleavable control compound containing only a single S atom in place of the disulfide (Compound No. 64-70) were incubated with 5 mM glutathione in PBS pH 7.5 at 37° C. At the indicated times, aliquots were taken from the reaction and the amount of released IMDQ assessed as described in Example S6.

Purified Cathepsin B (5 µM; R&D Systems, Minneapolis Minn., Cat. No. 953-CY) in 10 mM acetate pH 5 buffer was activated with 4 mM DTT/EDTA by incubation for 15 minutes at 37° C. Then the solution was made 80 µM with Compound No. 64-54 and 64-54a and the reaction was allow to proceed at 37° C. At the indicated times, aliquots were taken from the reaction and the amount of released IMDQ assessed as described in Example S8.

Results

Figure 4:
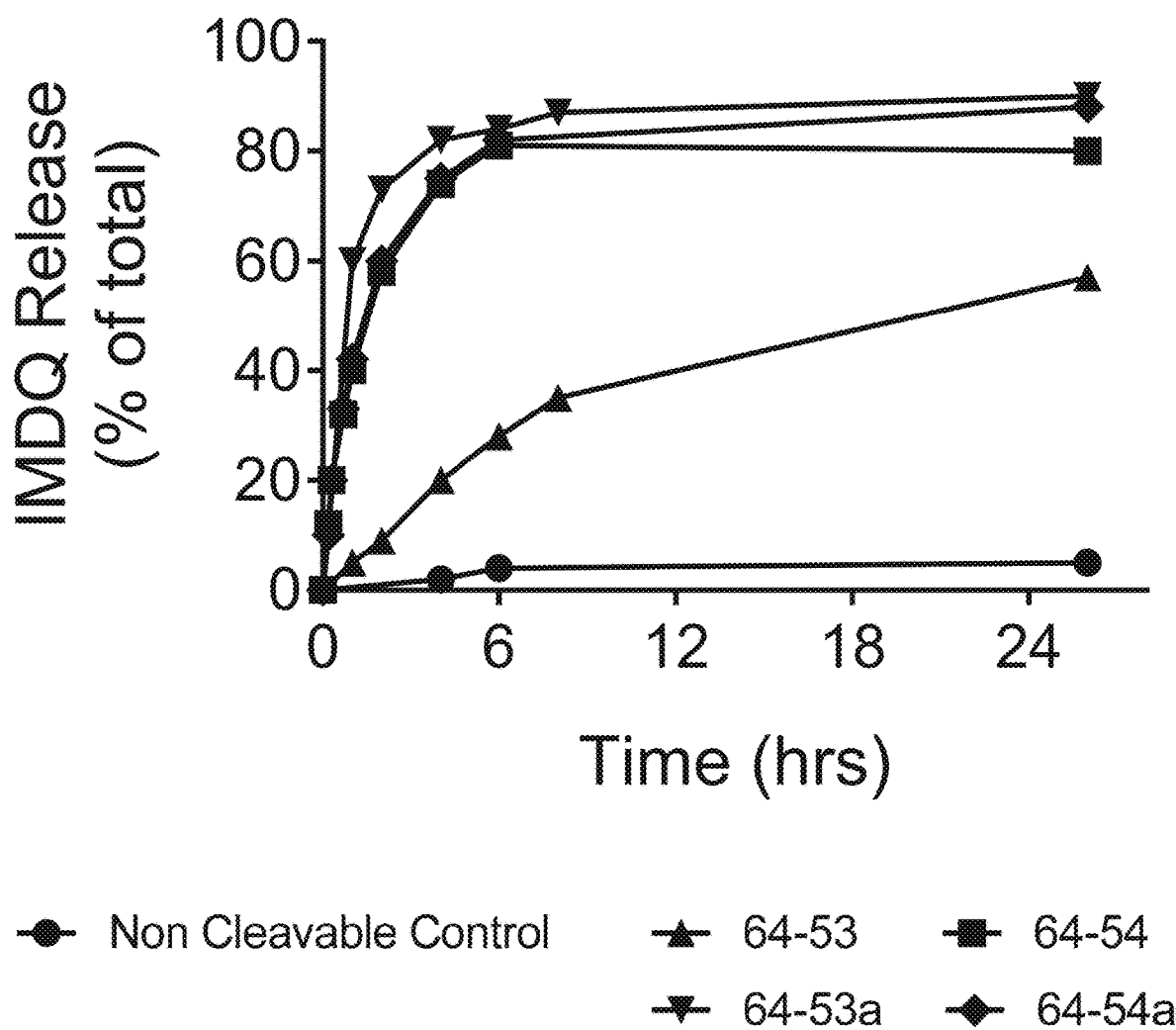
FIG. 4 shows the in vitro release of IMDQ (as a percentage of the total IMDQ) over time from Compound No. 64-53, Compound No. 64-53a, Compound No. 64-54, and Compound No. 64-54a, or a variant with no cleavable linker following incubation with glutathione or 5 µM Cathepsin B, respectively.

The non-cleavable control compound demonstrated low levels of IMDQ release over a 26 hour incubation period, whereas Compound No. 64-53, which contains the dimethyl disulfide cleavable linker, demonstrated up to about 60% IMDQ release in the presence of excess glutathione over the same time frame (FIG. 4). Compound No. 64-53a, which contains the mono-methyl disulfide variant, demonstrated up to about 80% IMDQ release under similar treatment conditions. Compound No. 64-54 and 64-54a demonstrated up to about 80% IMDQ release in the presence of excess Cathepsin B by the 6 hour incubation time point. These data demonstrate that the dipeptide and disulfide-based cleavable linker moieties in these constructs are performing (e.g., releasing unmodified IMDQ) in the expected manner.

Example B1a

In Vitro Cleavage of Compound Nos. 64-54a, 64-54b, and 64-54c by Cathepsin B

Methods

Purified Cathepsin B (30 nM; R&D Systems, Minneapolis Minn., Cat. No. 953-CY) in 10 mM acetate pH 5 buffer was activated with 4 mM DTT/1 mM EDTA by incubation for 15 minutes at 37° C. Then the solution was made 6 µM with Compound Nos. 64-54a, 64-54b, and 64-54c and the reaction was allow to proceed at 37° C. At the indicated times, aliquots were harvested and the amount of released IMDQ assessed as described in Example S5.

Results

Figure 4A:
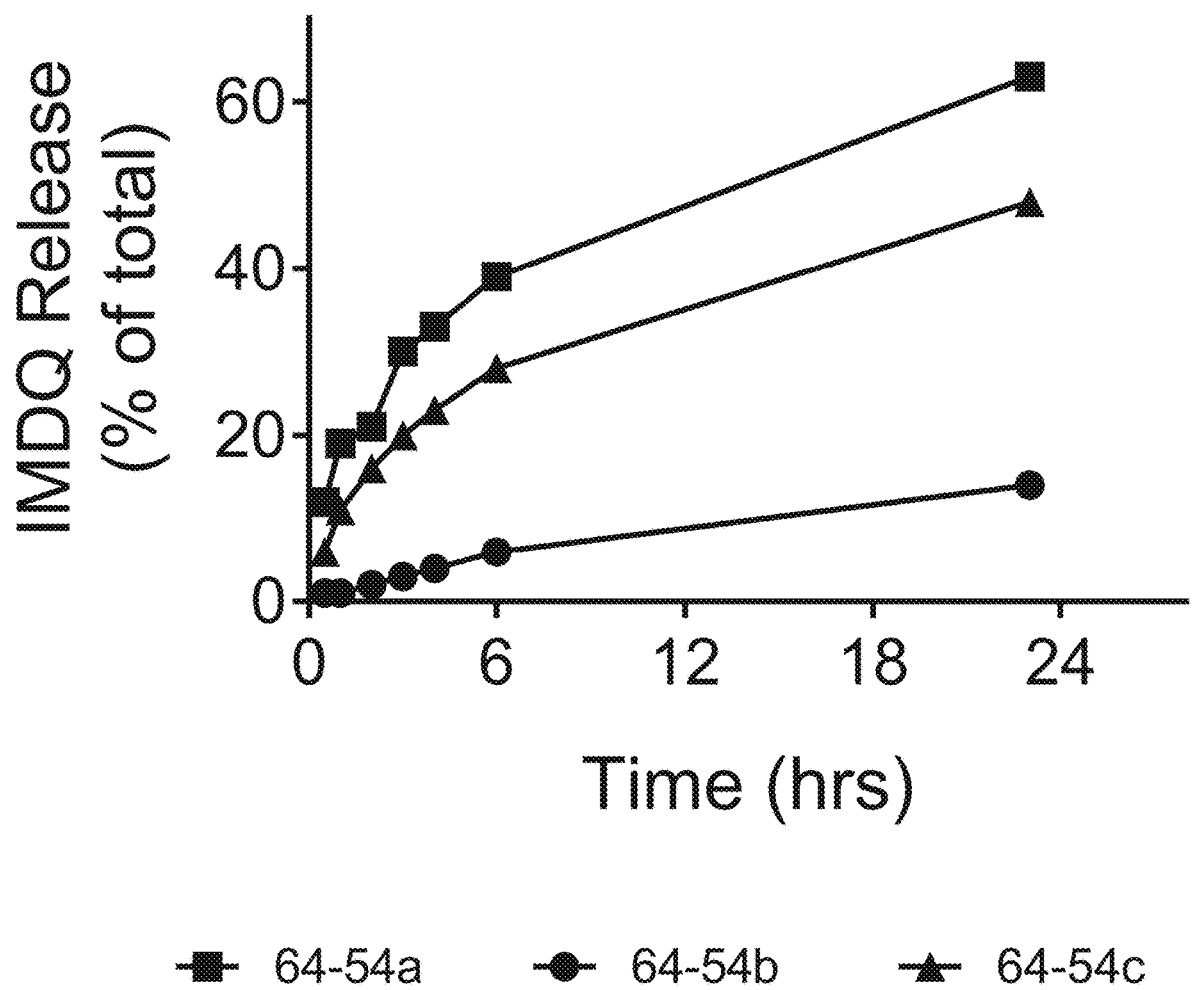
FIG. 4A shows the in vitro release of IMDQ (as a percentage of the total IMDQ) over time from Compound Nos. 64-53a, 64-53b, and 64-54c following incubation with 30 nM Cathepsin B.

Compound No. 64-54a, an embodiment of the invention where in formula (I) the TLR7/8 agonist D is IMDQ, the self-eliminating linker $L^1$ is a para-amino benzyl carbamate moiety, the cleavable linker $L^2$ is a valine-citrulline dipeptide, the conjugation linker $L^3$ is a triazole-PEG$_4$ moiety, and F is an amine-modified Ficoll nanoparticle, demonstrated the highest release levels (63%) of the unmodified chemical form of IMDQ when incubated with Cathepsin B enzyme for 23 hours (FIG. 4A). Compound No. 64-54b, an embodiment of the invention where in formula (I) the TLR7/8 agonist D is IMDQ, $L^1$ is a bond, the cleavable linker $L^2$ is a valine-citrulline dipeptide, the conjugation linker $L^3$ is a triazole-PEG$_{12}$ moiety, and F is an amine-modified Ficoll nanoparticle, demonstrated the lowest release levels (14%) of the unmodified chemical form of IMDQ when incubated with Cathepsin B enzyme for 23 hours. Compound No. 64-54c, an embodiment of the invention where in formula (I) the TLR7/8 agonist D is IMDQ, the self-eliminating linker $L^1$ is a para-amino benzyl carbamate moiety, the cleavable linker $L^2$ is a valine-citrulline dipeptide, the conjugation linker $L^3$ is a triazole moiety, and F is an amine-modified Ficoll nanoparticle, demonstrated an intermediate level of release (48%) of the unmodified chemical form of IMDQ when incubated with Cathepsin B enzyme for 23 hours. These data demonstrate that variation of the chemical structure of $L^1$ or $L^3$ in Ficoll conjugated compounds of the formula (I) can lead to variations in the rate of in vitro release of the unmodified chemical form of IMDQ (the TLR7/8 agonist D).

Example B2

Local vs. Systemic Immune Activation Following a Single Subcutaneous Injection into Wild-Type Mice Methods For serum cytokine and gene expression assays, BALB/c mice (n=3/group) were injected subcutaneously in the right hind footpad with 0.04, 0.2, 1, or 5 ms of IMDQ molar equivalents of IMDQ, Compound No. 64-53, Compound No. 64-54, or PBS (pH 7.5) as a vehicle control. Blood was drawn after 2 hours, serum samples were prepared and the IL-6, IL-12p40, and TNFα protein levels were measured by ELISA. Lower limit of quantification (LLOQ) for each of these assays was 31.3 pg/mL, and the dotted lines on graphs represent the LLOQ multiplied by serum dilution factor. Popliteal lymph nodes (draining node for the site of injection) were removed after 6 hours and stored in RNAlater (Qiagen, Hilden Del.) prior to tissue homogenization and isolation of RNA for gene expression analysis by TaqMan® using a StepOnePlus Real Time PCR system (Applied Biosystems, Foster City Calif.). Gene expression data are expressed as fold increase in gene induction relative to PBS control (mean±SEM).

For flow cytometry assays, BALB/c mice (n=3/group) were injected in both hind footpads with either 1.8 µg of IMDQ molar equivalents of IMDQ, Compound No. 64-53, Compound No. 64-54, or a PBS control (n=6/group for the control). Popliteal lymph nodes and spleens were harvested after 24 hours, and single cell suspensions were prepared for subsequent staining and analysis by flow cytometry using antibodies to cell surface markers to identify different APCs and lymphocyte cell populations. The biological effect of IMDQ, Compound No. 64-53, and Compound No. 64-54 was evaluated by measuring effects on the APC maturation marker CD86.

In Vivo Gene Expression Results

Figure 5:
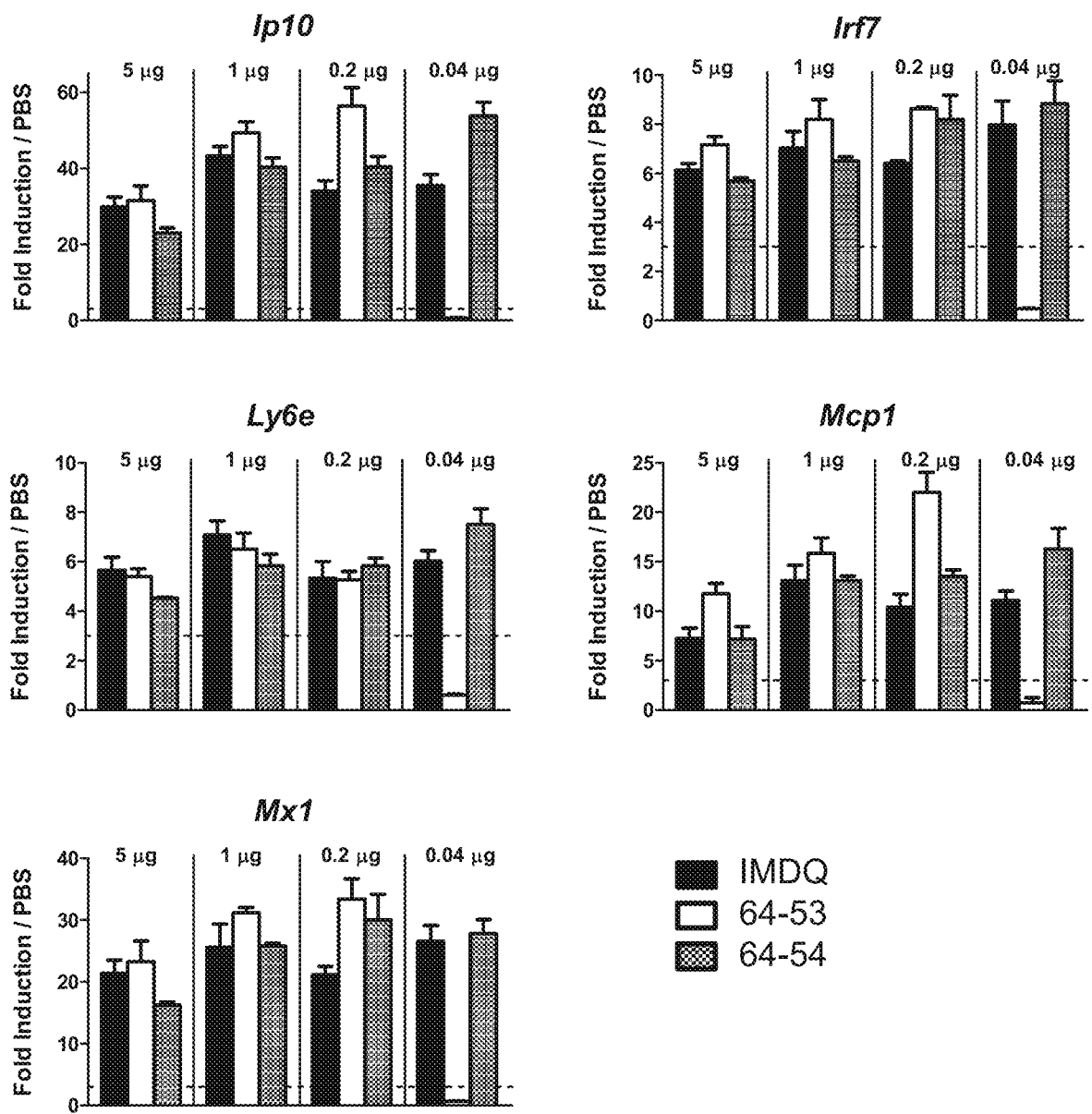
FIG. 5 shows induction of interferon-associated genes in the popliteal lymph nodes of BALB/c mice 24 hours after a single subcutaneous footpad injection of Compound No. 64-53, Compound No. 64-54, or an equimolar amount of unconjugated IMDQ.

Wild-type mice naturally lack functional TLR8, so only TLR7-mediated gene induction is measured by this readout. These in vivo data demonstrated that both Compound No. 64-53 and Compound No. 64-54 have relatively similar potency to IMDQ for induction of interferon-related genes in the popliteal lymph nodes (FIG. 5), although responses to Compound No. 64-53 were absent at the lowest dose (0.04 µg) whereas both IMDQ and Compound No. 64-54 induced gene expression at that dose.

In Vivo Serum Cytokine Results

Figure 6:
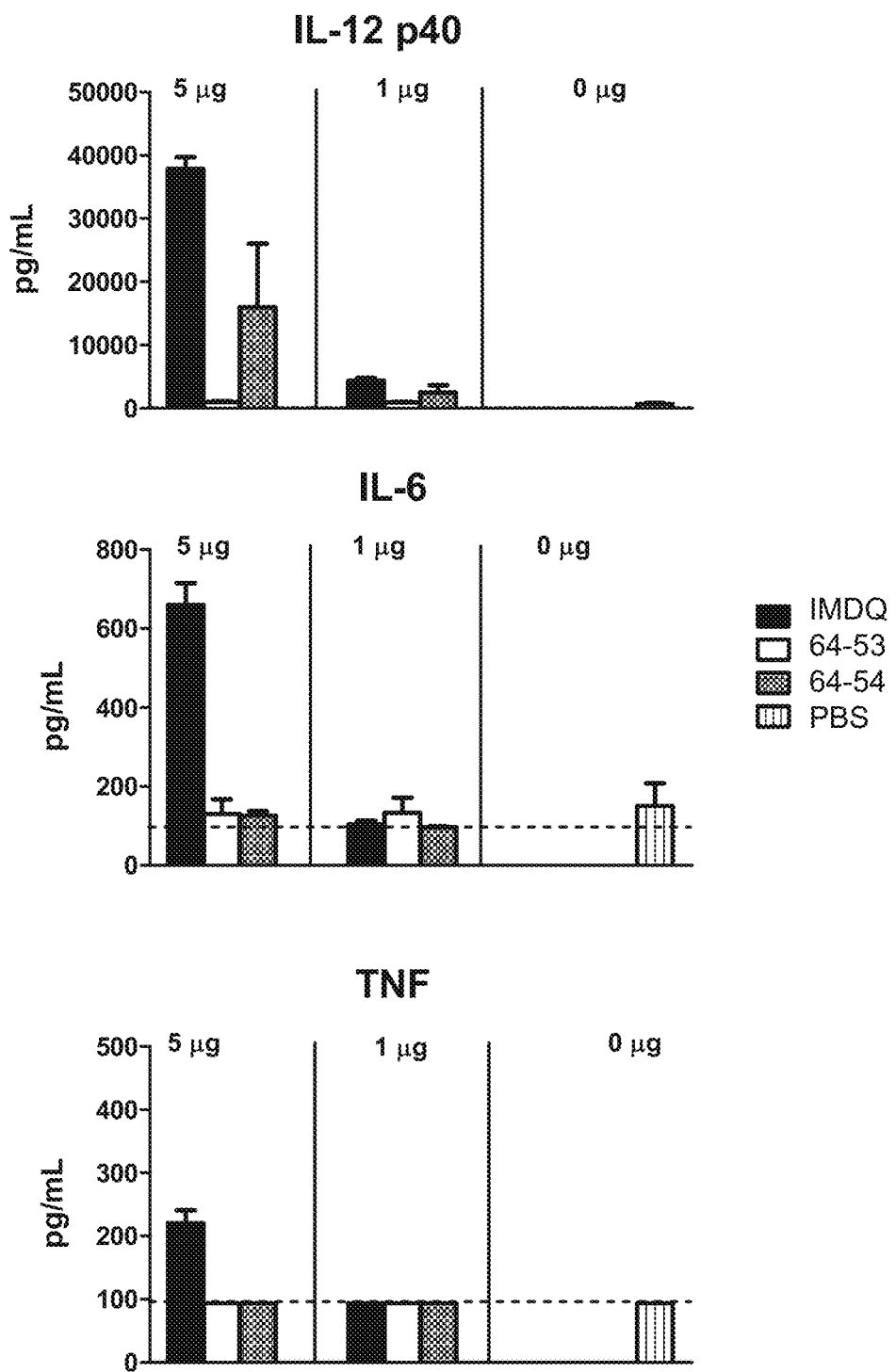
FIG. 6 shows the concentrations of the cytokines IL-12p40, IL-6, and TNFα in the serum of BALB/c mice 2 hours after a single subcutaneous footpad injection of Compound No. 64-53, Compound No. 64-54, an equimolar concentration of unconjugated IMDQ, or PBS vehicle control.

Small molecule TLR7/8 agonists such as IMDQ are known to quickly distribute to the systemic compartment from the site of injection where they rapidly induce TLR7-dependent pro-inflammatory cytokine responses in spleen and liver cells; detected in the serum as increases in certain cytokine levels. Plasma was harvested 2 hours after footpad injection of different doses of Compound No. 64-53, Compound No. 64-54, or IMDQ in BALB/c mice, serum was prepared, and the samples were assayed for circulating cytokine levels. As expected, injection of 5 µg IMDQ rapidly induced elevated levels of IL-12p40, IL-6 and TNFα in the serum (FIG. 6). This response was dose-dependent, with only IL-12p40 demonstrating levels above background after injection of 1 μg IMDQ. The 5 ug dose of Compound No. 64-54 also induced IL-12p40, albeit at lower levels compared to IMDQ. However, in contrast to IMDQ, Compound No. 64-54 did not induce IL-6 or TNFα above background levels at any dose. Compound No. 64-53 did not induce significant levels of serum cytokines over background at any dose. These data suggest that conjugation of the TLR7/8 agonist moiety IMDQ to a nanoparticle conjugation moiety Ficoll prevented the rapid systemic distribution of IMDQ, and the associated increase in systemic cytokine levels, compared to equimolar quantities of IMDQ.

In Vivo Antigen Presenting Cell Maturation Marker Expression Levels

Figure 7:
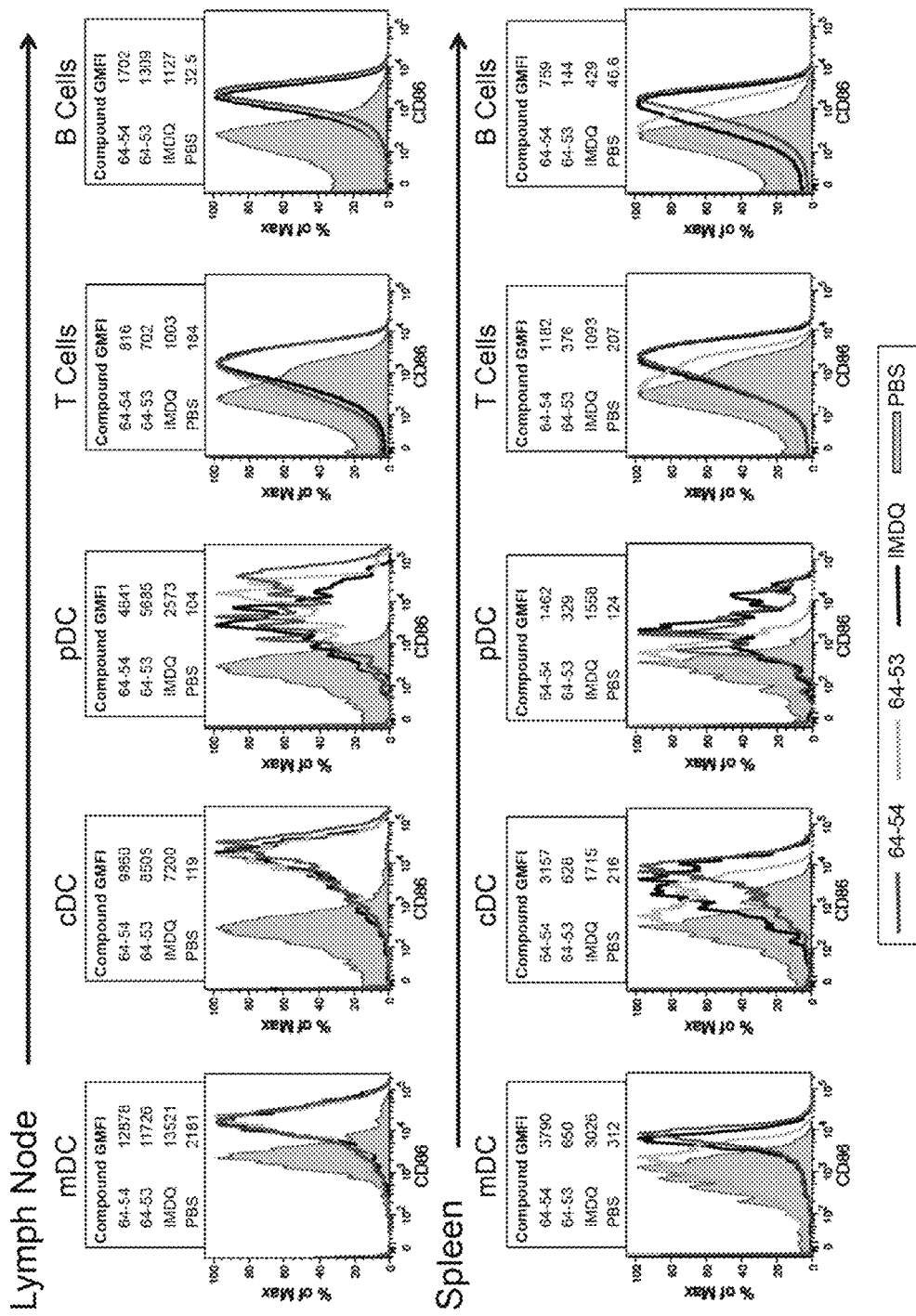
FIG. 7 shows induction of the maturation marker CD86 on various antigen presenting cells in the popliteal lymph node and spleen 24 hours after a single subcutaneous footpad injection of Compound No. 64-53, Compound No. 64-54, an equimolar amount of inconjugated IMDQ, or PBS vehicle control.

Compound No. 64-53, Compound No. 64-54, and IMDQ all induced activation/maturation of cells in popliteal lymph nodes at 24 hours after a subcutaneous footpad injection as measured by increase in the expression level of the APC maturation marker CD86, indicating comparable TLR7-mediated biological effects in the lymph nodes proximal to the injection site (FIG. 7). However, in the spleen (i.e., distal to the injection site), expression levels of CD86 were comparable in mice injected with IMDQ or Compound No. 64-54, but much lower on the APCs of mice injected with Compound No. 64-53. These findings are consistent with differences in serum cytokine responses between the two compounds at 2 hours post injection, and suggest that Compound No. 64-54 can be cleaved extracellularly, at least partially, thus allowing some systemic distribution of the IMDQ molecule. Similar trends were observed with CD80 expression (data not shown).

Example B2a

Local Immune Activation in Tumors Following a Single Intratumoral Injection in Syngeneic CT26 Tumor-Bearing Wild-Type Mice Methods Changes in TLR7-mediated interferon-related and pro-inflammatory gene expression in sub-cutaneous tumors were assessed by RT-PCR following a single intratumoral administration of IMDQ, or Compound Nos. 64-54a and 64-54b, into syngeneic CT26 colon carcinoma-bearing wild type BALB/c mice. All in vivo procedures were conducted in accordance with approved Institutional Animal Care and Use Committee (IACUC) protocols. The animals were housed in a facility that is accredited by the Association for Accreditation and Laboratory Animal Care (AALAC, Frederick, Md.). Wild-type female Balb/c mice (15-20 gm) were obtained from Envigo (Hayward, Calif.) and acclimated for 2-3 days prior to use.

Pharmaceutical compositions were made by solubilizng 200 μg of the indicated compound in 1 mL of PBS. The pharmaceutical compositions were 0.2 μm filtered sterilized and demonstrated to be free of endotoxin by Limulus Amebocyte Lysate assay (EndoSafe MCS; Charles River, Wilmington Mass.). On day 0, mice were anesthetized with 1% isoflurane and 80,000 CT26 tumor cells in 200 uL of RMPI-1640 culture media plus 2.5% fetal bovine serum were injected subcutaneously in the right flank. Tumors were allowed to grow until they were 100-200 mm$^3$, at which point animals were assigned to groups to begin treatment (N=5 per group). Mice were then given a single intratumoral injection with 25 uL of each pharmaceutical composition containing 5,000 μg of IMDQ, 5,000 μg IMDQ equivalent mass of Compound Nos. 64-54a and 64-54b, and a PBS vehicle control. At the indicated times tumors were removed and stored in RNAlater (Qiagen, Hilden Del.), they were then homogenized and RNA isolated for gene expression analysis by TaqMan® qPCR assay using a StepOnePlus Real-time PCR system (Applied Biosystems, Foster City Calif.). Gene expression data are expressed as the fold increase in gene induction relative to the PBS vehicle control (mean±SEM, N=5).

In Vivo Gene Expression Results

Figure 5A:
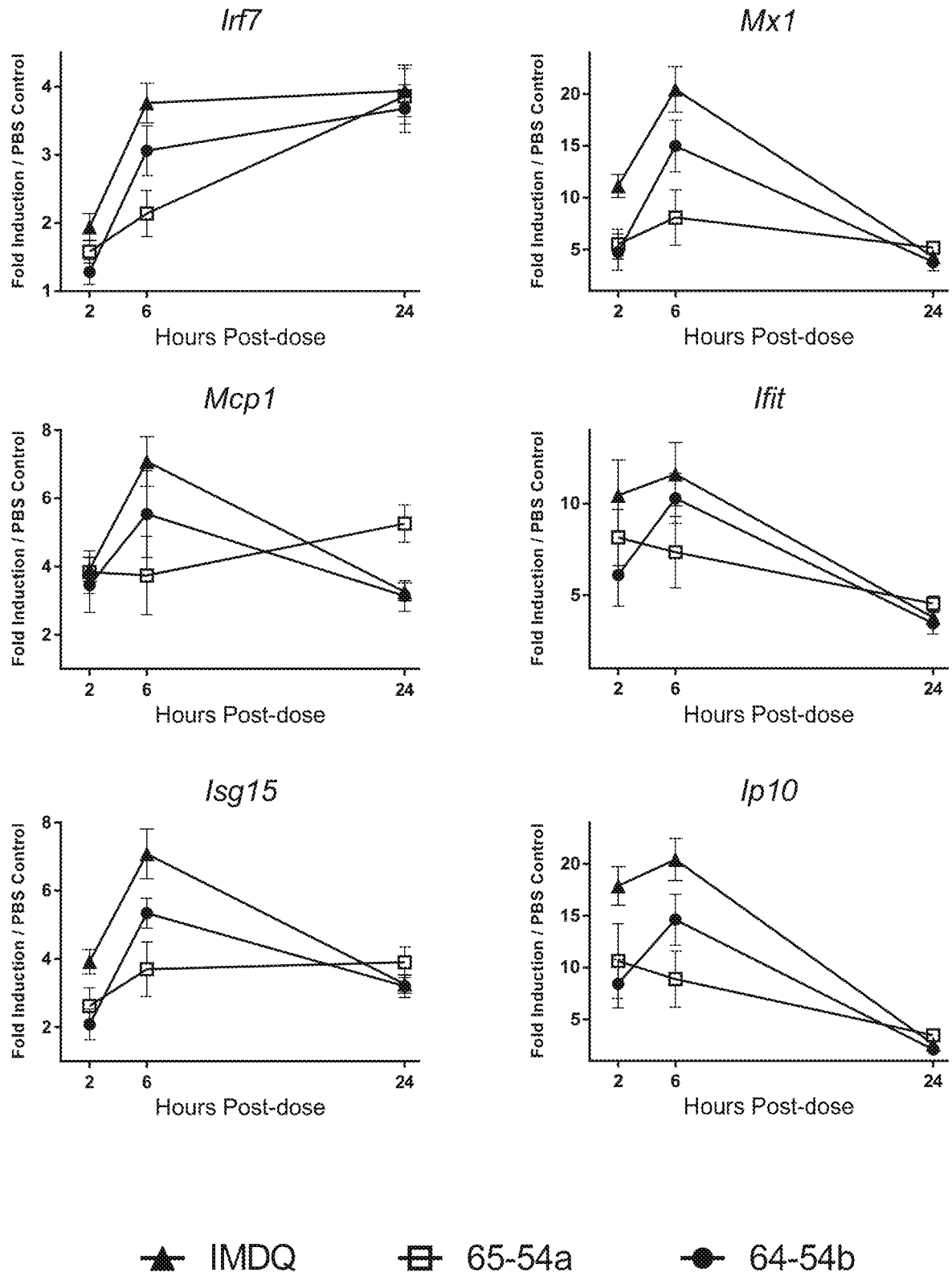
FIG. 5A shows induction of interferon-associated genes over time in CT26 tumors subcutaneously implanted in BALB/c mice after a single bolus intratumoral injection of Compound No. 64-54a, Compound No. 64-54b, or an IMDQ equivalent mass of unconjugated IMDQ. Datapoints are expressed as the fold gene expression over a PBS injected control, N=5 mice.
Figure 5B:
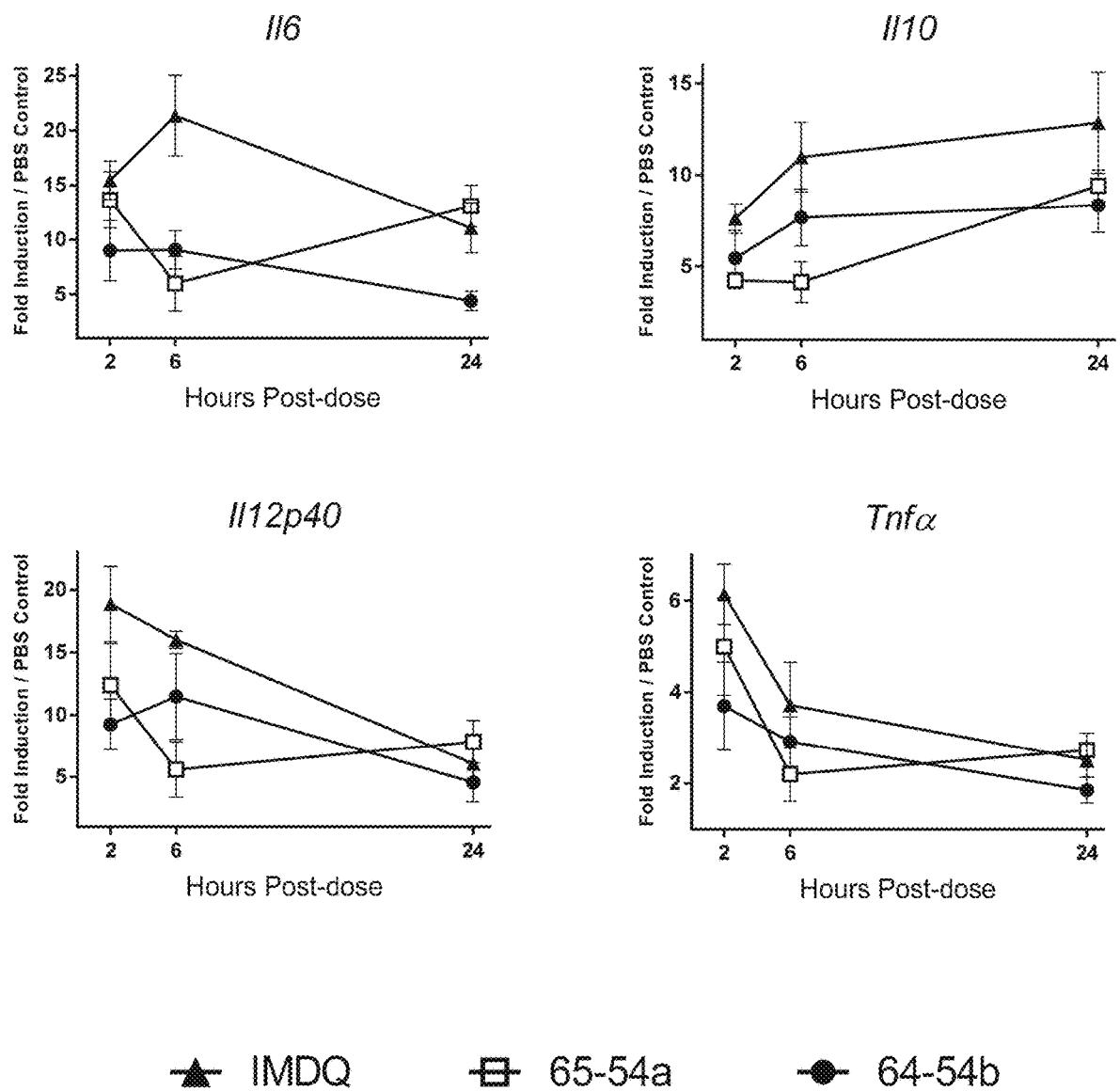
FIG. 5B shows induction of pro-inflammatory genes over time in CT26 tumors subcutaneously implanted in BALB/c mice after a single bolus intratumoral injection of Compound No. 64-54a, Compound No. 64-54b, or an IMDQ equivalent mass of unconjugated IMDQ. Datapoints are expressed as the fold gene expression over a PBS injected control, N=5 mice.

Wild-type mice naturally lack functional TLR8, so only TLR7-mediated gene induction is measured in this assay. Both Compound Nos. 64-54a and 64-54b demonstrated similar potency and kinetics of activation to IMDQ for the in vivo induction of interferon-related (FIG. 5A) and pro-inflammatory (FIG. 5B) genes in CT26 tumors. These data are consistent with the interpretation that the unmodified chemical form of IMDQ is being released from the Ficoll-conjugated, Cathepsin B sensitive cleavable linker containing Compound Nos. 64-54a and 64-54b within the tumor microenvironment subsequently activating TLR7-mediated gene responses in tumor-resident immune cells.

Example B3

Tumor Growth Inhibition Following Repeat Dose Intratumoral Administration of Compound Nos. 64-53a, 64-54a, and 64-10a into Syngeneic CT26 Tumor Bearing Balb/c Mice The effect of weekly intratumoral doses of Compound No. 64-53a, Compound No. 64-54a, Compound No. 64-10a, or a PBS vehicle control on tumor growth inhibition was assessed in syngeneic CT26 colon carcinoma-bearing Balb/c mice. Compound No. 64-53a differs from Compound No. 64-53 in that it contains a monomethyl group adjacent to the disulfide cleavable linker rather than the disulfide variant. Compound No. 64-54a differs from Compound No. 64-54 in that it contains a (PEG)$_4$ to the N-terminus of the peptide cleavable linker rather than a (PEG)$_{12}$ variant. Compound No. 64-10a is an alkyl chain variant of IMDQ with comparable TLR7 in vitro potency (2 nM v. 1 nM EC$_{50}$). Compound No. 64-10a is the free amine (i.e., unconjugated) form of Compound No. 64-10, the structure of which is shown in Table 1. All in vivo procedures were conducted in accordance with approved Institutional Animal Care and Use Committee (IACUC) protocols. The animals were housed in a facility that is accredited by the Association for Accreditation and Laboratory Animal Care (AALAC, Frederick, Md.). Wild-type female Balb/c mice (15-20 g) were obtained from Envigo (Hayward, Calif.) and acclimated for 2-3 days prior to use.

Methods

On day 0, mice were anesthetized with 1% isoflurane and 80,000 CT26 tumor cells in 200 μL of RMPI-1640 culture media plus 2.5% FBS were injected subcutaneously in the right flank. Tumors were allowed to grow until they were ~50 mm$^3$, at which point animals were assigned to groups, 8 mice per group, to begin treatment. Mice were injected intratumorally on days 8, 16, and 23 with 25 μL of a pharmaceutical composition comprising 1 μg molar equivalent of IMDQ for Compound Nos. 64-53a and 64-54a in PBS, or 0.63 ug molar equivalent of IMDQ for Compound No. 64-10a formulated in 95% sesame oil/5% ethanol (v/v), or a PBS vehicle control. Tumor sizes were measured twice weekly from day 7 through day 27 with calipers, with tumor volumes calculated using the following formula: length, multiplied by width, multiplied by width, divided by 2.
Results Wild-type mice naturally lack functional TLR8, so only TLR7-mediated anti-tumor efficacy is measured in this assay. Compound Nos. 64-53a, 64-54a, and 64-10a demonstrated significant CT26 tumor growth control compared to the vehicle control (FIG. 8, Panel A). In addition, on day 27, three days after the final dose, the 3 compounds demonstrated comparable levels of tumor growth inhibition (FIG. 8, Panel B); note that the dose of Compound No. 64-10a was slightly lower than the other 2 compounds. These tumor efficacy data are consistent with the interpretation that after intratumoral administration of the two examplars of compounds of formula (I), cleavage of the cleavable linker within the tumor microenvironment leads to release of the original (i.e., unconjugated) TLR7/8 agonist moiety, IMDQ. The levels of tumor growth control demonstrated by Compound Nos. 64-53a and 64-54a was comparable to that observed for Compound No. 64-10a, an alkyl chain modified variant of IMDQ with equal in vitro and in vivo TLR7 agonist potency to IMDQ (data not shown).

Example B4

Figure 9:
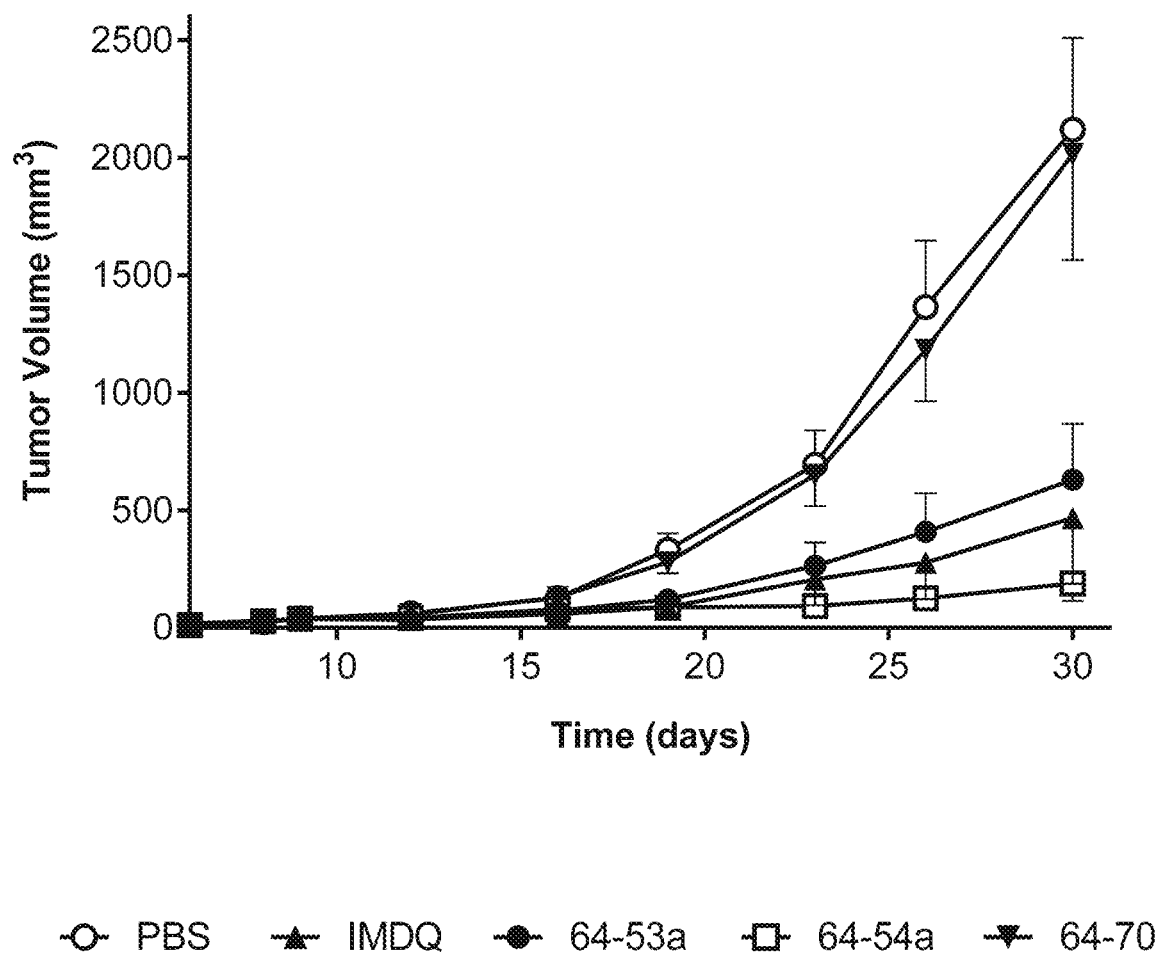
FIG. 9 shows the effect on tumor growth of weekly intratumoral administration of an IMDQ equivalent mass of unconjugated IMDQ, Compound No. 64-53a, Compound No. 64-54a, Compound No. 64-70, or PBS vehicle control to syngeneic CT26 tumor bearing BALB/c mice with a single subcutaneous tumor. Time is days post tumor implantation and datapoints are the average+/−standard error of the mean for groups of 8 mice.

Tumor Growth Inhibition Following Repeat Dose Intratumoral Administration of IMDQ, and Compound Nos. 64-53a, 64-54a, and 64-70 into Syngeneic CT26 Tumor Bearing Balb/c Mice The effect of weekly intratumoral doses of IMDQ, Compound Nos. 64-53a, Compound No. 64-54a, or Compound No. 64-70, or a PBS vehicle control on tumor growth inhibition was assessed in syngeneic CT26 colon carcinoma-bearing Balb/c mice bearing a tumor in a single flank. Compound No. 64-53a contains a monomethyl group adjacent to the disulfide cleavable linker $L^2$ in formula 1 and Compound No. 64-54a contains the valine-citrulline cleavable linker as $L^2$ in formula 1; in both instances the Compounds contain IMDQ as D in formula (I), a para-amino benzyl carbamate moiety as $L^1$ in formula (I), and are conjugated to Ficoll via differing conjugation linkers $L^3$ in formula (I). Compound No. 64-70 is a non-cleavable variant. All in vivo procedures were conducted in accordance with approved Institutional Animal Care and Use Committee (IACUC) protocols. The animals were housed in a facility that is accredited by the Association for Accreditation and Laboratory Animal Care (AALAC, Frederick, Md.). Wild-type female Balb/c mice (15-20 g) were obtained from Envigo (Hayward, Calif.) and acclimated for 2-3 days prior to use.
Methods On experimental day 0, mice were anesthetized with 1% isoflurane and 80,000 CT26 tumor cells in 200 µL of RMPI-1640 culture media plus 2.5% FBS were injected subcutaneously in the right flank. Tumors were allowed to grow until they were ~50 mm³, at which point animals were assigned to groups, 8 mice per group, to begin treatment. Mice were injected intratumorally on days 9, 16, 23 and 28 with 25 µL of a pharmaceutical composition comprising 500 ng of IMDQ in PBS, 500 ng IMDQ equivalent mass of Compound Nos. 64-54a, 64-53a, or 64-70 in PBS, or a PBS vehicle control. Tumor sizes were measured twice weekly from day 7 through day 30 with calipers, with tumor volumes calculated using the following formula: length, multiplied by width, multiplied by width, divided by 2.
Results Wild-type mice naturally lack functional TLR8, so only TLR7-mediated anti-tumor efficacy is measured in this assay. Compound No. 64-70 demonstrated no CT26 tumor growth inhibition compared to the vehicle control (FIG. 9); this is consistent with the expected lack of in situ release of the unmodified chemical form of IMDQ from this Compound. Compounds Nos. 64-54a and 64-53a demonstrated comparable tumor growth inhibition to equal molar quantities of the unmodified chemical form of IMDQ. These data are consistent with the interpretation that cleavage of the cleavable linker (disulfide or valine-citrulline) within the tumor microenvironment leads to release of the unmodified chemical form of IMDQ which activates TLR7-mediated gene responses in tumor-resident immune cells leading to anti-tumor efficacy (see e.g., Singh et al. 2014, *J. Immunol.* 193:4722-4731).

Example B5

Tumor Growth Inhibition Following Repeat Dose Intratumoral Administration of Varying Doses of Compound Nos. 64-54a and 64-54b into Syngeneic CT26 Tumor Bearing Balb/c Mice The effect of varying dose levels of weekly intratumoral doses Compound Nos. 64-54a, or 64-54b, or a PBS vehicle control on tumor growth inhibition was assessed in syngeneic CT26 colon carcinoma-bearing Balb/c mice bearing a tumor in a single flank. Compound No. 64-54a is an embodiment of the invention where in formula (I) the TLR7/8 agonist D is IMDQ, the self-eliminating linker $L^1$ is a para-amino benzyl carbamate moiety, the cleavable linker $L^2$ is a valine-citrulline dipeptide, the conjugation linker $L^3$ is an triazole-PEG$_4$ moiety, and F is a Ficoll nanoparticle. Compound No. 64-54b is the same, except for the presence of a PEG$_{12}$ moiety and $L^1$ is a bond. As shown in Example B1a, these chemical modifications lead to differences in the rate of in vitro release of IMDQ following incubation with Cathepsin B enzyme. All in vivo procedures were conducted in accordance with approved Institutional Animal Care and Use Committee (IACUC) protocols. The animals were housed in a facility that is accredited by the Association for Accreditation and Laboratory Animal Care (AALAC, Frederick, Md.). Wild-type female Balb/c mice (15-20 g) were obtained from Envigo (Hayward, Calif.) and acclimated for 2-3 days prior to use.
Methods On experimental day 0, mice were anesthetized with 1% isoflurane and 80,000 CT26 tumor cells in 200 µL of RMPI-1640 culture media plus 2.5% FBS were injected subcutaneously in the right flank. Tumors were allowed to grow until they were ~35 mm³, at which point animals were assigned to groups, 8 mice per group, to begin treatment. Mice were injected intratumorally on days 9, 16, 23 and 28 with a pharmaceutical composition comprising 30, 125 or 500 ng of IMDQ equivalent mass of Compound Nos. 64-54a or 64-54b in 10 µL PBS, or a 10 µL PBS vehicle control. Tumor sizes were measured twice weekly from day 7 through day 30 with calipers, with tumor volumes calculated using the following formula: length, multiplied by width, multiplied by width, divided by 2.
Results Wild-type mice naturally lack functional TLR8, so only TLR7-mediated anti-tumor efficacy is measured in this assay. Compounds Nos. 64-54a and 64-54b demonstrated comparable tumor growth inhibition that was dose dependent (FIG. 10). These data are consistent with the interpretation that the anti-tumor efficacy of Compounds Nos. 64-54a and 64-54b was independent of the in vitro rate of cleavage of the valine-citrulline cleavable linker, and subsequent release of the unmodified chemical form of IMDQ, within the tumor microenvironment.

Example B6

Tumor Growth Inhibition Following Intratumoral Administration of Repeat Doses of IMDQ and Compound No. 64-54a, in Combination with an Immune Checkpoint Inhibitor, in Syngeneic CT26 Tumor Bearing Balb/c Mice The effect of weekly intratumoral doses of IMDQ or Compound No. 64-54a in combination with intraperitoneally delivered anti-mouse PD-1 (CD279) antibody (an immune checkpoint inhibitor; Bio X Cell, Lebanon N.H.), on injected and distal tumor growth inhibition was assessed in syngeneic CT26 colon carcinoma-bearing Balb/c mice bearing two tumors in contralateral flanks. Compound No. 64-54a is an embodiment of the invention where in formula (I) the TLR7/8 agonist D is IMDQ, the self-eliminating linker $L^1$ is a para-amino benzyl carbamate moiety, the cleavable linker $L^2$ is a valine-citrulline dipeptide, the conjugation linker $L^3$ is an triazole-PEG$_4$ moiety, and F is a Ficoll nanoparticle. All in vivo procedures were conducted in accordance with approved Institutional Animal Care and Use Committee (IACUC) protocols. The animals were housed in a facility that is accredited by the Association for Accreditation and Laboratory Animal Care (AALAC, Frederick, Md.). Wild-type female Balb/c mice (15-20 g) were obtained from Envigo (Hayward, Calif.) and acclimated for 2-3 days prior to use.

Methods

On experimental day 0, mice were anesthetized with 1% isoflurane, and 80,000 CT26 tumor cells in 200 uL of RMPI-1640 culture media plus 2.5% fetal bovine serum were injected subcutaneously in both the right and left flanks. Tumors (left and right) were allowed to grow until day 9, when the right and left flank tumor sizes had reached approximately 35 mm$^3$, at which point mice were injected intraperitoneally with 250 μg of anti-PD-1 antibody formulated in PBS or a PBS vehicle control. The anti-PD-1 treatments were repeated on experimental days 12, 16, 20, 23, and 28. On experimental day 15, when the right (injected) and left (distal) flank tumors had reached approximately 100 mm$^3$, mice were randomized into treatment groups with 10 mice per group. The anti-PD-1 and PBS treatment groups were additionally injected intratumorally in the right flank tumor only with 10 uL of a pharmaceutical composition comprising 500 ng of IMDQ or IMDQ equivalent mass of Compound No. 64-54a in PBS on days 15, 18, 22, and 27. Tumor sizes were measured twice weekly from days 15 through day 30 with calipers, with tumor volumes calculated using the formula: length, multiplied by width, multiplied by width, divided by 2.

Results

Figure 11:
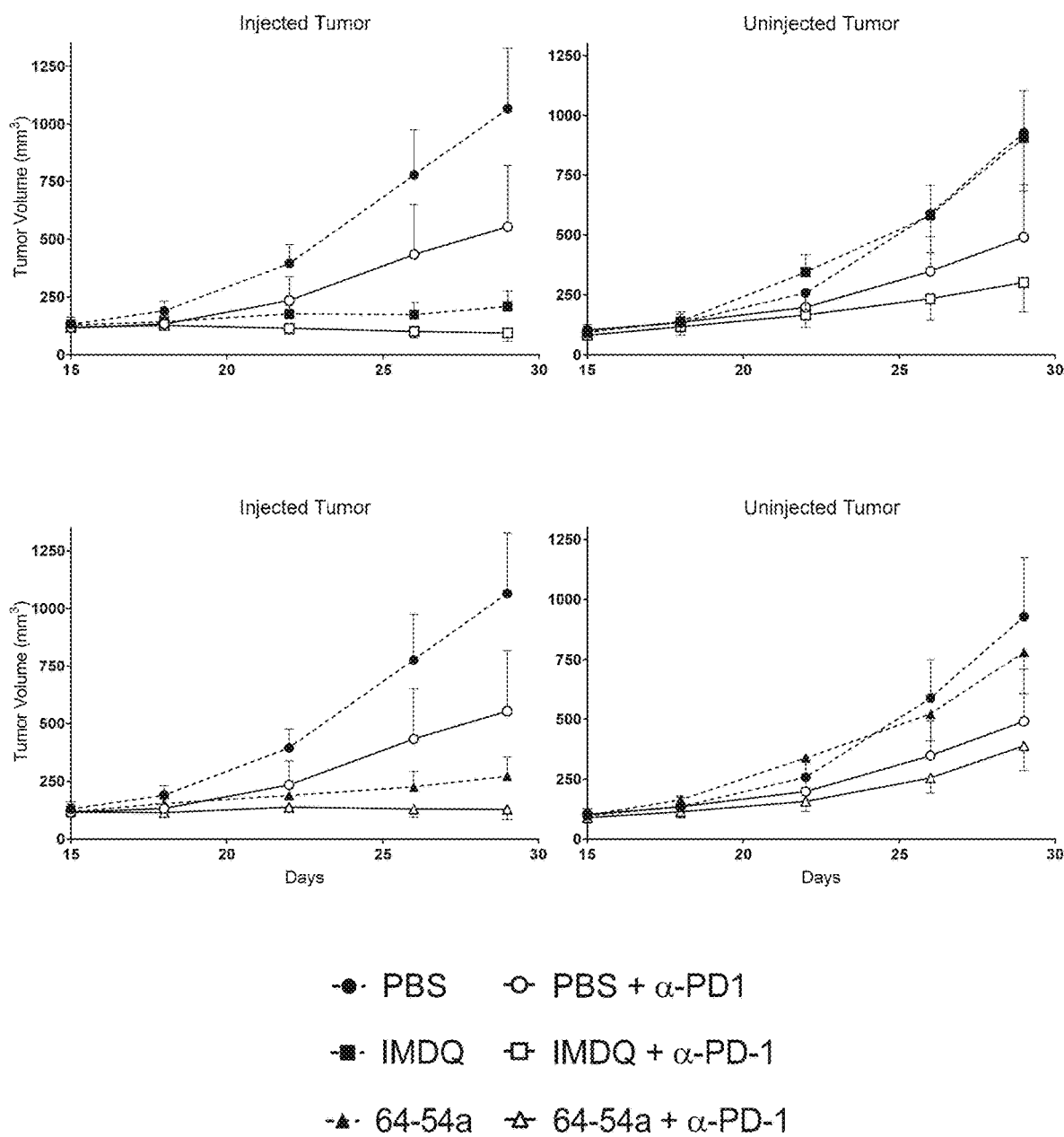
FIG. 11 shows the effect on tumor growth of weekly intratumoral administration of 500 ng of IMDQ, 500 ng of an IMDQ equivalent mass of Compound No. 64-54a, or a PBS vehicle control, plus or minus twice weekly administration of an immune checkpoint inhibitor, to syngeneic CT26 tumor bearing BALB/c mice with two contralateral, subcutaneous tumors. Time is days post tumor implantation and datapoints are the average+/−standard error of the mean for groups of 10 mice.

Wild-type mice naturally lack functional TLR8, so only TLR7-mediated anti-tumor efficacy is measured in this assay. In the injected tumor, IMDQ and Compound No. 64-54a administered in combination with anti-PD-1 treatment demonstrated comparable improvements in tumor growth control over either agent administered individually (FIG. 11, left-hand panels). Similarly in the uninjected tumor, IMDQ and Compound No. 64-54a administered in combination with anti-PD-1 treatment demonstrated comparable improvements in tumor growth control over either agent administered individually (FIG. 11, right-hand panels). These data are consistent with the interpretation that Compound No. 64-54a released the unmodified chemical form of IMDQ within the injected tumor microenvironment, and that the active TLR7 agonist in the presence of immune checkpoint inhibition modulated the innate and adaptive immune responses in the tumor microenvironment leading to effective systemic anti-tumor efficacy (see e.g., Wang et al. 2016, *Proc. Nat. Acad. Sci. USA* 113:E7240-E7249).

All publications, including patents, patent applications, and scientific articles mentioned in this specification, are herein incorporated by reference in their entirety for all purposes to the same extent as if each individual publication, including patent, patent application, or scientific article, were specifically and individually indicated to be incorporated by reference.

Although the foregoing invention has been described in some detail by way of illustration and example for purposes of clarity of understanding, it will be apparent to those skilled in the art that certain changes and modifications will be practiced in light of the above teaching. Therefore, the following synthetic and biological examples should not be construed as limiting the scope of the present disclosure, which is delineated by the appended claims.

We claim:

1. A compound of formula (I):

wherein:
D is a TLR7/8 agonist moiety;
$L^1$ is a self-eliminating linker;
$L^2$ is a cleavable linker;
$L^3$ is a conjugation linker;
W is O, S, or $N^{10}$;
$R^{10}$ is H or $C_1$-$C_8$ alkyl;
x is an integer from 1 to 500;
F is a conjugation moiety; and
the TLR7/8 agonist moiety is a 1H-imidazo[4,5-c]quinoline derivative.

2. The compound of claim 1, wherein D is of the formula (D-1):

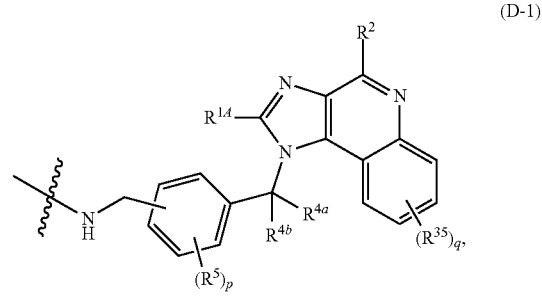

wherein:
$R^{14}$ is $C_1$-$C_8$ alkyl, $C_1$-$C_8$ hydroxyalkyl, or $C_3$-$C_8$ cycloalkyl;
$R^2$ is $NHR^{2a}$, where $R^{2a}$ is H or $C_1$-$C_8$ alkyl;
each $R^{35}$ is independently halogen or $C_1$-$C_8$ alkyl;
$R^{4a}$ and $R^{4b}$ are independently H or $C_1$-$C_8$ alkyl;
each $R^5$ is independently halogen or $C_1$-$C_8$ alkyl;
p and q are independently 0, 1, 2, 3, or 4; and
the wave line represents the point of attachment of D in formula (I).

3. The compound of claim 1, wherein D is of the formula (D-2):

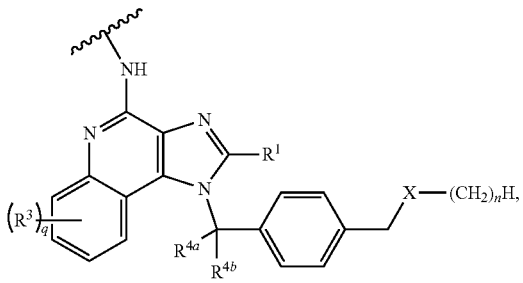

(D-2)

wherein:
n is an integer from 4 to 21;
X is —NH— or —NH(C=O)—;
$R^1$ is $C_3$-$C_6$ alkyl, $(CH_2)_pOR^{1a}$, $(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;
each $R^3$ is independently halogen, $C_1$-$C_8$ alkyl, —($C_1$-$C_7$ alkylene)-$NH_2$, or —$CH_2$-phenylene-$CH_2NH_2$;
q is 0, 1, 2, 3, or 4;
$R^{4a}$ and $R^{4b}$ are independently H or $C_1$-$C_8$ alkyl; and
the wave line represents the point of attachment of D in formula (I).

4. The compound of claim 1, wherein D is of the formula (D-2a) or (D-2b):

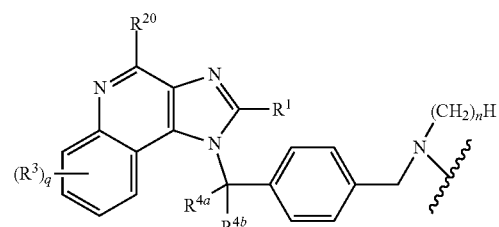

(D-2a)

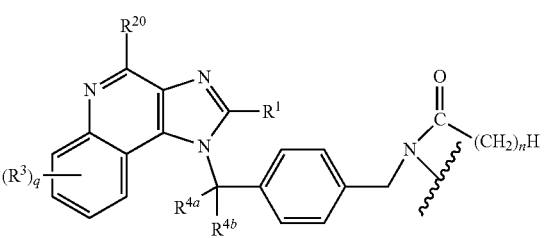

(D-2b)

wherein:
n is an integer from 4 to 21;
$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;
$R^{20}$ is $NHR^{20a}$; where $R^{20a}$ is H, OH, $NH_2$, or methyl;
each $R^3$ is independently halogen, $C_1$-$C_8$ alkyl, —($C_1$-$C_7$ alkylene)-$NH_2$, or —$CH_2$-phenylene-$CH_2NH_2$;
q is 0, 1, 2, 3, or 4;
$R^{4a}$ and $R^{4b}$ are independently H or $C_1$-$C_8$ alkyl; and
the wave line represents the point of attachment of D in formula (I).

5. The compound of claim 3, wherein X is —NH—.
6. The compound of claim 3, wherein n is an integer from 4 to 15.
7. The compound of claim 3, wherein n is 4, 5, 6, or 7.
8. The compound of claim 3, wherein X is —NH(C=O)—.
9. The compound of claim 3, wherein n is 11, 12, 13, or 14.
10. The compound of claim 3, wherein $R^1$ is $C_3$-$C_6$ alkyl.
11. The compound of claim 10, wherein $R^1$ is n-butyl.
12. The compound of claim 3, wherein $R^1$ is —$(CH_2)_pOR^{1a}$.
13. The compound of claim 3, wherein $R^1$ is —$(CH_2)_pNHR^{1b}$.
14. The compound of claim 3, wherein $R^1$ is —$(CH_2)_pR^{1c}$.
15. The compound of claim 3, wherein q is 0.
16. The compound of claim 3, wherein q is 1 and $R^3$ is $C_1$-$C_8$ alkyl.
17. The compound of claim 3, wherein $R^{4a}$ and $R^{4b}$ are each H.
18. The compound of claim 1, wherein D is of the formula (D-3):

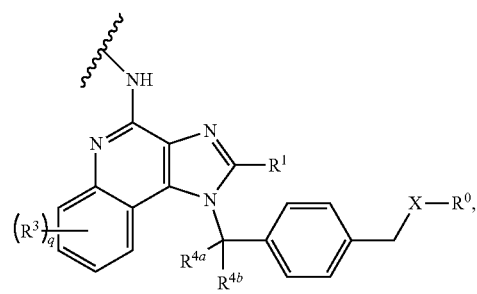

(D-3)

wherein:
$R^0$ is $C_4$-$C_{21}$ hydrocarbyl optionally substituted by 1 to 4 halogen atoms;
X is —NH— or —NH(C=O)—;
$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;
each $R^3$ is independently halogen, $C_1$-$C_8$ alkyl, —($C_1$-$C_7$ alkylene)-$NH_2$, or —$CH_2$-phenylene-$CH_2NH_2$;
q is 0, 1, 2, 3, or 4;
$R^{4a}$ and $R^{4b}$ are independently H or $C_1$-$C_8$ alkyl; and
the wave line represents the point of attachment of D in formula (I).

19. The compound of claim 1, wherein D is of the formula (D-3a) or (D-3b):

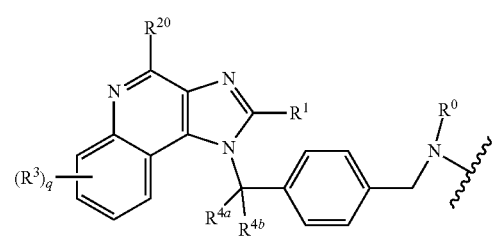

(D-3a)

-continued (D-3b)

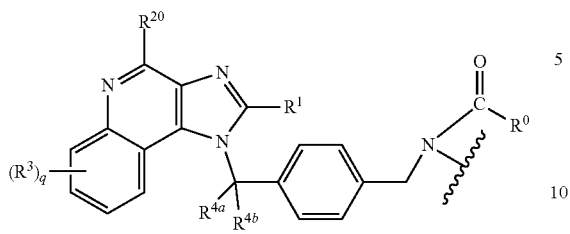

wherein:
R⁰ is $C_4$-$C_{21}$ hydrocarbyl optionally substituted by 1 to 4 halogen atoms;
$R^1$ is $C_3$-$C_6$ alkyl, —$(CH_2)_pOR^{1a}$, —$(CH_2)_pNHR^{1b}$, or —$(CH_2)_pR^{1c}$; where $R^{1a}$ and $R^{1b}$ are independently $C_1$-$C_3$ alkyl; $R^{1c}$ is $C_3$-$C_4$ cycloalkyl; and p is 1 or 2;
$R^{20}$ is $NHR^{20a}$, where $R^{20a}$ is H, OH, $NH_2$, or methyl;
each $R^3$ is independently halogen, $C_1$-$C_8$ alkyl, —($C_1$-$C_7$ alkylene)-$NH_2$, or —$CH_2$-phenylene-$CH_2NH_2$;
q is 0, 1, 2, 3, or 4;
$R^{4a}$ and $R^{4b}$ are independently H or $C_1$-$C_8$ alkyl; and
the wave line represents the point of attachment of D in formula (I).

20. The compound of claim 18, wherein X is —NH (C=O)—.

21. The compound of claim 18, wherein X is —NH—.

22. The compound of claim 18, wherein R⁰ is $C_4$-$C_{14}$ hydrocarbyl optionally substituted by 1 to 2 halogen atoms.

23. The compound of claim 18, wherein R⁰ is branched $C_4$-$C_{14}$ alkyl, —$(CH_2)_z(C(CH_3)_2)R^4$, or —$(CH_2)_mR^4$; m is 0, 1, 2, or 3; z is 1 or 2; and $R^4$ is $C_3$-$C_8$ cycloalkyl optionally substituted by 1 to 4 groups independently selected from the group consisting of $C_1$-$C_4$ alkyl, $C_1$-$C_4$ alkylene, and halogen.

24. The compound of claim 18, wherein R⁰ is branched $C_4$-$C_{14}$ alkyl.

25. The compound of claim 23, wherein R⁰ is —$(CH_2)_mR^4$.

26. The compound of claim 25, wherein m is 2.

27. The compound of claim 25, wherein m is 1.

28. The compound of claim 23, wherein R⁰ is —$(CH_2)_z(C(CH_3)_2)R^4$.

29. The compound of claim 28, wherein z is 1.

30. The compound of claim 25, wherein $R^4$ is cyclopropyl, cyclobutyl, or cyclopentyl.

31. The compound of claim 25, wherein $R^4$ is $C_3$-$C_6$ cycloalkyl optionally substituted by 1 to 3 groups independently selected from the group consisting of methyl, methylene, and halogen.

32. The compound of claim 25, wherein $R^4$ is $C_3$-$C_8$ cycloalkyl.

33. The compound of claim 25, wherein $R^4$ is cyclopropyl optionally substituted by 1 to 3 groups independently selected from the group consisting of methyl and methylene.

34. The compound of claim 25, wherein m is 0 and $R^4$ is cyclohexyl optionally substituted by 1 to 3 groups independently selected from the group consisting of methyl and methylene.

35. The compound of claim 18, wherein R⁰ is selected from the group consisting of:

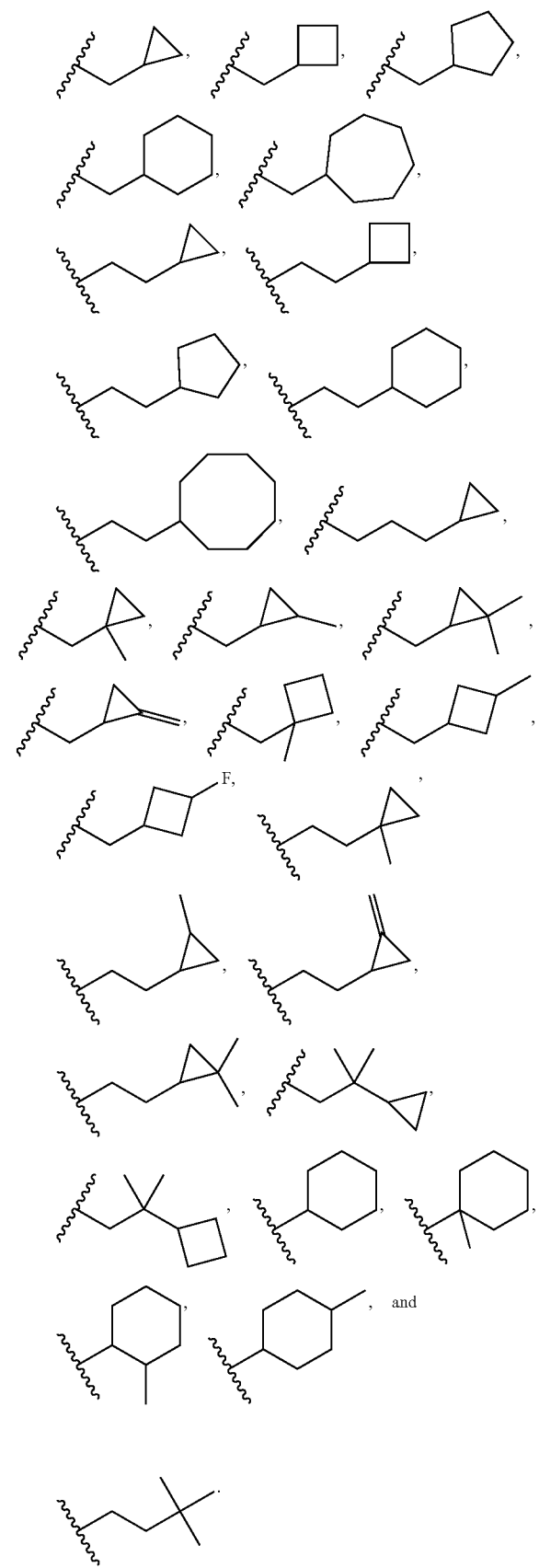

36. The compound of claim 1, wherein D is:
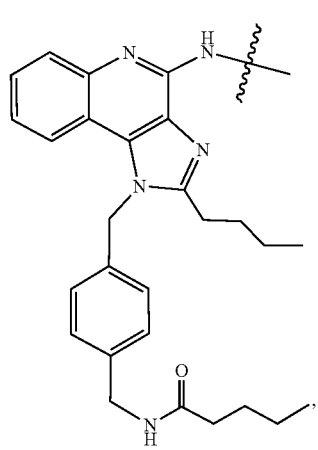
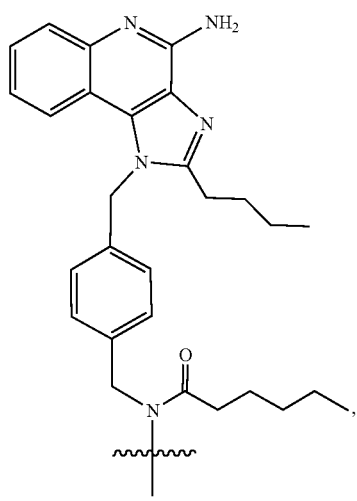
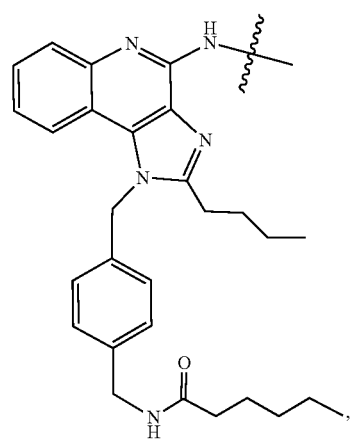
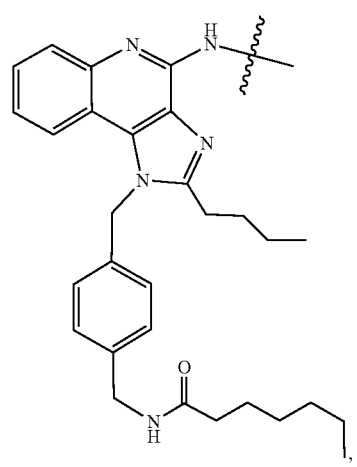
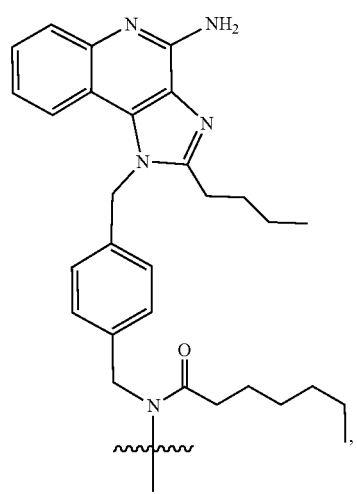

245
-continued
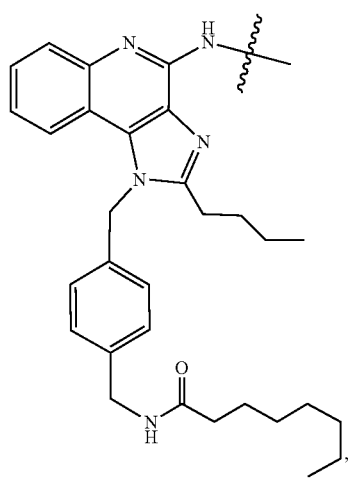
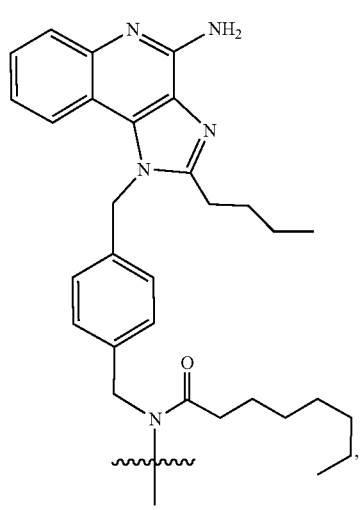
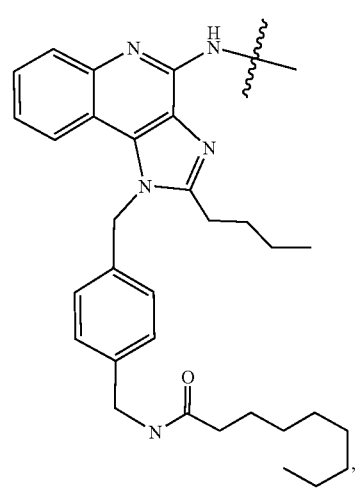
246
-continued
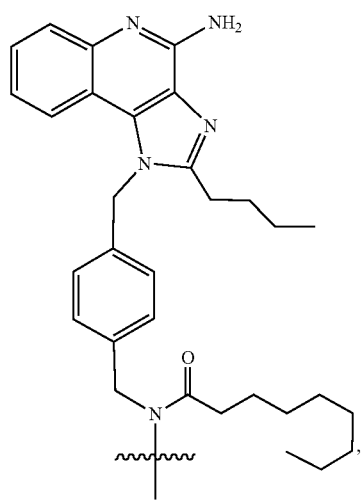
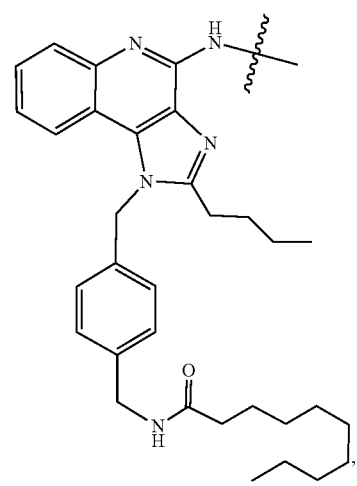
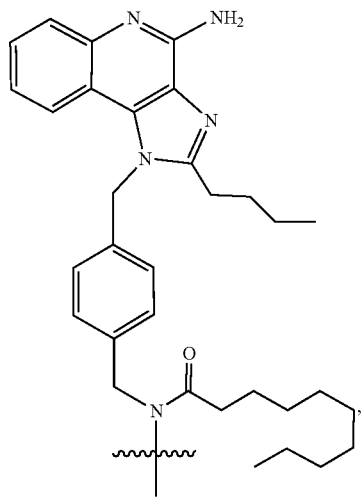

247
-continued
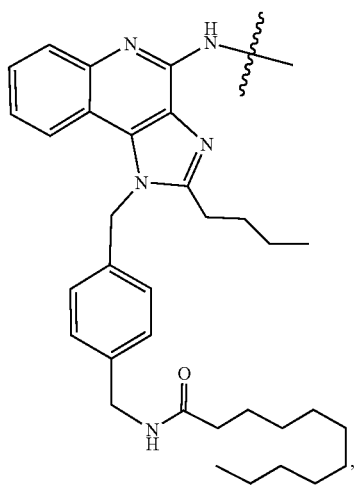
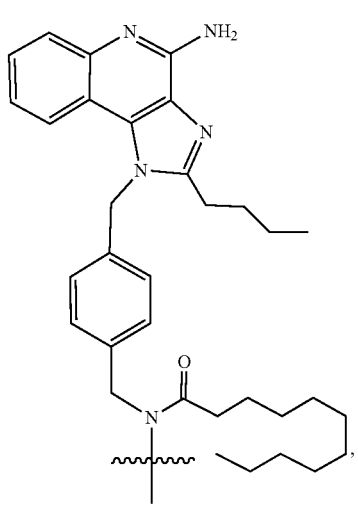
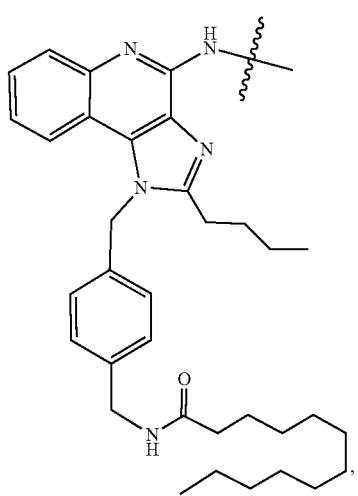
248
-continued
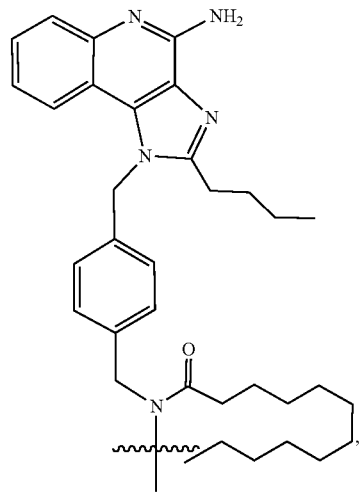
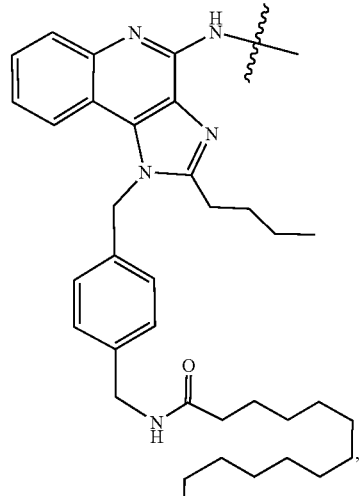

249
-continued
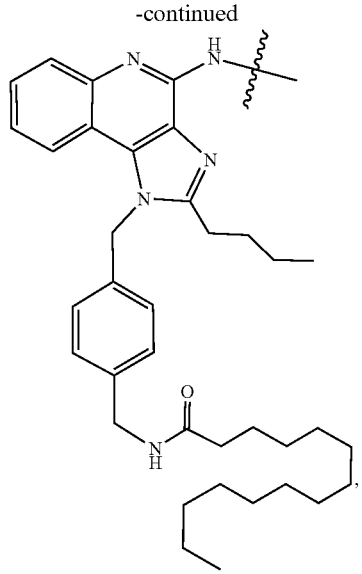
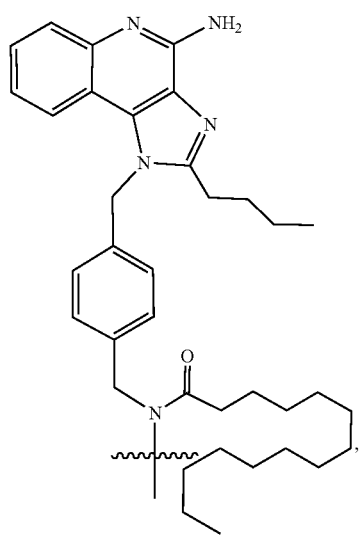
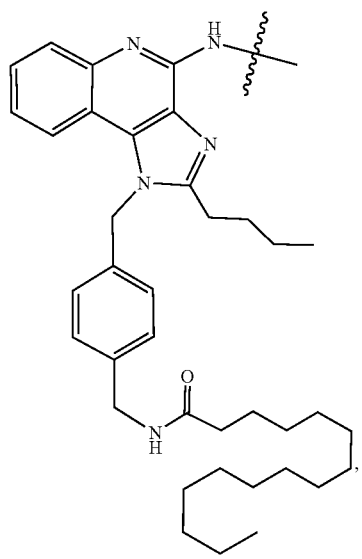
250
-continued
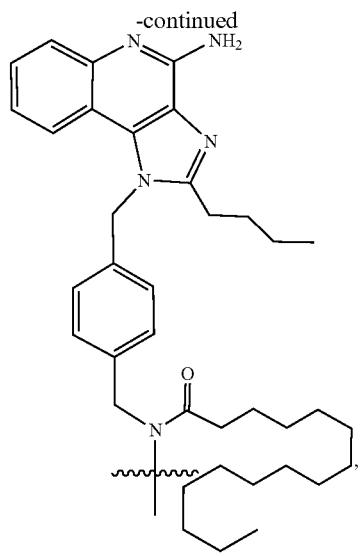
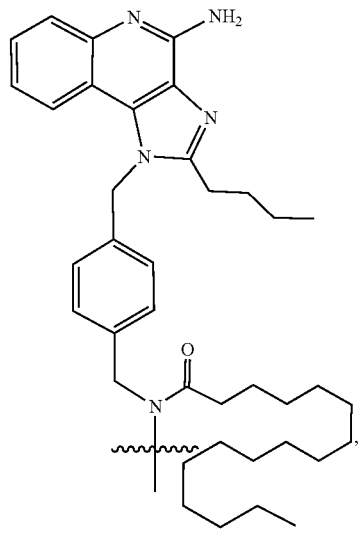

251
-continued
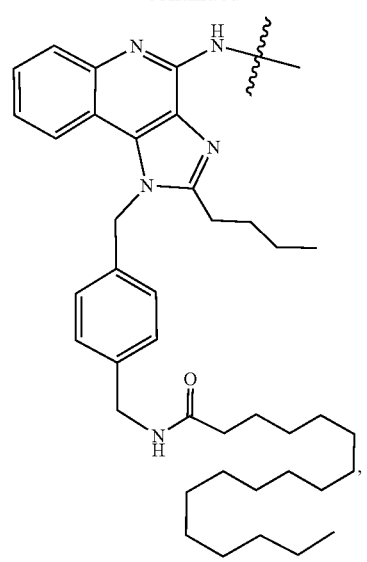
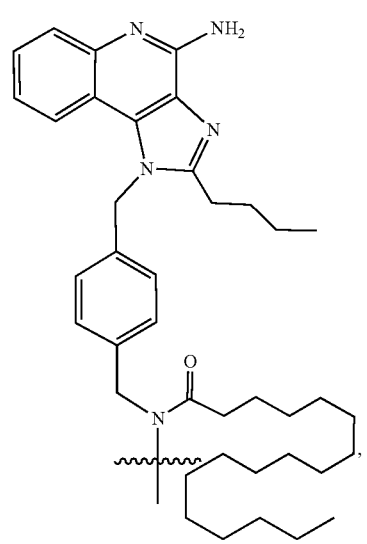
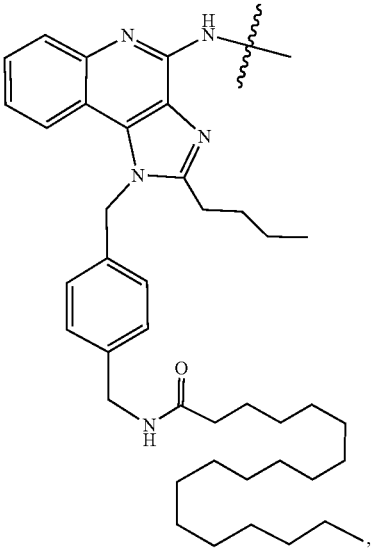
252
-continued
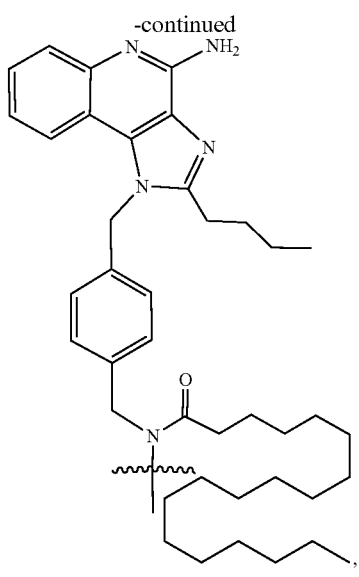
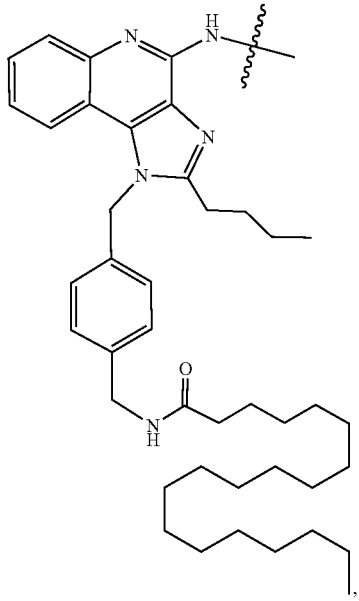
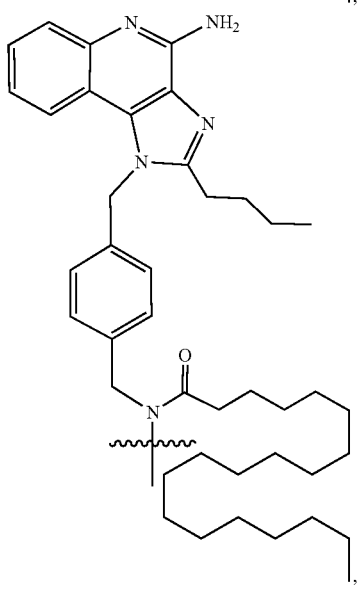

253
-continued
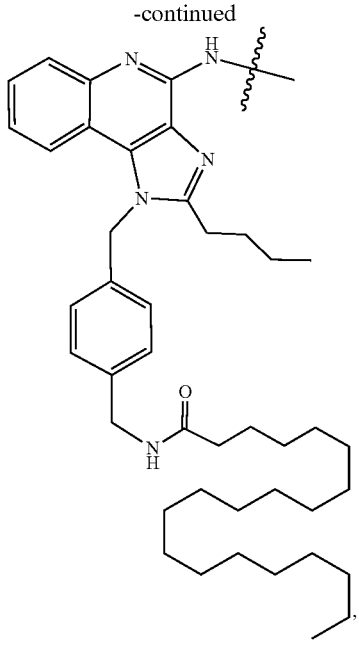
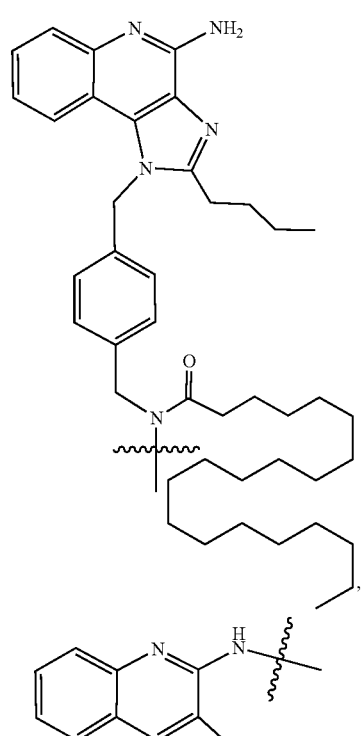
254
-continued
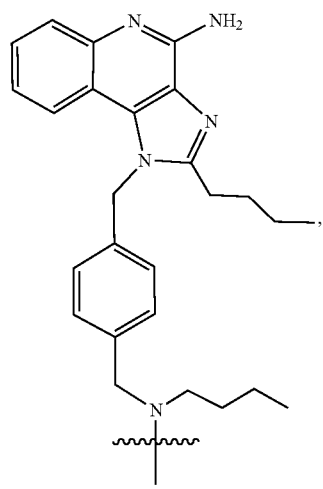
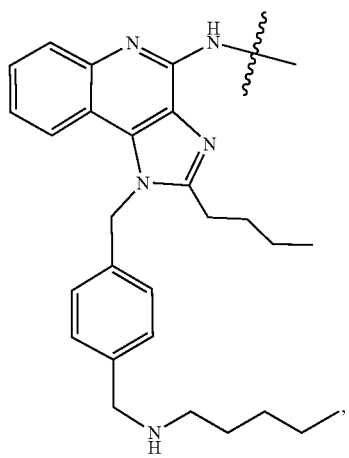
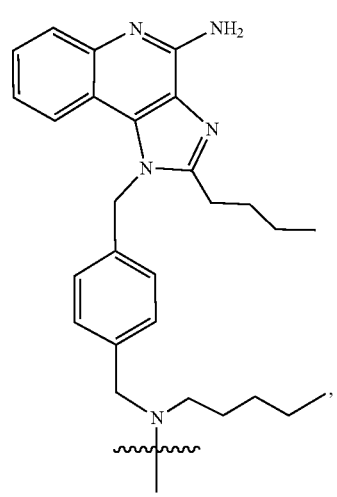

255
-continued
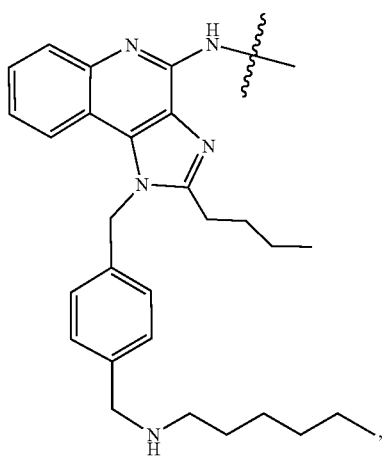
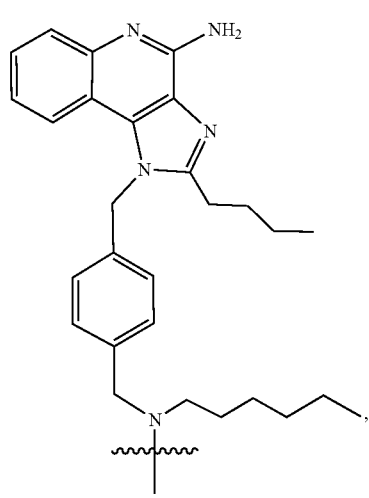
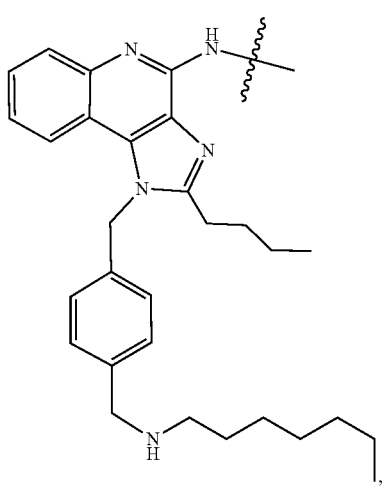
256
-continued
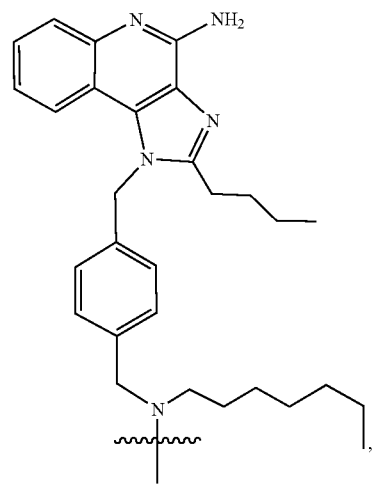
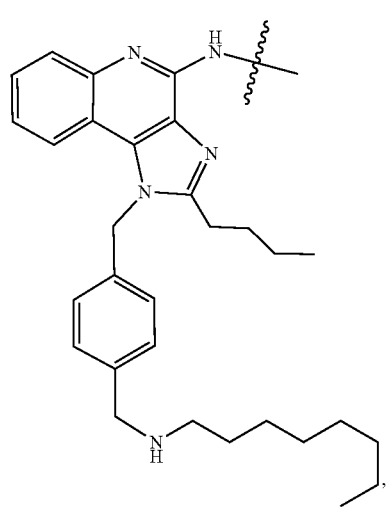
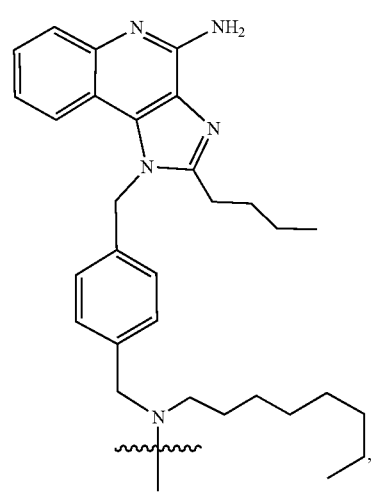

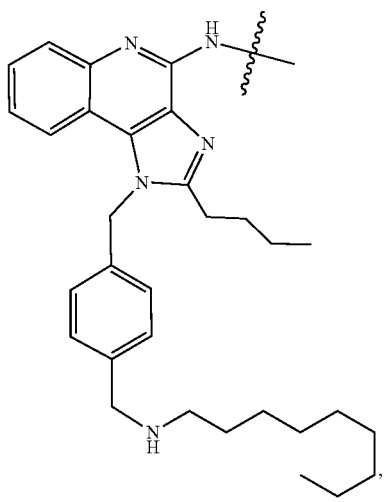
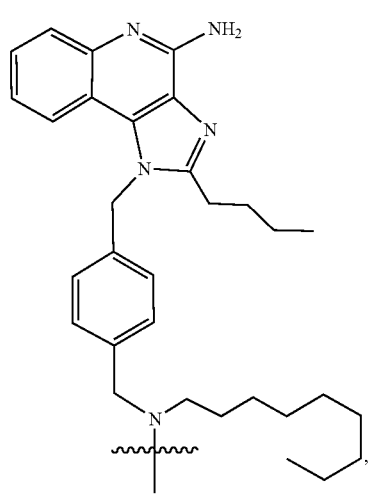
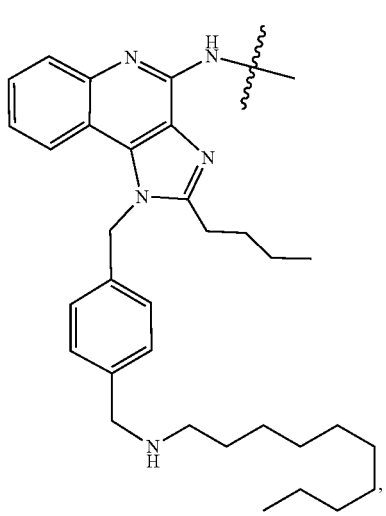
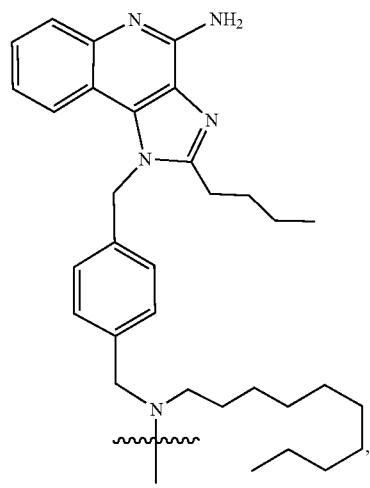
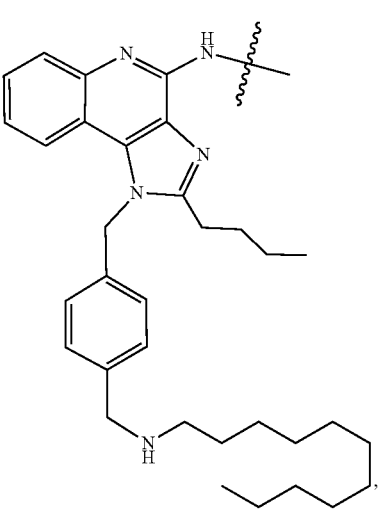
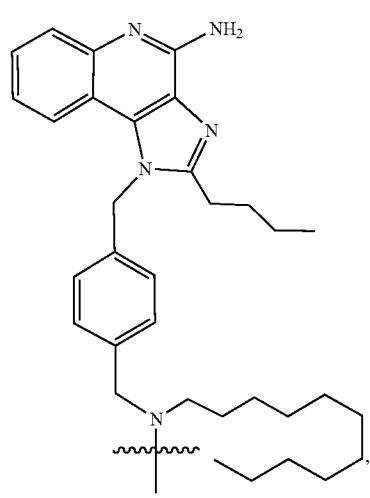

259
-continued
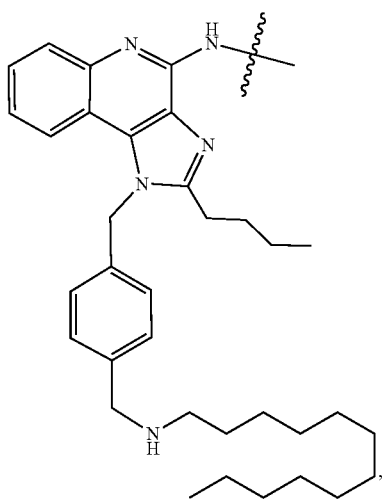
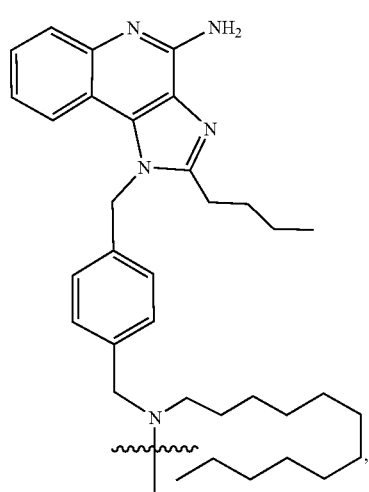
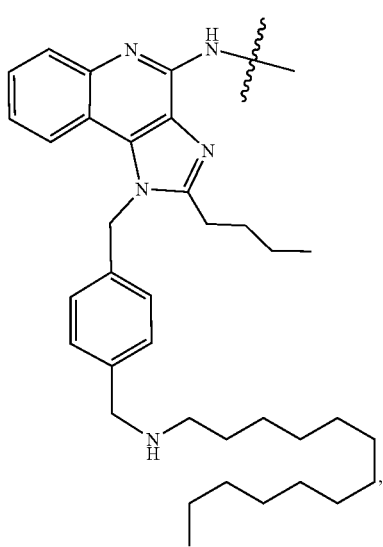
260
-continued
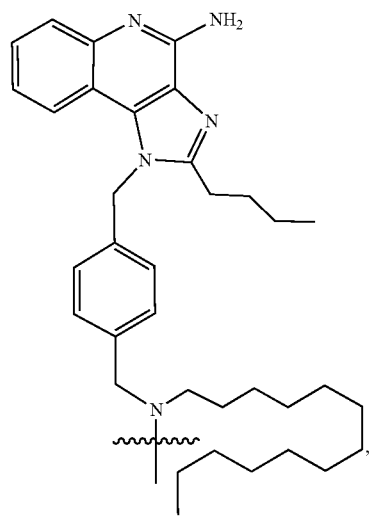
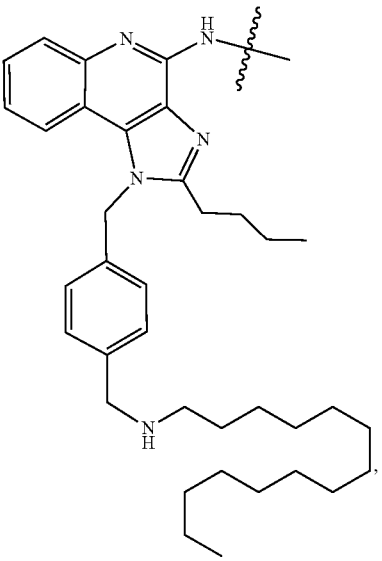
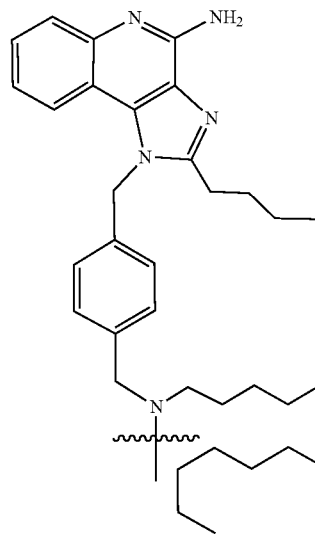

261
-continued
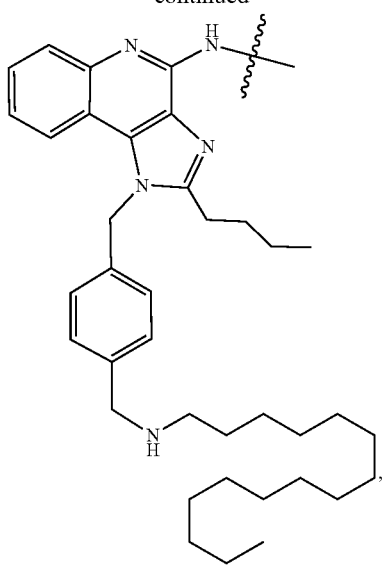
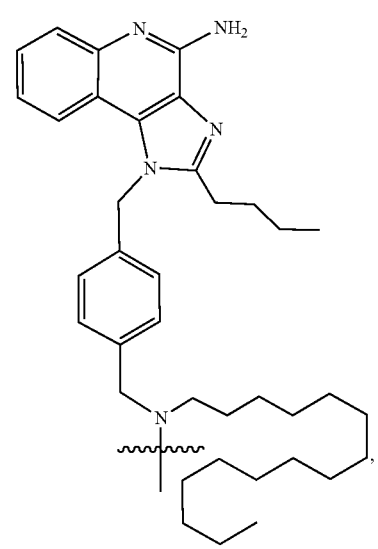
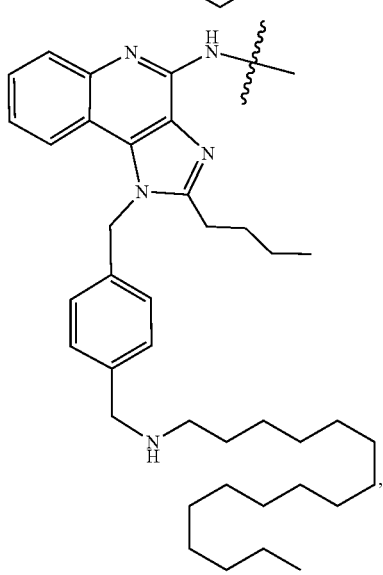
262
-continued
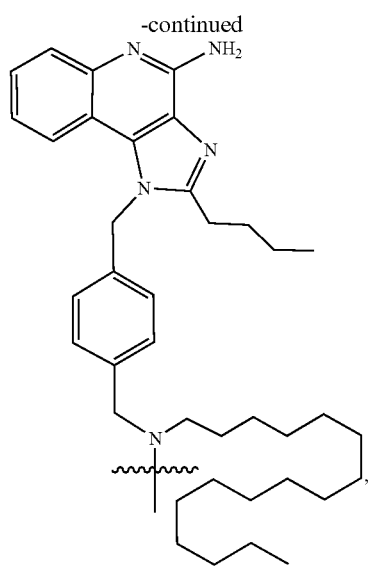
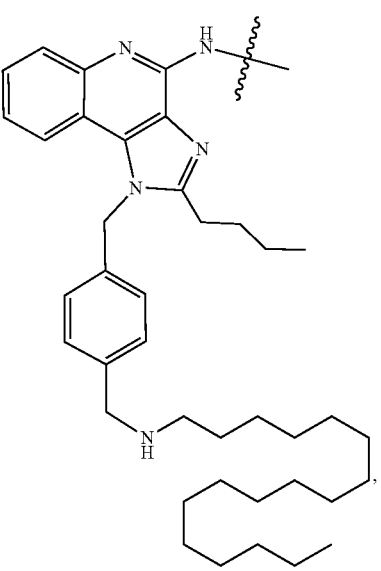
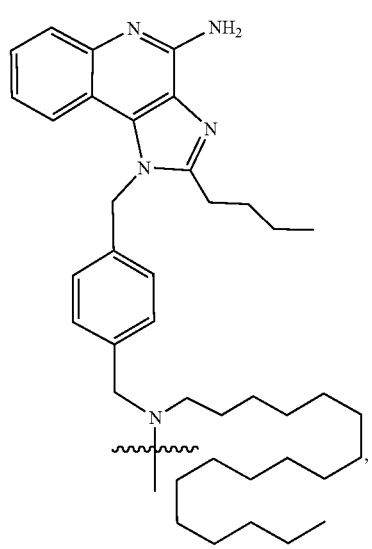

263
-continued
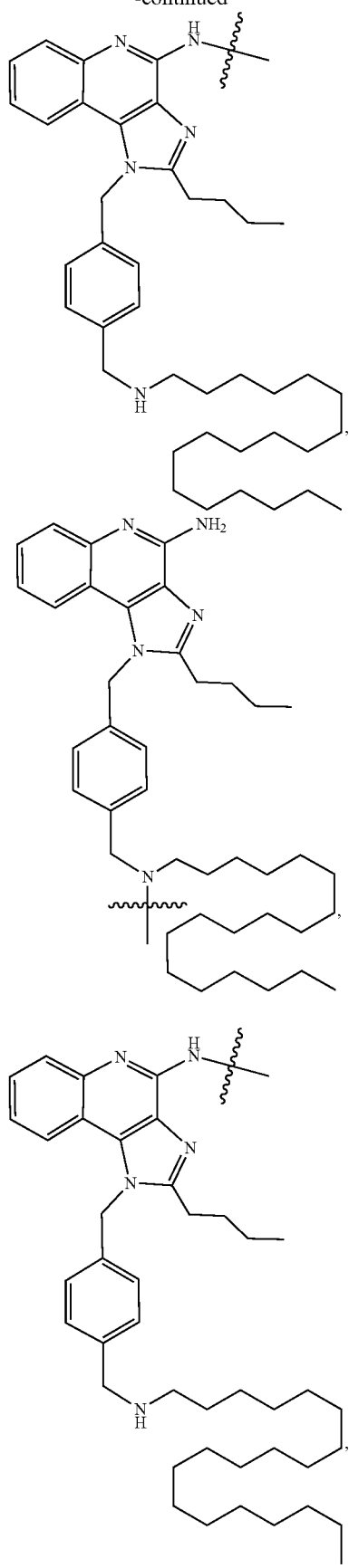
264
-continued
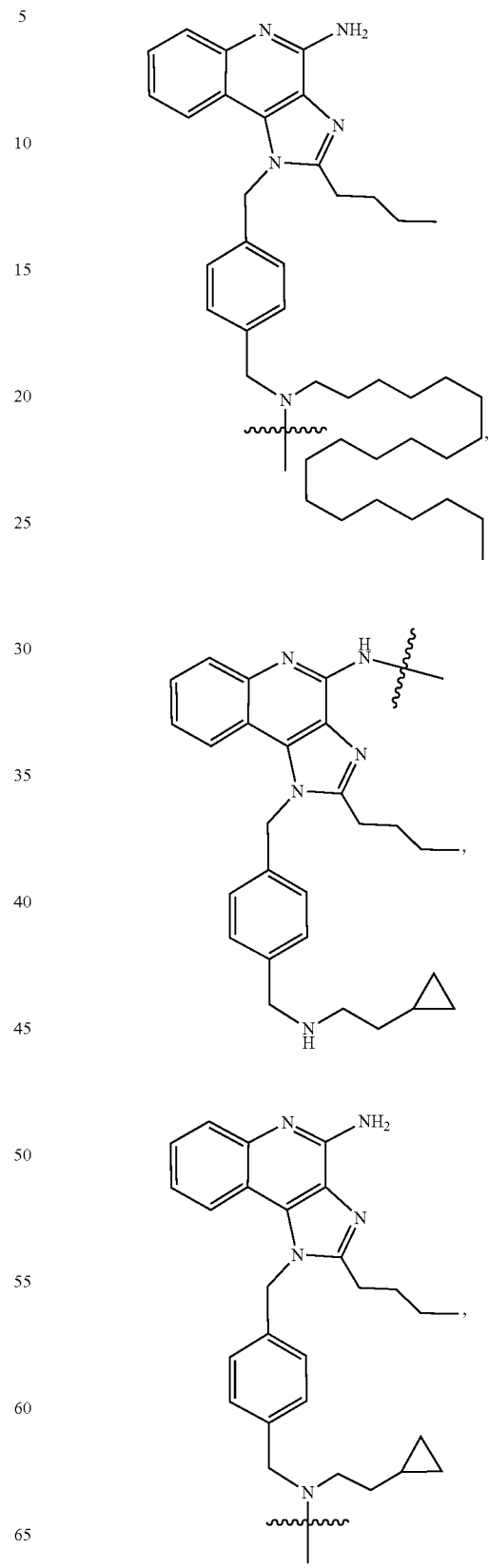

265
-continued
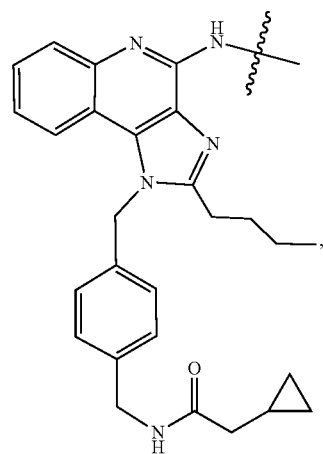
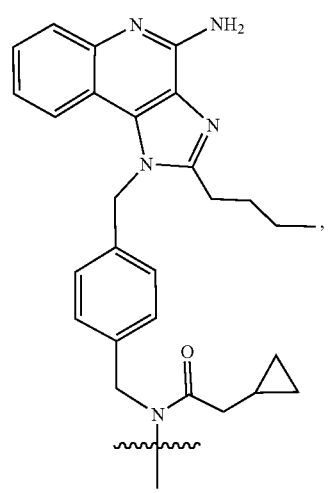
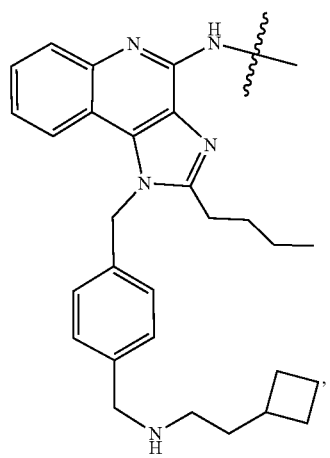
266
-continued
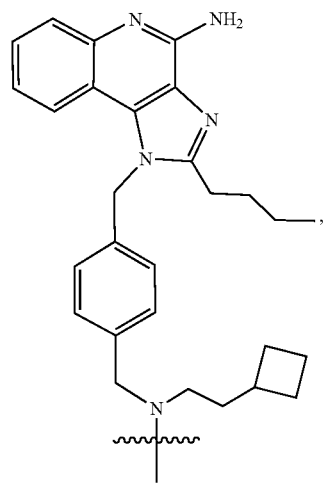
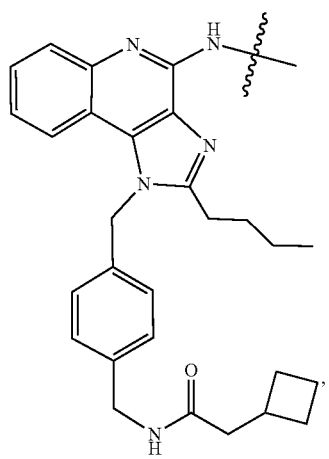
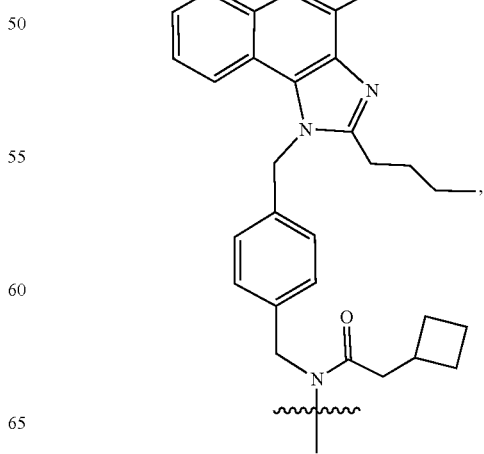

267
-continued
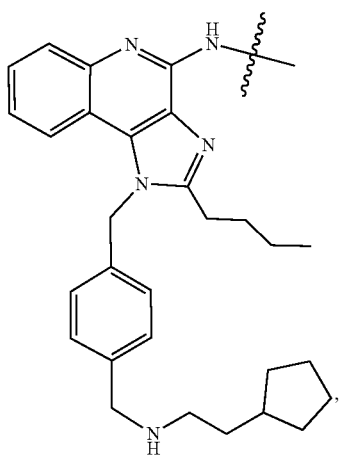
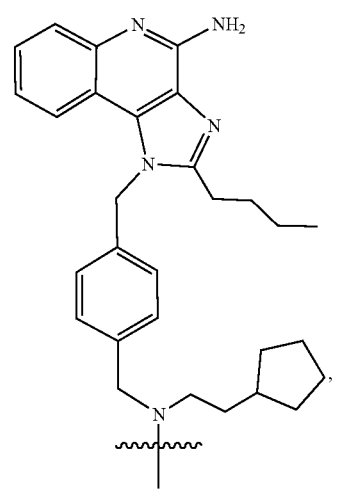
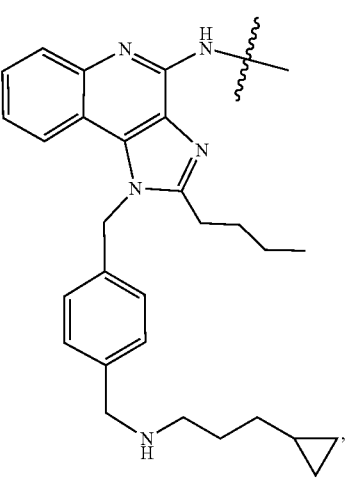
268
-continued
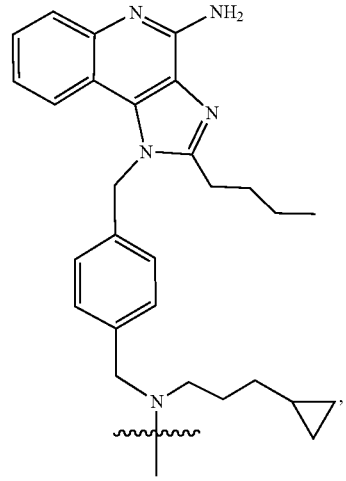
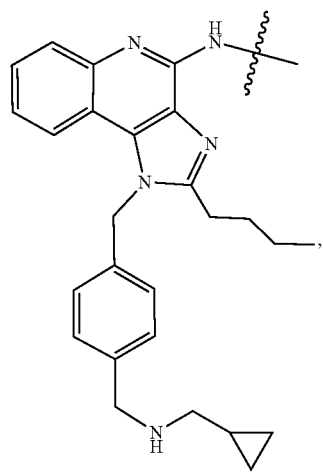
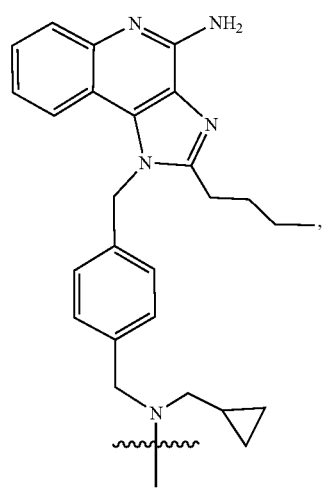

269
-continued
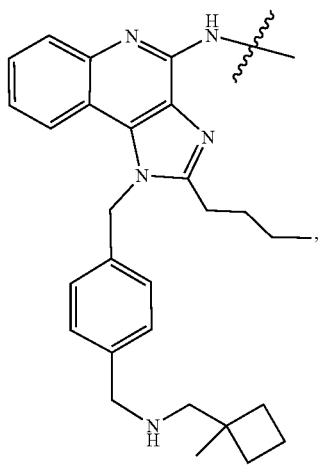
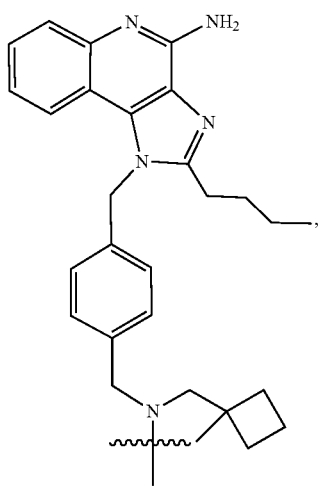
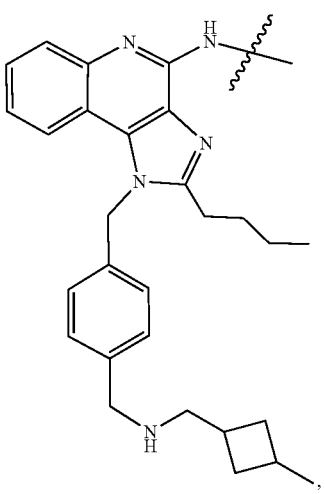
270
-continued
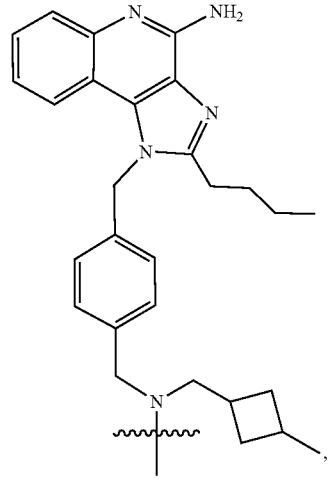
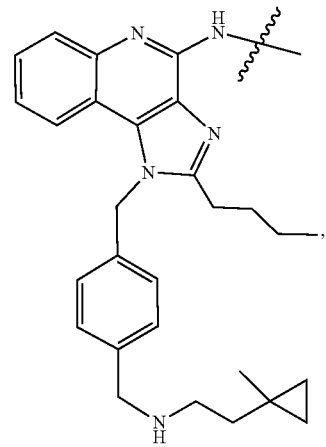
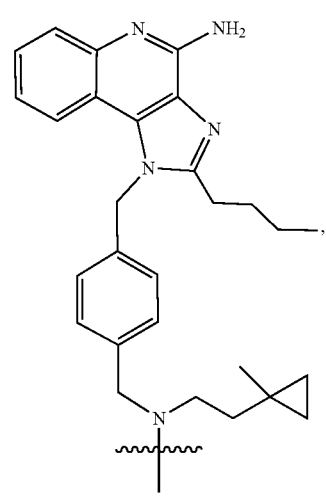

271
-continued
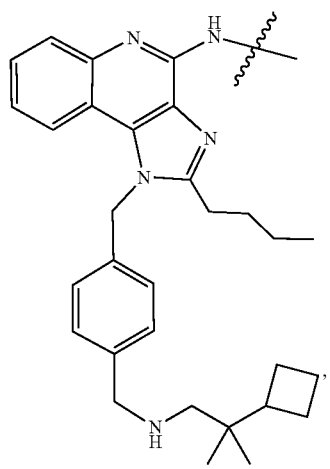
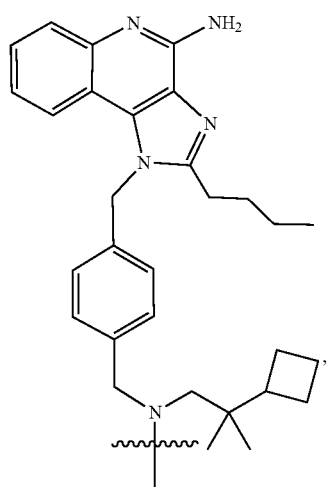
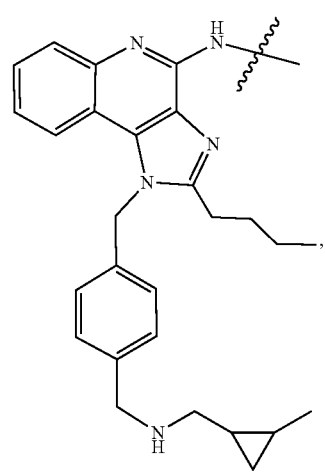
272
-continued
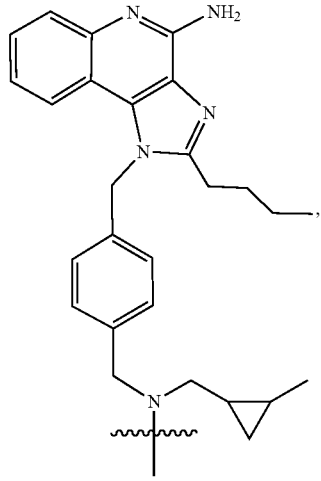
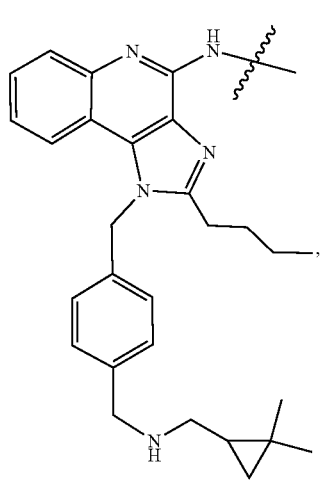
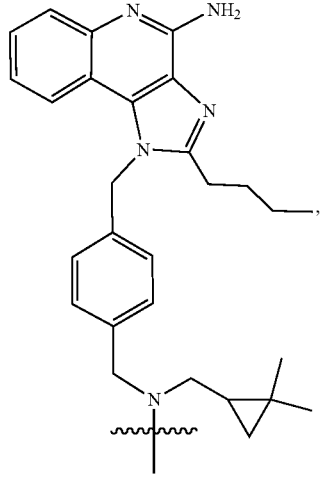

273
-continued
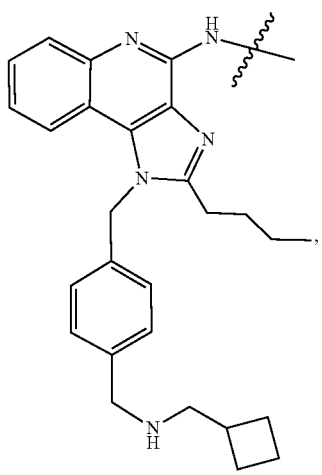
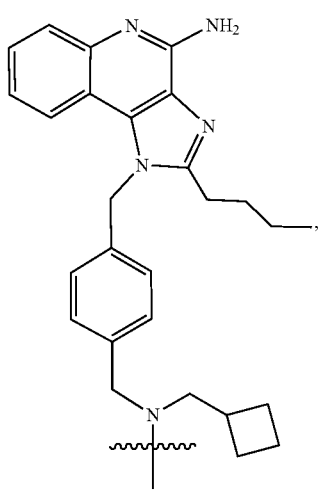
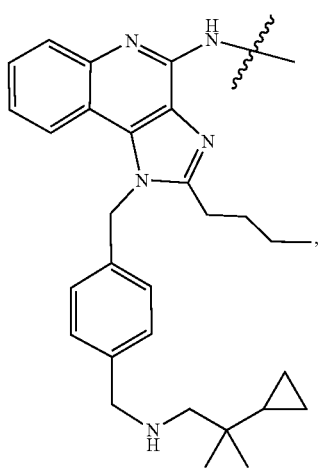
274
-continued
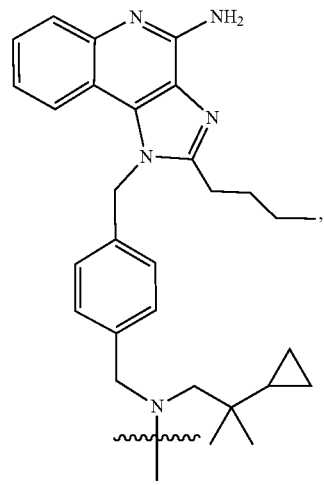
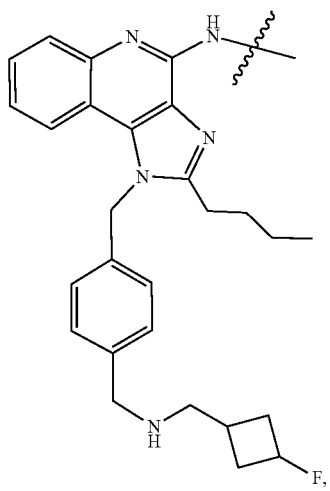
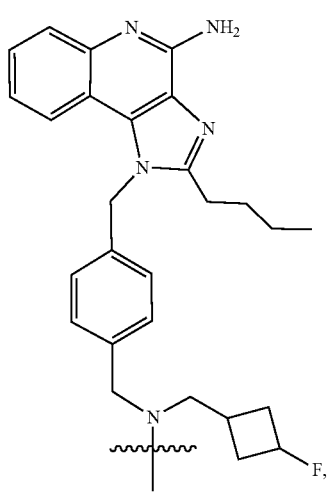

-continued

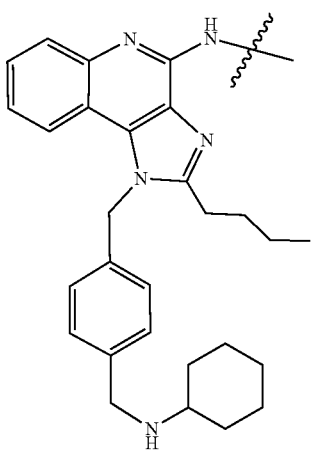

or

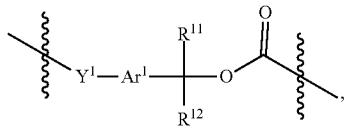

37. The compound of claim 1, wherein L¹ is of the formula (L-1):

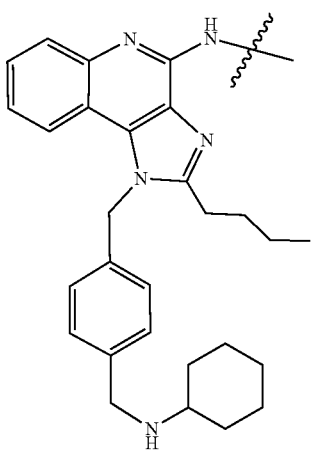
(Note: replaced)

wherein Y¹ is S, O, or NH; Ar¹ is an optionally substituted arylene; and R¹¹ and R¹² are independently H or optionally substituted $C_1$-$C_8$ alkyl.

38. The compound of claim 37, wherein Ar¹ is optionally substituted 1,4-phenylene or optionally substituted 1,2-phenylene.

39. The compound of claim 37, wherein R¹¹ and R¹² are each H.

40. The compound of claim 37, wherein Y¹ is NH.

41. The compound of claim 40, wherein L¹ is

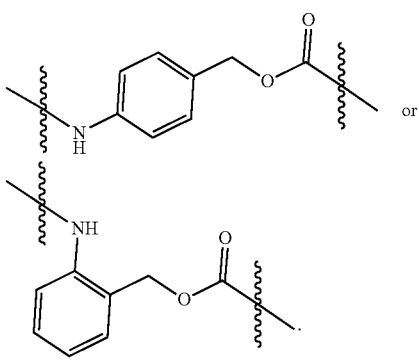

42. The compound of claim 37, wherein Y¹ is S.
43. The compound of claim 42, wherein L¹ is

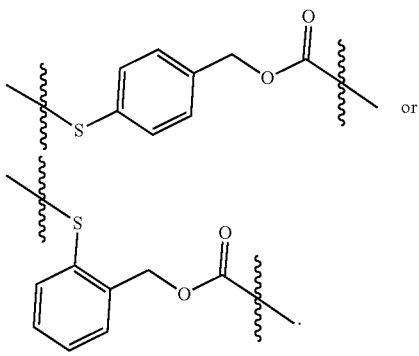

44. The compound of claim 1, wherein L¹-D is:

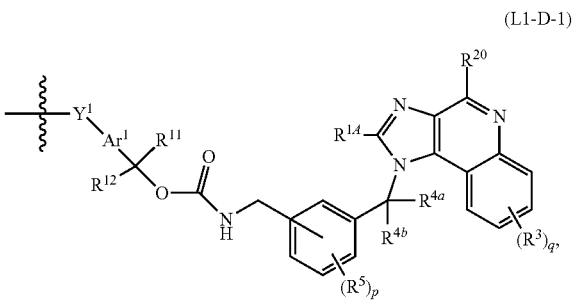
(L1-D-1)

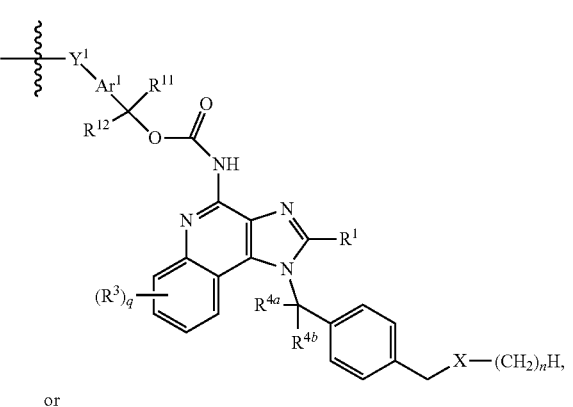
(L1-D-2)

or (L1-D-3)
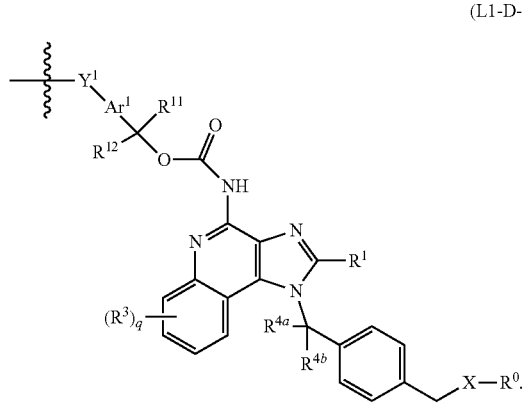
45. The compound of claim 1, wherein $L^1$-D is:
(L1-D-2a)
(L1-D-2b)
(L1-D-3a)
(L1-D-3b)
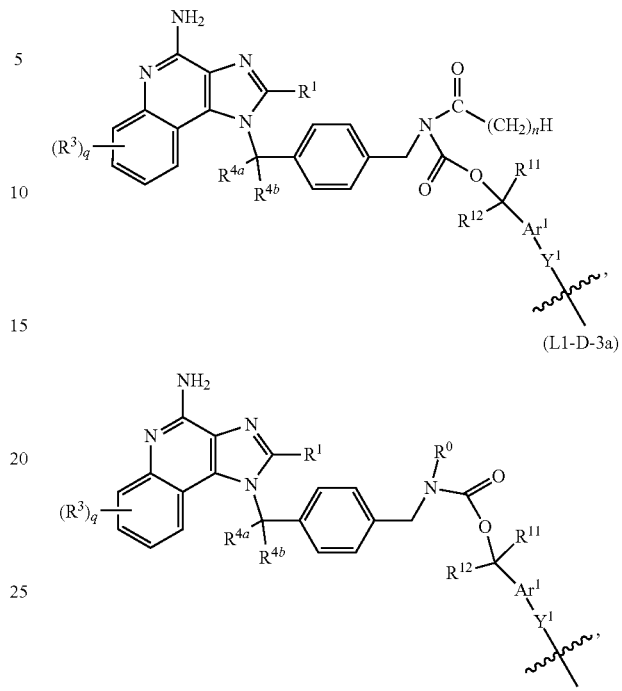
46. The compound of claim 1, wherein $L^1$-D is
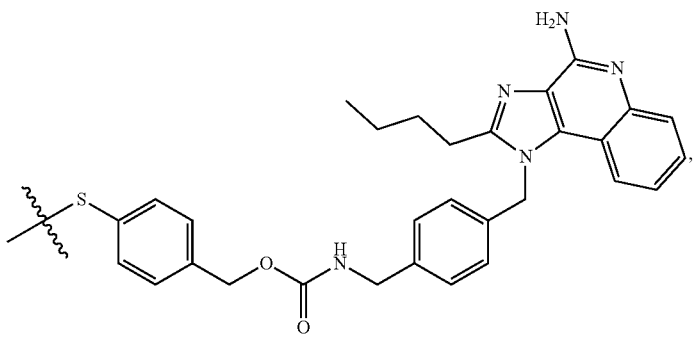

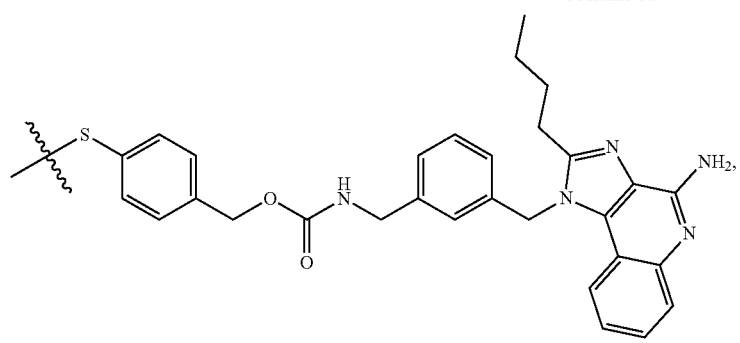
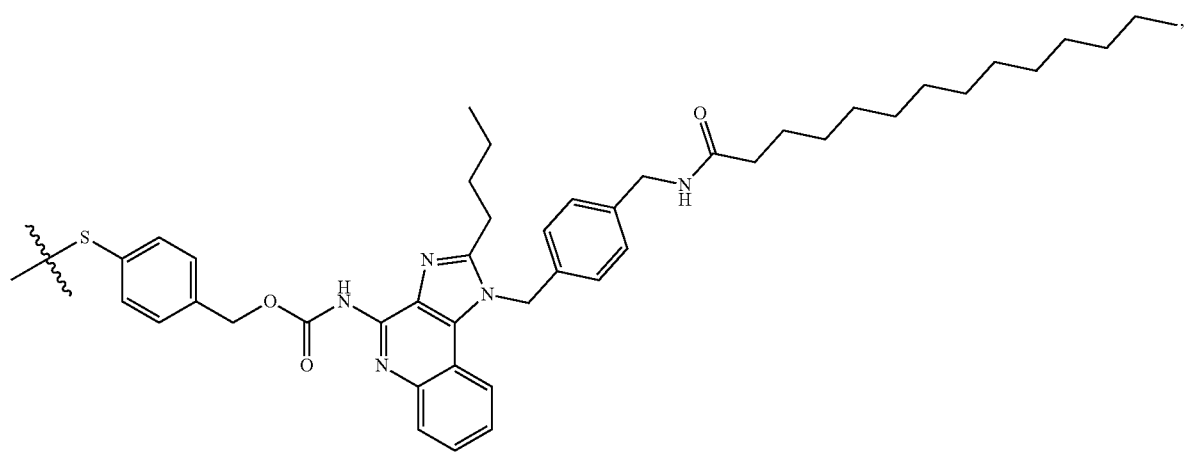
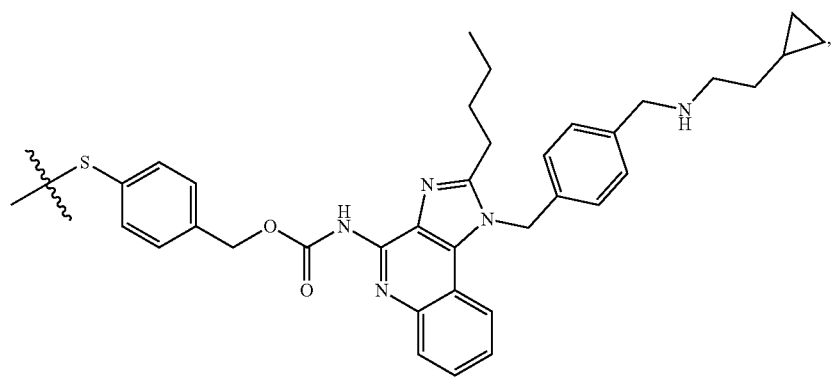
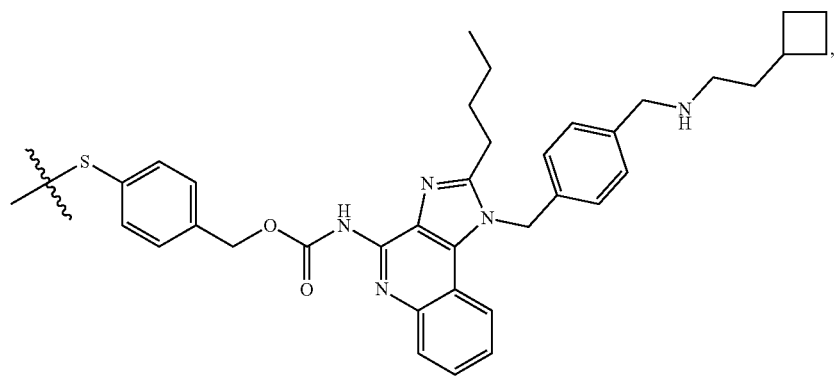

-continued
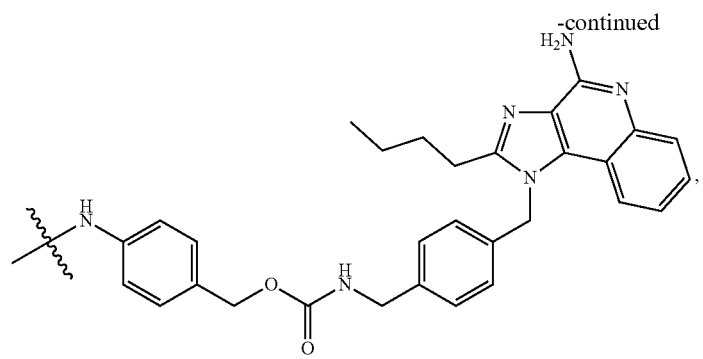
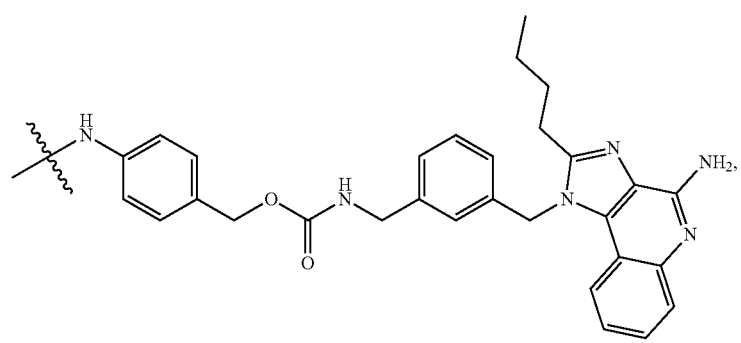
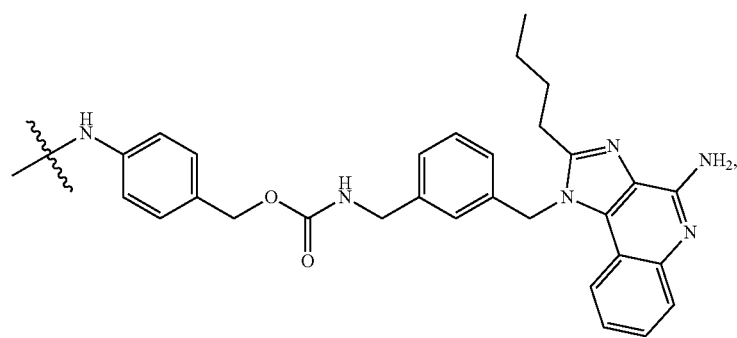
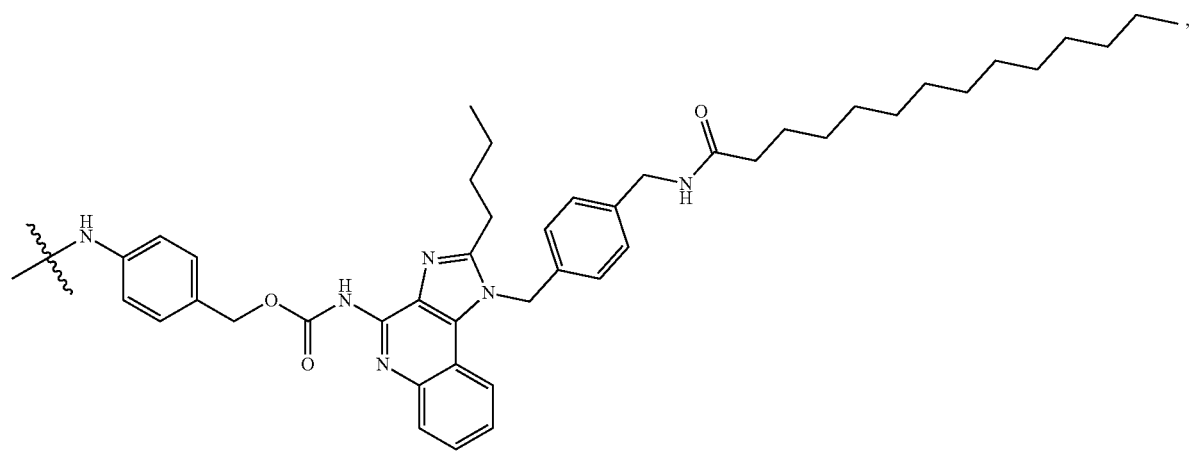

-continued
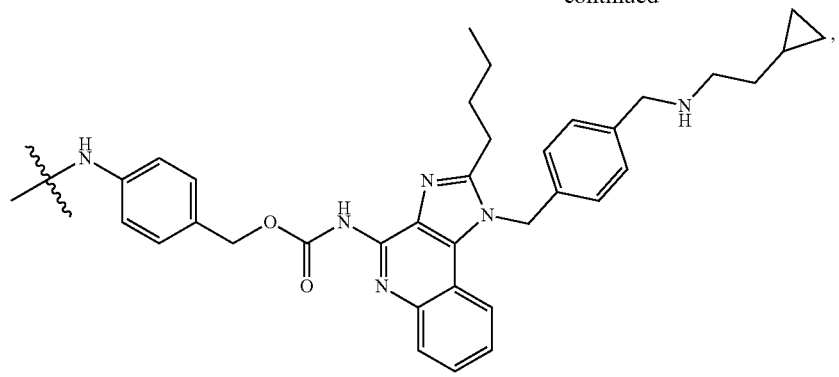
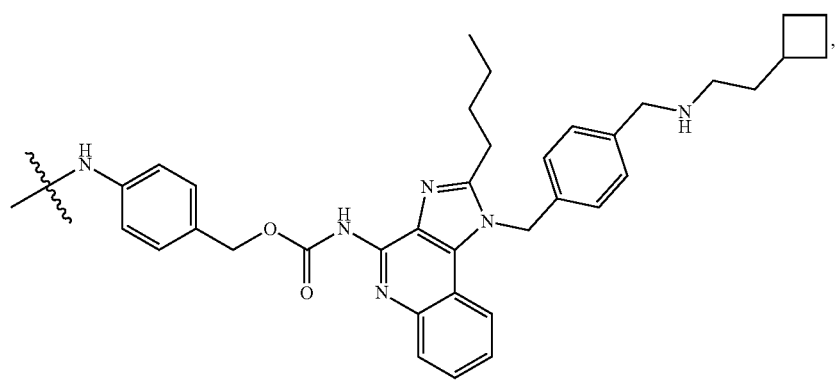
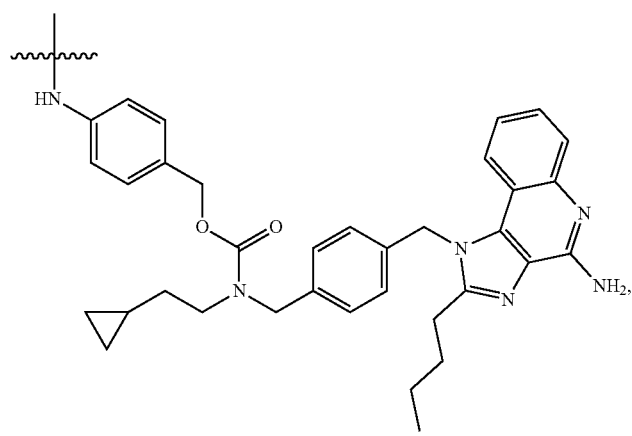
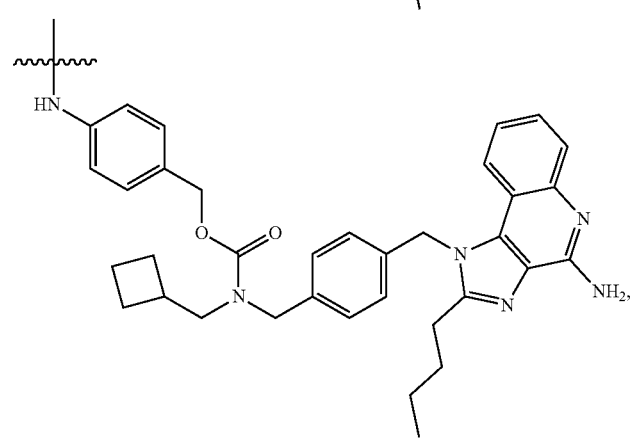

-continued

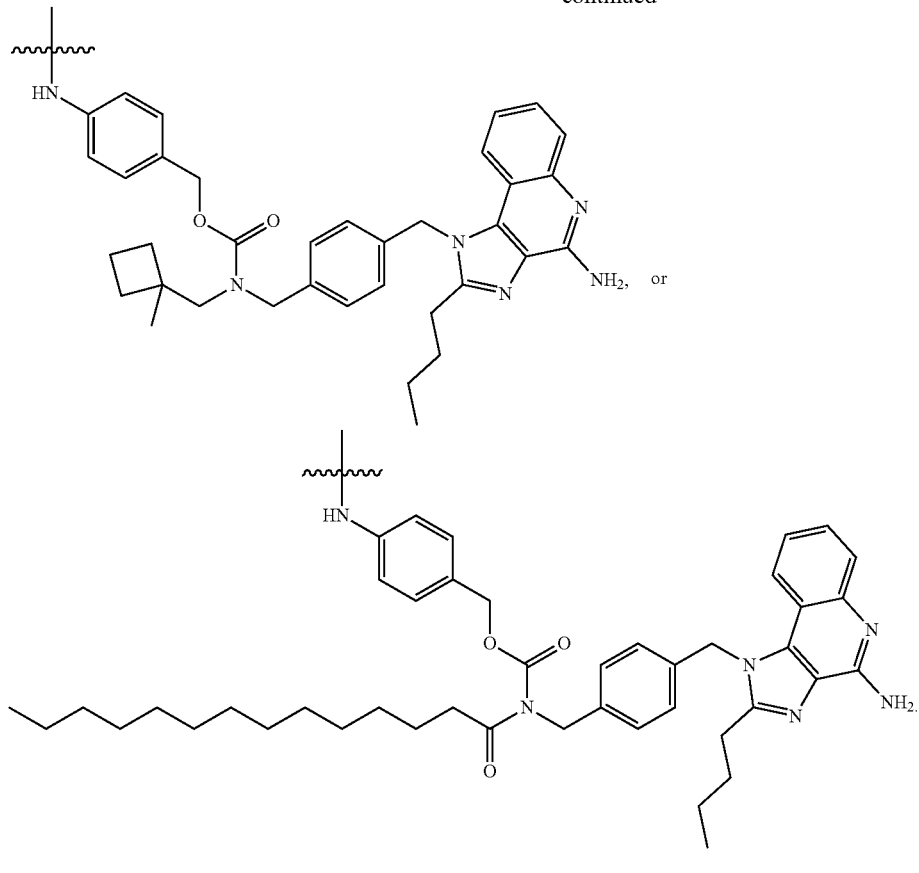

47. The compound of claim 1, wherein $L^2$ is of the formula (L-2):

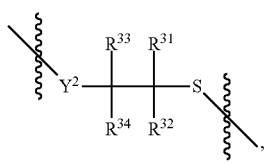
(L-2)

wherein $Y^2$ is $NR^{30}$, O, or S; and $R^{30}$, $R^{31}$, $R^{32}$, $R^{33}$ and $R^{34}$ are independently H, $C_1$-$C_8$ alkyl, or $C_3$-$C_8$ cycloalkyl.

48. The compound of claim 47, wherein $L^2$ is

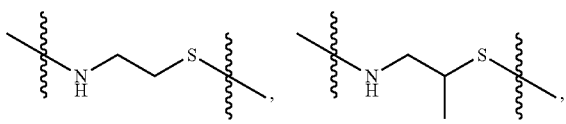

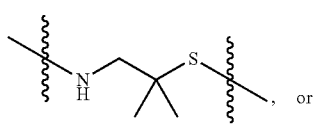

-continued

49. The compound of claim 1, wherein $L^2$ is a peptide linker.

50. The compound of claim 49, wherein $L^2$ is a peptide linker cleavable by one or more endosomal or lysosomal peptidase(s) or protease(s), or one or more pericellular peptidase(s) or protease(s), that are expressed by cells in the tumor microenvironment.

51. The compound of claim 50, wherein $L^2$ is a peptide linker cleavable by an endosomal cathepsin or a pericellular protease.

52. The compound of claim 51, wherein the endosomal cathepsin or pericellular protease is selected from the group consisting of Cathepsin B, urokinase-type plasminogen activator (uPA), membrane-type serine protease 1 (matriptase), matriptase-2, and legumain.

53. The compound of claim 52, wherein the peptide linker cleavable by Cathepsin B comprises the amino acid sequence $AA_1$-$AA_2$-$AA_3$-$AA_4$, wherein:
  $AA_1$ is absent, alanine, β-alanine, isoleucine, leucine, valine, or glycine;
  $AA_2$ is absent, alanine, β-alanine, isoleucine, leucine, or valine;
  $AA_3$ is alanine, β-alanine, isoleucine, leucine, or valine; and AA$_4$ is arginine, serine, alanine, β-alanine leucine, ornithine, or citrulline.

54. The compound of claim 53, wherein L$^2$ is

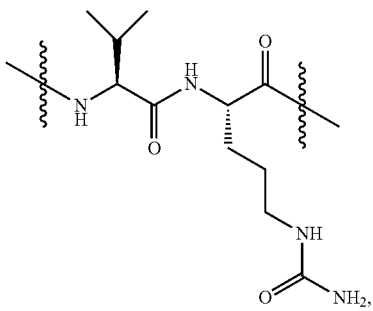

-continued

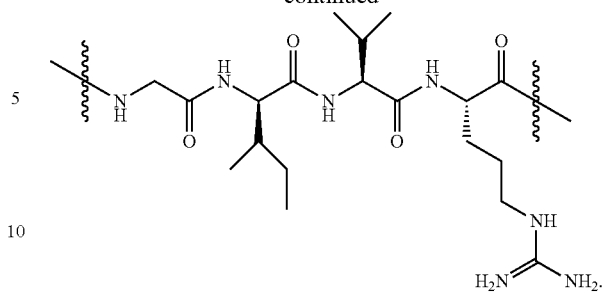

55. The compound of claim 52, wherein L$^2$ is peptide linker cleavable by urokinase-type plasminogen activator (uPA), membrane-type serine protease 1 (matriptase), matriptase-2, and/or legumain.

56. The compound of claim 55, wherein L$^2$ is

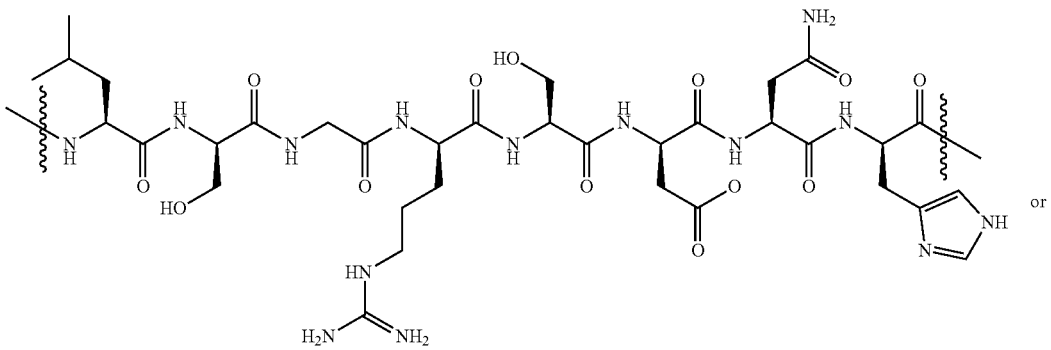

or

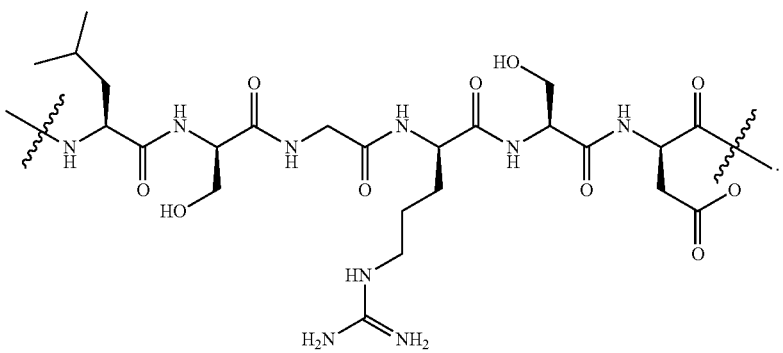

-continued

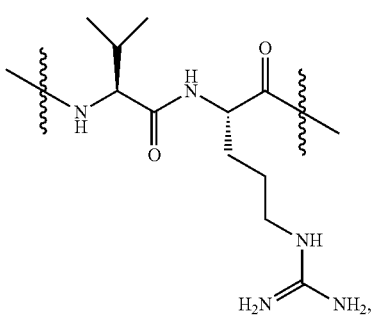

or

57. The compound of claim 1, wherein L$^3$ is -L$^3$a-Y$^3$-L$^{3b}$-, wherein Y$^3$, L$^{3a}$, and L$^{ab}$ are independently optional spacer fragments.

58. The compound of claim 57, wherein Y$^3$ is:

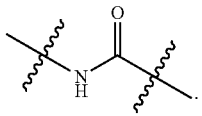 [SMILES: *NC(*)=O]

.

59. The compound of claim 57, wherein $Y^3$ is:

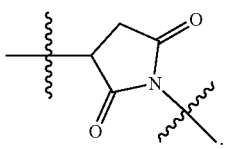 [SMILES: *C1CC(=O)N(*)C1=O]

60. The compound of claim 57, wherein $Y^3$ is:

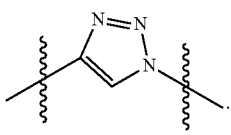 [SMILES: *c1cn(*)nn1]

61. The compound of claim 57, wherein $Y^3$ is:

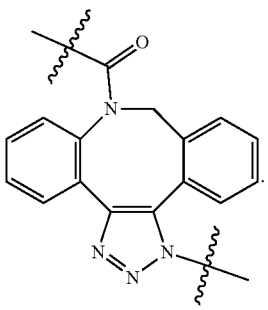 [SMILES: *C(=O)N1Cc2ccccc2-c2c(nnn2*)-c2ccccc21]

62. The compound of claim 57, wherein $L^{3a}$ is absent.

63. The compound of claim 57, wherein $L^{3a}$ is:

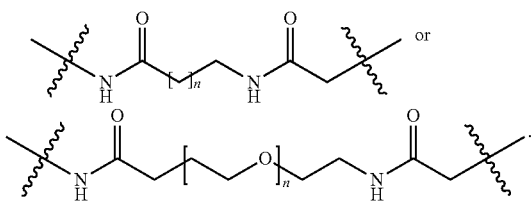

64. The compound of claim 57, wherein $L^{3a}$ is:

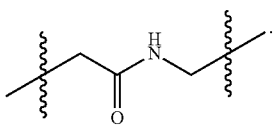 [SMILES: *CNC(=O)C*]

65. The compound of claim 57, wherein $L^{3a}$ is:

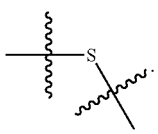 [SMILES: *S*]

66. The compound of claim 57, wherein $L^{3b}$ is an acyl spacer fragment of the formula:

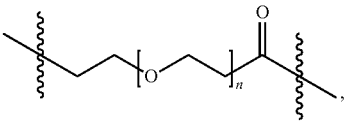

or a PEG-acyl spacer fragment of the formula:

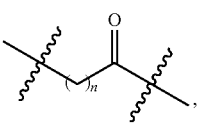

where n is 0 to 200.

67. The compound of claim 66, wherein $L^{3b}$ is an acyl spacer fragment of the formula:

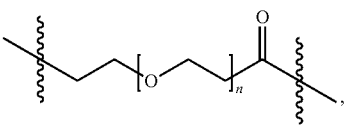

or a PEG-acyl spacer fragment of the formula:

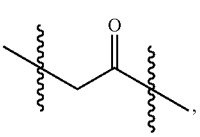

where n is 0 to 200.

68. The compound of claim 57, wherein $L^3$ is

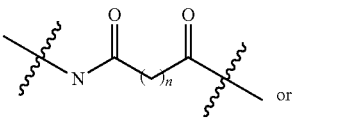

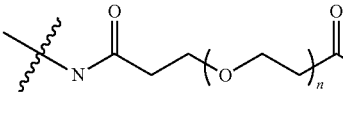

wherein n is 0 to 200.

69. The compound of claim 57, wherein $L^3$ is

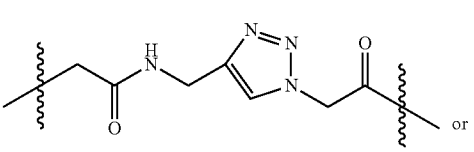

or

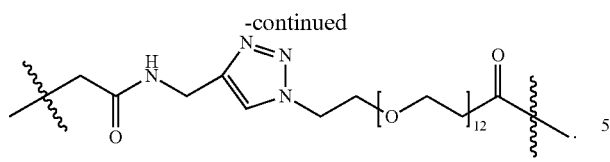
70. The compound of claim 57, wherein L³ is:
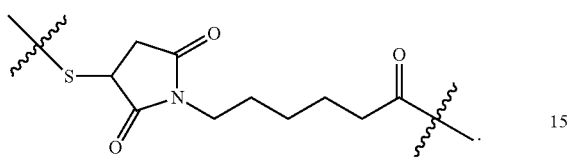
71. The compound of claim 57, wherein L³ is:
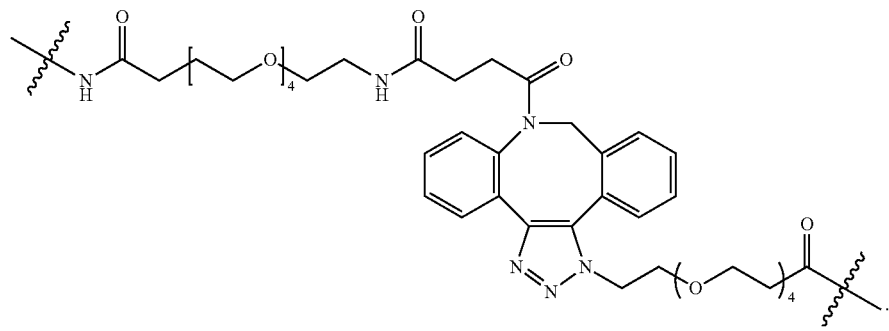
72. The compound of claim 1, wherein the -L³-L²-L¹-D moiety is:
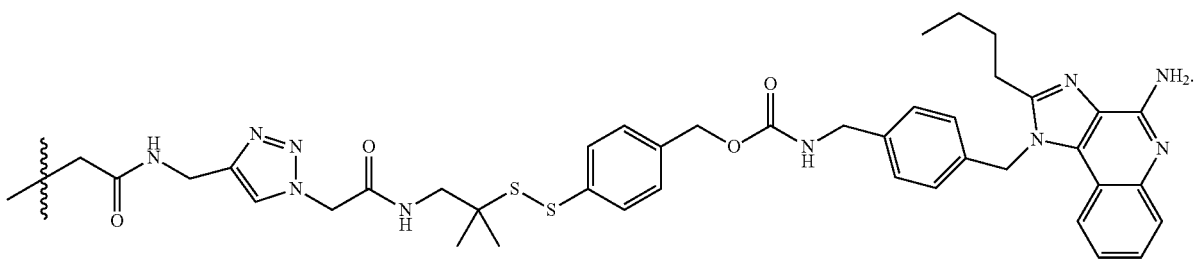 [SMILES: *CC(=O)NCc1cn(CC(=O)NCC(C)(C)SSc2ccc(COC(=O)NCc3ccc(Cn4c(CCCC)nc5c(N)nc6ccccc6c54)cc3)cc2)nn1]
73. The compound of claim 1, wherein the -L³-L²-L¹-D moiety is:
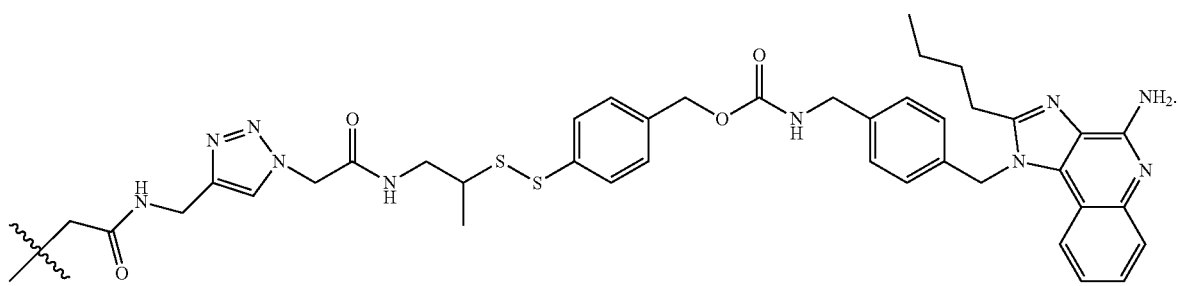 [SMILES: *CC(=O)NCc1cn(CC(=O)NCC(C)SSc2ccc(COC(=O)NCc3ccc(Cn4c(CCCC)nc5c(N)nc6ccccc6c54)cc3)cc2)nn1]

74. The compound of claim 1, wherein the -L³-L²-L¹-D moiety is:

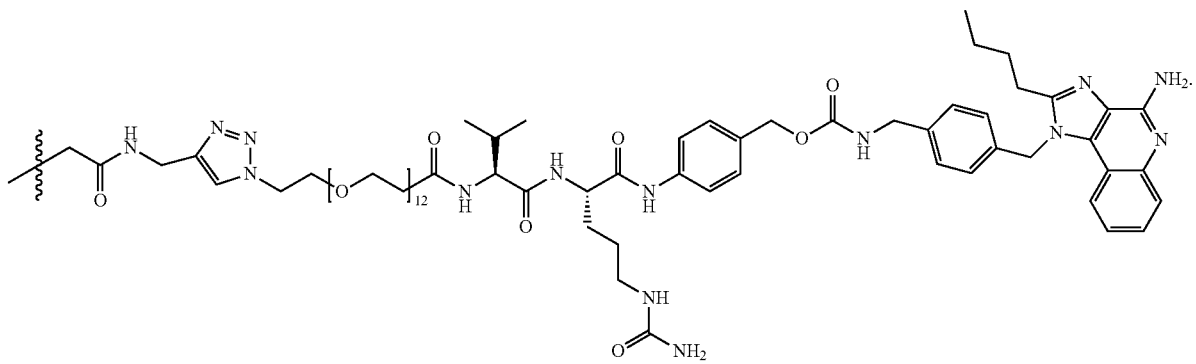

75. The compound of claim 1, wherein the -L³-L²-L¹-D moiety is:

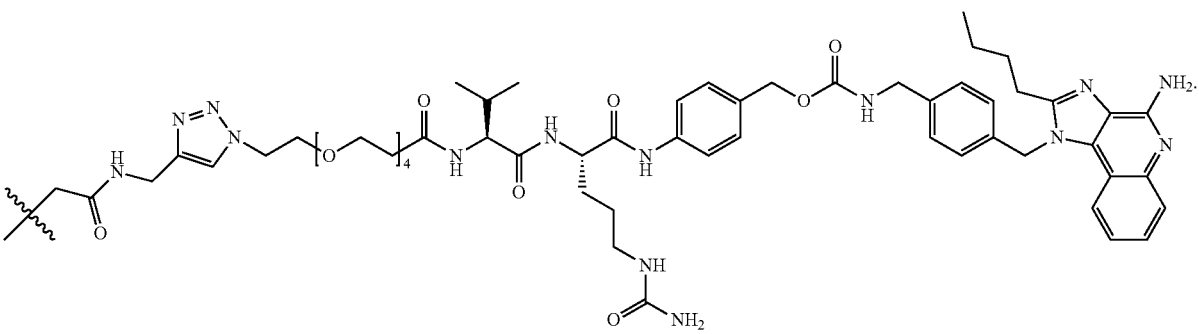

76. The compound of claim 1, wherein F is a tumor targeting agent.

77. The compound of claim 76, wherein the tumor targeting agent is an antibody or binding ligand, which preferentially binds to tumor cell surface antigens, unique structural elements of the tumor microenvironment extracellular matrix, or unique structural elements of the tumor vasculature.

78. The compound of claim 76, wherein F possesses physical properties or chemical modifications of the surface designed to cause preferential distribution to and/or retention in the tumor microenvironment.

79. The compound of claim 76, wherein F is an antibody of the IgG1, 2, or 4 class, or a derivative or a fragment thereof.

80. The compound of claim 79, wherein F is a bivalent monospecific antibody, a bivalent bispecific antibody, or a derivative without Fc regions selected from the group consisting of single-chain variable fragments (scFv), tandem divalent-scFvs, diabodies, tandem trivalent-scFvs, triabodies, and bispecific tandem divalent-scFvs, and x in formula (I) is an integer between 1 and 10.

81. The compound of claim 1, wherein F is an agent that promotes local retention of the compound of formula (I).

82. The compound of claim 81, wherein F is a liposome, virus-like particle, nanoparticle, microparticle, macromolecule or supramolecule, dendrimer, or polypeptide.

83. The compound of claim 81, wherein F is a branched copolymer of sucrose and epichlorohydrin having a molecular weight of about 100,000 to about 700,000 daltons.

84. The compound of claim 83, wherein the molecular weight is about 300,000 to about 500,000 daltons.

85. The compound of claim 83, wherein W is 0, and x is an integer from 3 to 500 in formula (I).

86. The compound of claim 85, wherein x is an integer from about 30 to 150.

87. The compound of claim 19, wherein D is:

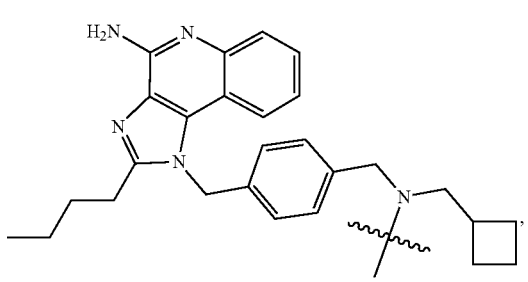

-continued

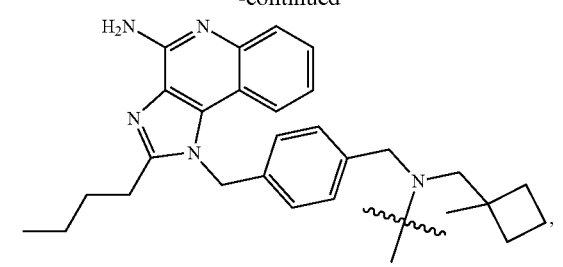

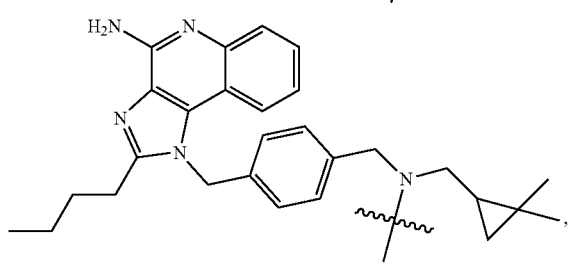

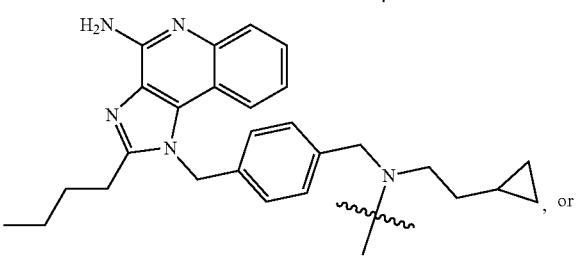

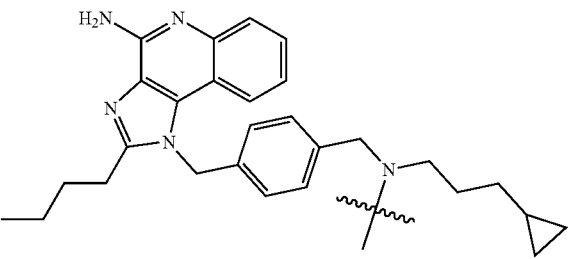

88. The compound of claim 19, wherein R⁰ is selected from the group consisting of:

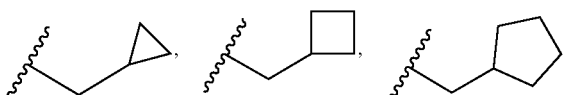

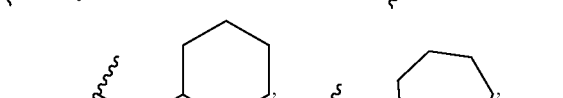

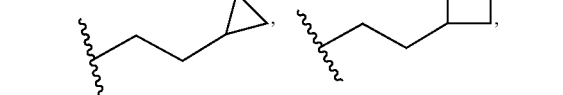

-continued

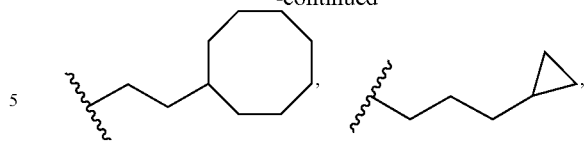

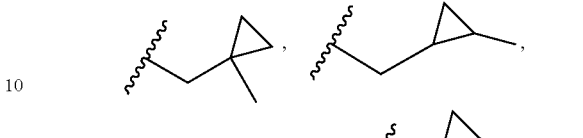

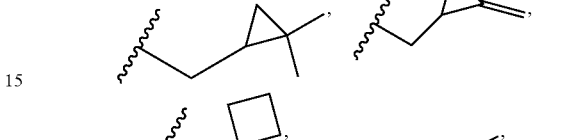

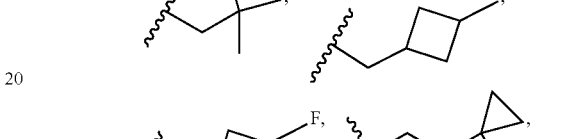

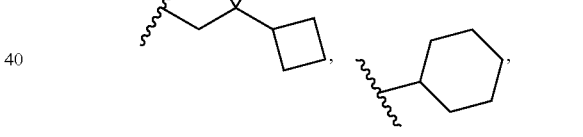

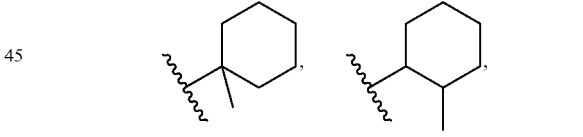

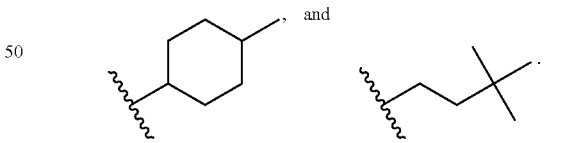

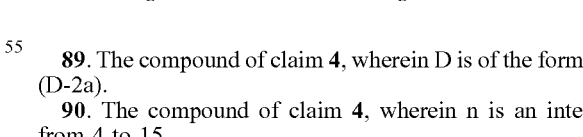

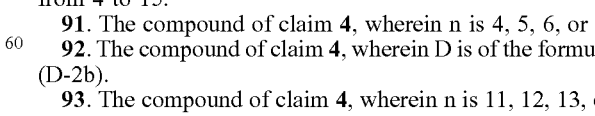

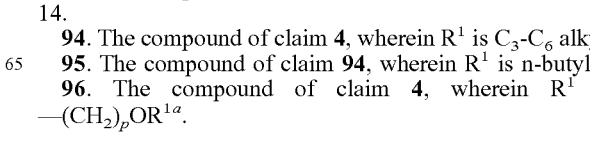

89. The compound of claim 4, wherein D is of the formula (D-2a).
90. The compound of claim 4, wherein n is an integer from 4 to 15.
91. The compound of claim 4, wherein n is 4, 5, 6, or 7.
92. The compound of claim 4, wherein D is of the formula (D-2b).
93. The compound of claim 4, wherein n is 11, 12, 13, or 14.
94. The compound of claim 4, wherein $R^1$ is $C_3$-$C_6$ alkyl.
95. The compound of claim 94, wherein $R^1$ is n-butyl.
96. The compound of claim 4, wherein $R^1$ is —$(CH_2)_p OR^{1a}$.

97. The compound of claim 4, wherein $R^1$ is —$(CH_2)_pNHR^{1b}$.

98. The compound of claim 4, wherein $R^1$ is —$(CH_2)_pR^{1c}$.

99. The compound of claim 4, wherein q is 0.

100. The compound of claim 4, wherein q is 1 and $R^3$ is $C_1$-$C_8$ alkyl.

101. The compound of claim 4, wherein $R^{4a}$ and $R^{4b}$ are each H.

102. The compound of claim 19, wherein D is of the formula (D-3b).

103. The compound of claim 19, wherein D is of the formula (D-3 a).

104. The compound of claim 19, wherein $R^0$ is $C_4$-$C_{14}$ hydrocarbyl optionally substituted by 1 to 2 halogen atoms.

105. The compound of claim 19, wherein $R^0$ is branched $C_4$-$C_{14}$ alkyl, —$(CH_2)_2(C(CH_3)_2)R^A$, or —$(CH_2)_mR^A$; m is 0, 1, 2, or 3; z is 1 or 2; and $R^A$ is $C_3$-$C_8$ cycloalkyl optionally substituted by 1 to 4 groups independently selected from the group consisting of $C_1$-$C_4$ alkyl, $C_1$-$C_4$ alkylene, and halogen.

106. The compound of claim 19, wherein $R^0$ is branched $C_4$-$C_{14}$ alkyl.

107. The compound of claim 105, wherein $R^0$ is —$(CH_2)_mR^A$.

108. The compound of claim 107, wherein m is 2.

109. The compound of claim 107, wherein m is 1.

110. The compound of claim 105, wherein $R^0$ is —$(CH_2)_2(C(CH_3)_2)R^A$.

111. The compound of claim 110, wherein z is 1.

112. The compound of claim 107, wherein $R^A$ is cyclopropyl, cyclobutyl, or cyclopentyl.

113. The compound of claim 107, wherein $R^A$ is $C_3$-$C_6$ cycloalkyl optionally substituted by 1 to 3 groups independently selected from the group consisting of methyl, methylene, and halogen.

114. The compound of claim 107, wherein $R^A$ is $C_3$-$C_6$ cycloalkyl.

115. The compound of claim 107, wherein $R^A$ is cyclopropyl optionally substituted by 1 to 3 groups independently selected from the group consisting of methyl and methylene.

116. The compound of claim 107, wherein m is 0 and $R^A$ is cyclohexyl optionally substituted by 1 to 3 groups independently selected from the group consisting of methyl and methylene.

117. A pharmaceutical composition comprising (i) the compound according to claim 1; and (ii) a pharmaceutically acceptable excipient.

118. A method for preparing the compound of claim 1, comprising:
reacting a compound of the formula (A):

$$F—[W-L^{3a}-Y^{3a}]_y \qquad (A)$$

with a compound of formula (B):

$$Y^{3b}-L^{3b}-L^2-L^1-D \qquad (B)$$

wherein y is an integer from 1 to 500; W, $L^2$, $L^1$, and D are as defined in claim 1; F is a particle-based conjugation moiety; $L^{3a}$ and $L^{3b}$ are optional spacer fragments; $Y^{3a}$ and $Y^{3b}$ are precursor moieties that react with each other to form spacer fragment $Y^3$; and $L^{3a}$, $Y^3$, and $L^{3b}$ are taken together to form $L^3$,
to form the compound of formula (I).

119. The method of claim 118, wherein $Y^{3a}$ is an alkyne group, $Y^{3b}$ is an azido group, and $Y^3$ is a 1,4-[1,2,3]triazolylene moiety.

120. The method of claim 118, wherein $L^{3a}$ is an amide spacer fragment, and $L^{3b}$ is an acyl spacer fragment or a PEG-acyl spacer fragment.

121. A method for preparing the compound of claim 1, comprising:
reacting a compound of formula (C):

$$F—[W']_x \qquad (C)$$

with a compound of formula (D):

$$L^3-L^2-L^1-D \qquad (D)$$

wherein x is an integer from 1 to 50; $L^3$, $L^2$, $L^1$, and D are as defined for the compound of formula (I); F is an antibody-based conjugation moiety; and W' is N, O, S, $N_3$, or alkyne, to form the compound of formula (I).

* * * * *